United States Patent
George et al.

(10) Patent No.: US 8,465,745 B2
(45) Date of Patent: Jun. 18, 2013

(54) CHIMERIC ANTIGENS FOR ELICITING AN IMMUNE RESPONSE

(75) Inventors: Rajan George, Edmonton (CA); Lorne Tyrrell, Edmonton (CA); Antoine Noujaim, Edmonton (CA); Dakun Wang, Edmonton (CA); Allan Ma, Edmonton (CA)

(73) Assignee: Akshaya Bio Inc. (CA)

( * ) Notice: Subject to any disclaimer, the term of this patent is extended or adjusted under 35 U.S.C. 154(b) by 0 days.

(21) Appl. No.: 13/209,979

(22) Filed: Aug. 15, 2011

(65) Prior Publication Data

US 2012/0070435 A1 Mar. 22, 2012

Related U.S. Application Data

(63) Continuation of application No. 10/912,969, filed on Aug. 5, 2004, now Pat. No. 8,025,873, which is a continuation-in-part of application No. PCT/IB2004/000373, filed on Feb. 14, 2004, and a continuation-in-part of application No. 10/365,620, filed on Feb. 13, 2003, now Pat. No. 8,029,803.

(60) Provisional application No. 60/423,578, filed on Nov. 5, 2002, provisional application No. 60/390,564, filed on Jun. 20, 2002.

(51) Int. Cl.
*A61K 39/395* (2006.01)
*A61K 39/29* (2006.01)
*A61K 39/00* (2006.01)

(52) U.S. Cl.
USPC ............... 424/143.1; 424/193.1; 424/228.1; 435/69.1

(58) Field of Classification Search
None
See application file for complete search history.

(56) References Cited

U.S. PATENT DOCUMENTS

| | | | |
|---|---|---|---|
| 4,088,748 A | 5/1978 | McAleer et al. |
| 4,181,713 A | 1/1980 | McAleer et al. |
| 4,235,871 A | 11/1980 | Papahadjopoulos et al. |
| 4,428,941 A | 1/1984 | Galibert et al. |
| 4,433,059 A | 2/1984 | Chang et al. |
| 4,501,728 A | 2/1985 | Geho et al. |
| 4,569,794 A | 2/1986 | Smith et al. |
| 4,599,230 A | 7/1986 | Milich et al. |
| 4,599,231 A | 7/1986 | Milich et al. |
| 4,722,840 A | 2/1988 | Valenzuela et al. |
| 4,816,249 A | 3/1989 | Levy et al. |
| 4,816,567 A | 3/1989 | Cabilly et al. |
| 4,837,028 A | 6/1989 | Allen |
| 4,877,830 A | 10/1989 | Dobeli et al. |
| 5,019,369 A | 5/1991 | Presant et al. |
| 5,023,252 A | 6/1991 | Hseih |
| 5,047,513 A | 9/1991 | Dobeli et al. |
| 5,053,224 A | 10/1991 | Koprowski et al. |
| 5,098,833 A | 3/1992 | Lasky et al. |
| 5,116,964 A | 5/1992 | Capon et al. |
| 5,155,027 A | 10/1992 | Sledziewski et al. |
| 5,196,194 A | 3/1993 | Rutter et al. |
| 5,216,131 A | 6/1993 | Lasky et al. |
| 5,225,538 A | 7/1993 | Capon et al. |
| 5,284,933 A | 2/1994 | Dobeli et al. |
| 5,310,663 A | 5/1994 | Dobeli et al. |
| 5,336,603 A | 8/1994 | Capon et al. |
| 5,346,994 A | 9/1994 | Chomczynski |
| 5,420,264 A | 5/1995 | Seed et al. |
| 5,428,130 A | 6/1995 | Capon et al. |
| 5,455,030 A | 10/1995 | Ladner et al. |
| 5,455,165 A | 10/1995 | Capon et al. |
| 5,514,582 A | 5/1996 | Capon et al. |
| 5,565,335 A | 10/1996 | Capon et al. |
| 5,567,584 A | 10/1996 | Sledziewski et al. |
| 5,589,466 A | 12/1996 | Felgner et al. |
| 5,686,600 A | 11/1997 | Carozzi et al. |
| 5,715,147 A | 2/1998 | Nagano |
| 5,750,375 A | 5/1998 | Sledziewski et al. |
| 5,792,463 A | 8/1998 | Valenzuela et al. |
| 5,840,844 A | 11/1998 | Lasky et al. |
| 5,843,725 A | 12/1998 | Sledziewski et al. |
| 5,928,902 A | 7/1999 | De Wilde et al. |
| 5,942,234 A | 8/1999 | Ralston et al. |
| 5,965,140 A | 10/1999 | Valenzuela et al. |
| 5,969,109 A | 10/1999 | Bona et al. |

(Continued)

FOREIGN PATENT DOCUMENTS

| WO | WO 92/01470 | 2/1992 |
|---|---|---|
| WO | WO 92/05793 | 4/1992 |

(Continued)

OTHER PUBLICATIONS

Adema et al., "Migration of dendritic cell based cancer vaccines: in vivo veritas?," Current Opinion in Immunology, 2005, vol. 17, pp. 1-5.

Akiyama et al., "Targeting apoptotic tumor cells to FcγR provides efficient and versatile vaccination against tumors by dendritic cells", J. Immunol., 2003, vol. 170, pp. 1641-1648.

Alter et al., "The Prevalence of Hepatitis C Virus Infection in the United States, 1988 through 1994"N. Eng. J. Med., 1999, vol. 341, pp. 556-562.

Alter et al., "Recovery, persistence and sequelae in hepatitis C virus infection: a perspective on long-term outcome", Semin. Liver Dis., 2000, vol. 20, pp. 17-35.

(Continued)

*Primary Examiner* — Bao Li
(74) *Attorney, Agent, or Firm* — Sheridan Ross P.C.

(57) ABSTRACT

Disclosed herein are compositions and methods for eliciting immune responses against antigens. In particular embodiments, the compounds and methods elicit immune responses against antigens that are otherwise recognized by the host as "self" antigens. The immune response is enhanced by presenting the host immune system with a chimeric antigen comprising an immune response domain and a target binding domain, wherein the target binding domain comprises a xenotypic antibody fragment. By virtue of the target binding domain, antigen presenting cells take up, process, and present the chimeric antigen, eliciting both a humoral and cellular immune response.

26 Claims, 65 Drawing Sheets

U.S. PATENT DOCUMENTS

| | | | |
|---|---|---|---|
| 5,977,315 | A | 11/1999 | Chatterjee et al. |
| 6,004,781 | A | 12/1999 | Seed |
| 6,018,026 | A | 1/2000 | Sledziewski et al. |
| 6,074,846 | A | 6/2000 | Ralston et al. |
| 6,074,852 | A | 6/2000 | Ralston et al. |
| 6,086,873 | A | 7/2000 | Sykes et al. |
| 6,087,476 | A | 7/2000 | Kenten et al. |
| 6,117,655 | A | 9/2000 | Capon et al. |
| 6,207,153 | B1 | 3/2001 | Dan et al. |
| 6,241,985 | B1 | 6/2001 | Madiyalakan et al. |
| 6,242,195 | B1 | 6/2001 | Idusogie et al. |
| 6,274,148 | B1 | 8/2001 | Ralston et al. |
| 6,277,375 | B1 | 8/2001 | Ward |
| 6,291,212 | B1 | 9/2001 | Sledziewski et al. |
| 6,291,646 | B1 | 9/2001 | Sledziewski et al. |
| 6,300,099 | B1 | 10/2001 | Sledziewski et al. |
| 6,323,323 | B1 | 11/2001 | Sledziewski et al. |
| 6,406,697 | B1 | 6/2002 | Capon et al. |
| 6,500,641 | B1 | 12/2002 | Chen et al. |
| 6,521,423 | B1 | 2/2003 | Houghton et al. |
| 6,555,114 | B1 | 4/2003 | Maertens et al. |
| 6,613,333 | B1 | 9/2003 | Leroux-Roels et al. |
| 6,689,355 | B2 | 2/2004 | Schultes et al. |
| 6,710,169 | B2 | 3/2004 | Capon et al. |
| 6,716,623 | B2 | 4/2004 | Chen et al. |
| 6,716,966 | B1 | 4/2004 | Madiyalakan |
| 6,808,901 | B1 | 10/2004 | Neuberger et al. |
| 6,838,281 | B2 | 1/2005 | Scott et al. |
| 7,067,110 | B1 | 6/2006 | Gillies et al. |
| 7,090,976 | B2 | 8/2006 | Anderson et al. |
| 7,105,303 | B2 | 9/2006 | Ralston et al. |
| 7,273,752 | B2 | 9/2007 | Chen et al. |
| 7,429,385 | B2 | 9/2008 | Houghton et al. |
| 7,601,516 | B2 | 10/2009 | Low |
| 7,754,208 | B2 | 7/2010 | Ledbetter et al. |
| 8,007,805 | B2 * | 8/2011 | George et al. ............. 424/178.1 |
| 8,025,873 | B2 * | 9/2011 | George et al. ............. 424/93.1 |
| 8,029,803 | B2 * | 10/2011 | George et al. ............. 424/227.1 |
| 2001/0044135 | A1 | 11/2001 | Stahl et al. |
| 2001/0048922 | A1 | 12/2001 | Romet-Lemonne et al. |
| 2002/0048583 | A1 | 4/2002 | Schultes et al. |
| 2003/0235536 | A1 | 12/2003 | Blumberg et al. |
| 2004/0001853 | A1 * | 1/2004 | George et al. ............. 424/189.1 |
| 2004/0047877 | A1 | 3/2004 | Leroux-Roels et al. |
| 2004/0063912 | A1 | 4/2004 | Blumberg et al. |
| 2005/0013828 | A1 * | 1/2005 | George et al. ............. 424/189.1 |
| 2005/0031628 | A1 * | 2/2005 | George et al. ............. 424/178.1 |
| 2005/0089843 | A1 | 4/2005 | Ralston et al. |
| 2009/0238822 | A1 | 9/2009 | George et al. |
| 2011/0223185 | A1 | 9/2011 | George et al. |

FOREIGN PATENT DOCUMENTS

| | | |
|---|---|---|
| WO | WO 96/01650 | 1/1996 |
| WO | WO 96/08570 | 3/1996 |
| WO | WO 96/40941 | 12/1996 |
| WO | WO 97/07218 | 2/1997 |
| WO | WO 97/36932 | 10/1997 |
| WO | WO 98/20141 | 5/1998 |
| WO | WO 99/65517 | 12/1999 |
| WO | WO 00/20460 | 4/2000 |
| WO | WO 01/07081 | 2/2001 |
| WO | WO 01/32714 | 5/2001 |
| WO | WO 01/32893 | 5/2001 |
| WO | WO 01/77137 | 10/2001 |
| WO | WO 01/85203 | 11/2001 |
| WO | WO 02/04484 | 1/2002 |
| WO | WO 02/056830 | 7/2002 |
| WO | WO 2004/004798 | 1/2004 |
| WO | WO 2004/100882 | 11/2004 |
| WO | WO 2004/101740 | 11/2004 |
| WO | WO 2004/108885 | 12/2004 |
| WO | WO 2005/001025 | 1/2005 |
| WO | WO 2005/014838 | 2/2005 |
| WO | WO 2005/073383 | 8/2005 |
| WO | WO 2005/087813 | 9/2005 |

OTHER PUBLICATIONS

Altmann et al., "Insect Cells as Hosts for the Expression of Recombinant Glycoproteins." Glycoconjugate Journal, 1999, vol. 16, pp. 109-123.

Andoniou et al., "Interation between conventional dendritic cells and natural killer cells is integral to the activation of effective antiviral immunity", Nature Immunol. Online, 2005, vol. 6, No. 10, pp. 1011-1019.

Apostolopoulos et al., "Aldehyde-mannan antigen complexes target the MHC class I antigen-presentation pathway", Eur. J. Immunol., 2000, vol. 30, pp. 1714-1723.

Apostolopoulos et al., "Role of the mannose receptor in the immune response," Curr. Mol. Med., 2001, vol. 1, pp. 469-474.

Arribillaga et al., "Enhancement of CD4 and CD8 immunity by anti-CD137 (4-1BB) monoclonal antibodies during hepatitis C vaccination with recombinant adenovirus", Vaccine, 2005, vol. 23, pp. 3493-3499.

Ashkenazi, et al., "Immunoadhesins as research tools and therapeutic agents", Curr. Op. Immunol., 1997, vol. 9, pp. 195-200.

Babiuk et al., "Needle-free topical electroporation improves gene expression from plasmids administered in porcine skin", Molecular Therapy, 2003, vol. 8, pp. 992-998.

Babiuk et al. "Electroporation improves the efficacy of DNA vaccines in large animals." Vaccine, 2002, 20: 3399-3408.

Babiuk et al., "Increased gene expression and inflammatory cell infiltration causedby electroporation are both important for improving the efficacy of DNA vaccines." J. Biotechnol, 2004, 110: 1-10.

Banchereau et al., "Dendritic cells and the control of immunity," Nature, 1998, vol. 392, pp. 245-252.

Bartenschlager, "Hepatitis C virus replicons: potential role for drug development", Nature Rev. Drug. Discov., 2002, vol. 1, pp. 911-916.

Bartenschlager et al., "Nonstructural Protein 3 of the Hepatitis C Virus Encodes a Serine-Type Proteinase Required for Cleavage at the NS3/4 and NS4/5 Junctions", J. Virol., 1993, vol. 67, pp. 3835-3844.

Bartenschlager et al., "Novel Insights into Hepatitis C Virus Replication and Persistence", Advances in Virus Research, 2004, vol. 63, pp. 71-180.

Barth et al., "Uptake and presentation of hepatitis C Virus-like particles by human dendritic cells", Blood, May 1, 2005, vol. 105, No. 9, pp. 3605-3614.

Batista et al., "The two membrane isoforms of human IgE assemble into functionally distinct B cell antigen receptors", J. Exp. Med., 1996, vol. 184, pp. 2197-2206.

Baumert et al., "Hepatitis C Virus Structural Proteins Assemble into Viruslike Particles in Insect Cells", Journal of Virology, 1998, vol. 72, No. 5, pp. 3827-3836.

Beasley, "Hepatitis B Virus. The major etiology of hepatocellular carcinoma," Cancer, 1988, vol. 61, No. 10, pp. 1942-1956.

Behrens et al., "Identification and properties of the RNA-dependent RNA polymerase of Hepatitis C virus", EMBO, 1996, vol. 15, pp. 12-22.

Berlyn et al., "Generation of CD4(+) and CD8(+) T lymphocyte responses by dendritic cells armed with PSA/anti-PSA (antigen/antibody) complexes," Clin. Immunol, 2001, vol. 101, No. 33, pp. 276-283.

Berzofsky et al., "Progress on new vaccine strategies against chronic viral infections", The Journal of Clinical Investigation, Aug. 2004, vol. 114, No. 4, pp. 450-462.

Biochemistry 4th Ed., Lubert Stryer ed., W. H. Freeman and Co., 1995, pp. 18-23.

Björklunda et al., "Characterization of recombinant human IgE-Fc fragments expressed in baculovirus-infected insect cells", Mol. Immunol., 2000, vol. 37, pp. 169-177.

Bonini, et al., "Targeting antigen in mature dendritic cells for simultaneous stimulation of CD4+ and CD8+ T cells", Journal Immunology, 2001, vol. 166, pp. 5250-5257.

Boruchov et al., "Activating and inhibitory IgC Fc receptors on human DCs mediate opposing functions", The Journal of Clinical Investigation, Oct. 2005, vol. 115, No. 10, pp. 2914-2923.

Bouige et al., "Molecular analysis of the modulatory factors of the response to HBsAg in mice as an approach to HBV vaccine enhancement", FEMS Immunology & Medical Microbiology, Jan. 1996, vol. 13, No. 1 p. 71-79.

Bowen et al., "Adaptive immune responses in acute and chronic hepatitis C virus infection." Nature, 2005, vol. 436, pp. 946-952.

Brown, "Hepatitis C and Liver transplantation", Nature, 2005, vol. 436, No. 7053, pp. 973-978.

Bruss et al., "Mapping a Region of the Large Envelope Protein Required for Hepatitis B Virion Maturation", J. Virol., 1994, vol. 68, No. 3, pp. 1643-1650.

Campton et al. "Tumor antigen presentation by dermal antigen-presenting cells", J. Invest. Dermatol., 2000, vol. 115, pp. 57-61.

Cao et al., "In Vivo Inhibition of Anti-Hepatitis B Virus Core Antigen (HBcAg) Immunoglobulin G Production by HBcAg-Specific CD4+ Th1-Type T-Cell Clones in a hu-PBL-NOD/SCID Mouse Model", Journal of Virology, Dec. 2001, vol. 75, No. 23, pp. 11449-11456.

Carroll, "The complement system in regulation of adaptive immunity", Nature Immunol., 2005, vol. 5, pp. 981-986.

Chamow et al., "Immunoadhesins: principles and applications", TIBTECH, 1996, vol. 14, pp. 52-60.

Chapman-Smith et al., "The enzyme biotinylation of proteins: a post-translational modification of exceptional specificity", TIBS, 1999, vol. 24, pp. 359-363.

Chisari, "Unscrambling hepatitis C virus-host interactions", Nature, Aug. 18, 2005, vol. 436, pp. 930-932.

Clarke, "Molecular virology of hepatitis C virus" J. Gen. Virol., 1997, vol. 78, pp. 2397-2410.

Cooper et al., "Analysis of a successful immune response against hepatitis C virus", Immunity, 1999, vol. 10, pp. 439-449.

Coughlan et al., "Enhanced proliferation of CD4+ T cells induced by dendritic cells following antigen uptake in the presence of specific antibody", Vetrinary Immunology and Immunopathology 49: 321-330,1996.

De Francesco et al., "Challenges and successes in developing new therapies for hepatitis C", Nature, 2005, vol. 436, pp. 953-960.

Delwaide et al., "Evidence-based medicine: treatment of chronic hepatitis C. Liege Study Group on Viral Hepatitis", Rev. Med. Liege, 2000, vol. 55, pp. 337-340 (Abstract).

Deres et al., "In vivo priming of virus-specific cytotoxic T lymphocytes with synthetic lipopeptide vaccine," Nature, 1989, vol. 342, pp. 561-564.

Dieckman et al. "High throughput methods for gene cloning and expression." Protein Expression and Purification published on line Jun. 19, 2002, vol. 25, No. 1, pp. 8-15.

Diepolder et al., "Possible mechanism involving T lymphocyte response to non-structural protein 3 in viral clearance in acute hepatitis C infection", Lancet, 1995, vol. 36, pp. 1006-1007.

Dodson et al., "Prevention of de novo hepatitis B infection in recipients of hepatic allografts from anti-HBc positive donors", Transplantation, 1999, vol. 68, No. 7, pp. 1058-1061.

Dolganiuc et al., "Hepatitis C Virus Core and Nonstructural Protein 3 Proteins Induce Pro- and Anti-inflammatory Cytokines and Inhibit Dendritic Cell Differentiation", J. Immunol., 2003, vol. 170, pp. 5615-5624.

Donnelly et al., "DNA vaccines." Annu. Rev. Immunol, 1997, vol. 15, pp. 617-648.

Dwyer et al., "Expression and characterization of a Dnase I-Fc fusion enzyme", Journal of Biological Chemistry, 1999, vol. 274, No. 14, pp. 9738-9743.

Encke et al., "Prophylactic and therapeutic vaccination with dendritic cells against hepatitis C virus infection", British Society for Immunology, Clinical and Experimental Immunology, 2005, vol. 142, pp. 362-369.

Ewen et al., "A novel cytotoxicity assay to evaluate antigen-specific CTL responses using a colorimetric substrate for Granzyme B" J. Immunol. Meth., 2003, vol. 276, pp. 89-101.

Eyles et al., "Stimulation of spleen cells in vitro by nanospheric particles containing antigen", Journal of Controlled Release, 2003, vol. 86, pp. 25-32.

"Faculty of Medicine Immunology Bookcase", Dalhousie University website, available at http://pim.medieine.dal.ealabfe.htm, pp. 1-2, published in 2005, modified on Nov. 29, 2006, printed Aug. 29, 2007.

Faith et al., "Targeting the dendritic cell: The key to immunotherapy in cancer?", British Society for Immunology, Clinical and Experimental Immunology, 2005, vol. 139, pp. 395-397.

Fanger, "Characterization of expression, cytokine regulation, and effector function of the high affinity IgG receptor FcγRl(CD64) expressed on human blood dendritic cells", Journal of Immunology, 1997, vol. 158, pp. 3090-3098.

Fanger et al., "Type I (CD64) and Type II (CD32) Fcγ receptor-mediated phagocytosis by human blood dendritic cells", Journal of Immunology, 1996, vol. 157, pp. 541-548.

Feld et al., "Mechanism of action of interferon and ribavirin in treatment of hepatitis C", Nature, 2005, vol. 436, pp. 967-972.

Feng et al., Database Embase 'Online!, Database accession No. EMB-2O03261340, "Construction and expression of chrimeid plasmid pHCV-IgFc", Elsevier Science Publishers and World Chinese Journal of Digestology, 11:6, pp. 697-700, Jun. 1, 2003 (Abstract).

Ferlazzo et al., "Dendritic cells generated either from CD34+ progenitor cells or from monocytes differ in their ability to activate antigen-specific CD8+ T cells", Journal of Immunology, 1999, vol. 163, pp. 3597-3604.

Finkleman et al., "Dendritic cells can present antigen in vivo in a tolerogenic or immunogenic fashion", Journal of Immunology, 1996, vol. 157, pp. 1406-1414.

Fong et al., "Dendritic cells in cancer immunotherapy", Annu. Rev. Immunol., 2000, vol. 18, pp. 245-273.

Fournillier et al., "Primary and memory T cell responses induced by hepatitis C Virus multiepitope long peptides", Vaccine, 2006, vol. 24, pp. 3153-3164.

Fried et al., "Peginterferon alfa-2a plus ribavirin for chronic hepatitis C virus infection." N. Engl. J. Med., 2002, vol. 347, No. 13, pp. 975-982.

Gale, Jr et al., "Evasion of intracellular host defence by hepatitis C virus", Nature, 2005, vol. 436, pp. 939-945.

Ganem, "Perspectives: Virology: The X files-one step closer to closure", Science, 2001, vol. 294, pp. 2299-2300.

Geijtenbeek et al., "Self- and nonself-recognition by C-type lectins on dendritic cells", Annu. Rev. Immunol., 2004, vol. 22, pp. 33-54.

George et al. "Chimigen Vaccines: A novel class of therapeutic vaccines for the treatment of chronic viral infections." International Meeting of the Molecular Biology of Hepatitis B Viruses, Sep. 7-10, 2003, Centro Congressi Giovanni XXIII, Bergamo, Italy, 1 page.

George et al., "A novel Class of Therapeutic Vaccines for the Treatment of Chronic Viral Infections: Evaluation in Ducks Chronically Infected with Duck Hepatitis B Virus (DHBV)", Hepdart 2003, Frontiers in Drug Development for Viral Hepatitis, Dec. 14-18,Kauai, Hawaii, USA., 1 page.

George et al. (2006) A new class of therapeutic vaccines for the treatment of chronic hepatitis B infections. In "Framing the Knowledge of Viral Hepatitis" Schinazi, R. F. Editor, 1HL Press USA, pp. 379-403.

George et al., "A New Class of Therapeutic Vaccines Produced in Insect Cells for the Treatment of Chronic Viral Infections", BioProcessing Journal, 2005, vol. 4, pp. 38-44.

George et al., "A new class of chimeric vaccines for the treatment of hepatitis C infections." 11th International Symposium on Hepatitis C and Related Viruses, Heidelberg, Germany, Oct. 3-7, 2004.

George et al., "Immunological Evaluation of a Novel Chimeric Therapeutic Vaccine for the Treatment of Chronic Hepatitis B Infections", International Meeting of the Molecular Biology of Hepatitis B Viruses, Woods Hole, MA, Oct. 24-27, 2004, 1 page.

Grakoui et al., "HCV persistence and immune evasion in the absence of memory T cell help", Science, 2003, vol. 302, pp. 659-662.

Grohmann et al., "CD40 litigation ablates the tolerogenic potential of lymphoid dendritic cells", Journal of Immunology, 2001, vol. 166, pp. 277-283.

Guermonprez et al., "Antigen presentation and T cell stimulation by dendritic cells", Annu. Rev. Immunol., 2002, vol. 20, pp. 621-667.

Gust et al., "Taxonomic classification of human hepatitis B virus," Intervirology, 1986, vol. 25, pp. 14-29.

Guyre et al., "Colocalization of FcγRI-targeted antigen with class I MHC: implications for antigen processing", J. Immunol., 2001, vol. 166, pp. 2469-2478.

Hahn, "Subversion of immune responses by hepatitis C virus: 25 immunomodulatory strategies beyond evasion'?", Curr. Opin. Immunol., 2003, vol. 15, pp. 443-449.

Hamann et al., "Phenotypic and functional separation of memory and effector human CD8+ T cells", J. Exp. Med., 1997, vol. 186, p. 1407.

Hameed et al., "Immunohistochemical identification of cytotoxic lymphocytes using human perforin monoclonal antibody" Am. J. Pathol., 1992, vol. 140, pp. 1025-1030.

Hartgers et al., "Toward a molecular understanding of dendritic cell immunobiology", Immunology Today, 2000, vol. 21, No. 11, pp. 542-545.

He, et al, "A novel human cancer vaccine elicits cellular responses to the tumor-associated antigen, human chorionic gonadotropin" Clin Cancer Res, 10(6): 1920-1927, (2004).

Hellström et al., "Significance of Pre-S2 Peptide of Hepatitis B Virus: Should it be in the Vaccine?", Prog. Med. Virol., 1998, vol. 35, pp. 76-106.

Henikoff et al., "Amino acid substitution matrices from protein blocks," PNAS, 1992, vol. 89, pp. 10915-10919.

Hewlett et al., "The coated pit and macropinocytic pathways serve distinct endosome populations." J. Cell Biology, 1994, vol. 124, pp. 689-703.

Hijikkata et al., "Gene mapping of the putative structural region of the hepatitis C virus genome by in vitro processing analysis", Proc. Natl. Acad. Sci. USA, 1991, vol. 88, pp. 5547-5551.

Hilgers et al. "Sulfolipo-cyclodextrin in squalane-in-water as a novel and safe vaccine adjuvant" Vaccine, 1999, vol. 17, pp. 219-228.

Hinrichsen, et al, "Short-term antiviral efficacy of BILN 2061, a hepatitis C 30 virus serine protease inhibitor, in hepatitis C genotype 1 patients", Gastroenterology, 2004, vol. 127, pp. 1347-1355.

Ho et al., "The likelihood of aggregation during protein renaturation can be assessed using the second viral coefficient", Prot. Sci., 2003, vol. 12, pp. 708-716.

Hochrein et al., "Differential production of IL-12, IFN-oc and IFN-y by mouse dendritic cell subsets", Journal of Immunology, 2001, vol. 166, pp. 5448-5455.

Hoofnagle, "Course and outcome of hepatitis C", Hepatology, 2002, vol. 36, pp. S21-S29.

Houghton et al., "Prospects for a vaccine against the hepatitis C virus", Nature, Aug. 18, 2005, vol. 436, pp. 961-966.

Iwasaki et al., "Toll-like receptor control of the adaptive immune responses", Nature Immunol., 2004, vol. 5, pp. 987-995.

Jefferis, "Glycosylation of Recombinant Antibody Therapeutics", Biotechnol. Prog., 2005, vol. 21, pp. 11-16.

Jenne et al., "Viral vectors for dendritic cell-based immunotherapy", Trends in Immunology, 2001, vol. 22, No. 2, pp. 102-107.

Jilg et al., "Novel hepatitis B vaccines", Vaccine, 1998, vol. 16, pp. s65-s68.

Jonuleit et al., "Dendritic cells as a tool to induce anergic and regulatory T cells", Trends in Immunology, 2001, vol. 22, No. 7, pp. 394-400.

Kane, "Global programme for control of hepatitis B infection", Vaccine, 1995, vol. 13 (Supplement 1), pp. S47-S49.

Koo et al. "Construction and expression of a bifunctional single-chain antibody against *Bacillus cereus* p6ores." Applied and Environmental Microbiology 1998, vol. 64, No. 7, pp. 2490-2496.

Kotenko et al. "Identification of the Functional Interleukin-22 (IL-22) Receptor Complex", Journal of Biological Chemistry, 2002, vol. 276, No. 4, pp. 2725-2732.
Kozak, "Adherence to the first-AUG rule when a second AUG codon follows closely upon the first," PNAS, 1995, vol. 92, pp. 2662-2666.
Kozak, "An analysis of 5'-noncoding sequences from 699 vertebrate messenger RNAs," NAR, 1987, vol. 15, No. 20, pp. 8125-8132.
Kozak, "Context Effects and Inefficient Initiation at Non-AUG Codons in Eucaryotic Cell-Free Translation Systems," Mol. Cell. Biol, 1989, vol. 9, No. 11, pp. 5073-5080.
Kozlowski, et al., "Lactacystin inhibits cathepsin A activity in melanoma cell lines", Tumour Biol., 2001, vol. 22, No. 4, pp. 211-215.
Lai et al., "DNA vaccines", Crit. Rev., Immunol., 1998, vol. 18, pp. 449-484.
Langhans et al., "Cytotoxic Capacity of Hepatitis C Virus (HVC)-specific Lymphocytes After in Vitro Immunization with HCV-Derived Lipopeptides", Cytometry Part A, 2005, vol. 65A, pp. 59-68.
Larsson et al. "Dendritic cells resurrect antigens from dead cells." Trends Immunol., 2001, vol. 22, No. 3, pp. 141-148.
Lauer et al., "Medical Progress: Hepatitis C Virus Infection", N. Engl. J. Med., 2001, vol. 345, No. 1, pp. 41-52.
Laupéze et al. "Differential expression of major histocompatibility complex class Ia, Ib, and II molecules on monocytes and raonocyte-derived dendritic and macrophagic cells." Hum. Immunol, 1999, vol. 60, pp. 591-597.
Lebensztein et al., "Current knowledge on treatment of chronic hepatitis B in children", Med. Sci. Monit., 2000, vol. 6, No. 1, pp. 198-203.
Lechner et al., "Analysis of successful immune responses in persons infected with hepatitis C virus.", J. Exp. Med., 2000, vol. 191, pp. 1499-1522.
Lei et al., "Structure-function analysis of human glucose-6-phosphatase, the enzyme deficient in glycogen storage disease type 1 a," J. Biol. Chem., 1995, vol. 270, No. 20, pp. 11882-11886.
Leyssen et al., "Perspectives for the Treatment of Infections with Flaviviridae", Clinical Microbiology Reviews, Jan. 2000, vol. 13, No. 1, pp. 67-82.
Li et al., "A novel HBV DNA vaccine based on T cell epitopes and its potential therapeutic effect in HBV transgenic mice", International Immunology, 2005, vol. 17, No. 10, pp. 1293-1302.
Liang et al., "Pathogenesis, Natural History, Treatment, and Prevention of Hepatitis C", Annals of Internal Medicine, Feb. 15, 2000, vol. 132, No. 4, pp. 296-305.
Lin, et al, "In vitro resistance studies of hepatitis C virus serine protease inhibitors, VX-950 and BILN 2061: structural analysis indicates different resistance 5 mechanisms", J. Biol. Chem, 2004, vol. 279, pp. 17508-17514.
Lindenbach, et al, Complete Replication of hepatitis C Virus in culture, Science, 2005, vol. 309, pp. 623-626.
Lindenbach et al., "Unravelling hepatitis C virus replication from genome to function", Nature, 2005, vol. 436, pp. 933-938.
Liu et al., "Dendritic cell lineage, plasticity and cross-regulation", Nature immunology, 2001, vol. 2, No. 7, pp. 585-589).
Lizée et al., "Tails of wonder: endocytic-sorting motifs key for exogenous antigen presentation" Trends Immunol., 2005, vol. 26, No. 3, pp. 141-149.
Lobe, et al, "Novel serine proteases encoded by two cytotoxic T lymphocyte-specific genes." Science , 1986, vol. 232, pp. 858-861.
Lohmann et al., "Processing pathways of 15 the hepatitis C virus proteins", J. Hepatol., 1996, vol. 24, pp. 11-19.
Loirat et al., "Multiepitopic HLA-A 0201-Restricted Immune Response Against Hepatitis B Surface Antigen After DNA-Based Immunization", The Journal of Immunology, 2000, vol. 165, No. 8, pp. 4748-4755.
Lorenz et al. "Anti-tumor immunity elicited by a recombinant vaccinia virus expressing CD70 (CD27L)" Hum. Gene Ther., 1999, vol. 10, pp. 1095-1103.
Lorenz et al., "Induction of Ani-Tumor Immunity Elicited yb Tumor Cells Expressing a Murine LFA-3 Analog via a Recombinant Vaccinia virus", Hum. Gene Ther., 1999, vol. 10, pp. 623-631.
Lu, et al, "Mutations conferring resistance to a potent hepatitis C virus serine protease inhibitors in vitro." Antimicrob Agents Chemother., 2004, vol. 48, pp. 2260-2266.
Lutsiak et al., "Analysis of poly(D,L-lactic-co-glycolic acid) nanosphere uptake by human dendritic cells and macrophages in vitro", Pharmaceutical Research, Oct. 2002, vol. 19, No. 10, pp. 1480-1487 (Abstract).
Maini et al., "The role of virus-specific CD8(+) cells in liver damage and viral control during persistent hepatitis B virus infection" J. Exp. Med., 2000, vol. 191, pp. 1269-1280.
Manns et al., "Peginterferon alfa-2b plus ribavirin compared with interferon alfa-2b plus ribavirin for initial treatment of chronic hepatitis C: a randomised trial," Lancet, 2001, vol. 358, pp. 958-965.
Marion, "Use of animal models to study hepatitis B virus." Prog. Med. Virol., 1988, vol. 35, pp. 43-75.
Mason et al. "Virus of Pekin Ducks with Structural and Biological Relatedness to Human Hepatitis B Virus", J. Virol., 1980, vol. 36, No. 3, pp. 829-836.
McCluskie et al., "Immunization Against Hepatitis B Virus by Mucosal Administration of Antigen-Antibody Complexes", Viral Immunology, 1998, vol. 11, No. 4, pp. 245-252.

McGreal et al., "Ligand recognition by antigen-presenting cell C-type lectin receptors", Current Opinion in Immunology, 2005, vol. 17, pp. 18-24.

McHutchison et al., "Current therapy for hepatitis C: pegylated interferon and ribavirin", Clin. Liver Dis., 2003, vol. 7, pp. 149-161.

Mehta, et al, "Protection against persistence of hepatitis C", 2002, Lancet, 2002, vol. 359, pp. 1478-1483.

Merad et al., "Differentiation of myeloid dendritic cells into CD8a-positive", Blood, 2000, vol. 96, No. 5, pp. 1865-1872.

Mercer, et al, "Hepatitis C virus replication in mice with chimeric human livers", Nat. Med., 2001, vol. 7, pp. 927-933.

Michel et al., "Therapeutic vaccination against chronic hepatitis B Virus infection", Journal of Clinical Virology, 2005, vol. 34, Suppl. 1, pp. S108-S114.

Middelberg, "Preparative protein refolding", Trends Biotech., 2002, vol. 20, pp. 437-443.

Mihailova et al., "Recombinant virus-like particles as a carrier of B- and T-cell epitopes of hepatitis C Virus (HCV)", Vaccine, 2006, pp. 1-9.

Moll et al., "Designed heterodimerizing leucine zippers with a range of pIs and stabilities up to 10-15 M.", Protein Science, 2001, vol. 10, pp. 649-655.

Moore et al., "Interleukin-10 and the interleukin-10 receptor", Annual Review Immunology, 2001, vol. 19, pp. 683-765.

Morris et al., "Incorporation of an Isoleucine Zipper Motif Enhances the Biiological Activity of Soluble CD40L (CD154)", The Journal of Biological Chemistry, Jan. 1999, vol. 274, No. 1, pp. 418-422.

Motyka et al., "CD8+ T Cell Responses to a Novel Class of Therapeutic Vaccines for the Treatment of Chronic Hepatitis B Infection", Abstract No. 2481,12th International Congress of Immunology and 4th Annual Conference of FOCIS, [online] Jul. 18-23, 2004 [retrieved Nov. 19, 2004] retrieved from the Internet URL: http://www.immuno2004.ore/onlineabstracts/index.htm.

Nagarajan et al., "Ligand binding and phagocytosis by CD16 (Fcy receptor III) isoforms", Journal of Biological Chemistry, 1995, vol. 270, No. 43, pp. 25672-25770.

Nestle et al., "Dendritic-cell-based therapeutic vaccination against cancer", Current Opinion in Immunlogy, 2005, vol. 17, pp. 1-7.

Neuhaus et al., "Multiple sclerosis: comparison of copolymer-1-reactive T cell lines from treated and untreated subjects reveals cytokine shift from T helper 1 to T helper 2 cells", PNAS, 2000, vol. 97, No. 13, pp. 7452-7457.

Newman et al. "Cytoplasmic delivery of a macromolecular fluorescent probe by poly (d, I-lactic-co-glycolic acid) microspheres." J. Biomed Mater Res., 2000, vol. 50, pp. 591-597.

Newman et al. "Ovalbumin peptide encapsulated in poly (d, I lactic-co-glycolic acid) microspheres is capable of inducing a T helper type 1 immune response." J. Control Release, 1998, vol. 54, pp. 49-59.

Newman et al. "Uptake of poly (D,L-lactic-co-glycolic acid) microspheres by antigen-presenting cells in vivo," J. Biomed Mater Res., 2002, vol. 603, pp. 480-486.

Novak et al., "Engagement of FceRI on human monocytes induces the production of IL-10 and prevents their differaetation in dendritic cells", Journal of Immunology, 2001, vol. 167, pp. 797-804.

Pawlotsky, "Diagnostic tests for hepatitis", J. Hepatol., 1999, vol. 31(suppl), pp. 71-79.

Peng et al., "Novel vaccines for the treatment of chronic HBV infection based on mycobacterial heat shock protein 70", Vaccine, 2006, vol. 24, pp. 887-896.

Penin et al. (2004) Structural Biology of hepatitis C virus. Hepatology 39: 5-19.

Polyak et al., "Hepatitis C Virus Nonstructural 5A Protein Induces Interleukin-8, Leading to Partial Inhibition of the Interferon-Induced Antiviral Response", J. Virol., 2001, vol. 75, pp. 6095-6106.

Post et al., "Clearance of Hepatitis C Viremia Associated with Cellular Immunity in the Absence of Seroconversion in the Hepatitis C Incidence and Transmission in Prisons Study Cohort", J. Infect. Dis., 2004, vol. 189, pp. 1846-1855.

Purcell, "The Hepatitis C Virus: Overview," Hepatology, 1997, vol. 26(3), pp. 11S-14S.

Qin et al. "Fcg receptor IIB on follicular dendritic cells regulates the B cell recall response", Journal of Immunology, 2000, vol. 164, pp. 6268-6275.

Quarantino et al., "Fully competent dendritic cells as inducers of T cell anergy in autoimmunity", PNAS, 2000, vol. 97, No. 20, pp. 10911-10916.

Ramakrishna et al., "Mannose receptor targeting of tumor antigen pmeII7 to human dendritic cells directs anti-melanoma T cell responses via multiple HLA molecules," J. Immunol, 2004, vol. 172, pp. 2845-2852.

Regnault et al., "Fcg receptor-mediated induction of dendritic cell maturation and major histocompatibility complex Class 1-restricted antigen presentation after immune complex internalization", Journal Exp. Medicine, 1999, vol. 189, No. 2, pp. 371-380.

Rehermann et al., "Immunology of hepatitis B and hepatitis C virus infection", Nature Rev. Immunol., 2005, vol. 5, pp. 215-229.

Reiser, et al, "Antiviral efficacy of NS3-serine protease inhibitor BILN-2061 in patients with chronic genotype 2 and 3 hepatitis C", Hepatology, 2005, vol. 41, pp. 832-835.

Roncarolo et al., "Differentation of T regulatory cells by immature dendritic cells", Journal Exp. Medicine, 2001, vol. 193, No. 2, pp. F5-F9.

Roque et al., "Antibodies and Genetically Engineered Related Molecules: Production and Purification", Biotechnol. Prog., 2004, vol. 20, pp. 639-654.

Rozema et al., "Artificial chaperone-assisted refolding of denatured-reduced lysozyme: Modulation of competition between renaturation and aggregation", Biochem., 1996, vol. 35, pp. 15760-15771.

Saito et. al., "Hepatitis C virus infection is associated with the development of hepatocellular carcinoma", PNAS USA, 1990, vol. 87, pp. 6547-6549.

Sarobe et al., "Abnormal priming of CD4(+) T cells by dendritic cells expressing hepatitis C virus core and El proteins" J. Virol., 2002, vol. 76, pp. 5062-5070.

Sarobe et al., "Hepatitis C virus structural proteins impair dendritic cell maturation and inhibit in vivo induction of cellular immune responses", J. Virol., 2002, vol. 77, pp. 10862-10871.

Schirmbeck et al. "Ongoing murine T1 or T2 immune responses to the hepatitis B surface antigen are excluded from the liver that expresses transgene-encoded hepatitis B surface antigen", J. Immunol., Apr. 15, 2000, vol. 164, No. 8), pp. 4235-4243.

Schultz et al., "Duck Hepatitis B Virus: An Invaluable Model System for HBV Infection", Advances in Virus Research, 2004, vol. 63, pp. 1-70.

Schuurhuis et al., "Antigen-antibody immune complexes empower dendritic cells to efficiently prime specific CD8+ CTL responses in vivo", Journal of Immunology, 2002, vol. 168, pp. 2240-2246.

Seeff, "Natural history of chronic hepatitis C", Hepatology, 2002, vol. 36, pp. s35-s46.

Shiraki et al. "Processing of hepatitis B virus surface antigen expressed by recombinant Oka varicella vaccine virus" J. General Virol. 1992, vol. 73, pp. 1401-1407.

Shoji et al., "Internal Processing of Hepatitis C Virus NS3 Protein" Virology, 1999, vol. 254, pp. 315-323.

Shoukry et al., "Cell-mediated immunity 15 and the outcome of hepatitis C virus infection", Ann. Rev. Microbiol, 2004, vol. 58, pp. 391-424.

Shoukry et al., "Memory CD8+ T cells are required for protection from persistent hepatitis C virus infection", J. Exp. Med., 2003, vol. 197, pp. 1645-1655.

Spaeny-Dekking et al., "Extracellular granzymes A and B in humans: detection of native species during CTL responses in vitro and in vivo", J. Immunol., 1988, vol. 160, p. 3610.

Sprengel et al. "Isolation and characterization of a hepatitis B virus endemic in herons." J. of Virol., 1988, vol. 62, No. 10, pp. 3832-3839.

Steinman et al. "Antigen capture, processing, and presentation by dendritic cells: recent cell biological studies." Hum. Immunol., 1999, vol. 60, No. 7, pp. 562-567.

Stevenson et al., "Vaccine therapy in NGL; Future Promises and Current Limitations", Leuk Lymphoma 44 Suppl 3: S85-90 (2003).

Strader, "Understudied populations with hepatitis C", Hepatology, 2002, vol. 36, pp. S226-S236.

Strader et al., (2004) "Diagnosis, management, and treatment of hepatitis C", Hepatology, 2004, vol. 39, pp. 1147-1171.

Summers et al. "A virus similar to human hepatitis B virus associated with hepatitis and hepatoma in woodchucks." Proc. Natl. Acad. Sci. USA, 1978, vol. 75, No. 9, pp. 4533-4537.

Szoka et al., "Comparative properties and methods of preparation of lipid vesicles (liposomes)", Ann. Rev. Biophys. Bioeng., 1980, vol. 9, pp. 467-508.

Takeda, et al., "Toll-like receptors", Annu. Rev. Immunol., 2003, vol. 21, pp. 335-376.

Tan et al., "How hepatitis C virus counteracts the interferon response: the jury is still out on NS5A" Virology, 2001, vol. 284, pp. 1-12.

Tarte et al., "Dendritic cell-based vaccine: a promising 5 approach for cancer immunotherapy", Leukemia, 1999, vol. 13, pp. 653-663.

Taylor et al., "Macrophage receptors and immune recognition", Annu. Rev. Immunol., 2005, vol. 23, pp. 901-944.

Taylor et al., "The mannose receptor: linking homeostasis and immunity through sugar recognition", Trends in Immunology, Feb. 2005, vol. 26, No. 2, pp. 104-110.

Thimme et al., "Determinants of viral clearance and persistence during acute hepatitis C virus infection", J. Exp. Med., 2002, vol. 194, pp. 1395-1406.

Thimme et al., "Viral and immunological determinants of hepatitis C virus clearance, persistence, and disease", Proc. Natl. Acad. Sci. USA, 2001, vol. 99, pp. 15661-15668.

Trozzi et al. "In vitro selection and characterization of hepatitis C virus serine protease variants resistant to an active-site peptide inhibitor", J. Virol., 2003, vol. 77, pp. 3669-3679.

Wakita et al., 2005 "Production of infectious hepatitis C virus in tissue culture from a cloned viral genome", Nature Med., 2005, vol. 11, pp. 791-796.

Wang et al., "Characterization of Immune Responses to a Novel Therapeutic Vaccine for the Treatment of Chronic Heaptitis B Virus Infections", Abstract No. 2293,12th International Congress of Immunology and 4th Annual Conference of FOCIS,(2004), [online] Jul. 18-23, 2004 [retrieved Nov. 19, 2004 ] retrieved from the Internet URL: http://www.immuno2004.ore/onlineabstracts/index.html (abstract).

Wang et al., "Induction of hepatitis C virus-specific cytotoxic T and B cell responses by dendritic cells expressing a modified antigen targeting receptor." World J. Gastroenterol,2005; 11(4):557-560.

Wei et al., "Development of the diagnostic immunossay to detect anti-PreS1 (21-47aa) antibody-a marker suggesting the health improvement of hepatitis B patients", Clinical Chemica Acta, 2002, vol. 317, pp. 159-169.

Wen et al., "Antigen-antibody complex as therapeutic vaccine for viral hepatitis B", Int. Rev. Immunol., 1999, vol. 18, pp. 251-258.

Wen et al., "Hepatitis B vaccine and anti-HBs complex as approach for vaccine therapy", The Lacent 1995, vol. 345, No. 8964, pp. 1575-1576.

Wetlaufer et al., "Control of aggregation in protein refolding: A variety of surfactants promote renaturation of carbonice anhydrase II", Prot. Sci., 1995, vol. 4, pp. 1535-1543.

Whitton et al., "The Regulation and Maturation of Antiviral Immune Responses", Advances in Virus Research, 2004, vol. 63, pp. 181-238.

Wieland et al., "Stealth and cunning: Hepatitis B and Hepatitis C viruses.", J. Virol., 2005, vol. 79, pp. 9369-9380.

Wild et al., "Primary prevention of hepatocellular carcinoma in developing countries", Mutation Res., 2000, vol. 462, pp. 381-393.

Wines et al. "The IgG Fc Contains Distinct Fc Receptor (FcR) Binding Sites: The Leukocyte Receptors Fc{gamma}RI and Fc{gamma}RIIa Bind to a Region in the Fc Distinct from That Recognized by Neonatal FcR and Protein A," J. Immuno., 2000, vol. 164, pp. 5313-5318.

Xu, et al, "Endoplasmic reticulum targeting sequence enhances HBV-specific cytotoxic T lympocytes induced by a CTL epitope-based DNA vaccine", Virology, 2005 vol. 334, pp. 255-263.

Yanagi, et al, "Transcripts from a single full-length cDNA clone of hepatitis C virus are infectious when directly transfected into the liver of a chimpanzee", Proc. Natl. Acad. Sci. USA, 1997, vol. 94, pp. 8738-8743.

Yotsuyanagi et al. "Prolonged Fecal Excretion of Hepatitis A Virus in Adult Patients With Hepatitis A as Determined by Polymerase Chain Reaction", Hepatology vol. 24, No. 1, 1996, pp. 10-13.

You, et al, "Targeting Dendritic Cells to Enhance DNA Vaccine Potency.", Cancer Research, 2001; vol. 61, pp. 3704-3711.

You et al., "A retrogen strategy for presentation of an intracellular tumor antigen as an exogenous antigen by dendritic cells induces potent antitumor T helper and CTL responses", Cancer Research, 2001, vol. 61, No. 1, pp. 197-205.

You et al., "Induction of vigorous helper and cytotoxic T cell as well as B cell responses by dentritic cells expressing a modified antigen targeting receptor-mediated intemalization pathway", Journal of Immunology, 165:8, pp. 4581-4591, Oct. 15, 2001.

Yu et al., "Priming with CpG-enriched plasmid and boosting with protein formulated with CpG oligodeoxynucleotides and Quil A induces strong cellular and humoral immune responses to hepatitis C virus NS3", J. Gen. Virol., 2004, vol. 85, pp. 1533-1543.

Zheng et al., "Therapeutic efficacy of hepatitis B surface antigen-antibodies-recombinant ONA composite in HBsAg transgenic mice", Vaccine, Jul., 2001, vol. 19, No. 30, pp. 4219-4225.

Zhong, et al, 2005 "Robust hepatitis C infection in vitro", Proc. Natl. Acad. Sci. USA, 2005, vol. 102, pp. 9294-9299.

Zhong et al., "A Study of Humoral Immune Responses Induced by Anti-HBs-HBsAg Immunogenic Complexes", Zhonghua Weishengwuxue He Mianyixue Zazhi (Chinese Journal of Microbiology and Immunology) ,1998, vol. 18, No. 4, pp. 331-335 (English Translation Provided).

Zhu et al., "MHC class 1-related neonatal Fc receptor for IgG is functionally expressed in monocytes, intestinal macrophages, and dendritic cells", Journal of Immunology, 2001, vol. 166, pp. 3266-3276.

Zou, "Regulatory T cells, tumour immunity and immunotherapy", Nat Rev Immunol., Apr. 2006, vol. 6, pp. 295-307.

Zuckerman, "More than third of world's population has been infected with hepatitis B virus", BMJ, 1999, vol. 318, No. 7192, p. 1213.

International Search Report for International (PCT) Application No. PCT/IB2004/000373, mailed Aug. 19, 2004.

Written Opinion for International (PCT) Application No. PCT/IB2004/000373, mailed Aug. 19, 2004.

International Preliminary Report on Patentability for International (PCT) Application No. PCT/IB2004/000373, issued Aug. 14, 2006.

* cited by examiner

TBD

Fig 6a. DNA sequence of TBD Protein expression cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC AAA GGC
CTA CGT CGA CGA GCT CAA CTA GTG CGG CCG CAA GGC GGC GGA TCC GTG
GAC AAG AAA ATT GTG CCC AGG GAT TGT GGT TGT AAG CCT TGC ATA TGT
ACA GTC CCA GAA GTA TCA TCT GTC TTC ATC TTC CCC CCA AAG CCC AAG
GAT GTG CTC ACC ATT ACT CTG ACT CCT AAG GTC ACG TGT GTT GTG GTA
GAC ATC AGC AAG GAT GAT CCC GAG GTC CAG TTC AGC TGG TTT GTA GAT
GAT GTG GAG GTG CAC ACA GCT CAG ACG CAA CCC CGG GAG GAG CAG TTC
AAC AGC ACT TTC CGC TCA GTC AGT GAA CTT CCC ATC ATG CAC CAG GAC
TGG CTC AAT GGC AAG GAG TTC AAA TGC AGG GTC AAC AGT GCA GCT TTC
CCT GCC CCC ATC GAG AAA ACC ATC TCC AAA ACC AAA GGC AGA CCG AAG
GCT CCA CAG GTG TAC ACC ATT CCA CCT CCC AAG GAG CAG ATG GCC AAG
GAT AAA GTC AGT CTG ACC TGC ATG ATA ACA GAC TTC TTC CCT GAA GAC
ATT ACT GTG GAG TGG CAG TGG AAT GGG CAG CCA GCG GAG AAC TAC AAG
AAC ACT CAG CCC ATC ATG GAC ACA GAT GGC TCT TAC TTC GTC TAC AGC
AAG CTC AAT GTG CAG AAG AGC AAC TGG GAG GCA GGA AAT ACT TTC ACC
TGC TCT GTG TTA CAT GAG GGC CTG CAC AAC CAC CAT ACT GAG AAG AGC
CTC TCC CAC TCT CCT GGG CTG CAA AGC TTG TCG AGA AGT ACT AGA GGA
TCA TAA
```

Fig 6b. Amino Acid sequence of TBD Protein

MSYYHHHHHHDYDIPTTENLYFQGAMDPEFKGLRRRAQLVRPQGGGSVDKKIVPRDCGCKPCIC
TVPEVSSVFIFPPKPKDVLTITLTPKVTCVVVDISKDDPEVQFSWFVDDVEVHTAQTQPREEQF
NSTFRSVSELPIMHQDWLNGKEFKCRVNSAAFPAPIEKTISKTKGRPKAPQVYTIPPPKEQMAK
DKVSLTCMITDFFPEDITVEWQWNGQPAENYKNTQPIMDTDGSYFVYSKLNVQKSNWEAGNTFT
CSVLHEGLHNHHTEKSLSHSPGLQSLSRSTRGS

Fig 8a. DNA Sequence of HBV S1/S2-TBD Protein expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCT ATG AAA AAA TGG
TCA TCA AAA CCT CGC AAA GGC ATG GGG ACG AAT CTT TCT GTT CCC AAC
CCT CTG GGA TTC TTT CCC GAT CAT CAG TTG GAC CCT GTA TTC GGA GCC
AAC TCA AAC AAT CCA GAT TGG GAC TTC AAC CCC ATC AAG GAC CAC TGG
CCA GCA GCC AAC CAG GTA GGA GTG GGA GCA TTC GGG CCA GGG TTC ACC
CCT CCA CAC GGC GGT GTT TTG GGG TGG AGC CCT CAG GCT CAG GGC ATG
TTG ACC CCA GTG TCA ACA ATT CCT CCT CCT GCC TCC GCC AAT CGG CAG
TCA GGA AGG CAG CCT ACT CCC ATC TCT CCA CCT CTA AGA GAC AGT CAT
CCT CAG GCC ATG CAG TGG AAT TCC ACT GCC TTC CAC CAA GCT CTG CAA
GAC CCC AGA GTC AGG GGT CTG TAT TTT CCT GCT GGT GGC TCC AGT TCA
GGA ACA GTA AAC CCT GCT CCG AAT ATT GCC TCT CAC ATC TCG TCA ATC
TCC GCG AGG ACC GGG GAC CCT GTG ACG AAC TCG CGG CCG CAA GGC GGC
GGA TCC GTG GAC AAG AAA ATT GTG CCC AGG GAT TGT GGT TGT AAG CCT
TGC ATA TGT ACA GTC CCA GAA GTA TCA TCT GTC TTC ATC TTC CCC CCA
AAG CCC AAG GAT GTG CTC ACC ATT ACT CTG ACT CCT AAG GTC ACG TGT
GTT GTG GTA GAC ATC AGC AAG GAT GAT CCC GAG GTC CAG TTC AGC TGG
TTT GTA GAT GAT GTG GAG GTG CAC ACA GCT CAG ACG CAA CCC CGG GAG
GAG CAG TTC AAC AGC ACT TTC CGC TCA GTC AGT GAA CTT CCC ATC ATG
CAC CAG GAC TGG CTC AAT GGC AAG GAG TTC AAA TGC AGG GTC AAC AGT
GCA GCT TTC CCT GCC CCC ATC GAG AAA ACC ATC TCC AAA ACC AAA GGC
AGA CCG AAG GCT CCA CAG GTG TAC ACC ATT CCA CCT CCC AAG GAG CAG
ATG GCC AAG GAT AAA GTC AGT CTG ACC TGC ATG ATA ACA GAC TTC TTC
CCT GAA GAC ATT ACT GTG GAG TGG CAG TGG AAT GGG CAG CCA GCG GAG
AAC TAC AAG AAC ACT CAG CCC ATC ATG GAC ACA GAT GGC TCT TAC TTC
GTC TAC AGC AAG CTC AAT GTG CAG AAG AGC AAC TGG GAG GCA GGA AAT
ACT TTC ACC TGC TCT GTG TTA CAT GAG GGC CTG CAC AAC CAC CAT ACT
GAG AAG AGC CTC TCC CAC TCT CCT GGG CTG CAA AGC TTG TCG AGA AGT
ACT AGA GGA TCA TAA
```

Fig 8b. Amino Acid sequence of HBV S1/S2-TBD Protein

```
MSYYHHHHHHDYDIPTTENLYFQGAMDPMKKWSSKPRKGMGTNLSVPNPLGFFPDHQLDPVFGA
NSNNPDWDFNPIKDHWPAANQVGVGAFGPGFTPPHGGVLGWSPQAQGMLTPVSTIPPPASANRQ
SGRQPTPISPPLRDSHPQAMQWNSTAFHQALQDPRVRGLYFPAGGSSSGTVNPAPNIASHISSI
SARTGDPVTNSRPQGGGSVDKKIVPRDCGCKPCICTVPEVSSVFIFPPKPKDVLTITLTPKVTC
VVVDISKDDPEVQFSWFVDDVEVHTAQTQPREEQFNSTFRSVSELPIMHQDWLNGKEFKCRVNS
AAFPAPIEKTISKTKGRPKAPQVYTIPPPKEQMAKDKVSLTCMITDFFPEDITVEWQWNGQPAE
NYKNTQPIMDTDGSYFVYSKLNVQKSNWEAGNTFTCSVLHEGLHNHHTEKSLSHSPGLQSLSRS
TRGS
```

Fig 9a. DNA Sequence of HBV S1/S2 Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCT ATG AAA AAA TGG
TCA TCA AAA CCT CGC AAA GGC ATG GGG ACG AAT CTT TCT GTT CCC AAC
CCT CTG GGA TTC TT

Fig 11a. DNA Sequence of HBV S1/S2/S-TBD Protein Expression Cassette

```
ATG TCG TAC TAC CAT CAC CAT CAC CAT CAC GAT TAC GAT ATC CCA ACG ACC
GAA AAC CTG TAT TTT CAG GGC GCC ATG GAT CCT ATG GGA GGT TGG TCA TCA
AAA CCT CGC AAA GGC ATG GGG ACG AAT CTT TCT GTT CCC AAC CCT CTG GGA
TTC TTT CCC GAT CAT CAG TTG GAC CCT GTA TTC GGA GCC AAC TCA AAC AAT
CCA GAT TGG GAC TTC AAC CCC ATC AAG GAC CAC TGG CCA GCA GCC AAC CAG
GTA GGA GTG GGA GCA TTC GGG CCA GGG TTC ACC CCT CCA CAC GGC GGT GTT
TTG GGG TGG AGC CCT CAG GCT CAG GGC ATG TTG ACC CCA GTG TCA ACA ATT
CCT CCT CCT GCC TCC GCC AAT CGG CAG TCA GGA AGG CAG CCT ACT CCC ATC
TCT CCA CCT CTA AGA GAC AGT CAT CCT CAG GCC ATG CAG TGG AAT TCC ACT
GCC TTC CAC CAA GCT CTG CAA GAC CCC AGA GTC AGG GGT CTG TAT TTT CCT
GCT GGT GGC TCC AGT TCA GGA ACA GTA AAC CCT GCT CCG AAT ATT GCC TCT
CAC ATC TCG TCA ATC TCC GCG AGG ACT GGG GAC CCT GTG ACG AAC ATG GAG
AAC ATC ACA TCA GGA TTC CTA GGA CCC CTG CTC GTG TTA CAG GCG GGG TTT
TTC TTG TTG ACA AGA ATC CTC ACA ATA CCG CAG AGT CTA GAC TCG TGG TGG
ACT TCT CTC AAT TTT CTA GGG GGA TCA CCC GTG TGT CTT GGC CAA AAT CGG
CAG TCC CCA ACC TCC AAT CAC TCA CCA ACC TCC TGT CCT CCA ATT TGT CCT
GGT TAT CGC TGG ATG TGT CTG CGG CGT TTT ATC ATA TTC CTC TTC ATC CTG
CTG CTA TGC CTC ATC TTC TTA TTG GTT CTT CTG GAT TAT CAA GGT ATG TTG
CCC GTT TGT CCT CTA ATT CCA GGA TCA ACA ACA ACC AGT ACG GGA CCA TGC
AAA ACC TGC ACG ACT CCT GCT CAA GGC AAC TCT ATG TTT CCC TCA TGT TGC
TGT ACA AAA CCT ACG GAT GGA AAT GCA CCT GTA TTC CCA TCG TCT
TGG GCT TTC GCA AAA TAC CTA TGG GAG TGG GCC TCA GTC CGT TTC TCT TGG
CTC AGT TTA CTA GTG CCA TTT GTT CAG TGG TTC GTA GGG CTT TCC CCC ACT
GTT TGG CTT TCA GCT ATA TGG ATG ATG TGG TAT TGG GGG CCA AGT CTG TAC
AGC ATC GTG AGT CCC TTT ATA CCG CTG TTA CCA ATT TTC TTT TGT CTC TGG
GTA TAC ATT TCG CGG CCG CAA GGC GGC GGA TCC GTG GAC AAG AAA ATT GTG
CCC AGG GAT TGT GGT TGT AAG CCT TGC ATA TGT ACA GTC CCA GAA GTA TCA
TCT GTC TTC ATC TTC CCC CCA AAG CCC AAG GAT GTG CTC ACC ATT ACT CTG
ACT CCT AAG GTC ACG TGT GTT GTG GTA GAC ATC AGC AAG GAT GAT CCC GAG
GTC CAG TTC AGC TGG TTT GTA GAT GAT GTG GAG GTG CAC ACA GCT CAG ACG
CAA CCC CGG GAG GAG CAG TTC AAC AGC ACT TTC CGC TCA GTC AGT GAA CTT
CCC ATC ATG CAC CAG GAC TGG CTC AAT GGC AAG GAG TTC AAA TGC AGG GTC
AAC AGT GCA GCT TTC CCT GCC CCC ATC GAG AAA ACC ATC TCC AAA ACC AAA
GGC AGA CCG AAG GCT CCA CAG GTG TAC ACC ATT CCA CCT CCC AAG GAG CAG
ATG GCC AAG GAT AAA GTC AGT CTG ACC TGC ATG ATA ACA GAC TTC TTC CCT
GAA GAC ATT ACT GTG GAG TGG CAG TGG AAT GGG CAG CCA GCG GAG AAC TAC
AAG AAC ACT CAG CCC ATC ATG GAC ACA GAT GGC TCT TAC TTC GTC TAC AGC
AAG CTC AAT GTG CAG AAG AGC AAC TGG GAG GCA GGA AAT ACT TTC ACC TGC
TCT GTG TTA CAT GAG GGC CTG CAC AAC CAC CAT ACT GAG AAG AGC CTC TCC
CAC TCT CCT GGG CTG CAA AGC TTG TCG AGA AGT ACT AGA GGA TCA TAA
```

Fig 11b. Amino Acid Sequence of HBV S1/S2/S/TBD Protein

MSYYHHHHHHDYDIPTTENLYFQGAMDPMGGWSSKPRKGMGTNLSVPNPLGFFPDHQLDPVFGA
NSNNPDWDFNPIKDHWPAANQVGVGAFGPGFTPPHGGVLGWSPQAQGMLTPVSTIPPPASANRQ
SGRQPTPISPPLRDSHPQAMQWNSTAFHQALQDPRVRGLYFPAGGSSSGTVNPAPNIASHISSI
SARTGDPVTNMENITSGFLGPLLVLQAGFFLLTRILTIPQSLDSWWTSLNFLGGSPVCLGQNSQ
SPTSNHSPTSCPPICPGYRWMCLRRFIIFLFILLLCLIFLLVLLDYQGMLPVCPLIPGSTTTST
GPCKTCTTPAQGNSMFPSCCCTKPTDGNCTCIPIPSSWAFAKYLWEWASVRFSWLSLLVPFVQW
FVGLSPTVWLSAIWMMWYWGPSLYSIVSPFIPLLPIFFCLWVYISRPQGGGSVDKKIVPRDCGC
KPCICTVPEVSSVFIFPPKPKDVLTITLTPKVTCVVVDISKDDPEVQFSWFVDDVEVHTAQTQP
REEQFNSTFRSVSELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMDTDGSYFVYSKLNVQKSNWEA
GNTFTCSVLHEGLHNHHTEKSLSHSPGLQSLSRSTRGS

Fig 12a. DNA Sequence of HBV S1/S2/S Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCT ATG GGA GGT TGG
TCA TCA AAA CCT CGC AAA GGC ATG GGG ACG AAT CTT TCT GTT CCC AAC
CCT CTG GGA TTC TT

TBD

Figure 14A:
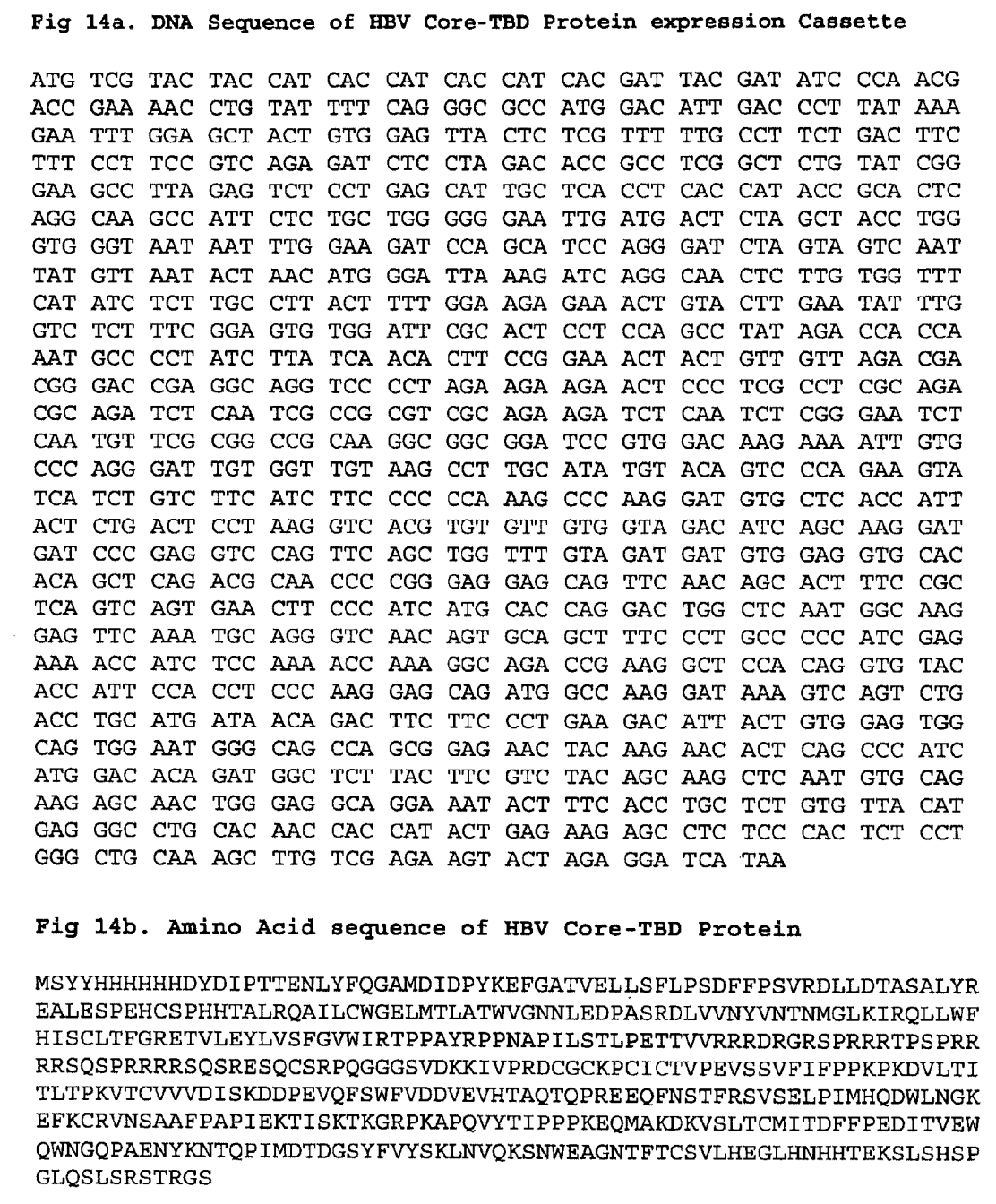

Fig 14a. DNA Sequence of HBV Core-TBD Protein expression Cassette

```
ATG TCG TAC TAC CAT CAC CAT CAC CAT CA

Fig 15a. DNA Sequence of HBV Core Protein expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAC ATT GAC CCT TAT AAA
GAA TTT GGA GCT ACT GTG GAG TTA CTC TCG TTT TTG CCT TCT GAC TTC
TTT CCT TCC GTC AGA GAT CTC CTA GAC ACC GCC TCG GCT CTG TAT CGG
GAA GCC TTA GAG TCT CCT GAG CAT TGC TCA CCT CAC CAT ACC GCA CTC
AGG CAA GCC ATT CTC TGC TGG GGG GAA TTG ATG ACT CTA GCT ACC TGG
GTG GGT AAT AAT TTG GAA GAT CCA GCA TCC AGG GAT CTA GTA GTC AAT
TAT GTT AAT ACT AAC ATG GGA TTA AAG ATC AGG CAA CTC TTG TGG TTT
CAT ATC TCT TGC CTT ACT TTT GGA AGA GAA ACT GTA CTT GAA TAT TTG
GTC TCT TTC GGA GTG TGG ATT CGC ACT CCT CCA GCC TAT AGA CCA CCA
AAT GCC CCT ATC TTA TCA ACA CTT CCG GAA ACT ACT GTT GTT AGA CGA
CGG GAC CGA GGC AGG TCC CCT AGA AGA AGA ACT CCC TCG CCT CGC AGA
CGC AGA TCT CAA TCG CCG CGT CGC AGA AGA TCT CAA TCT CGG GAA TCT
CAA TGT TCG CGG CCG CTT TCG AAT CTA GAG CCT GCA GTC TCG AGG CAT
GCG GTA CCA AGC TTG TCG AGA AGT ACT AGA GGA TCA TAA
```

Fig 15b. Amino Acid sequence of HBV Core Protein

MSYYHHHHHHDYDIPTTENLYFQGAMDIDPYKEFGATVELLSFLPSDFFPSVRDLLDTASALYR
EALESPEHCSPHHTALRQAILCWGELMTLATWVGNNLEDPASRDLVVNYVNTNMGLKIRQLLWF
HISCLTFGRETVLEYLVSFGVWIRTPPAYRPPNAPILSTLPETTVVRRRDRGRSPRRRTPSPRR
RRSQSPRRRRSQSRESQCSRPLSNLEPAVSRHAVPSLSRSTRGS

TBD

Fig 17a. DNA Sequence of DHBV PreS-TBD Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC ATG GGG
CAA CAT CCA GCA AAA TCA ATG GAC GTC AGA CGG ATA GAA GGA GGA GAA
ATA CTG TTA AAC CAA CTT GCC GGA AGG ATG ATC CCA AAA GGG ACT TTG
ACA TGG TCA GGC AAG TTT CCA ACA CTA GAT CAC GTG TTA GAC CAT GTG
CAA ACA ATG GAG GAG ATA AAC ACC CTC CAG AAT CAG GGA GCT TGG CCT
GCT GGG GCG GGA AGG AGA GTA GGA TTA TCA AAT CCG ACT CCT CAA GAG
ATT CCT CAG CCC CAG TGG ACT CCC GAG GAA GAC CAA AAA GCA CGC GAA
GCT TTT CGC CGT TAT CAA GAA GAA AGA CCA CCG GAA ACC ACC ACC ATT
CCT CCG TCT TCC CCT CCT CAG TGG AAG CTA CAA CCC GGG GAC GAT CCA
CTC CTG GGA AAT CAG TCT CTC CTC GAG ACT CAT CCG CTA TAC CAG TCA
GAA CCA GCG GTG CCA GTG ATA AAA ACT CCC CCC TTG AAG AAG AAA ACG
CGG CCG CAA GGC GGC GGA TCC GTG GAC AAG AAA ATT GTG CCC AGG GAT
TGT GGT TGT AAG CCT TGC ATA TGT ACA GTC CCA GAA GTA TCA TCT GTC
TTC ATC TTC CCC CCA AAG CCC AAG GAT GTG CTC ACC ATT ACT CTG ACT
CCT AAG GTC ACG TGT GTT GTG GTA GAC ATC AGC AAG GAT GAT CCC GAG
GTC CAG TTC AGC TGG TTT GTA GAT GAT GTG GAG GTG CAC ACA GCT CAG
ACG CAA CCC CGG GAG GAG CAG TTC AAC AGC ACT TTC CGC TCA GTC AGT
GAA CTT CCC ATC ATG CAC CAG GAC TGG CTC AAT GGC AAG GAG TTC AAA
TGC AGG GTC AAC AGT GCA GCT TTC CCT GCC CCC ATC GAG AAA ACC ATC
TCC AAA ACC AAA GGC AGA CCG AAG GCT CCA CAG GTG TAC ACC ATT CCA
CCT CCC AAG GAG CAG ATG GCC AAG GAT AAA GTC AGT CTG ACC TGC ATG
ATA ACA GAC TTC TTC CCT GAA GAC ATT ACT GTG GAG TGG CAG TGG AAT
GGG CAG CCA GCG GAG AAC TAC AAG AAC ACT CAG CCC ATC ATG GAC ACA
GAT GGC TCT TAC TTC GTC TAC AGC AAG CTC AAT GTG CAG AAG AGC AAC
TGG GAG GCA GGA AAT ACT TTC ACC TGC TCT GTG TTA CAT GAG GGC CTG
CAC AAC CAC CAT ACT GAG AAG AGC CTC TCC CAC TCT CCT GGG CTG CAA
AGC TTG TCG AGA AGT ACT AGA GGA TCA TAA
```

Fig 17b. Amino Acid Sequence of DHBV PreS-TBD Protein

MSYYHHHHHHDYDIPTTENLYFQGAMDPEFMGQH

Fig 18a. DNA Sequence of DHBV PreS Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC
ATG GGG CAA CAT CCA GCA AAA TCA ATG GAC GTC AGA CGG ATA GAA
GGA GGA GAA ATA CTG TTA AAC CAA CTT GCC GGA AGG ATG ATC CCA AAA
GGG ACT TTG ACA TGG TCA GGC AAG TTT CCA ACA CTA GAT CAC GTG TTA
GAC CAT GTG CAA ACA ATG GAG GAG ATA AAC ACC CTC CAG
AAT CAG GGA GCT TGG CCT GCT GGG GCG GGA AGG AGA GTA GGA TTA TCA
AAT CCG ACT CCT CAA GAG ATT CCT CAG CCC CAG TGG ACT CCC GAG GAA
GAC CAA AAA GCA CGC GAA GCT TTT CGC CGT TAT CAA GAA GAA AGA CCA
CCG GAA ACC ACC ACC ATT CCT CCG TCT TCC CCT CCT CAG TGG AAG CTA
CAA CCC GGG GAC GAT CCA CTC CTG GGA AAT CAG TCT CTC CTC GAG ACT
CAT CCG CTA TAC CAG TCA GAA CCA GCG GTG
CCA GTG ATA AAA ACT CCC CCC TTG AAG AAG AAA ACG CGG CCG CTT TCG
AAT CTA GAG CCT GCA GTC TCG AGG CAT GCG GTA CCA AGC TTG TCG AGA
AGT ACT AGA GGA TCA TAA
```

Fig 18b. Amino Acid Sequence of DHBV PreS Protein

MSYYHHHHHHDYDIPTTENLYFQGAMDPEFMGQHPAKSMDVRRIEGGEILLNQLAGRMIPKGTL
TWSGKFPTLDHVLDHVQTMEEINTLQNQGAWPAGAGRRVGLSNPTPQEIPQPQWTPEEDQKARE
AFRRYQEERPPETTTIPPSSPPQWKLQPGDDPLLGNQSLLETHPLYQSEPAVPVIKTPPLKKKT
RPLSNLEPAVSRHAVPSLSRSTRGS

Fig 20a. DNA Sequence of DHBV PreS/S-TBD Protein expression Cassette

```
ATG TCG TAC TAC CAT CAC CAT CAC CAT CAC GAT TAC GAT ATC CCA ACG ACC GAA AAC
CTG TAT TTT CAG GGC GCC ATG GAT CCG GAA TTC ATG GGG CAA CAT CCA GCA AAA TCA
ATG GAC GTC AGA CGG ATA GAA GGA GGA GAA ATA CTG TTA AAC CAA CTT GCC GGA AGG
ATG ATC CCA AAA GGG ACT TTG ACA TGG TCA GGC AAG TTT CCA ACA CTA GAT CAC GTG
TTA GAC CAT GTG CAA ACA ATG GAG GAG ATA AAC ACC CTC CAG AAT CAG GGA GCT TGG
CCT GCT GGG GCG GGA AGG AGA GTA GGA TTA TCA AAT CCG ACT CCT CAA GAG ATT CCT
CAG CCC CAG TGG ACT CCC GAG GAA GAA CAA AAA GCA CGC GAA GCT TTT CGC CGT TAT
CAA GAA GAA AGA CCA CCG GAA ACC ACC ACC ATT CCT CCG TCT TCC CCT CCT CAG TGG
AAG CTA CAA CCC GGG GAC GAT CCA CTC CTG GGA AAT CAG TCT CTC CTC GAG ACT CAT
CCG CTA TAC CAG TCA GAA CCA GCG GTG CCA GTG ATA AAA ACT CCC CCC TTG AAG AAG
AAA ATG TCT GGT ACC TTC GGG GGA ATA CTA GCT GGC CTA ATC GGA TTA CTG GTA AGC
TTT TTC TTG TTG ATA AAA ATT CTA GAA ATA CTG AGG AGG CTA GAT TGG TGG TGG ATT
TCT CTC AGT TCT CCA AAG GGA AAA ATG CAA TGC GCT TTC CAA GAT ACT GGA GCC CAA
ATC TCT CCA CAT TAC GTA GGA TCT TGC CCG TGG GGA TGC CCA GGA TTT CTT TGG ACC
TAT CTC AGG CTT TTT ATC ATC TTC CTC TTA ATC CTG CTA GTA GCA GCA GGC TTG CTG
TAT CTG ACG GAC AAC GGG TCT ACT ATT TTA GGA AAG CTC CAA TGG GCG TCG GTC TCA
GCC CTT TTC TCC TCC ATC TCT TCA CTA CTG CCC TCG GAT CCG AAA TCT CTC GTC GCT
TTA ACG TTT GGA CTT TCA CTT ATA TGG ATG ACT TCC TCT TCT GCC ACC CAA ACG CTC
GTC ACC TTA ACG CAA TTA GCC ACG CTG TCT GCT CTT TTT TAC AAG AGT TCG CGG CCG
CAA GGC GGC GGA TCC GTG GAC AAG AAA ATT GTG CCC AGG GAT TGT GGT TGT AAG CCT
TGC ATA TGT ACA GTC CCA GAA GTA TCA TCT GTC TTC ATC TTC CCC CCA AAG CCC AAG
GAT GTG CTC ACC ATT ACT CTG ACT CCT AAG GTC ACG TGT GTT GTG GTA GAC ATC AGC
AAG GAT GAT CCC GAG GTC CAG TTC AGC TGG TTT GTA GAT GAT GTG GAG GTG CAC ACA
GCT CAG ACG CAA CCC CGG GAG GAG CAG TTC AAC AGC ACT TTC CGC TCA GTC AGT GAA
CTT CCC ATC ATG CAC CAG GAC TGG CTC AAT GGC AAG GAG TTC AAA TGC AGG GTC AAC
AGT GCA GCT TTC CCT GCC CCC ATC GAG AAA ACC ATC TCC AAA ACC AAA GGC AGA CCG
AAG GCT CCA CAG GTG TAC ACC ATT CCA CCT CCC AAG GAG CAG ATG GCC AAG GAT AAA
GTC AGT CTG ACC TGC ATG ATA ACA GAC TTC TTC CCT GAA GAC ATT ACT GTG GAG TGG
CAG TGG AAT GGG CAG CCA GCG GAG AAC TAC AAG AAC ACT CAG CCC ATC ATG GAC ACA
GAT GGC TCT TAC TTC GTC TAC AGC AAG CTC AAT GTG CAG AAG AGC AAC TGG GAG GCA
GGA AAT ACT TTC ACC TGC TCT GTG TTA CAT GAG GGC CTG CAC AAC CAC CAT ACT GAG
AAG AGC CTC TCC CAC TCT CCT GGG CTG CAA AGC TTG TCG AGA AGT ACT AGA GGA TCA
TAA
```

Fig 20b. Amino Acid sequence of DHBV PreS/S-TBD Protein

MSYYHHHHHHDYDIPTTENLYFQGAMDPEFMGQHPAKSMDVRRIEGGEILLNQLAGRMIPKGTLTWSGKFPTLDHVL
DHVQTMEEINTLQNQGAWPAGAGRRVGLSNPTPQEIPQPQWTPEEEQKAREAFRRYQEERPPETTTIPPSSPPQWKL
QPGDDPLLGNQSLLETHPLYQSEPAVPVIKTPPLKKKMSGTFGGILAGLIGLLVSFFLLIKILEILRRLDWWWISLS
SPKGKMQCAFQDTGAQISPHYVGSCPWGCPGFLWTYLRLFIIFLLILLVAAGLLYLTDNGSTILGKLQWASVSALFS
SISSLLPSDPKSLVALTFGLSLIWMTSSSATQTLVTLTQLATLSALFYKSSRPQGGGSVDKKIVPRDCGCKPCICTV
PEVSSVFIFPPKPKDVLTITLTPKVTCVVVDISKDDPEVQFSWFVDDVEVHTAQTQPREEQFNSTFRSVSELPIMHQ
DWLNGKEFKCRVNSAAFPAPIEKTISKTKGRPKAPQVYTIPPPKEQMAKDKVSLTCMITDFFPEDITVEWQWNGQPA
ENYKNTQPIMDTDGSYFVYSKLNVQKSNWEAGNTFTCSVLHEGLHNHHTEKSLSHSPGLQSLSRSTRGS

Fig 21a. DNA Sequence of DHBV PreS/S Protein expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC ATG GGG
CAA CAT CCA GCA AAA TCA ATG GAC GTC AGA CGG ATA GAA GGA GGA GAA
ATA CTG TTA AAC CAA CTT GCC GGA AGG ATG ATC CCA AAA GGG ACT TTG
ACA TGG TCA GGC AAG TTT CCA ACA CTA GAT CAC GTG TTA GAC CAT GTG
CAA ACA ATG GAG GAG ATA AAC ACC CTC CAG AAT CAG GGA GCT TGG CCT
GCT GGG GCG GGA AGG AGA GTA GGA TTA TCA AAT CCG ACT CCT CAA GAG
ATT CCT CAG CCC CAG TGG ACT CCC GAG GAA GAC CAA AAA GCA CGC GAA
GCT TTT CGC CGT TAT CAA GAA GAA AGA CCA CCG GAA ACC ACC ACC ATT
CCT CCG TCT TCC CCT CCT CAG TGG AAG CTA CAA CCC GGG GAC GAT CCA
CTC CTG GGA AAT CAG TCT CTC CTC GAG ACT CAT CCG CTA TAC CAG TCA
GAA CCA GCG GTG CCA GTG ATA AAA ACT CCC CCC TTG AAG AAG AAA ATG
TCT GGT ACC TTC GGG GGA ATA CTA GCT GGC CTA ATC GGA TTA CTG GTA
AGC TTT TTC TTG TTG ATA AAA ATT CTA GAA ATA CTG AGG AGG CTA GAT
TGG TGG TGG ATT TCT CTC AGT TCT CCA AAG GGA AAA ATG CAA TGC GCT
TTC CAA GAT ACT GGA GCC CAA ATC TCT CCA CAT TAC GTA GGA TCT TGC
CCG TGG GGA TGC CCA GGA TTT CTT TGG ACC TAT CTC AGG CTT TTT ATC
ATC TTC CTC TTA ATC CTG CTA GTA GCA GCA GGC TTG CTG TAT CTG ACG
GAC AAC GGG TCT ACT ATT TTA GGA AAG CTC CAA TGG GCG TCG GTC TCA
GCC CTT TTC TCC TCC ATC TCT TCA CTA CTG CCC TCG GAT CCG AAA TCT
CTC GTC GCT TTA ACG TTT GGA CTT TCA CTT ATA TGG ATG ACT TCC TCC
TCT GCC ACC CAA ACG CTC GTC ACC TTA ACG CAA TTA GCC ACG CTG TCT
GCT CTT TTT TAC AAG AGT TCG CGG CCG CTT TCG AAT CTA GAG CCT GCA
GTC TCG AGG CAT GCG GTA CCA AGC TTG TCG AGA AGT ACT AGA GGA TCA
TAA
```

Figure 21b. Amino Acid sequence of DHBV PreS/S Protein

MSYYHHHHHHDYDIPTTENLYFQGAMDPEFMGQHPAKSMDVRRIEGGEILLNQLAGRMIPKGTL
TWSGKFPTLDHVLDHVQTMEEINTLQNQGAWPAGAGRRVGLSNPTPQEIPQPQWTPEEDQKARE
AFRRYQEERPPETTTIPPSSPPQWKLQPGDDPLLGNQSLLETHPLYQSEPAVPVIKTPPLKKKM
SGTFGGILAGLIGLLVSFFLLIKILEILRRLDWWWISLSSPKGKMQCAFQDTGAQISPHYVGSC
PWGCPGFLWTYLRLFIIFLLILLVAAGLLYLTDNGSTILGKLQWASVSALFSSISSLLPSDPKS
LVALTFGLSLIWMTSSSATQTLVTLTQLATLSALFYKSSRPLSNLEPAVSRHAVPSLSRSTRGS

Fig 23a. DNA Sequence of DHBV Core-TBD Protein expression Cassette

```
ATG TCG TAC TAC CA

Figure 24. Nucleotide and Amino Acid Sequences of the ORF of
DHBV Core Protein in the plasmid pFastBac HTa-DHBV Core Fig 24a. DNA Sequence of DHBV Core Protein expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT ATC AAT GCT TCT AGA
GCC TTA GCC AAT GTG TAT GAT CTA CCA GAT GAT TTC TTT CCA AAA ATA
GAT GAT CTT GTT AGA GAT GCT AAA GAC GCT TTA GAG CCT TAT TGG AAA
TCA GAT TCA ATA AAG AAA CAT GTT TTG ATT GCA ACT CAC TTT GTG GAT
CTC ATT GAA GAC TTC TGG CAG ACT ACA CAG GGC ATG CAT GAA ATA GCC
GAA TCA TTA AGA GCT GTT ATA CCT CCC ACT ACT ACT CCT GTT CCA CCG
GGT TAT CTT ATT CAG CAC GAG GAA GCT GAA GAG ATA CCT TTG GGA GAT
TTA TTT AAA CAC CAA GAA GAA AGG ATA GTA AGT TTC CAA CCC GAC TAT
CCG ATT ACG GCT AGA ATT CAT GCT CAT TTG AAA GCT TAT GCA AAA ATT
AAC GAG GAA TCA CTG GAT AGG GCT AGG AGA TTG CTT TGG TGG CAT TAC
AAC TGT TTA CTG TGG GGA GAA GCT CAA GTT ACT AAC TAT ATT TCT CGT
TTG CGT ACT TGG TTG TCA ACT CCT GAG AAA TAT AGA GGT AGA GAT GCC
CCG ACC ATT GAA GCA ATC ACT AGA CCA ATC CAG GTG GCT CAG GGA GGC
AGA AAA ACA ACT ACG GGT ACT AGA AAA CCT CGT GGA CTC GAA CCT AGA
AGA AGA AAA GTT AAA ACC ACA GTT GTC TAT GGG AGA AGA CGT TCA AAG
TCC CGG GAA AGG AGA GCC CCT ACA CCC CAA CGT GCG GGC TCC CCT CTC
CCA CGT AGT TCG AGC AGC CAC CAT AGA TCT CCC TCG CCT AGG AAA TCG
CGG CCG CTT TCG AAT CTA GAG CCT GCA GTC TCG AGG CAT GCG GTA CCA
AGC TTG TCG AGA AGT ACT AGA GGA TCA TAA
```

Fig 24b. Amino Acid sequence of DHBV Core Protein

```
MSYYHHHHHHDYDIPTTENLYFQGAMDINASRALANVYDLPDDFFPKIDDLVRDAKDALEPYWK
SDSIKKHVLIATHFVDLIEDFWQTTQGMHEIAESLRAVIPPTTTPVPPGYLIQHEEAEEIPLGD
LFKHQEERIVSFQPDYPITARIHAHLKAYAKINEESLDRARRLLWWHYNCLLWGEAQVTNYISR
LRTWLSTPEKYRGRDAPTIEAITRPIQVAQGGRKTTTGTRKPRGLEPRRRKVKTTVVYGRRRSK
SRERRAPTPQRAGSPLPRSSSSHHRSPSPRKSRPLSNLEPAVSRHAVPSLSRSTRGS
```

Figure 25. Effect of HBV sAg-Murine Fc Conjugate
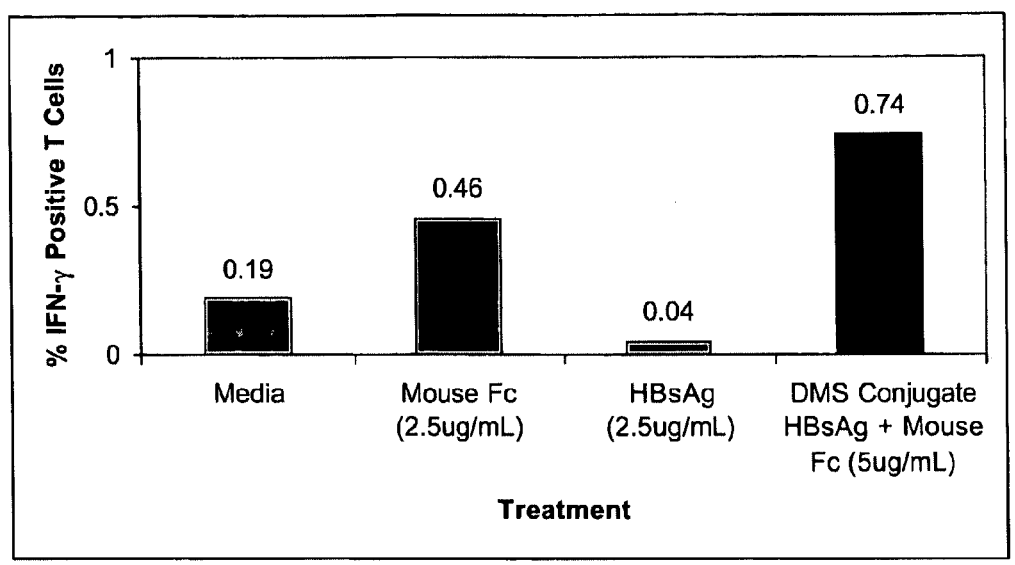

Figure 26. DC Maturation (CD83 level) with S1/S2-TBD and its Components
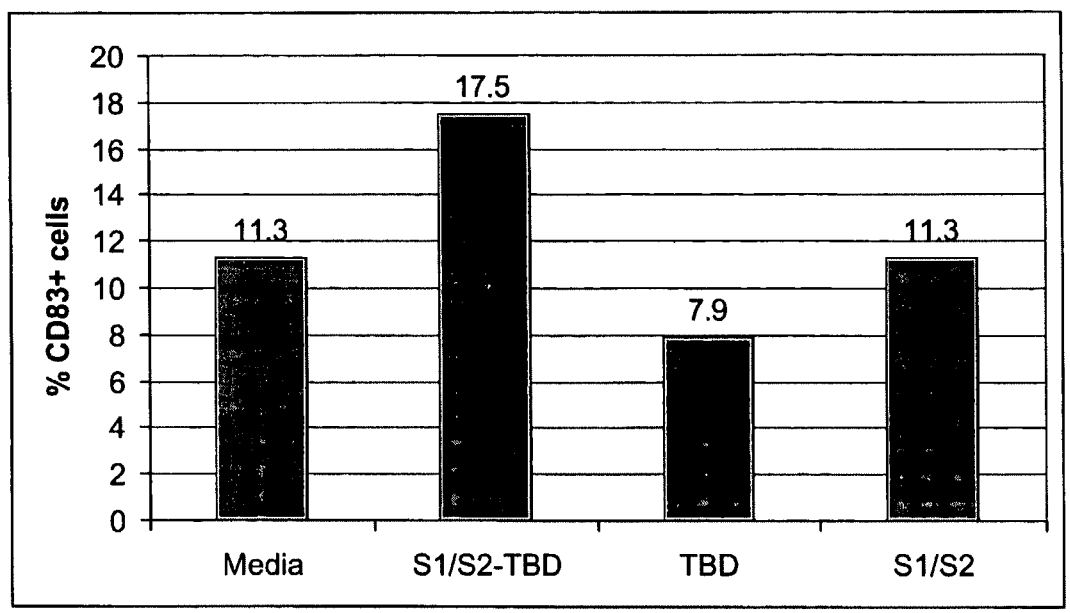

Figure 27. Expression of HLA-DR (Class II) on DCs
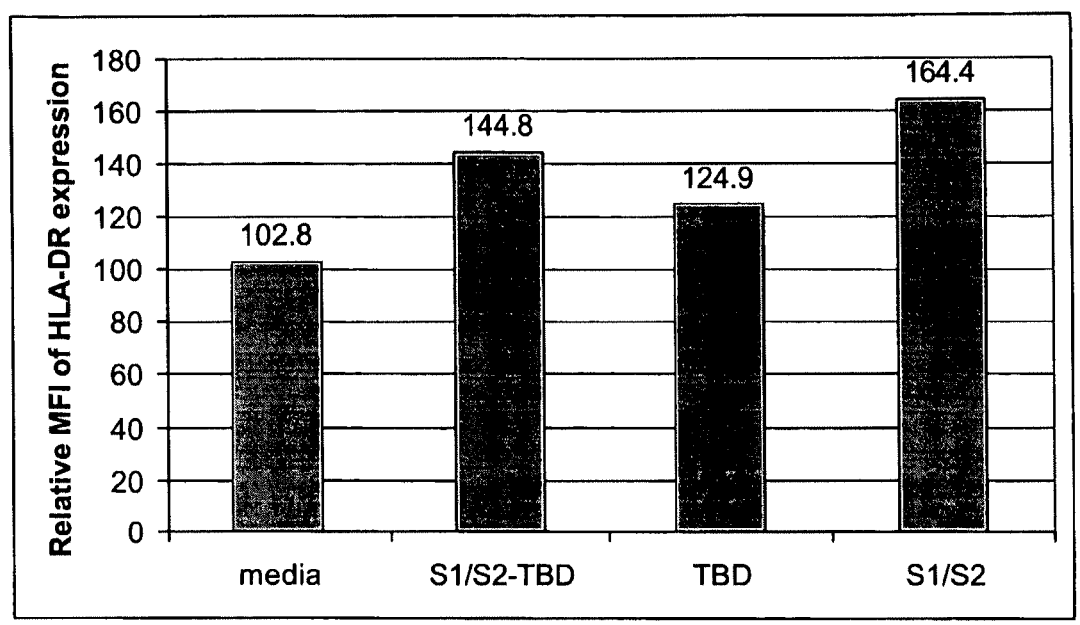

Fig. 28: T Cell Stimulation by DCs Loaded with S1/S2-TBD or its Components

Fig. 29: Time Course of the Stimulation of T Cells by Ag-Fc Conjugate
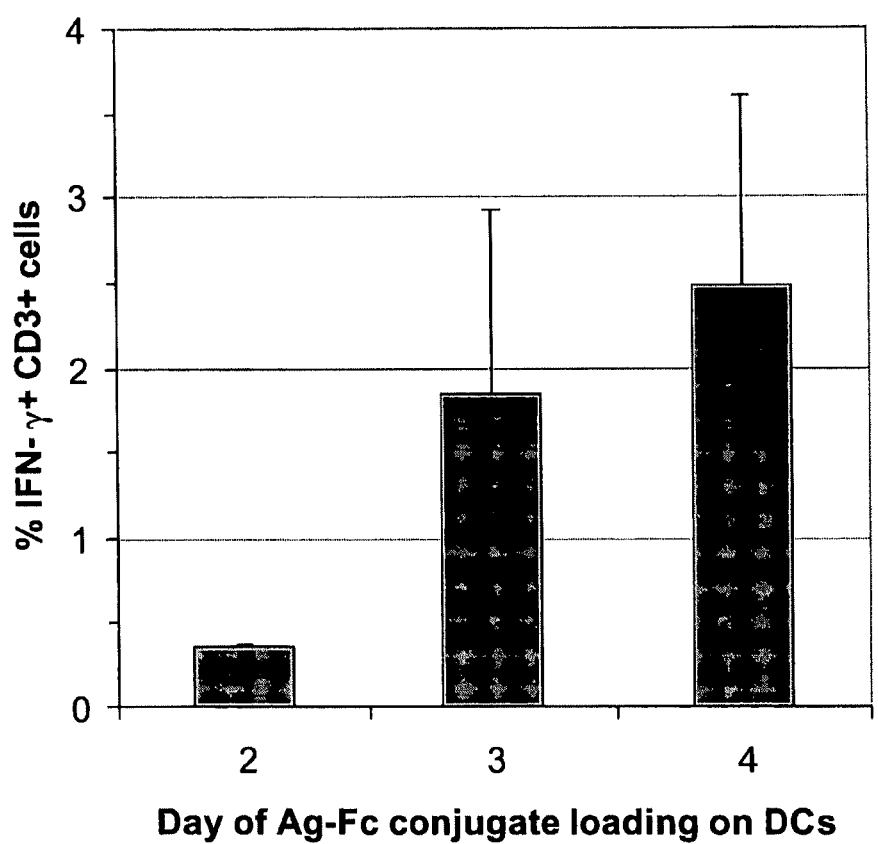

Figure 30. Time Course of Expression of Antigen Binding Receptors on Maturing DCs
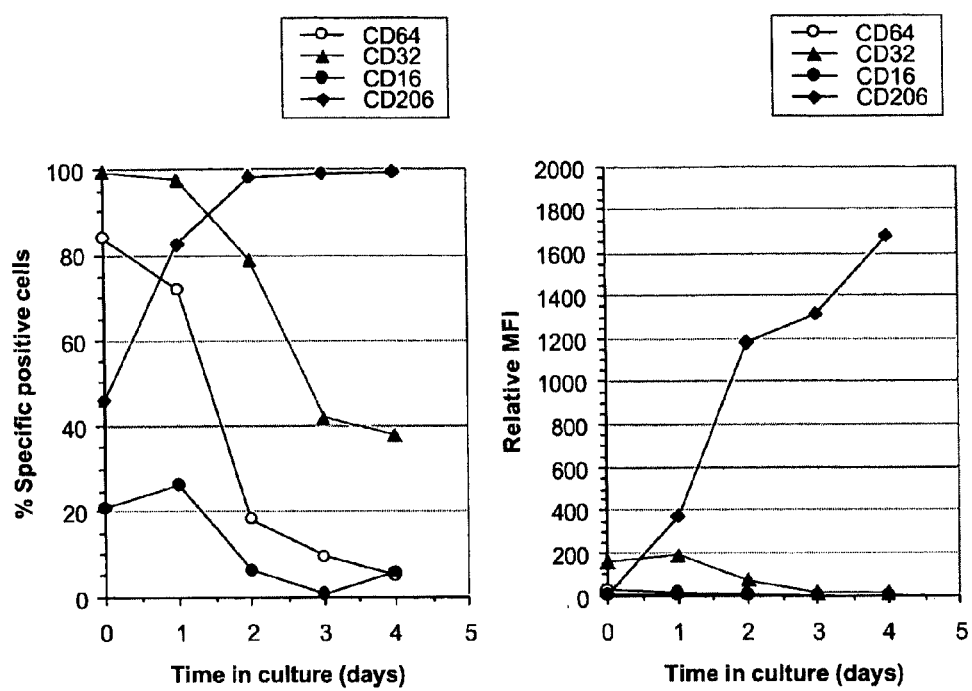

Figure 31. Time Course of the Expression of Various DC Activation Markers
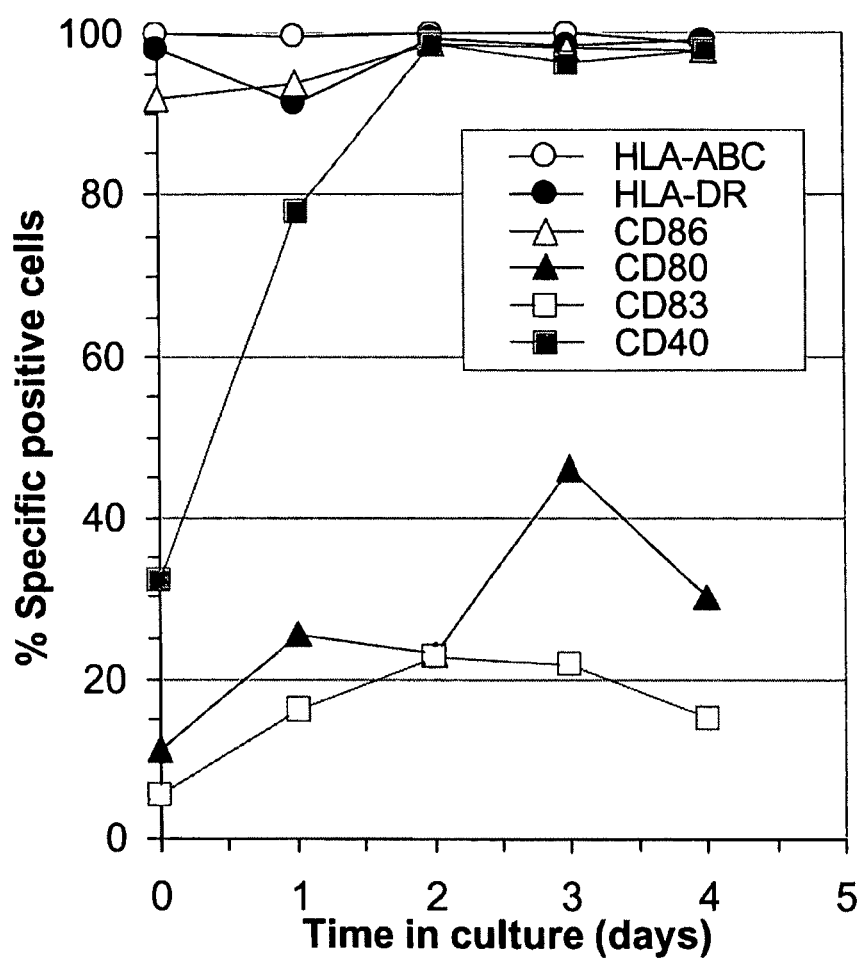

Figure 32. Comparison of S1/S2-TBD, IgG1 and IgG2a Binding to DCs over Time

Figure 33. Comparison of HBV S1/S2-TBD, IgG1 and IgG2a binding to maturing DCs on Day 1

Figure 34. Comparison of S1/S2-TBD, IgG2a and IgG1 Binding to Maturing DCs on Day 4

Figure 35: Comparison of the Uptake of S1/S2-TBD, IgG1 and IgG2a as a Function of Concentration
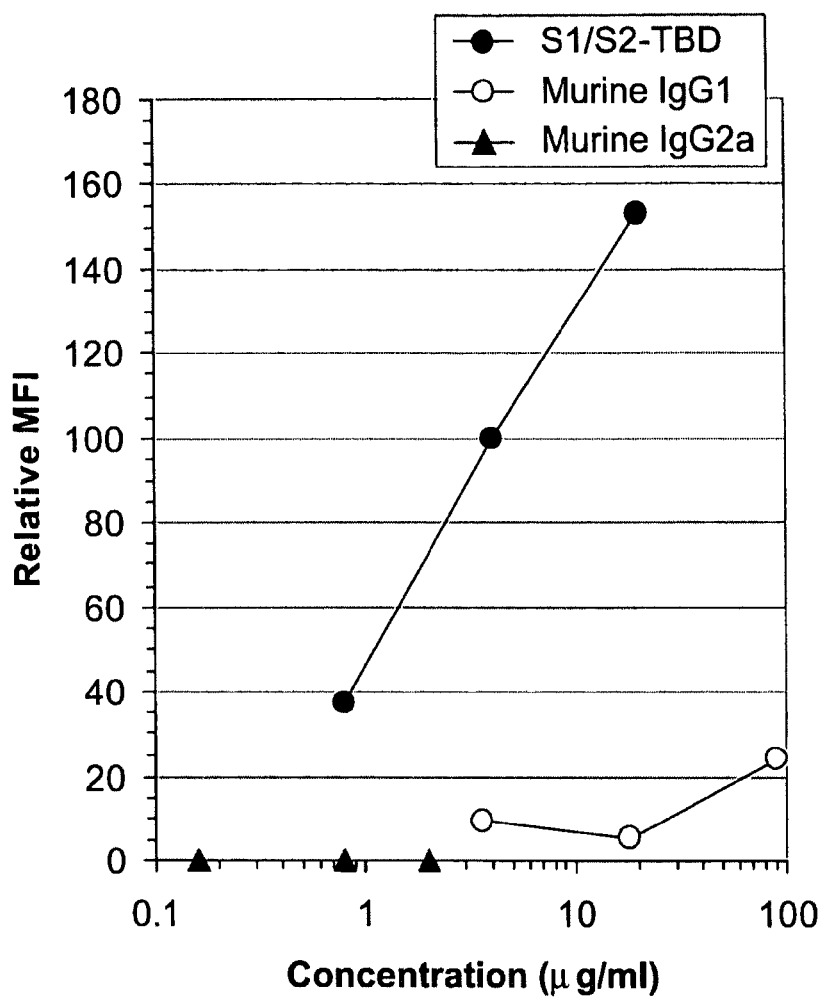

Figure 36: Correlation of S1/S2-TBD Binding to CD32 and CD206 Expression on DC

Figure 37. Binding of S1/S2-TBD to DCs is Abolished by Mouse Fcγ.

Figure 38. Glycosylation of S1/S2 Antigen Increases the Uptake via CD206 Receptor Figure 39. Intracellular IFN-? Positive T Cells after Antigen Presentation by DCs Loaded with S1/S2-TBD or its Components Figure 40. Secretion of IFN-γ by T Cells after Antigen Presentation by DCs Loaded with S1/S2-TBD or its Components Figure 41. Intracellular IFN-γ Positive T Cells as a Function of S1/S2-TBD Concentration
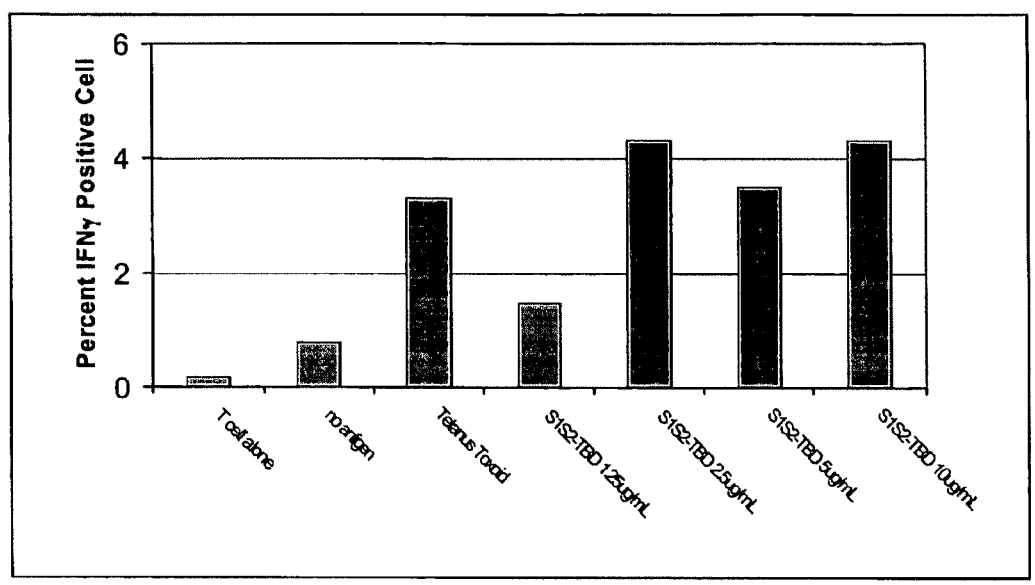

Figure 42. Secretion of IFN-γ by T Cells as a Function of S1/S2-TBD Concentration Figure 43. Effect of Glycosylation on Intracellular IFN-? Production in T cells
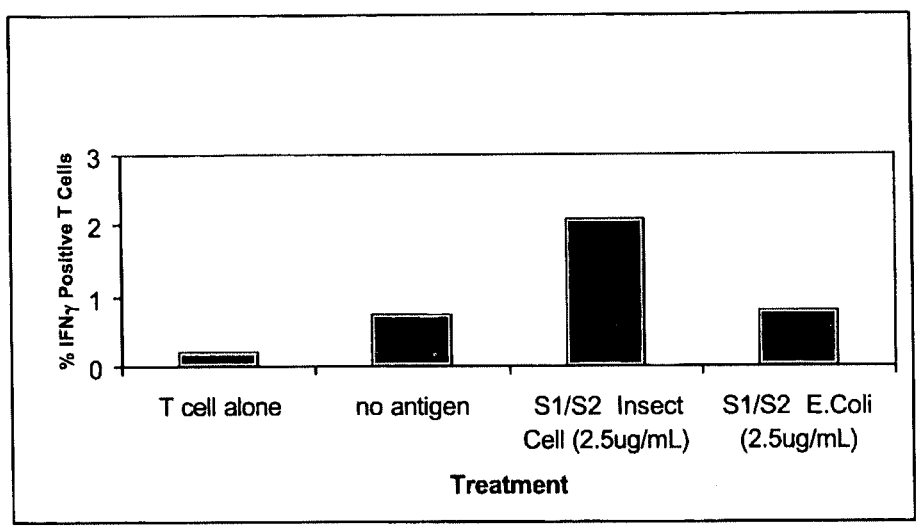

Figure 44. Effect of Glycosylation on IFN-? Secretion by T cells
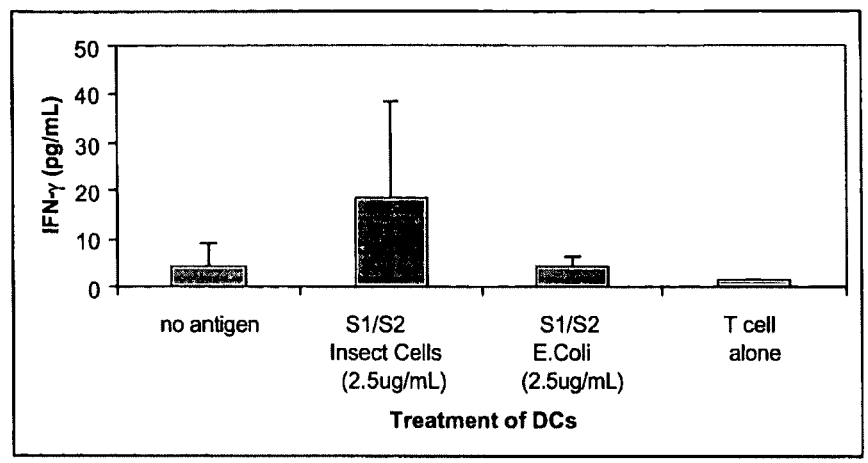

Fig. 45a. DNA sequence of HCV Core(1-191) Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC ATG AGC
ACG AAT CCT AAA CCT CAA AGA AAA ACC AAA CGT AAC ACC AAC CGT CGC
CCA CAG GAC GTC AAG TTC CCG GGT GGC GGT CAG ATC GTT GGT GGA GTT
TAC TTG TTG CCG CGC AGG GGC CCT AGA TTG GGT GTG CGC GCG ACG AGG
AAG ACT TCC GAG CGG TCG CAA CCT CGA GGT AGA CGT CAG CCT ATC CCC
AAG GCA CGT CGG CCC GAG GGC AGG ACC TGG GCT CAG CCC GGG TAC CCT
TGG CCC CTC TAT GGC AAT GAG GGT TGC GGG TGG GCG GGA TGG CTC CTG
TCT CCC CGT GGC TCT CGG CCT AGC TGG GGC CCC ACA GAC CCC CGG CGT
AGG TCG CGC AAT TTG GGT AAG GTC ATC GAT ACC CTT ACG TGC GGC TTC
GCC GAC CTC ATG GGG TAC ATA CCG CTC GTC GGC GCC CCT CTT GGA GGC
GCT GCC AGG GCC CTG GCG CAT GGC GTC CGG GTT CTG GAA GAC GGC GTG
AAC TAT GCA ACA GGG AAC CTT CCT GGT TGC TCT TTC TCT ATC TTC CTT
CTG GCC CTG CTC TCT TGC CTG ACT GTG CCC GCT TCA GCC GGA CTA GTG
CGG CCG CTT TCG AAT CTA GAG CCT GCA GTC TCG AGG CAT GCG GTA CCA
AGC TTG TCG AGA AGT ACT AGA GGA TCA TAA
```

Fig. 45b. Amino Acid Sequence of HCV Core(1-191) Protein.

```
M S Y Y H H H H H H D Y D I P T
T E N L Y F Q G A M D P E F M S
T N P K P Q R K T K R N T N R R
P Q D V K F P G G G Q I V G G V
Y L L P R R G P R L G V R A T R
K T S E R S Q P R G R R Q P I P
K A R R P E G R T W A Q P G Y P
W P L Y G N E G C G W A G W L L
S P R G S R P S W G P T D P R R
R S R N L G K V I D T L T C G F
A D L M G Y I P L V G A P L G G
A A R A L A H G V R V L E D G V
N Y A T G N L P G C S F S I F L
L A L L S C L T V P A S A G L V
R P L S N L E P A V S R H A V P
S L S R S T R G S
```

Figure 46A:
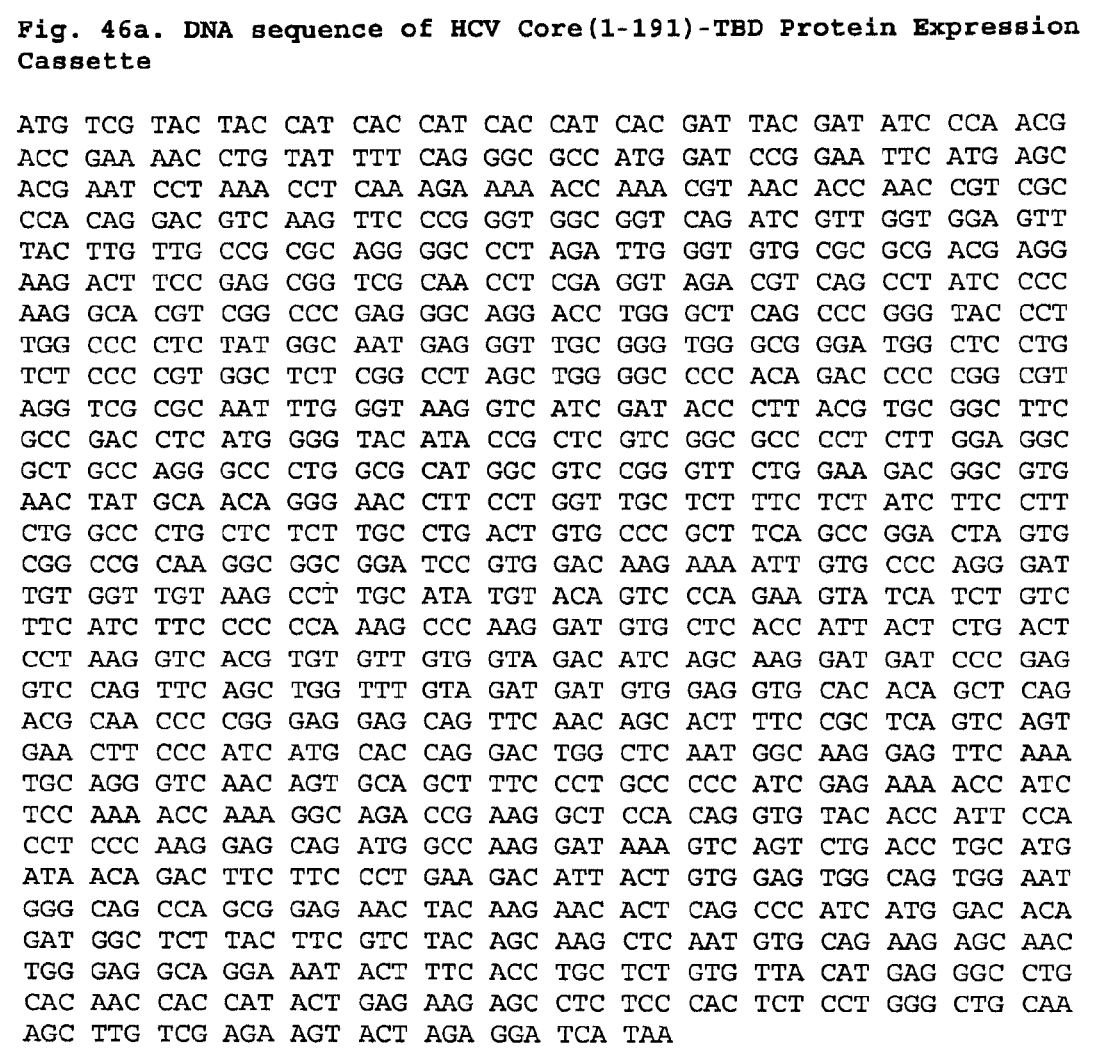

Fig. 46a. DNA sequence of HCV Core(1-191)-TBD Protein Expression Cassette

```
ATG TCG TAC TAC CAT C

Fig. 46b. Amino acid sequence of HCV Core(1-191)-TBD Protein.

```
M S Y Y H H H H H H D Y D I P T
T E N L Y F Q G A M D P E F M S
T N P K P Q R K T K R N T N R R
P Q D V K F P G G G Q I V G G V
Y L L P R R G P R L G V R A T R
K T S E R S Q P R G R R Q P I P
K A R R P E G R T W A Q P G Y P
W P L Y G N E G C G W A G W L L
S P R G S R P S W G P T D P R R
R S R N L G K V I D T L T C G F
A D L M G Y I P L V G A P L G G
A A R A L A H G V R V L E D G V
N Y A T G N L P G C S F S I F L
L A L L S C L T V P A S A G L V
R P Q G G G S V D K K I V P R D
C G C K P C I C T V P E V S S V
F I F P P K P K D V L T I T L T
P K V T C V V V D I S K D D P E
V Q F S W F V D D V E V H T A Q
T Q P R E E Q F N S T F R S V S
E L P I M H Q D W L N G K E F K
C R V N S A A F P A P I E K T I
S K T K G R P K A P Q V Y T I P
P P K E Q M A K D K V S L T C M
I T D F F P E D I T V E W Q W N
G Q P A E N Y K N T Q P I M D T
D G S Y F V Y S K L N V Q K S N
W E A G N T F T C S V L H E G L
H N H H T E K S L S H S P G L Q
S L S R S T R G S
```

Fig. 47a. DNA sequence of HCV Core(1-177) Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC ATG AGC
ACG AAT CCT AAA CCT CAA AGA AAA ACC AAA CGT AAC ACC AAC CGT CGC
CCA CAG GAC GTC A

Fig. 48a. DNA sequence of HCV Core(1-177)-TBD Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG gaa ttc ATG AGC
ACG AAT CCT AAA CCT CAA AGA AAA ACC AAA CGT AAC ACC AAC CGT CGC
CCA CAG GAC GTC AAG TTC CCG GGT GGC GGT CAG ATC GTT GGT GGA GTT
TAC TTG TTG CCG CGC AGG GGC CCT AGA TTG GGT GTG CGC GCG ACG AGG
AAG ACT TCC GAG CGG TCG CAA CCT CGA GGT AGA CGT CAG CCT ATC CCC
AAG GCA CGT CGG CCC GAG GGC AGG ACC TGG GCT CAG CCC GGG TAC CCT
TGG CCC CTC TAT GGC AAT GAG GGT TGC GGG TGG GCG GGA TGG CTC CTG
TCT CCC CGT GGC TCT CGG CCT AGC TGG GGC CCC ACA GAC CCC CGG CGT
AGG TCG CGC AAT TTG GGT AAG GTC ATC GAT ACC CTT ACG TGC GGC TTC
GCC GAC CTC ATG GGG TAC ATA CCG CTC GTC GGC GCC CCT CTT GGA GGC
GCT GCC AGG GCC CTG GCG CAT GGC GTC CGG GTT CTG GAA GAC GGC GTG
AAC TAT GCA ACA GGG AAC CTT CCT GGT TGC TCT TTC TCT ATC TTC gga
cta gtG CGG CCG CAA GGC GGC GGA TCC GTG GAC AAG AAA ATT GTG CCC
AGG GAT TGT GGT TGT AAG CCT TGC ATA TGT ACA GTC CCA GAA GTA TCA
TCT GTC TTC ATC TTC CCC CCA AAG CCC AAG GAT GTG CTC ACC ATT ACT
CTG ACT CCT AAG GTC ACG TGT GTT GTG GTA GAC ATC AGC AAG GAT GAT
CCC GAG GTC CAG TTC AGC TGG TTT GTA GAT GAT GTG GAG GTG CAC ACA
GCT CAG ACG CAA CCC CGG GAG GAG CAG TTC AAC AGC ACT TTC CGC TCA
GTC AGT GAA CTT CCC ATC ATG CAC CAG GAC TGG CTC AAT GGC AAG GAG
TTC AAA TGC AGG GTC AAC AGT GCA GCT TTC CCT GCC CCC ATC GAG AAA
ACC ATC TCC AAA ACC AAA GGC AGA CCG AAG GCT CCA CAG GTG TAC ACC
ATT CCA CCT CCC AAG GAG CAG ATG GCC AAG GAT AAA GTC AGT CTG ACC
TGC ATG ATA ACA GAC TTC TTC CCT GAA GAC ATT ACT GTG GAG TGG CAG
TGG AAT GGG CAG CCA GCG GAG AAC TAC AAG AAC ACT CAG CCC ATC ATG
GAC ACA GAT GGC TCT TAC TTC GTC TAC AGC AAG CTC AAT GTG CAG AAG
AGC AAC TGG GAG GCA GGA AAT ACT TTC ACC TGC TCT GTG TTA CAT GAG
GGC CTG CAC AAC CAC CAT ACT GAG AAG AGC CTC TCC CAC TCT CCT GGG
CTG CAA AGC TTG TCG AGA AGT ACT AGA GGA TCA TAA
```

Fig. 48b. Amino Acid Sequence of HCV Core (1-177)-TBD Protein.

```
M  S  Y  Y  H  H  H  H  H  H  D  Y  D  I  P  T
T  E  N  L  Y  F  Q  G  A  M  D  P  E  F  M  S
T  N  P  K  P  Q  R  K  T  K  R  N  T  N  R  R
P  Q  D  V  K  F  P  G  G  G  Q  I  V  G  G  V
Y  L  L  P  R  R  G  P  R  L  G  V  R  A  T  R
K  T  S  E  R  S  Q  P  R  G  R  R  Q  P  I  P
K  A  R  R  P  E  G  R  T  W  A  Q  P  G  Y  P
W  P  L  Y  G  N  E  G  C  G  W  A  G  W  L  L
S  P  R  G  S  R  P  S  W  G  P  T  D  P  R  R
R  S  R  N  L  G  K  V  I  D  T  L  T  C  G  F
A  D  L  M  G  Y  I  P  L  V  G  A  P  L  G  G
A  A  R  A  L  A  H  G  V  R  V  L  E  D  G  V
N  Y  A  T  G  N  L  P  G  C  S  F  S  I  F  G
L  V  R  P  Q  G  G  G  S  V  D  K  K  I  V  P
R  D  C  G  C  K  P  C  I  C  T  V  P  E  V  S
S  V  F  I  F  P  P  K  P  K  D  V  L  T  I  T
L  T  P  K  V  T  C  V  V  V  D  I  S  K  D  D
P  E  V  Q  F  S  W  F  V  D  D  V  E  V  H  T
A  Q  T  Q  P  R  E  E  Q  F  N  S  T  F  R  S
V  S  E  L  P  I  M  H  Q  D  W  L  N  G  K  E
F  K  C  R  V  N  S  A  A  F  P  A  P  I  E  K
T  I  S  K  T  K  G  R  P  K  A  P  Q  V  Y  T
I  P  P  P  K  E  Q  M  A  K  D  K  V  S  L  T
C  M  I  T  D  F  F  P  E  D  I  T  V  E  W  Q
W  N  G  Q  P  A  E  N  Y  K  N  T  Q  P  I  M
D  T  D  G  S  Y  F  V  Y  S  K  L  N  V  Q  K
S  N  W  E  A  G  N  T  F  T  C  S  V  L  H  E
G  L  H  N  H  H  T  E  K  S  L  S  H  S  P  G
L  Q  S  L  S  R  S  T  R  G  S
```

Fig. 49a. DNA sequence of HCV NS5A Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC TCC GGT
TCC TGG CTA AGG GAC ATC TGG GAC TGG ATA TGC GAG GTG CTG AGC GAC
TTT AAG ACC TGG CTG AAA GCC AAG CTC ATG CCA CAA CTG CCT GGG ATT
CCC TTT GTG TCC TGC CAG CGC GGG TAT AGG GGG GTC TGG CGA GGA GAC
GGC ATT ATG CAC ACT CGC TGC CAC TGT GGA GCT GAG ATC ACT GGA CAT
GTC AAA AAC GGG ACG ATG AGG ATC GTC GGT CCT AGG ACC TGC AGG AAC
ATG TGG AGT GGG ACG TTC CCC ATT AAC GCC TAC ACC ACG GCC CCC TGT
ACT CCC CTT CCT GCG CCG AAC TAT AAG TTC GCG CTG TGG AGG GTG TCT
GCA GAG GAA TAC GTG GAG ATA AGG CGG GTG GGG GAC TTC CAC TAC GTA
TCG GGT ATG ACT ACT GAC AAT CTT AAA TGC CCG TGC CAG ATC CCA TCG
CCC GAA TTT TTC ACA GAA TTG GAC GGG GTG CGC CTA CAC AGG TTT GCG
CCC CCT TGC AAG CCC TTG CTG CGG GAG GAG GTA TCA TTC AGA GTA GGA
CTC CAC GAG TAC CCG GTG GGG TCG CAA TTA CCT TGC GAG CCC GAA CCG
GAC GTA GCC GTG TTG ACG TCC ATG CTC ACT GAT CCC TCC CAT ATA ACA
GCA GAG GCG GCC GGG AGA AGG TTG GCG AGA GGG TCA CCC CCT TCT ATG
GCC AGC TCC TCG GCT AGC CAG CTG TCC GCT CCA TCT CTC AAG GCA ACT
TGC ACC GCC AAC CAT GAC TCC CCT GAC GCC GAG CTC ATA GAG GCT AAC
CTC CTG TGG AGG CAG GAG ATG GGC GGC AAC ATC ACC AGG GTT GAG TCA
GAG AAC AAA GTG GTG ATT CTG GAC TCC TTC GAT CCG CTT GTG GCA GAG
GAG GAT GAG CGG GAG GTC TCC GTA CCT GCA GAA ATT CTG CGG AAG TCT
CGG AGA TTC GCC CGG GCC CTG CCC GTC TGG GCG CGG CCG GAC TAC AAC
CCC CCG CTA GTA GAG ACG TGG AAA AAG CCT GAC TAC GAA CCA CCT GTG
GTC CAT GGC TGC CCG CTA CCA CCT CCA CGG TCC CCT CCT GTG CCT CCG
CCT CGG AAA AAG CGT ACG GTG GTC CTC ACC GAA TCA ACC CTA TCT ACT
GCC TTG GCC GAG CTT GCC ACC AAA AGT TTT GGC AGC TCC TCA ACT TCC
GGC ATT ACG GGC GAC AAT ACG ACA ACA TCC TCT GAG CCC GCC CCT TCT
GGC TGC CCC CCC GAC TCC GAC GTT GAG TCC TAT TCT TCC ATG CCC CCC
CTG GAG GGG GAG CCT GGG GAT CCG GAT CTC AGC GAC GGG TCA TGG TCG
ACG GTC AGT AGT GGG GCC GAC ACG GAA GAT GTC GTG TGC GGA CTA GTG
CGG CCG CTT TCG AAT CTA GAG CCT GCA GTC TCG AGG CAT GCG GTA CCA
AGC TTG TCG AGA AGT ACT AGA GGA TCA TAA
```

Fig. 49b. Amino Acid Sequence of HCV NS5A Protein.

```
M  S  Y  Y  H  H  H  H  H  H  D  Y  D  I  P  T
T  E  N  L  Y  F  Q  G  A  M  D  P  E  F  S  G
S  W  L  R  D  I  W  D  W  I  C  E  V  L  S  D
F  K  T  W  L  K  A  K  L  M  P  Q  L  P  G  I
P  F  V  S  C  Q  R  G  Y  R  G  V  W  R  G  D
G  I  M  H  T  R  C  H  C  G  A  E  I  T  G  H
V  K  N  G  T  M  R  I  V  G  P  R  T  C  R  N
M  W  S  G  T  F  P  I  N  A  Y  T  T  G  P  C
T  P  L  P  A  P  N  Y  K  F  A  L  W  R  V  S
A  E  E  Y  V  E  I  R  R  V  G  D  F  H  Y  V
S  G  M  T  T  D  N  L  K  C  P  C  Q  I  P  S
P  E  F  F  T  E  L  D  G  V  R  L  H  R  F  A
P  P  C  K  P  L  L  R  E  E  V  S  F  R  V  G
L  H  E  Y  P  V  G  S  Q  L  P  C  E  P  E  P
D  V  A  V  L  T  S  M  L  T  D  P  S  H  I  T
A  E  A  A  G  R  R  L  A  R  G  S  P  P  S  M
A  S  S  S  A  S  Q  L  S  A  P  S  L  K  A  T
C  T  A  N  H  D  S  P  D  A  E  L  I  E  A  N
L  L  W  R  Q  E  M  G  G  N  I  T  R  V  E  S
E  N  K  V  V  I  L  D  S  F  D  P  L  V  A  E
E  D  E  R  E  V  S  V  P  A  E  I  L  R  K  S
R  R  F  A  R  A  L  P  V  W  A  R  P  D  Y  N
P  P  L  V  E  T  W  K  K  P  D  Y  E  P  P  V
V  H  G  C  P  L  P  P  P  R  S  P  P  V  P  P
P  R  K  K  R  T  V  V  L  T  E  S  T  L  S  T
A  L  A  E  L  A  T  K  S  F  G  S  S  S  T  S
G  I  T  G  D  N  T  T  T  S  S  E  P  A  P  S
G  C  P  P  D  S  D  V  E  S  Y  S  S  M  P  P
L  E  G  E  P  G  D  P  D  L  S  D  G  S  W  S
T  V  S  S  G  A  D  T  E  D  V  V  C  G  L  V
R  P  L  S  N  L  E  P  A  V  S  R  H  A  V  P
S  L  S  R  S  T  R  G  S
```

Figure 50A:
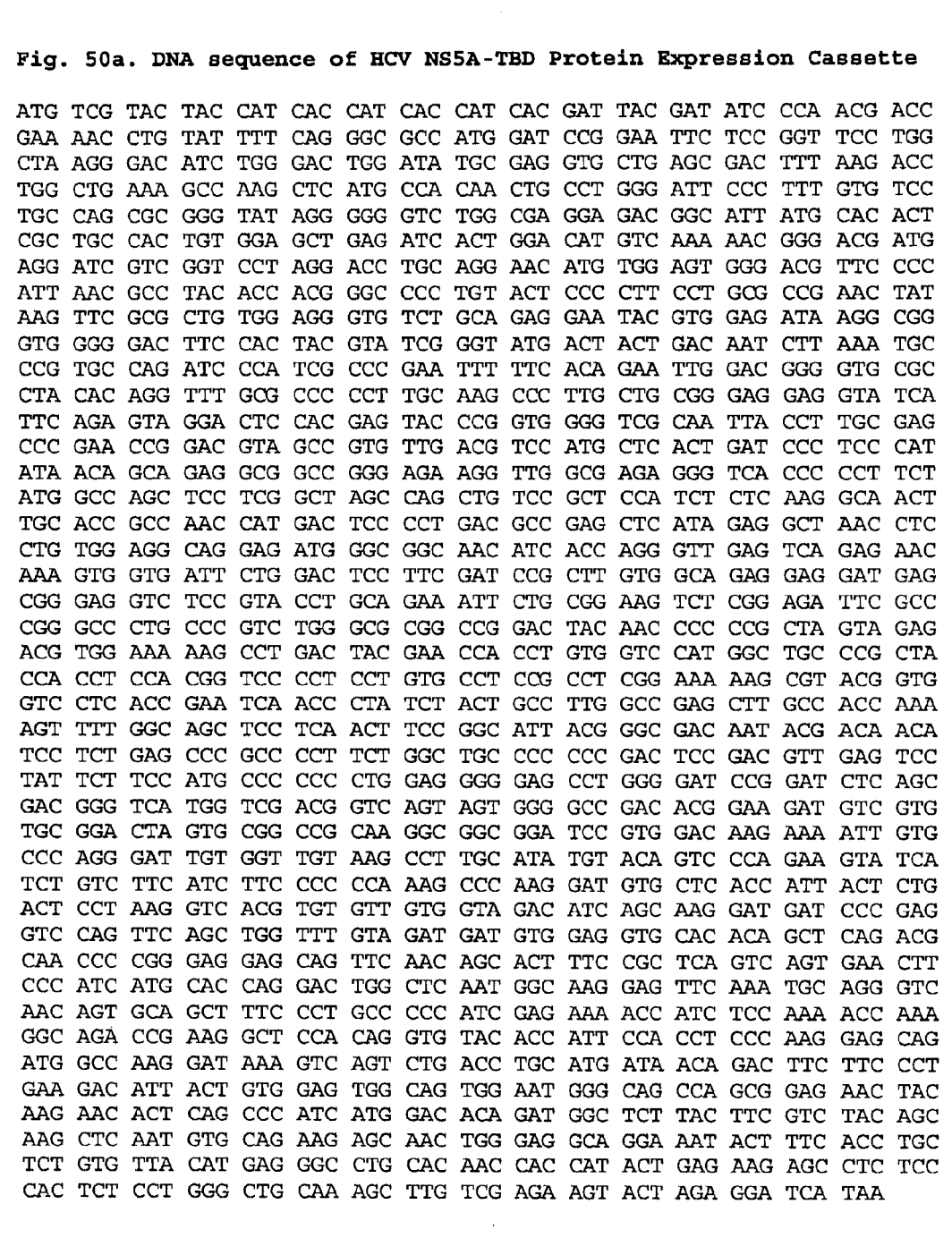

Fig. 50a. DNA sequence of HCV NS5A-TBD Protein Expression Cassette

```
ATG TCG TAC TAC CAT CAC CAT CAC CAT

Fig. 50b. Amino Acid Sequence of HCV NS5A-TBD Protein.

```
M  S  Y  Y  H  H  H  H  H  H  D  Y  D  I  P  T  T  E
N  L  Y  F  Q  G  A  M  D  P  E  F  S  G  S  W  L  R
D  I  W  D  W  I  C  E  V  L  S  D  F  K  T  W  L  K
A  K  L  M  P  Q  L  P  G  I  P  F  V  S  C  Q  R  G
Y  R  G  V  W  R  G  D  G  I  M  H  T  R  C  H  C  G
A  E  I  T  G  H  V  K  N  G  T  M  R  I  V  G  P  R
T  C  R  N  M  W  S  G  T  F  P  I  N  A  Y  T  T  G
P  C  T  P  L  P  A  P  N  Y  K  F  A  L  W  R  V  S
A  E  E  Y  V  E  I  R  R  V  G  D  F  H  Y  V  S  G
M  T  T  D  N  L  K  C  P  C  Q  I  P  S  P  E  F  F
T  E  L  D  G  V  R  L  H  R  F  A  P  P  C  K  P  L
L  R  E  E  V  S  F  R  V  G  L  H  E  Y  P  V  G  S
Q  L  P  C  E  P  E  P  D  V  A  V  L  T  S  M  L  T
D  P  S  H  I  T  A  E  A  A  G  R  R  L  A  R  G  S
P  P  S  M  A  S  S  S  A  S  Q  L  S  A  P  S  L  K
A  T  C  T  A  N  H  D  S  P  D  A  E  L  I  E  A  N
L  L  W  R  Q  E  M  G  G  N  I  T  R  V  E  S  E  N
K  V  V  I  L  D  S  F  D  P  L  V  A  E  E  D  E  R
E  V  S  V  P  A  E  I  L  R  K  S  R  R  F  A  R  A
L  P  V  W  A  R  P  D  Y  N  P  P  L  V  E  T  W  K
K  P  D  Y  E  P  P  V  V  H  G  C  P  L  P  P  P  R
S  P  P  V  P  P  P  R  K  K  R  T  V  V  L  T  E  S
T  L  S  T  A  L  A  E  L  A  T  K  S  F  G  S  S  S
T  S  G  I  T  G  D  N  T  T  S  S  E  P  A  P  S
G  C  P  P  D  S  D  V  E  S  Y  S  S  M  P  P  L  E
G  E  P  G  D  P  D  L  S  D  G  S  W  S  T  V  S  S
G  A  D  T  E  D  V  V  C  G  L  V  R  P  Q  G  G  G
S  V  D  K  K  I  V  P  R  D  C  G  C  K  P  C  I  C
T  V  P  E  V  S  S  V  F  I  F  P  P  K  P  K  D  V
L  T  I  T  L  T  P  K  V  T  C  V  V  V  D  I  S  K
D  D  P  E  V  Q  F  S  W  F  V  D  D  V  E  V  H  T
A  Q  T  Q  P  R  E  E  Q  F  N  S  T  F  R  S  V  S
E  L  P  I  M  H  Q  D  W  L  N  G  K  E  F  K  C  R
V  N  S  A  A  F  P  A  P  I  E  K  T  I  S  K  T  K
G  R  P  K  A  P  Q  V  Y  T  I  P  P  P  K  E  Q  M
A  K  D  K  V  S  L  T  C  M  I  T  D  F  F  P  E  D
I  T  V  E  W  Q  W  N  G  Q  P  A  E  N  Y  K  N  T
Q  P  I  M  D  T  D  G  S  Y  F  V  Y  S  K  L  N  V
Q  K  S  N  W  E  G  N  T  F  T  C  S  V  L  H  E
G  L  H  N  H  H  T  E  K  S  L  S  H  S  P  G  L  Q
S  L  S  R  S  T  R  G  S
```

FIG. 51A. DNA SEQUENCE OF HCV E1 PROTEIN EXPRESSION CASSETTE

```
ATG TCG TAC TAC CAT CAC CAT CAC CAT CAC

Figure 52A:
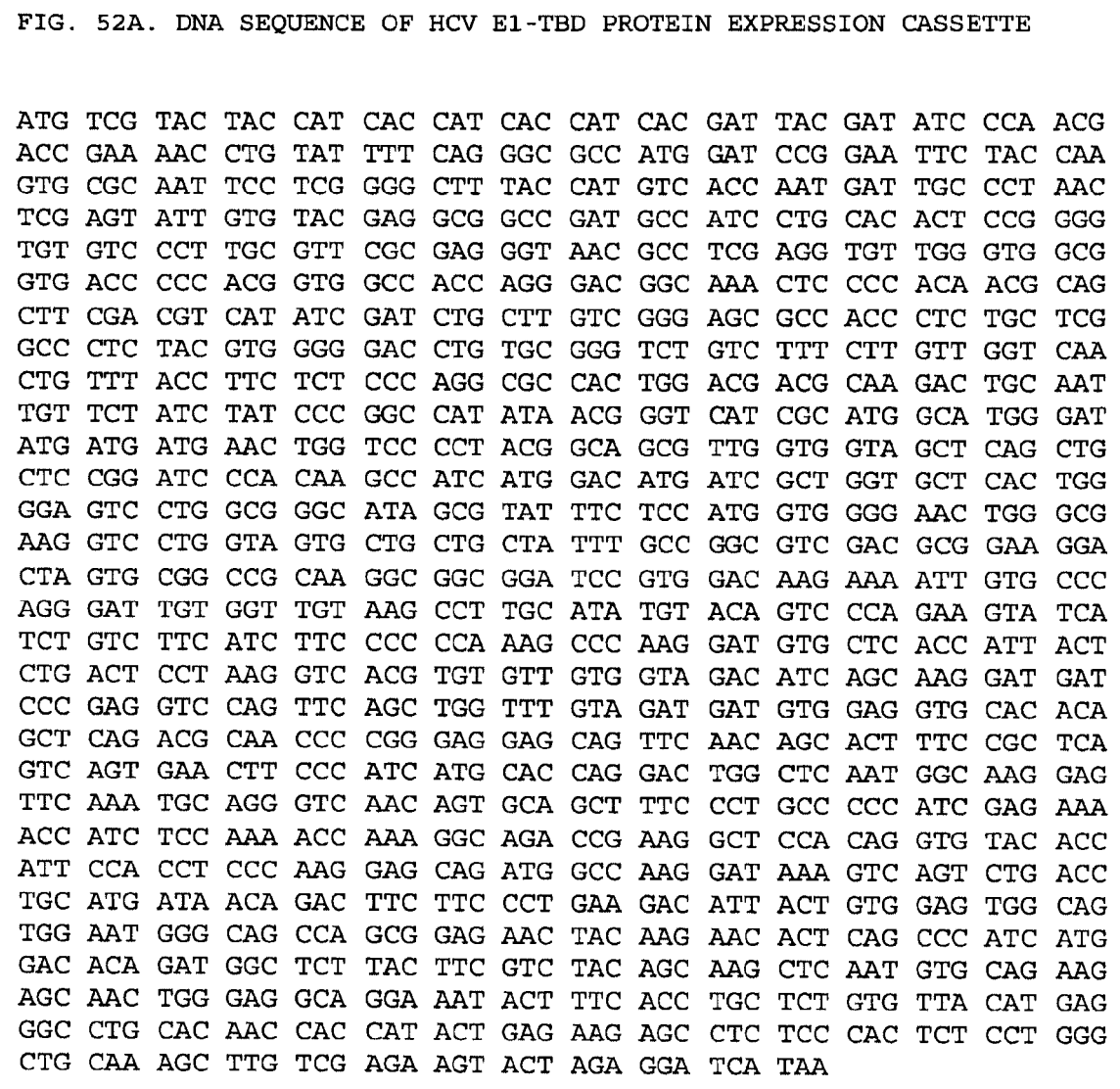

FIG. 52A. DNA SEQUENCE OF HCV E1-TBD PROTEIN EXPRESSION CASSETTE

```
ATG TCG TA

Fig. 52b. Amino Acid Sequence of HCV E1-TBD Protein

```
M  S  Y  Y  H  H  H  H  H  H  D  Y  D  I  P  T
T  E  N  L  Y  F  Q  G  A  M  D  P  E  F  Y  Q
V  R  N  S  S  G  L  Y  H  V  T  N  D  C  P  N
S  S  I  V  Y  E  A  A  D  A  I  L  H  T  P  G
C  V  P  C  V  R  E  G  N  A  S  R  C  W  V  A
V  T  P  T  V  A  T  R  D  G  K  L  P  T  T  Q
L  R  R  H  I  D  L  L  V  G  S  A  T  L  C  S
A  L  Y  V  G  D  L  C  G  S  V  F  L  V  G  Q
L  F  T  F  S  P  R  R  H  W  T  T  Q  D  C  N
C  S  I  Y  P  G  H  I  T  G  H  R  M  A  W  D
M  M  M  N  W  S  P  T  A  A  L  V  V  A  Q  L
L  R  I  P  Q  A  I  M  D  M  I  A  G  A  H  W
G  V  L  A  G  I  A  Y  F  S  M  V  G  N  W  A
K  V  L  V  V  L  L  L  F  A  G  V  D  A  E  G
L  V  R  P  Q  G  G  G  S  V  D  K  K  I  V  P
R  D  C  G  C  K  P  C  I  C  T  V  P  E  V  S
S  V  F  I  F  P  P  K  P  K  D  V  L  T  I  T
L  T  P  K  V  T  C  V  V  V  D  I  S  K  D  D
P  E  V  Q  F  S  W  F  V  D  D  V  E  V  H  T
A  Q  T  Q  P  R  E  E  Q  F  N  S  T  F  R  S
V  S  E  L  P  I  M  H  Q  D  W  L  N  G  K  E
F  K  C  R  V  N  S  A  A  F  P  A  P  I  E  K
T  I  S  K  T  K  G  R  P  K  A  P  Q  V  Y  T
I  P  P  P  K  E  Q  M  A  K  D  K  V  S  L  T
C  M  I  T  D  F  F  P  E  D  I  T  V  E  W  Q
W  N  G  Q  P  A  E  N  Y  K  N  T  Q  P  I  M
D  T  D  G  S  Y  F  V  Y  S  K  L  N  V  Q  K
S  N  W  E  A  G  N  T  F  T  C  S  V  L  H  E
G  L  H  N  H  H  T  E  K  S  L  S  H  S  P  G
L  Q  S  L  S  R  S  T  R  G  S
```

FIG. 53A. DNA SEQUENCE OF HCV E2 PROTEIN EXPRESSION CASSETTE

ATGTCGTACTACCATCACCATCACCATCACGATTACGATATCCCAACGACCGAAAACCTG
TATTTTCAGGGCGCCATGGATCCGGAATTCACCCACGTCACCGGGGGAAATGCCGGCCGC
ACCACGGCTGGGCTTGTTGGTCTCCTTACACCAGGCGCCAAGCAGAACATCCAACTGATC
AACACCAACGGCAGTTGGCACATCAATAGCACGGCCTTGAATTGCAATGAAAGCCTTAAC
ACCGGCTGGTTAGCAGGGCTCTTCTATCAACACAAATTCAACTCTTCAGGCTGTCCTGAG
AGGTTGGCCAGCTGCCGACGCCTTACCGATTTTGCCCAGGGCTGGGGTCCTATCAGTTAT
GCCAACGGAAGCGGCCTCGACGAACGCCCCTACTGCTGGCACTACCCTCCAAGACCTTGT
GGCATTGTGCCCGCAAAGAGCGTGTGTGGCCCGGTATATTGCTTCACTCCCAGCCCCGTG
GTGGTGGGAACGACCGACAGGTCGGGCGCGCCTACCTACAGCTGGGGTGCAAATGATACG
GATGTCTTCGTCCTTAACAACACCAGGCCACCGCTGGGCAATTGGTTCGGTTGTACCTGG
ATGAACTCAACTGGATTCACCAAAGTGTGCGGAGCGCCCCCTTGTGTCATCGGAGGGGTG
GGCAACAACACCTTGCTCTGCCCCACTGATTGCTTCCGCAAACATCCGGAAGCCACATAC
TCTCGGTGCGGCTCCGGTCCCTGGATTACACCCAGGTGCATGGTCGACTACCCGTATAGG
CTTTGGCACTATCCTTGTACCATCAATTACACCATATTCAAAGTCAGGATGTACGTGGGA
GGGGTCGAGCACAGGCTGGAAGCGGCCTGCAACTGGACGCGGGGCGAACGCTGTGATCTG
GAAGACAGGGACAGGTCCGAGCTCAGCCCGTTGCTGCTGTCCACCACACAGTGGCAGGTC
CTTCCGTGTTCTTTCACGACCCTGCCAGCCTTGTCCACCGGCCTCATCCACCTCCACCAG
AACATTGTGGACGTGCAGTACTTGTACGGGGTAGGGTCAAGCATCGCGTCCTGGGCCATT
AAGTGGGAGTACGTCGTTCTCCTGTTCCTTCTGCTTGCAGACGCGCGCGTCTGCTCCTGC
TTGTGGATGATGTTACTCATATCCCAAGCGGAGGCGGCTGGACTAGTGCGGCCGCTTTCG
AATCTAGAGCCTGCAGTCTCGAGGCATGCGGTACCAAGCTTGTCGAGAAGTACTAGAGGA
TCATAA

Fig. 53b. Amino Acid Sequence of HCV E2 Protein

MSYYHHHHHHDYDIPTTENLYFQGAMDPEFTHVTGGNAGRTTAGLVGLLTPGAKQNIQLINTNG
SWHINSTALNCNESLNTGWLAGLFYQHKFNSSGCPERLASCRRLTDFAQGWGPISYANGSGLDE
RPYCWHYPPRPCGIVPAKSVCGPVYCFTPSPVVVGTTDRSGAPTYSWGANDTDVFVLNNTRPPL
GNWFGCTWMNSTGFTKVCGAPPCVIGGVGNNTLLCPTDCFRKHPEATYSRCGSGPWITPRCMVD
YPYRLWHYPCTINYTIFKVRMYVGGVEHRLEAACNWTRGERCDLEDRDRSELSPLLLSTTQWQV
LPCSFTTLPALSTGLIHLHQNIVDVQYLYGVGSSIASWAIKWEYVVLLFLLLADARVCSCLWMM
LLISQAEAAGLVRPLSNLEPAVSRHAVPSLSRSTRGS

Fig. 54a. DNA Sequence of HCV E2-TBD Protein Expression Cassette

```
ATG TCG TAC TAC CAT CAC CAT CAC CAT CAC GAT TAC GAT

Fig. 54b. Amino Acid Sequence of HCV E2-TBD Protein

```
M  S  Y  Y  H  H  H  H  H  H  D  Y  D  I  P  T
T  E  N  L  Y  F  Q  G  A  M  D  P  E  F  T  H
V  T  G  G  N  A  G  R  T  T  A  G  L  V  G  L
L  T  P  G  A  K  Q  N  I  Q  L  I  N  T  N  G
S  W  H  I  N  S  T  A  L  N  C  N  E  S  L  N
T  G  W  L  A  G  L  F  Y  Q  H  K  F  N  S  S
G  C  P  E  R  L  A  S  C  R  R  L  T  D  F  A
Q  G  W  G  P  I  S  Y  A  N  G  S  G  L  D  E
R  P  Y  C  W  H  Y  P  P  R  P  C  G  I  V  P
A  K  S  V  C  G  P  V  Y  C  F  T  P  S  P  V
V  V  G  T  T  D  R  S  G  A  P  T  Y  S  W  G
A  N  D  T  D  V  F  V  L  N  N  T  R  P  P  L
G  N  W  F  G  C  T  W  M  N  S  T  G  F  T  K
V  C  G  A  P  P  C  V  I  G  G  V  G  N  N  T
L  L  C  P  T  D  C  F  R  K  H  P  E  A  T  Y
S  R  C  G  S  G  P  W  I  T  P  R  C  M  V  D
Y  P  Y  R  L  W  H  Y  P  C  T  I  N  Y  T  I
F  K  V  R  M  Y  V  G  G  V  E  H  R  L  E  A
A  C  N  W  T  R  G  E  R  C  D  L  E  D  R  D
R  S  E  L  S  P  L  L  L  S  T  T  Q  W  Q  V
L  P  C  S  F  T  T  L  P  A  L  S  T  G  L  I
H  L  H  Q  N  I  V  D  V  Q  Y  L  Y  G  V  G
S  S  I  A  S  W  A  I  K  W  E  Y  V  V  L  L
F  L  L  L  A  D  A  R  V  C  S  C  L  W  M  M
L  L  I  S  Q  A  E  A  A  G  L  V  R  P  Q  G
G  G  S  V  D  K  K  I  V  P  R  D  C  G  C  K
P  C  I  C  T  V  P  E  V  S  S  V  F  I  F  P
P  K  P  K  D  V  L  T  I  T  L  T  P  K  V  T
C  V  V  V  D  I  S  K  D  D  P  E  V  Q  F  S
W  F  V  D  D  V  E  V  H  T  A  Q  T  Q  P  R
E  E  Q  F  N  S  T  F  R  S  V  S  E  L  P  I
M  H  Q  D  W  L  N  G  K  E  F  K  C  R  V  N
S  A  A  F  P  A  P  I  E  K  T  I  S  K  T  K
G  R  P  K  A  P  Q  V  Y  T  I  P  P  P  K  E
Q  M  A  K  D  K  V  S  L  T  C  M  I  T  D  F
F  P  E  D  I  T  V  E  W  Q  W  N  G  Q  P  A
E  N  Y  K  N  T  Q  P  I  M  D  T  D  G  S  Y
F  V  Y  S  K  L  N  V  Q  K  S  N  W  E  A  G
N  T  F  T  C  S  V  L  H  E  G  L  H  N  H  H
T  E  K  S  L  S  H  S  P  G  L  Q  S  L  S  R
S  T  R  G  S
```

Fig. 55a. DNA Sequence of HCV E1E2 Protein Expression Cassette

```
ATG TCG TAC TAC CAT CAC CAT CAC CAT CAC GAT TAC GAT ATC CCA ACG
ACC GAA AAC CTG TAT TTT CAG GGC GCC ATG GAT CCG GAA TTC TAC CAA
GTG CGC AAT TCC TCG GGG CTT TAC CAT GTC ACC AAT GAT TGC CCT AAC
TCG AGT ATT GTG TAC GAG GCG GCC GAT GCC ATC CTG CAC ACT CCG GGG
TGT GTC CCT TGC GTT CGC GAG GGT AAC GCC TCG AGG TGT TGG GTG GCG
GTG ACC CCC ACG GTG GCC ACC AGG GAC GGC AAA CTC CCC ACA ACG CAG
CTT CGA CGT CAT ATC GAT CTG CTT GTC GGG AGC GCC ACC CTC TGC TCG
GCC CTC TAC GTG GGG GAC CTG TGC GGG TCT GTC TTT CTT GTT GGT CAA
CTG TTT ACC TTC TCT CCC AGG CGC CAC TGG ACG ACG CAA GAC TGC AAT
TGT TCT ATC TAT CCC GGC CAT ATA ACG GGT CAT CGC ATG GCA TGG GAT
ATG ATG ATG AAC TGG TCC CCT ACG GCA GCG TTG GTG GTA GCT CAG CTG
CTC CGG ATC CCA CAA GCC ATC ATG GAC ATG ATC GCT GGT GCT CAC TGG
GGA GTC CTG GCG GGC ATA GCG TAT TTC TCC ATG GTG GGG AAC TGG GCG
AAG GTC CTG GTA GTG CTG CTG CTA TTT GCC GGC GTC GAC GCG GAA ACC
CAC GTC ACC GGG GGA AAT GCC GGC CGC ACC ACG GCT GGG CTT GTT GGT
CTC CTT ACA CCA GGC GCC AAG CAG AAC ATC CAA CTG ATC AAC ACC AAC
GGC AGT TGG CAC ATC AAT AGC ACG GCC TTG AAT TGC AAT GAA AGC CTT
AAC ACC GGC TGG TTA GCA GGG CTC TTC TAT CAA CAC AAA TTC AAC TCT
TCA GGC TGT CCT GAG AGG TTG GCC AGC TGC CGA CGC CTT ACC GAT TTT
GCC CAG GGC TGG GGT CCT ATC AGT TAT GCC AAC GGA AGC GGC CTC GAC
GAA CGC CCC TAC TGC TGG CAC TAC CCT CCA AGA CCT TGT GGC ATT GTG
CCC GCA AAG AGC GTG TGT GGC CCG GTA TAT TGC TTC ACT CCC AGC CCC
GTG GTG GTG GGA ACG ACC GAC AGG TCG GGC GCG CCT ACC TAC AGC TGG
GGT GCA AAT GAT ACG GAT GTC TTC GTC CTT AAC AAC ACC AGG CCA CCG
CTG GGC AAT TGG TTC GGT TGT ACC TGG ATG AAC TCA ACT GGA TTC ACC
AAA GTG TGC GGA GCG CCC CCT TGT GTC ATC GGA GGG GTG GGC AAC AAC
ACC TTG CTC TGC CCC ACT GAT TGC TTC CGC AAA CAT CCG GAA GCC ACA
TAC TCT CGG TGC GGC TCC GGT CCC TGG ATT ACA CCC AGG TGC ATG GTC
GAC TAC CCG TAT AGG CTT TGG CAC TAT CCT TGT ACC ATC AAT TAC ACC
ATA TTC AAA GTC AGG ATG TAC GTG GGA GGG GTC GAG CAC AGG CTG GAA
GCG GCC TGC AAC TGG ACG CGG GGC GAA CGC TGT GAT CTG GAA GAC AGG
GAC AGG TCC GAG CTC AGC CCG TTG CTG CTG TCC ACC ACA CAG TGG CAG
GTC CTT CCG TGT TCT TTC ACG ACC CTG CCA GCC TTG TCC ACC GGC CTC
ATC CAC CTC CAC CAG AAC ATT GTG GAC GTG CAG TAC TTG TAC GGG GTA
GGG TCA AGC ATC GCG TCC TGG GCC ATT AAG TGG GAG TAC GTC GTT CTC
CTG TTC CTT CTG CTT GCA GAC GCG CGC GTC TGC TCC TGC TTG TGG ATG
ATG TTA CTC ATA TCC CAA GCG GAG GCG GCT GGA CTA GTG CGG CCG CTT
TCG AAT CTA GAG CCT GCA GTC TCG AGG CAT GCG GTA CCA AGC TTG TCG
AGA AGT ACT AGA GGA TCA TAA
```

Fig. 55b. Amino Acid Sequence of HCV E1E2 Protein

```
M  S  Y  Y  H  H  H  H  H  H  D  Y  D  I  P  T
T  E  N  L  Y  F  Q  G  A  M  D  P  E  F  Y  Q
V  R  N  S  S  G  L  Y  H  V  T  N  D  C  P  N
S  S  I  V  Y  E  A  A  D  A  I  L  H  T  P  G
C  V  P  C  V  R  E  G  N  A  S  R  C  W  V  A
V  T  P  T  V  A  T  R  D  G  K  L  P  T  T  Q
L  R  R  H  I  D  L  L  V  G  S  A  T  L  C  S
A  L  Y  V  G  D  L  C  G  S  V  F  L  V  G  Q
L  F  T  F  S  P  R  R  H  W  T  T  Q  D  C  N
C  S  I  Y  P  G  H  I  T  G  H  R  M  A  W  D
M  M  M  N  W  S  P  T  A  A  L  V  V  A  Q  L
L  R  I  P  Q  A  I  M  D  M  I  A  G  A  H  W
G  V  L  A  G  I  A  Y  F  S  M  V  G  N  W  A
K  V  L  V  V  L  L  L  F  A  G  V  D  A  E  T
H  V  T  G  G  N  A  G  R  T  T  A  G  L  V  G
L  L  T  P  G  A  K  Q  N  I  Q  L  I  N  T  N
G  S  W  H  I  N  S  T  A  L  N  C  N  E  S  L
N  T  G  W  L  A  G  L  F  Y  Q  H  K  F  N  S
S  G  C  P  E  R  L  A  S  C  R  R  L  T  D  F
A  Q  G  W  G  P  I  S  Y  A  N  G  S  G  L  D
E  R  P  Y  C  W  H  Y  P  P  R  P  C  G  I  V
P  A  K  S  V  C  G  P  V  Y  C  F  T  P  S  P
V  V  V  G  T  T  D  R  S  G  A  P  T  Y  S  W
G  A  N  D  T  D  V  F  V  L  N  N  T  R  P  P
L  G  N  W  F  G  C  T  W  M  N  S  T  G  F  T
K  V  C  G  A  P  P  C  V  I  G  G  V  G  N  N
T  L  L  C  P  T  D  C  F  R  K  H  P  E  A  T
Y  S  R  C  G  S  G  P  W  I  T  P  R  C  M  V
D  Y  P  Y  R  L  W  H  Y  P  C  T  I  N  Y  T
I  F  K  V  R  M  Y  V  G  G  V  E  H  R  L  E
A  A  C  N  W  T  R  G  E  R  C  D  L  E  D  R
D  R  S  E  L  S  P  L  L  L  S  T  T  Q  W  Q
V  L  P  C  S  F  T  T  L  P  A  L  S  T  G  L
I  H  L  H  Q  N  I  V  D  V  Q  Y  L  Y  G  V
G  S  S  I  A  S  W  A  I  K  W  E  Y  V  V  L
L  F  L  L  L  A  D  A  R  V  C  S  C  L  W  M
M  L  L  I  S  Q  A  E  A  A  G  L  V  R  P  L
S  N  L  E  P  A  V  S  R  H  A  V  P  S  L  S
R  S  T  R  G  S
```

Figure 56A:
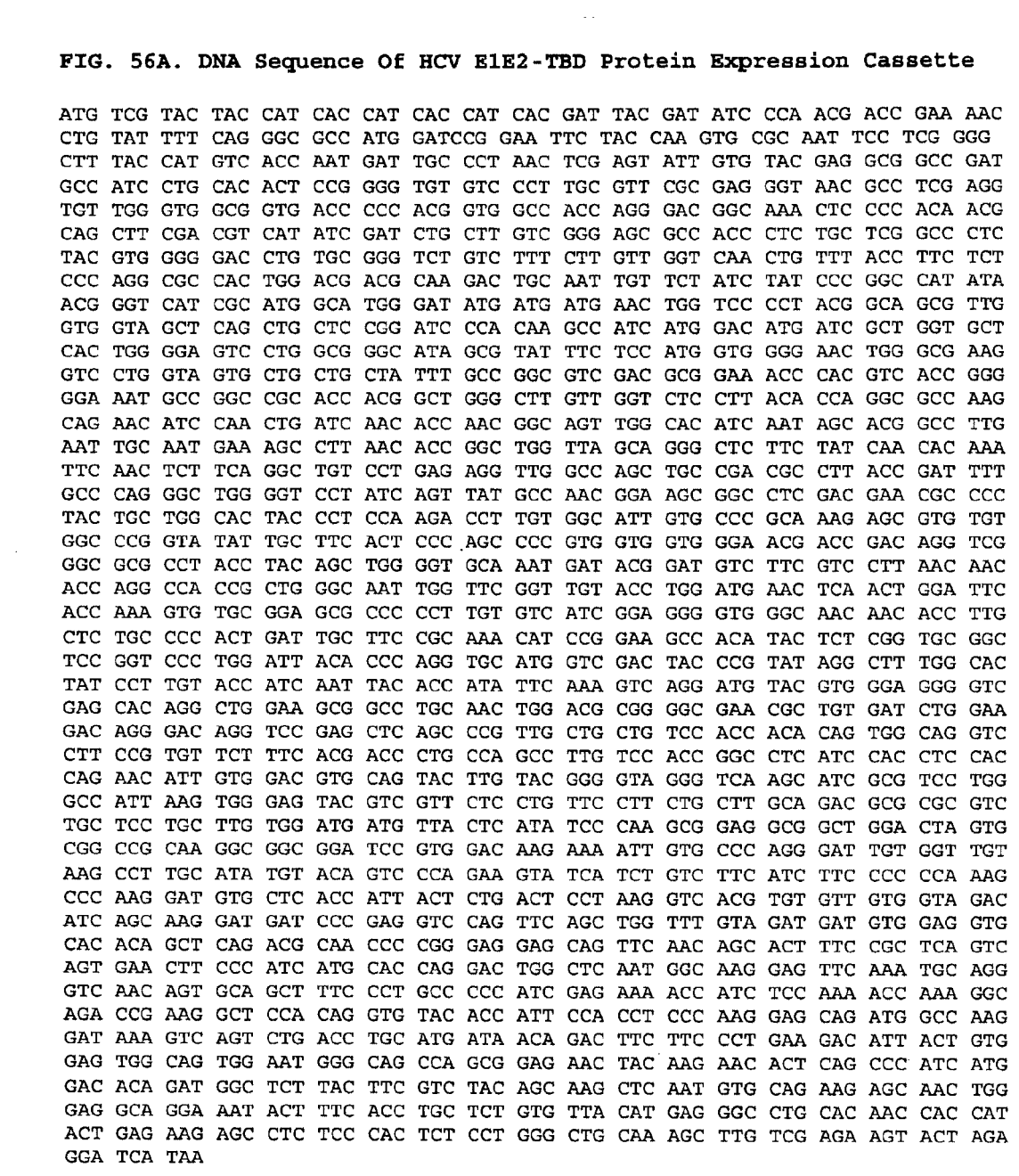

FIG. 56A. DNA Sequence Of HCV E1E2-TBD Protein Expression Cassette

```
ATG TCG TAC TAC CAT CAC CAT

Fig. 56b. Amino Acid Sequence of HCV E1E2-TBD Protein

```
M S Y Y H H H H H H D Y D I P T T E N L
Y F Q G A M D P E F Y Q V R N S S G L Y
H V T N D C P N S S I V Y E A A D A I L
H T P G C V P C V R E G N A S R C W V A
V T P T V A T R D G K L P T T Q L R R H
I D L L V G S A T L C S A L Y V G D L C
G S V F L V G Q L F T F S P R R H W T T
Q D C N C S I Y P G H I T G H R M A W D
M M M N W S P T A A L V V A Q L L R I P
Q A I M D M I A G A H W G V L A G I A Y
F S M V G N W A K V L V V L L L F A G V
D A E T H V T G G N A G R T T A G L V G
L L T P G A K Q N I Q L I N T N G S W H
I N S T A L N C N E S L N T G W L A G L
F Y Q H K F N S S G C P E R L A S C R R
L T D F A Q G W G P I S Y A N G S G L D
E R P Y C W H Y P P R P C G I V P A K S
V C G P V Y C F T P S P V V V G T T D R
S G A P T Y S W G A N D T D V F V L N N
T R P P L G N W F G C T W M N S T G F T
K V C G A P P C V I G G V G N N T L L C
P T D C F R K H P E A T Y S R C G S G P
W I T P R C M V D Y P Y R L W H Y P C T
I N Y T I F K V R M Y V G G V E H R L E
A A C N W T R G E R C D L E D R D R S E
L S P L L L S T T Q W Q V L P C S F T T
L P A L S T G L I H L H Q N I V D V Q Y
L Y G V G S S I A S W A I K W E Y V V L
L F L L A D A R V C S C L W M M L L L I
S Q A E A A G L V R P Q G G G S V D K K
I V P R D C G C K P C I C T V P E V S S
V F I F P P K P K D V L T I T L T P K V
T C V V V D I S K D D P E V Q F S W F V
D D V E V H T A Q T Q P R E E Q F N S T
F R S V S E L P I M H Q D W L N G K E F
K C R V N S A A F P A P I E K T I S K T
K G R P K A P Q V Y T I P P P K E Q M A
K D K V S L T C M I T D F F P E D I T V
E W Q W N G Q P A E N Y K N T Q P I M D
T D G S Y F V Y S K L N V Q K S N W E A
G N T F T C S V L H E G L H N H H T E K
S L S H S P G L Q S L S R S T R G S
```

CHIMERIC ANTIGENS FOR ELICITING AN IMMUNE RESPONSE

RELATED APPLICATIONS

The present application is a continuation of U.S. patent application Ser. No. 10/912,969, filed Aug. 5, 2004, now U.S. Pat. No. 8,025,873, which is a continuation-in-part of International Patent Application Serial No. PCT/IB2004/000373, filed Feb. 14, 2004. U.S. patent application Ser. No. 10/912,969 is also a continuation-in-part of U.S. patent application Ser. No. 10/365,620, filed Feb. 13, 2003, now U.S. Pat. No. 8,029,803, which claims the benefit of U.S. Provisional Patent Application Ser. No. 60/423,578, filed Nov. 5, 2002 and U.S. Provisional Patent Application Ser. No. 60/390,564, filed Jun. 20, 2002, each of the above-identified disclosures are incorporated fully herein by reference.

INTRODUCTION

1. Technical Field

The present invention relates to chimeric antigens (fusion proteins) for targeting and activating antigen presenting cells. In particular, the invention describes compositions and methods that contain or use one or more fusion proteins that contain a pre-selected HBV antigen or HCV antigen, and a xenotypic immunoglobulin fragment, wherein the fusion molecule is capable of binding and activating antigen presenting cells, especially dendritic cells.

2. Background

Viral infectious diseases are major public healthcare issues. Human Hepatitis B virus (HBV) is a member of a family of DNA viruses that primarily infect the liver (Gust, et al., *Intervirology* 25:14-29 (1986). Other members of this family are woodchuck hepatitis B virus (WHV) (Summers, et al., *Proc Natl Acad Sci USA* 75(9): 4533-7 (1978)), duck hepatitis B virus (DHBV) (Mason, et al., *J Virol* 36(3): 829-36 (1980)) and heron hepatitis B virus (HHBV) (Sprengel, et al., *J Virol* 62(10): 3832-9 (1988)). These viruses share a common morphology and replication mechanisms, but are species specific for infectivity (Marion, *Prog Med. Virol.* 35:43-75 (1988)).

HBV primarily infects liver cells and can cause acute and chronic liver disease resulting in cirrhosis and hepatocellular carcinoma. Infection occurs through blood and other body fluids. Approximately 90% of the individuals infected by HBV are able to clear the infection, while the remaining 10% become chronic carriers of the virus with a high probability of developing cirrhosis of the liver and hepatocellular carcinoma. The World Health Organization statistics show that more than 2 billion people have been infected by HBV and among these, 370 million are chronically infected by the virus (Beasley, *Cancer* 61(10):1942-56 (1988); Kane *Vaccine* 12:547-49 (1995)). Prophylactic vaccines based on HBV surface antigen (HBsAg) have been very effective in providing protective immunity against HBV infections. These vaccines have been developed from HBsAg purified from plasma of chronic HBV carriers, produced by recombinant DNA techniques as well as through the use of synthetic peptides (see, e.g. U.S. Pat. Nos. 4,599,230 and 4,599,231). These vaccines are highly effective in the prevention of infection, but are ineffective in eradicating established chronic infections.

Human Hepatitis B Virus (HBV) belongs to the family of Hepadnaviruses. Other members of this family are Duck Hepatitis B Virus (DHBV), Woodchuck Hepatitis Virus (WHV) Ground Squirrel Hepatitis B Virus (GSHV) and Heron Hepatitis B Virus (HHBV). Although these viruses have similar morphology and replication mechanism, they are fairly species specific. Consequently, they infect only very closely related species. These viruses have a DNA genome ranging in size from 3.0-3.2 Kb, with overlapping reading frames to encode several proteins. HBV genome encodes several proteins. Among these, the surface antigens: Large (S1/S2/S), Medium (S2/S) and Small (S) are proposed to be involved in the binding of the virus to the cellular receptors for uptake. The Core protein (Core) forms capsids, which encapsulate the partially double stranded DNA genome. Polymerase/Reverse Transcriptase (Pol) protein is a multifunctional enzyme necessary for the replication of the virus. The X protein has been proposed to have many properties, including the activation of Src kinases (Ganem, *Science* 294 (5550):2299-300 (2001)). The present invention describes DNA sequences and amino acid compositions of the surface antigen proteins S1/S2, S1/S2/S as well as Core protein fusion proteins with a xenotypic monoclonal antibody (mAb) fragment.

DHBV, another member of the hepadnaviral family, infects pekin ducks, is species specific, and has served as an animal model for studying the hepatitis B viruses. DHBV has a DNA genome and it codes for surface antigens PreS and PreS/S, Core protein (Core) and Polymerase/Reverse Transcriptase. The present invention also describes DNA sequences and deduced amino acid sequences of fusion proteins of the PreS, PreS/S and Core proteins with a fragment of a xenotypic mAb. These fusion proteins can be used to elicit a broad immune response in chronic viral infections, thus as therapeutic vaccine.

Hepatitis C virus (HCV) is a member of the flaviviridae family of RNA viruses. The route of infection is via blood and body fluids and over 50% of the patients become chronic carriers of the virus. Persistent infection results in chronic active hepatitis, which may lead to liver cirrhosis and hepatocellular carcinoma (Saito et. al., *PNAS USA* 87:6547-6549 (1990)).

Approximately 170 million people worldwide are chronic carriers of HCV (Wild and Hall, *Mutation Res.* 462: 381-393 (2000)). There is no prophylactic vaccine available at present. Current therapy is interferon α-2b and ribavirin, either alone or as combination therapy. The significant side effects for interferon treatment and the development of mutant strains are major drawbacks to the current therapy. Moreover, interferon therapy is effective only in 20% of the patients. Therapeutic vaccines to enhance host immune system to eliminate chronic HCV infection will be a major advancement in the treatment of this disease.

HCV genome is a positive sense single stranded RNA molecule of approximately 9.5 Kb in length. This RNA, which contains both 5' and 3' untranslated regions, codes for a single polyprotein that is cleaved into individual proteins and catalyzed by both viral and host proteases (Clarke, *J. Gen. Virol.* 78: 2397-2410 (1997)). The structural proteins are Core, Envelope E1 & E2 and P7. The non-structural proteins are NS2, NS3, NS4A, NS4B, NS5A and NS5B. Core forms capsids. E1, E2 are envelope proteins, also called "Hypervariable region" due to the high rate of mutations. NS3 is a Serine Protease, the target of several protease inhibitors as antivirals for HCV. NS5B is the RNA Polymerase enzyme. NS5A has recently been suggested to have a direct role in the replication of the virus in the host by counteracting the interferon response (Tan, and Katze, *Virology* 284:1-12 (2001)) that augments the immune function.

When a healthy host (human or animal) encounters an antigen (such as a protein derived from a bacterium, virus or parasite), normally the host initiates an immune response.

This immune response can be a humoral response and/or a cellular response. In the humoral response antibodies are produced by B cells and are secreted into the blood and/or lymph in response to an antigenic stimulus. The antibody then neutralizes the antigen, e.g. a virus, by binding specifically to antigens on its surface, marking it for destruction by phagocytotic cells and/or complement-mediated mechanisms. The cellular response is characterized by the selection and expansion of specific helper and cytotoxic T-lymphocytes capable of directly eliminating the cells that contain the antigen.

In many individuals, the immune system does not respond to certain antigens. When an antigen does not stimulate the production of a specific antibody and/or killer T cells, the immune system is unable to prevent the resultant disease. As a result, the infectious agent, e.g. a virus, can establish a chronic infection and the host immune system becomes tolerant to the antigens produced by the virus. The mechanism by which the virus evades the host immune machinery is not clearly established. The best-known examples of chronic viral infections include Hepatitis B, Hepatitis C, Human Immunodeficiency Virus, Human Papilloma Virus and Herpes Simplex Virus.

In chronic states of viral infections, the virus escapes the host immune system. Viral antigens are recognized as "self," and thus not recognized by the antigen-presenting cells. The lack of proper presentation of the appropriate viral antigen to the host immune system may be a contributing factor. The success in eliminating the virus will result from the manner in which the antigen is processed and presented by the antigen presenting cells (APCs) and the involvement of the regulatory and cytotoxic T cells. The major participant in this process is the Dendritic Cell (DC), which captures and processes antigens, expresses lymphocyte co-stimulatory molecules, migrates to lymphoid organs, and secretes cytokines to initiate immune responses. Dendritic cells also control the proliferation of B and T lymphocytes, which are the mediators of immunity (Steinman, et al., *Hum Immunol* 60(7):562-7 (1999)). The generation of a cytotoxic T lymphocyte (CTL) response is critical in the elimination of the virus infected cells and thus a cure of the infection.

Antigen presenting cells process the encountered antigens differently depending on the localization of the antigen (Steinman et al., 1999, supra). Exogenous antigens are processed within the endosomes of the APC and the generated peptide fragments are presented on the surface of the cell complexed with Major Histocompatibility Complex (MHC) Class II. The presentation of this complex to CD4$^+$ T cells stimulates the CD4$^+$ T helper cells. As a result, cytokines secreted by the helper cells stimulate B cells to produce antibodies against the exogenous antigen (humoral response). Immunizations using antigens typically generate antibody response through this endosomal antigen processing pathway.

On the other hand, intracellular antigens are processed in the proteasome and the resulting peptide fragments are presented as complexes with MHC Class I on the surface of APCs. Following binding of this complex to the co-receptor CD8 molecule, antigen presentation to CD8$^+$ T cells occurs which results in a cytotoxic T lymphocyte (CTL) immune response to remove the host cells that carry the antigen.

In patients with chronic viral infections, since the virus is actively replicating, viral antigens will be produced within the host cell. Secreted antigens will be present in the circulation. As an example, in the case of chronic HBV carriers, virions and HBV surface antigens and a surrogate for core antigens (in the form of e-antigen) can be detected in the blood. An effective therapeutic vaccine should be able to induce strong CTL responses against an intracellular antigen or an antigen delivered into the appropriate cellular compartment so as to activate the MHC Class I processing pathway. An effective prophylactic vaccine will induce a strong humoral immune response, thus producing antibodies to neutralize circulating virions.

These findings would suggest that a therapeutic vaccine that can induce a strong CTL response should be processed through the proteasomal pathway and presented via the MHC Class I (Larsson, et al., *Trends Immunol* 22(3):141-8 (2001)). This can be achieved either by producing the antigen within the host cell, or it can be delivered to the appropriate cellular compartment so that it gets processed and presented so as to elicit a cellular response. Several approaches have been documented in the literature for the intracellular delivery of the antigen. Among these, viral vectors (Lorenz, et al., *Hum Gene Ther* 10(7):1095-103 (1999)), the use of cDNA-transfected cells (Donnelly, et al., *Annu Rev Immunol* 15: 617-48 (1997)) as well as the expression of the antigen through injected cDNA vectors (Lai and Bennett, *Crit. Rev Immunol* 18(5): 449-84 (1998); U.S. Pat. No. 5,589,466), have been documented. Further, DNA vaccines expressing antigens targeted to dendritic cells have been described (You, et al., *Cancer Res* 61:3704-3711 (2001)).

Delivery vehicles capable of carrying the antigens to the cytosolic compartment of the cell for MHC Class I pathway processing have also been used. The use of adjuvants to achieve the same goal has been described in detail by (Hilgers, et al., *Vaccine* 17(3):219-28 (1999)) Another approach is the use of biodegradable microspheres in the cytoplasmic delivery of antigens (Newman, et al., *J Biomed Mater Res* 50(4):591-7 (2000)), exemplified by the generation of a Th1 immune response against ovalbumin peptide (Newman, et al., *J Control Release* 54(1):49-59 (1998); Newman, et al., *J Biomed Mater Res* 50(4): 591-7 (2000)). It has also been shown that PLGA nanospheres are taken up by the most potent antigen presenting cells, dendritic cells (Newman, et al., *J Biomed Mater Res* 60(3): 480-6 (2002)).

Dendritic cells derived from blood monocytes, by virtue of their capability as professional antigen presenting cells have been shown to have great potential as immune modulators that stimulate primary T cell response (Steinman, et al., *Hum Immunol* 60(7): 562-7 (1999); Banchereau and Steinman, *Nature* 392(6673):245-52 (1998)). This property of the DCs to capture, process, present the antigen and stimulate naive T cells has made them very important tools for therapeutic vaccine development (Laupeze, et al., *Hum Immunol* 60(7): 591-7 (1999)). Targeting of the antigen to the DCs is the crucial step in the antigen presentation and the presence of receptors on the DCs for the Fc region of monoclonal antibodies have been exploited for this purpose (Regnault, et al., *J Exp Med* 189(2): 371-80 (1999)). Examples of this approach include ovarian cancer mAb-B43.13, Anti-PSA antibody as well as Anti-HBV antibody antigen complexes (Wen, et al., *Int Rev Immunol* 18(3): 251-8 (1999)). Cancer immunotherapy using DCs loaded with tumor associated antigens have been shown to produce tumor-specific immune responses and anti-tumor activity (Campton, et al., *J Invest Dermatol* 115(1):57-61 (2000); Fong and Engleman, *Annu Rev Immunol* 18: 245-73 (2000)). Promising results were obtained in clinical trials in vivo using tumor-antigen-pulsed DCs (Tarte and Klein, *Leukemia* 13(5): 653-63 (1999)). These studies clearly demonstrate the efficacy of using DCs to generate immune responses against cancer antigens.

The primary goal in antiviral therapy is the complete elimination of the infectious virus. In the case of chronic hepatitis B, this will result in the eradication of hepatitis B viremia, the arrest of progressive liver injury, normalization of liver transaminase activity, resolution of hepatic inflammation, elimination of HBV cccDNA (covalently closed circular DNA) reservoir, and improve the quality of life of the patient.

Two forms of antiviral therapies are currently in use for the treatment of chronic hepatitis B infections. First, antiviral compounds, particularly nucleoside analogues, which are DNA chain terminators, suppress the viral replication resulting in a decrease in HBV DNA and HBV antigens. The effectiveness of the antiviral compound depends on the level of immune help from the host. The second therapy involves the use of immune modulators, such as interferons (e.g., interferon α-2b), to stimulate the immune system into mounting a generalized humoral and cellular response against the viral infection.

The most widely used antiviral nucleoside agent is lamivudine, a cytosine analogue that acts as a chain terminator and inhibits HBV replication. The drug is well tolerated and has marked virus-suppressive activity in the majority of patients; complete clearance of the virus occurs if the patient has elevated levels of liver inflammatory enzymes. This suggests that a strong involvement of the host immune system is needed to clear the HBV infection. While lamivudine suppresses HBV replication in HBV carriers, replication recurs if therapy is stopped. The emergence of resistant mutants also is a possibility.

Interferons are biologic response modifiers that have a variety of therapeutic activities, including antiviral, immunomodulatory, and antiproliferative effects. They enhance T cell helper activity, cause maturation of B lymphocytes, inhibit T cell suppressors, and enhance HLA type I expression. While interferons have only mild to moderate virus-suppressive activities, they induce a generalized, non-specific but clinically important immune response in receptive individuals.

The indications for interferon therapy are specific: patients must be HbeAg-positive, have detectable HBV DNA in the serum, and have a serum ALT level double the upper limit of normal. When these patients are treated with a standard course of interferon-α therapy (30-35 MU interferon/week for 16-26 weeks), the response rate is 40-50%. A response is defined as loss of HBeAg, development of anti-HBe, loss of HBV DNA (by non-PCR assays), and normalization of ALT. A sustained response encompasses the foregoing outcomes plus generating effective immune responses. The responses are usually durable, are associated with improvement in liver histology, and produce a better long-term outcome, e.g., with fewer patients progressing to cirrhosis and/or hepatocellular carcinoma.

For most chronic hepatitis B patients, monotherapy with a standard 16 week course of interferon-α or a one year course of lamivudine is effective in only 30-40% of patients. It is reasonable to assume that combining the antiviral effect of one drug with a second agent promoting immune modulation may improve the response rate beyond that seen with either agent alone. However, in order to produce more effective and specific immune responses against chronic hepatitis B infections than are currently achievable with current biological response modifiers, an agent that induces highly specific cellular immune responses directed against cells harboring the viruses, viral antigens or cccDNA must be employed. The chimeric antigens described in the present invention are such agents.

The goals of treatment of chronic hepatitis C include eradication of the HCV infection, improvement or normalization of liver histology, prevention of progression of the viral liver infection to cirrhosis and hepatocellular carcinoma, extension of patient survival, improvement of the quality of life, and a reduction in the size of the infectious pool of hepatitis C virus patients in order to reduce the wide spread transmission of the disease.

Two forms of treatment of chronic hepatitis C are currently in use: pegylated interferon-α used alone and conventional or pegylated interferon-α used in combination with ribavirin. Ribavirin is a purine nucleoside analogue that as monotherapy has little effect on HCV viremia, despite the fact that it significantly reduces serum ALT levels in patients. While the exact nature of the synergism of ribavirin and interferon has not been elucidated, the efficacy of the combination exceeds that of either agent used alone.

While the mechanism of action of ribavirin in hepatitis C infection is not understood, a number of mechanisms have been proposed including: (a) the enhancement of host T cell-mediated immunity against viral infection through switching the T cell phenotype from type 2 to type 1; (b) the inhibition of the host enzyme inosine monophosphate dehydrogenase (IMPDH); (c) the direct inhibition of HCV, including NS5B-encoded RNA-dependent RNA polymerase (RdRp); and (d) its action as an RNA mutagen that drives a rapidly mutating RNA virus over the threshold to "error catastrophe."

Interferons are biologic response modifiers that have a variety of therapeutic activities including antiviral, immunomodulatory, and antiproliferative effects. They enhance T cell helper activity, cause maturation of B lymphocytes, inhibit T cell suppressors, and enhance HLA type I expression. While interferons have only mild to moderate virus-suppressive activities, they induce a generalized, non-specific but clinically important immune response in receptive individuals that reduces viral levels.

The treatment options for previously untreated patients with hepatitis C include pegylated interferon monotherapy and a combination of conventional or pegylated interferon with ribavirin. The overall sustained response rate (SR) of ribavirin combined with conventional interferon α-2b therapy for 48 weeks is about 40%. The SR for patients infected with genotype 2 or 3 patients is about 60%, whereas the SR is about 30% for patients infected with genotype 1 (Lauer and Walker, NEJMed 345:41-42 (2001)). However, the combination is associated with significantly more side effects than conventional interferon alone. Up 20% of patients receiving the combination required a reduction of dose or discontinuation of therapy because of the side effects. Nevertheless, the combination represents a significant improvement in the treatment of chronic hepatitis C and has become the current standard of care.

Conventional interferon-α is rapidly cleared from the circulation by the kidneys. During the first 12 hours after interferon administration, interferon-α causes the viral levels to decrease significantly, but after that time, the viral levels begin to increase because of low blood levels of interferon. Sustained viral suppression can be achieved by the administration of pegylated interferon, which is administered only once a week and produces constant blood levels of interferon for 7 days. Thus, there is no need for the daily dosing that is required with conventional interferon. Per the Peg-Intron® product insert, the overall SR in previously untreated chronic hepatitis C patients who received pegylated interferon for 48 weeks was about 39%, which is comparable to the previously reported SR with combined conventional interferon α-2b and ribavirin combination (Rebetron®).

In studies comparing combined pegylated interferon and ribavirin to the Rebetron® combination, the pegylated interferon and ribavirin combinations appeared to be more effective, especially in patients infected with HCV genotype 1. For patients infected with this genotype, the sustained response rate (SR) was about 45% for the pegylated interferon and ribavirin combination compared with about 35% for the Rebetron® combination. As expected, the overall response rates in HCV genotype 2 or 3 patients for each of these treatment groups were better than those obtained with HCV genotype 1 patients (SR 60% to 80%).

In a trial comparing Rebetron® with varying doses of PEG-Intron® (pegylated interferon α-2a) and ribavirin, the patients were predominately male Caucasians, more frequently infected with HCV genotype 1, and had a mean age of 44 years (Mann, et al., *Lancet* 358:958-965 (2001)). The best-sustained virologic response of 54% was obtained with PEG-Intron® plus ribavirin given for 48 weeks. Patients with HCV genotype 1 had an SR of about 40%, while patients with HCV genotypes 2 and 3 after 48 weeks of therapy had the best sustained virologic response rate of approximately 80%, regardless of whether they received Rebetron® or PEG-Intron® and ribavirin. Adverse events in the PEG-Intron® plus ribavirin group that were more than 10% more frequent than in the standard interferon and ribavirin group included fever, nausea, and injection site reaction. Twelve percent of patients on PEG-Intron® plus ribavirin required dose modifications due to an adverse event, while 34% had dose modifications due to a lab abnormality.

In another large, multinational, multicenter trial of plus ribavirin, the three arms of the study were Pegasys® plus placebo, standard interferon α-2b plus ribavirin (Rebetron®), and Pegasys® plus ribavirin, which were all given for 48 weeks (Fried et al., *N Engl J. Med.* 347(13):975-982 (2002)). There were 1,149 predominantly male patients in the trial with an average age of about 40; 12% to 15% of patients had cirrhosis and approximately two-thirds had infection with HCV genotype 1. The overall sustained virologic response with Pegasys® plus ribavirin was 56% compared to 30% in the Pegasys® plus placebo group, and 45% in the standard interferon α-2b plus ribavirin (Rebetron®) group. Patients with HCV genotype I had a 46% SR with Pegasys® plus ribavirin, while patients with genotypes 2 and 3 had a 76% SR. Fever, myalgia, rigors, and depression were relatively less frequent with Pegasys® plus ribavirin compared to standard interferon α-2b plus ribavirin (Rebetron®). In the Pegasys® plus ribavirin group, the rate of discontinuation of therapy due to an adverse event was 7% and due to a lab abnormality was 3%.

Despite vigorous treatment with the current standard combination therapy of interferon-α and ribavirin, there are still a large proportion of patients with chronic HCV who do not respond. In order to produce an improved sustained response rate in the treatment of chronic hepatitis C infection, an agent that induces highly specific cellular immune responses directed against cells harboring the hepatitis C viruses must be employed. Such an agent is the chimeric antigen hepatitis C vaccine.

There is no prophylactic vaccine available to prevent new HCV infections. The attempts to develop preventative vaccines using the envelope proteins of HCV have been unsuccessful due to the high rate of mutation of the virus. Similarly, no therapeutic vaccine is available for the treatment of existing and/or chronic HCV infections. Chimeric antigens described in the present invention incorporating immunological attributes of HBV antigen and xenotypic monoclonal antibody have been shown to elicit both a strong humoral and strong cellular immune response against viral antigen in animal models. Chimeric antigens described in the present invention incorporating HCV antigens and xenotypic monoclonal antibody fragment could be used for prophylaxis and/or treatment.

SUMMARY OF THE INVENTION

The present invention pertains to compositions and methods for targeting and activating antigen presenting cells, one of the first steps in eliciting an immune response. The compositions of the present invention include a novel class of bifunctional molecules designated as "chimeric antigens") that include an immune response domain (IRD), for example a recombinant protein, linked to a target binding domain (TBD), for example, a xenotypic antibody fragment portion. More specifically, the chimeric antigens are molecules that couple viral antigens, such as Hepatitis B Core or surface proteins, to a xenotypic Fc fragment, such as a murine immunoglobulin G fragment.

The compositions and methods of the present invention are useful for targeting and activating antigen presenting cells. The present invention may be useful for inducing cellular and humoral host immune responses against any viral antigen associated with a chronic viral infection, including but not limited to Hepatitis B, Hepatitis C, Human Immunodeficiency Virus, Human Papilloma Virus (HPV), and Herpes Simplex Virus. The invention may also be applicable to prophylactic vaccines, especially for viral disease, and to all autologous antigens in diseases such as cancer and autoimmune disorders.

The present invention relates to chronic infectious diseases, and in particular to chronic HBV infections. The presentation of HBV antigens to elicit a cellular or humoral immune response by the use of vaccine molecules designed to target the vaccines to DCs whereby the HBV-associated antigens treated as "self" during the chronic infection will be recognized as "foreign" and the host's immune system will mount a CTL response to eliminate HBV-infected cells is provided. At the same time, the antibody response to the circulating HBV antigen will bind to the antigen and remove it from the circulation. Accordingly, the present invention is designed to produce vaccines that can induce a broad immune response in patients who have chronic viral infections such as HBV.

One or more embodiments of the present invention include one or more chimeric antigens suitable for initiating an immune response against Hepatitis B virus (HBV). In these embodiments of the invention, selected HBV antigens are linked to fragments of xenotypic antibodies. The resulting chimeric antigens are capable of targeting and activating antigen presenting cells, such as dendritic cells.

One or more embodiments of the present invention include one or more chimeric antigens suitable for initiating an immune response against Hepatitis C virus (HCV). In these embodiments of the invention, selected HCV antigens are linked to fragments of antibodies. The resulting chimeric antigens are capable of targeting and activating antigen presenting cells, such as dendritic cells.

The present invention also includes methods for cloning and producing fusion proteins in a heterologous expression system. In preferred embodiments of the invention, the cloning and production methods introduce unique post-translational modifications including, but not limited to glycosylation on the expressed fusion proteins.

In order to provide efficient presentation of the antigens, the inventors have developed a novel murine monoclonal antibody Fc fragment-antigen (viral antigenic protein/peptide) fusion protein. This molecule, by virtue of the Fc fragment is recognized at a higher efficiency by the antigen-presenting cells (dendritic cells) as xenotypic, and the viral antigen is processed and presented as complexes with Major Histocompatibility Complex (MHC) Class I. This processing and antigen presentation is expected to result in the up-regulation of the response by cytotoxic T-lymphocytes, resulting in the elimination of virus-infected cell population. In addition, due to antigen presentation by MHC Class II molecules, humoral response also aids in the antibody response to the viral infection.

The bifunctional nature of the molecule helps to target the antigen to the proper antigen-presenting cells (dendritic cells), making it a unique approach in the therapy of chronic infectious diseases by specifically targeting the antigen presenting cells with the most effective stoichiometry of antigen to antibody. This is useful to the development of therapeutic vaccines to cure chronic viral infections such as Hepatitis B, Hepatitis C, Human Immunodeficiency Virus, Human Papilloma Virus and Herpes Simplex Virus, and may also be applicable to all autologous antigens in diseases such as cancer and autoimmune disorders.

The administration of these fusion proteins can elicit a broad immune response from the host, including both cellular and humoral responses. Thus, they can be used as therapeutic vaccines to treat subjects that are immune tolerant to a particular infection.

One aspect of the invention provides chimeric antigens for eliciting an immune response, said chimeric antigen comprising an immune response domain and a target binding domain, wherein the target binding domain comprises a xenotypic antibody fragment. The immune response can be a humoral and/or cellular response, elicited in vivo or ex vivo. In the case where a cellular response is elicited, the immune response can be a Th1 response, a Th2 response and/or a CTL response. The chimeric antigen can comprise more than one immune response domain, or an immune response domain that can confer immunity to more than one antigen. In certain embodiments, the chimeric antigen of the invention further comprises a 6×His-peptide, a protease cleavage site, and/or a linker for linking the immune response domain and the target binding domain. In preferred embodiments, the immune response domain comprises one or more immunogenic portions of a protein selected from the group consisting of a hepatitis B virus (HBV) protein, a duck hepatitis B virus (DHBV) protein, a hepatitis C virus (HCV) protein or a protein from Human Papilloma Virus (HPV), Human Immunodeficiency Virus (HIV), Herpes Simplex Virus (HSV) or a cancer antigen. In other preferred embodiments, the xenotypic antibody fragment comprises an Fc fragment, an antibody hinge region, a portion of or an entire $C_H1$ domain, a portion of or an entire $C_H2$ domain and/or a portion of or an entire $C_H3$ domain. In a particularly preferred embodiment, the xenotypic antibody fragment is a mouse antibody fragment. The target binding domain, optionally, can also comprise a 6×His tag, a protease cleavage site (preferably a rTEV protease cleavage site) and/or a linker for linking the immune response domain and the target binding domain. The linker may be leucine zippers, biotin/avidin or a covalent peptide linkage, such as SRPQGGGS (SEQ ID NO: 28). In a preferred embodiment, the chimeric antigen is glycosylated. The immune response domain and/or the target binding domain can be glycosylated. In a particularly preferred embodiment, the chimeric antigen is mannose glycosylated by either high mannose glycosylation or by pauci mannose glycosylation.

Another aspect of the invention provides chimeric antigens for eliciting an immune response to HBV, said chimeric antigen comprising an immune response domain and a target binding domain, wherein the immune response domain comprises a protein selected from the group consisting of a HBV Core protein, a HBV S protein, a HBV S1 protein, a HBV S2 protein, and combinations thereof, and wherein the target binding domain comprises a xenotypic antibody fragment. The immune response can be a humoral and/or cellular response, elicited in vivo or ex vivo. When a cellular response is elicited, the immune response can be a Th1 response and or a Th2 response.

Yet another aspect of the invention relates to chimeric antigens for eliciting an immune response to DHBV, said chimeric antigens comprising an immune response domain and a target binding domain, wherein the immune response domain comprises a protein selected from the group consisting of a DHBV Core protein, a DHBV Pre-S protein, a DHBV PreS/S protein, and combinations thereof, and wherein the target binding domain comprises a xenotypic antibody fragment. The immune response can be a humoral and/or cellular response, elicited in vivo or ex vivo. When a cellular response is elicited, the immune response can be a Th1 response and or a Th2 response.

An aspect of the invention provides chimeric antigens for eliciting an immune response to HCV, said chimeric antigens comprising an immune response domain and a target binding domain, wherein the immune response domain comprises a protein selected from the group consisting of a HCV Core (1-191) protein, a HCV Core (1-177) protein, a HCV E1 protein, a HCV E2 protein, a HCV E1-E2 protein, a HCV NS3 protein, a HCV NS5A protein, and combinations thereof, and wherein the target binding domain comprises a xenotypic antibody fragment. The immune response can be a humoral and/or cellular response, elicited in vivo or ex vivo. When a cellular response is elicited, the immune response can be a Th1 response and or a Th2 response.

Another aspect of the invention provides methods of enhancing antigen presentation in antigen presenting cells, said method comprising administering, to the antigen presenting cells, a chimeric antigen that comprises an immune response domain and a target binding domain, wherein the target binding domain comprises a xenotypic antibody fragment. In a preferred embodiment, the antigen presenting cells are dendritic cells.

An aspect of the invention relates to methods of activating antigen presenting cells comprising contacting an antigen presenting cell with a chimeric antigen that comprises an immune response domain and a target binding domain, wherein the target binding domain comprises a xenotypic antibody fragment. The antigen presenting cell can be contacted with the chimeric antigen in vivo or ex vivo. In another preferred embodiment, the contacting takes place in a human.

Yet another aspect of the invention provides methods of eliciting an immune response, said method comprising administering to a subject a composition comprising a chimeric antigen that comprises an immune response domain and a target binding domain, wherein the target binding domain comprises a xenotypic antibody fragment. The immune response can be a humoral and/or cellular response, elicited in vivo or ex vivo. When a cellular response is elicited, the immune response can be a Th1 response and/or a Th2 response. In a preferred embodiment, the cellular immune response is a Th1 response, a Th2 response or both a Th1 and a Th2 response.

Another aspect of the invention provides methods of treating immune-treatable conditions comprising administering, to a subject in need thereof, a chimeric antigen that comprises an immune response domain and a target binding domain, wherein the target binding domain comprises a xenotypic antibody fragment. Preferably, the immune-treatable condition is an infection or a cancer. More preferably, the immune-treatable condition is a viral infection, even more preferably, a chronic viral infection. Most preferably, the immune-treatable condition is a chronic hepatitis B viral infection or a chronic hepatitis C viral infection. For the treatment of HBV, preferably the immune response domain comprises an antigenic portion of a protein selected from the group consisting of a HBV Core protein, a HBV S protein, a HBV S1 protein, a HBV S2 protein, and combinations thereof. For the treatment of HCV, preferably the immune response domain comprises an antigenic portion of a protein selected from the group consisting of a HCV Core (1-191) protein, a HCV Core (1-177) protein, a HCV E1 protein, a HCV E2 protein, a HCV E1-E2 protein, a HCV NS3 protein, a HCV NS5A protein, and combinations thereof.

Another aspect of the invention provides methods of vaccinating a subject against an infection comprising administering to the subject a chimeric antigen that comprises an immune response domain and a target binding domain, wherein the target binding domain comprises a xenotypic antibody fragment. Preferably, the infection is a viral infection. The method of the invention can prophylactically vaccinate the animal against the infection or therapeutically vaccinate a subject having a preexisting infection.

Yet another aspect of the invention provides polynucleotides encoding a chimeric antigen, said polynucleotide comprising a first polynucleotide portion encoding an immune response domain and a second polynucleotide portion encoding a target binding domain, wherein the target binding domain comprises a xenotypic antibody fragment. In one embodiment, the polynucleotide comprises a nucleotide sequence selected from the group consisting of nucleotides 1 to 1326 of SEQ ID NO: 31, nucleotides 1 to 2004 of SEQ ID NO: 35, nucleotides 1 to 1350 of SEQ ID NO: 39, nucleotides 1 to 1293 of SEQ ID NO: 43, nucleotides 1 to 1794 of SEQ ID NO: 47, nucleotides 1 to 1581 of SEQ ID NO: 51, nucleotides 1 to 1389 of SEQ ID NO: 57, nucleotides 1 to 1347 of SEQ ID NO: 61, nucleotides 1 to 2157 of SEQ ID NO: 65, nucleotides 1 to 1395 of SEQ ID NO: 69, nucleotides 1 to 1905 of SEQ ID NO: 73 and nucleotides 1 to 2484 of SEQ ID NO: 77. Yet another embodiment provides polynucleotides that encodes a chimeric antigen that is at least 90% identical to an amino acid sequence selected from the group consisting of amino acids 1 to 442 of SEQ ID NO: 32, amino acids 1 to 668 of SEQ ID NO: 36, amino acids 1 to 450 of SEQ ID NO: 40, amino acids 1 to 431 of SEQ ID NO: 44, amino acids 1 to 598 of SEQ ID NO: 48, amino acids 1 to 527 of SEQ ID NO: 52, amino acids 1 to 463 of SEQ ID NO: 58, amino acids 1 to 449 of SEQ ID NO: 62, amino acids 1 to 719 of SEQ ID NO: 66, amino acids 1 to 465 of SEQ ID NO: 70, amino acids 1 to 635 of SEQ ID NO: 74 and amino acids 1 to 828 of SEQ ID NO: 78. One preferred embodiment includes polynucleotides that selectively hybridize under stringent conditions to a polynucleotide having a nucleotide sequence selected from the group consisting of SEQ ID NO: 31, 35, 39, 43, 47, 51, 57, 61, 65, 69, 73 and 77.

The invention also provides microorganisms and cell lines comprising a polynucleotide of the invention. Preferably, the microorganism or cell line is a eukaryotic microorganism or cell line. More preferably the microorganism or cell line is a non-mammalian eukaryotic microorganism or cell line. In a preferred embodiment the microorganism or cell line is a yeast, a plant cell line or an insect cell line. In a particularly preferred embodiment, the cell line is an insect cell line selected from the group consisting of Sf9, Sf21, *Drosophila* S2 and High Five™.

One aspect of the invention provides methods for producing a chimeric antigen comprising (a) providing a microorganism or cell line that comprises a polynucleotide encoding a chimeric antigen; and (b) culturing said microorganism or cell line under conditions whereby the chimeric antigen is expressed. Preferably, the microorganism or cell line is eukaryotic, more preferably a non-mammalian eukaryotic, microorganism or cell line. In a preferred embodiment, the microorganism or cell line is a yeast, a plant cell line or an insect cell line. In a particularly preferred embodiment, the cell line is an insect cell line selected from the group consisting of Sf9, Sf21, *Drosophila* S2 and High Five™. In another particularly preferred embodiment, the yeast is selected from the group consisting of *Saccharomyces cerevisiae, Schizosaccharomyces pombe, Pichia pastoris*, and *Pichia august*.

Another aspect of the invention relates to articles of manufacture comprising a chimeric antigen of the invention and instructions for administering the chimeric antigen to a subject, in need thereof.

Yet another aspect of the invention relates to a pharmaceutical composition comprising a pharmaceutically acceptable excipient and a chimeric antigen that comprises an immune response domain and a target binding domain comprising a xenotypic antibody fragment. Preferably the pharmaceutical composition is formulated for parenteral, transdermal, intradermal, nasal, pulmonary or oral administration.

DESCRIPTION OF DRAWINGS

FIG. 1b illustrates a particularly preferred embodiment, in which the chimeric antigen comprises a 6×His tag and peptide linker in addition to the IRD and TBD.

FIG. 6a provides the nucleotide sequences of the open reading frame encoding the TBD of FIG. 5 (SEQ ID NO: 29). FIG. 6b provides the amino acid sequence of the TBD of FIG. 5 (SEQ ID NO: 30).

FIG. 8a provides the nucleotide and deduced amino acid sequences of the chimeric antigen molecule of FIG. 7 (SEQ ID NO: 31). FIG. 8b provides the amino acid sequence of the chimeric antigen of FIG. 7 (SEQ ID NO: 32).

FIG. 9 shows the nucleotide (FIG. 9a; SEQ ID NO: 33) and deduced amino acid (FIG. 9b; SEQ ID NO: 34) sequences of HBV S1/S2 protein, expressed as described in Example 2.

FIG. 11 shows the nucleotide (FIG. 11a; SEQ ID NO: 35) and deduced amino acid (FIG. 11b; SEQ ID NO: 36) sequences of the chimeric antigen molecule of FIG. 10.

FIG. 12 shows the nucleotide (FIG. 12a; SEQ ID NO: 37) and deduced amino acid (FIG. 12b; SEQ ID NO: 38) sequences of the HBV S1/S2/S protein, expressed as described in Example 3.

FIG. 14 shows the nucleotide (FIG. 14a; SEQ ID NO: 39) and deduced amino acid (FIG. 14b; SEQ ID NO: 40) sequences of the chimeric antigen molecule of FIG. 13.

FIG. 15 shows the nucleotide (FIG. 15a; SEQ ID NO: 41) and deduced amino acid (FIG. 15b; SEQ ID NO: 42) sequences of the HBV Core protein, expressed as described in Example 4.

FIG. 17 shows the nucleotide (FIG. 17a; SEQ ID NO: 43) and deduced amino acid (FIG. 17b; SEQ ID NO: 44) sequences of the chimeric antigen molecule of FIG. 16.

FIG. 18 shows the nucleotide (FIG. 18a; SEQ ID NO: 45) and deduced amino acid (FIG. 18b; SEQ ID NO: 46) sequences of the DHBV PreS protein, expressed as described in Example 5.

FIG. 20 shows the nucleotide (FIG. 20a; SEQ ID NO: 47) and deduced amino acid (FIG. 20b; SEQ ID NO: 48) sequences of the chimeric antigen molecule of FIG. 19.

FIG. 21 shows the nucleotide (FIG. 21a; SEQ ID NO: 49) and deduced amino acid (FIG. 21b; SEQ ID NO: 50) sequences of the DHBV PreS/S protein, expressed as described in Example 6.

FIG. 23 shows the nucleotide (FIG. 23a; SEQ ID NO: 51) and deduced amino acid (FIG. 23b; SEQ ID NO: 52) sequences of the chimeric antigen molecule of FIG. 22.

FIG. 24 shows the nucleotide (FIG. 24a; SEQ ID NO: 53) and deduced amino acid (FIG. 24b; SEQ ID NO: 54) sequences of the DHBV Core protein, expressed as described in Example 7.

FIG. 25 shows that a chimeric antigen embodiment of the invention can be taken up by dendritic cells.

FIG. 26 shows that dendritic cells maturation is higher in the presence of a chimeric antigen of the present invention (S1/S2-TBD), as compared to the target binding domain (TBD) alone, or the immune response domain (S1/S2) alone.

FIG. 27 shows the expression of MHC Class II by dendritic cells in response to the chimeric antigen (S1/S2-TBD), the target binding domain alone (TBD) or the immune response domain alone (S1/S2).

FIG. 28 shows that a cellular response is generated after contact with dendritic cells activated with a chimeric antigen of the present invention.

FIG. 29 shows T cell stimulation by a chimeric antigen of the present invention over a period of 2-4 days.

FIG. 30 shows a time course of expression of antigen binding receptors on maturing dendritic cells.

FIG. 31 shows a time course of expression of various dendritic cells activation markers.

FIG. 32 shows the comparison of binding of HBV S1/S2-TBD, IgG1, and IgG2 to dendritic cells over time.

FIG. 33 shows a comparison of HBV S1/S2-TBD, IgG1, and IgG2a binding to maturing dendritic cells on day 1.

FIG. 34 shows the comparison of HBV S1/S2-TBD, IgG1, and IgG2a binding to maturing dendritic cells on day 4.

FIG. 35 shows the comparison of uptake between HBV S1/S2-TBD, IgG1, and IgG2 as a function of concentration.

FIG. 36 shows the correlation of HBV S1/S2-TBD binding to CD32 and CD206 expression on dendritic cells.

FIG. 37 demonstrates that the binding of HBV S1/S2-TBD to CD32 and CD206 receptors on dendritic cells is abolished by Fcγ fragment.

FIG. 38 shows that glycosylation of S1/S2 antigen increases the uptake by dendritic cells via the CD206 receptor.

FIG. 39 shows an increase in intracellular interferon-γ positive T cells after antigen presentation.

FIG. 40 shows an increase in secretion of interferon-γ after antigen presentation.

FIG. 41 shows an increase in intracellular interferon-γ positive T cells as a function of S1/S2-TBD concentration FIG. 42 shows interferon-γ secretion by T cells as a function of S1/S2-TBD concentration.

FIG. 43 shows the effect of glycosylation on intracellular interferon-γ production in T cells.

FIG. 44 shows the effect of glycosylation on interferon-γ secretion by T cells.

FIG. 45 shows the nucleotide (FIG. 45*a*; SEQ ID NO: 55) and amino acid (FIG. 45*b*; SEQ ID NO: 56) sequences of the ORF of HCV Core (1-191) in the plasmid pFastBac HTa-HCV.

FIG. 46 shows the nucleotide (FIG. 46*a*; SEQ ID NO: 57) and amino acid (FIG. 46*b*; SEQ ID NO: 58) sequences of the ORF of HCV Core-TBD in the plasmid pFastBac HTa-HCV-TBD.

FIG. 47 shows the nucleotide (FIG. 47*a*; SEQ ID NO: 59) and amino acid (FIG. 47*b*; SEQ ID NO: 60) sequences of the ORF of HCV Core (1-177) in the plasmid pFastBac HTa-HCV-Core (1-177).

FIG. 48 shows the nucleotide (FIG. 48*a*; SEQ ID NO: 61) and amino acid (FIG. 48*b*; SEQ ID NO: 62) sequences of the ORF of HCV Core-TBD protein in the plasmid pFastBac HTa-HCV-Core-TBD.

FIG. 49 shows the nucleotide (FIG. 49*a*; SEQ ID NO: 63) and amino acid (FIG. 49*b*; SEQ ID NO: 64) sequences of the ORF of HCV NS5A in the plasmid pFastBac HTa-HCV-NS5A.

FIG. 50 shows the nucleotide (FIG. 50*a*; SEQ ID NO: 65) and amino acid (FIG. 50*b*; SEQ ID NO: 66) sequences of the ORF of HCV NS5A-TBD in the plasmid pFastBac HTa-HCV-NS5A-TBD FIG. 51 shows the nucleotide (FIG. 51*a*; SEQ ID NO: 67) and amino acid (FIG. 51*b*; SEQ ID NO: 68) sequences of the ORF of HCV E1 in the plasmid pFastBac HTa-HCV-E1.

FIG. 52 shows the nucleotide (FIG. 52a; SEQ ID NO: 69) and amino acid (FIG. 52b; SEQ ID NO: 70) sequences of the ORF of HCV E1-TBD in the plasmid pFastBac HTa-HCV-E1-TBD.

FIG. 53 shows the nucleotide (FIG. 53a; SEQ ID NO: 71) and amino acid (FIG. 53b; SEQ ID NO: 72) sequences of the ORF of HCV E2 in the plasmid pFastBac HTa-HCV-E2.

FIG. 54 shows the nucleotide (FIG. 54a; SEQ ID NO: 73) and amino acid (FIG. 54b; SEQ ID NO: 74) sequences of the ORF of HCV E2-TBD in the plasmid pFastBac HTa-HCV-E2-TBD.

FIG. 55 shows the nucleotide (FIG. 55a; SEQ ID NO: 75) and amino acid (FIG. 55b; SEQ ID NO: 76) sequences of the ORF of HCV E1/E2 in the plasmid pFastBac HTa-HCV-E1/E2.

FIG. 56 shows the nucleotide (FIG. 56a; SEQ ID NO: 77) and amino acid (FIG. 56b; SEQ ID NO: 78) sequences of the ORF of HCV E1/E2-TBD in the plasmid pFastBac HTa-HCV-E1/E2-TBD.

DETAILED DESCRIPTION

A. Overview

Figure 1A:
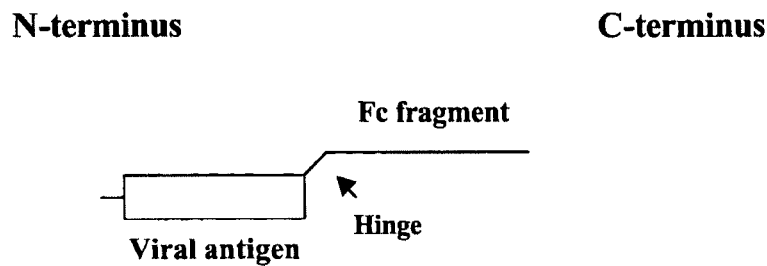
FIG. 1a provides a schematic diagram illustrating the structure of the chimeric antigen of the present invention as a monomer, wherein the chimeric antigen has two portions, namely an antigen and a xenotypic murine Fc fragment. In a preferred embodiment, a hinge region is present.
Figure 1B:
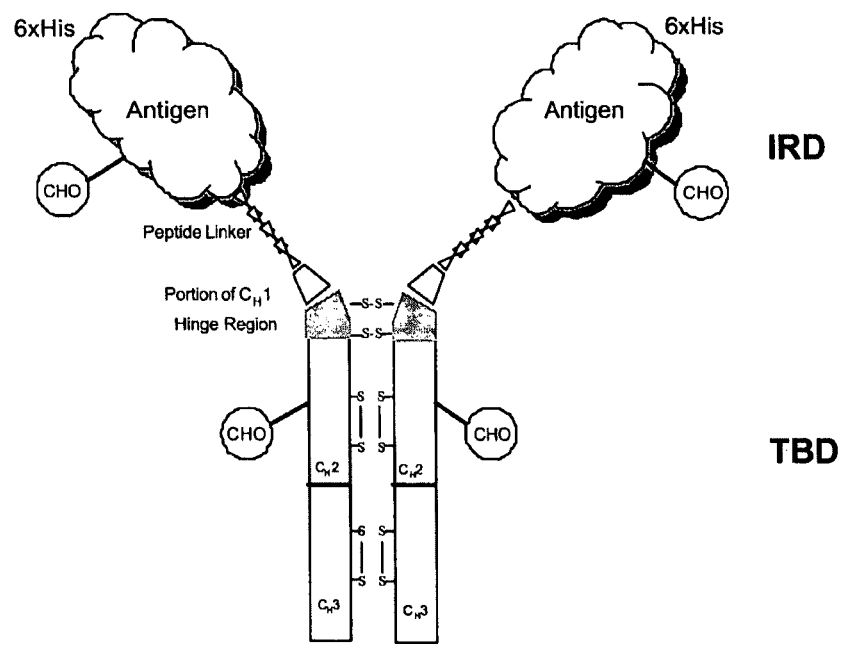
FIG. 1b provides a schematic diagram illustrating the structure of the chimeric antigen of FIG. 1 in its normal, assembled state as a dimer.
Figure 2A:
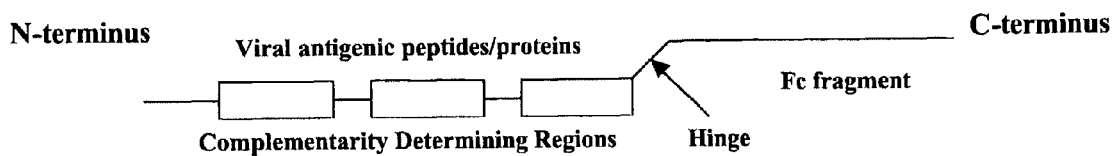
FIG. 2a provides a schematic diagram illustrating the structure of an exemplary modified chimeric antigen as a monomer, wherein the chimeric antigen has two portions, namely a modified viral antigen portion which incorporates any viral antigen or antigens, antigenic protein fragments or peptides, or any of these with glycosylation at specific sites, and a xenotypic binding agent, namely a murine Fc fragment with the hinge region present.
Figure 2B:
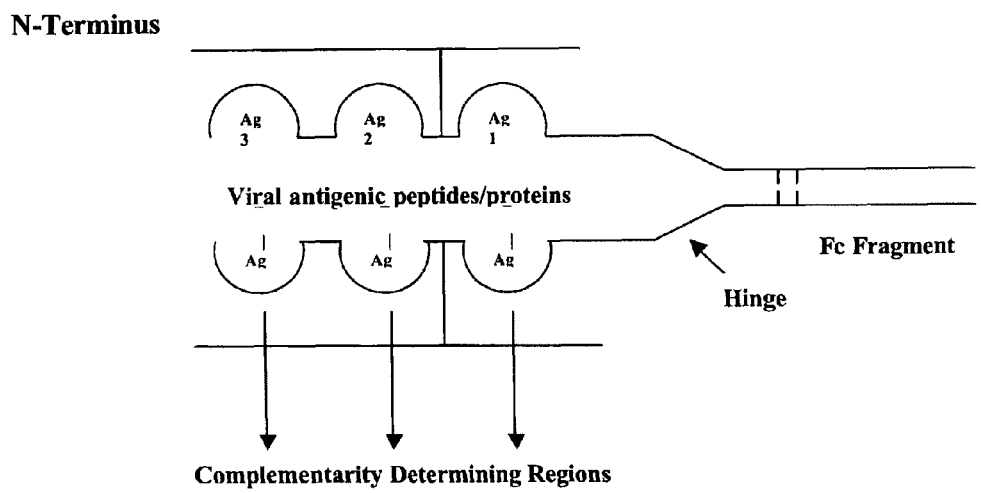
FIG. 2b is a schematic diagram illustrating the structure of the modified chimeric antigen of FIG. 2a in its normal, assembled state as a dimer. The abbreviations "Ag1," "Ag2," and "Ag3" represent different viral antigenic peptides or proteins.
Figure 3A:
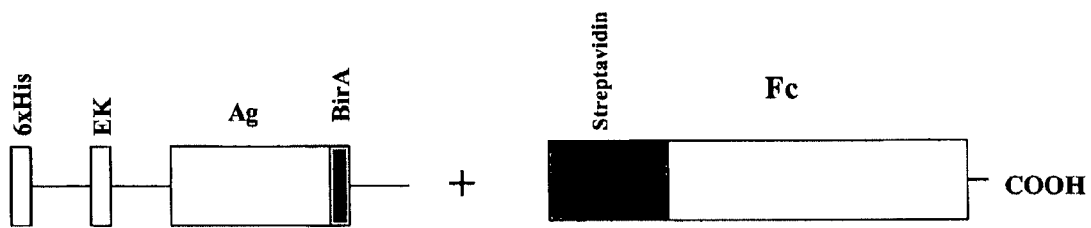
FIG. 3a provides a schematic diagram illustrating the structure of a modified biotinylated immune response domain comprising an antigen and a fusion protein of a streptavidin and a target binding domain comprising a Fc fragment with the hinge region present.
Figure 3B:
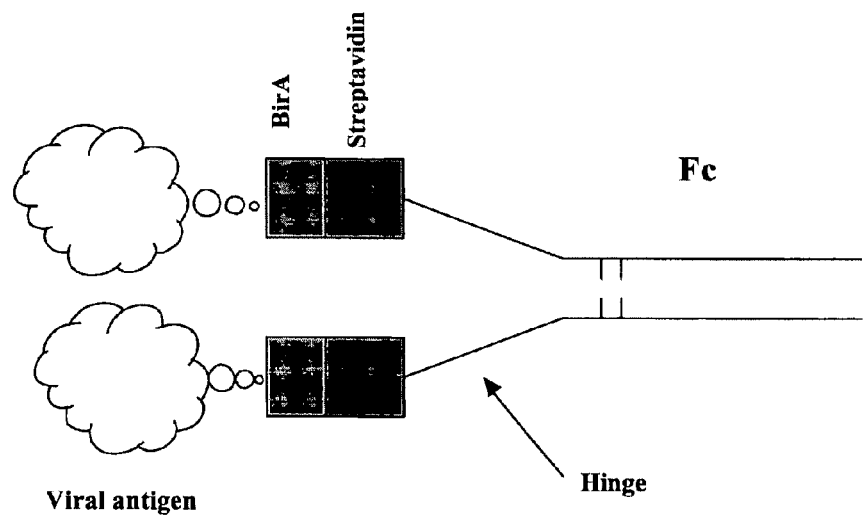
FIG. 3b provides a schematic diagram illustrating the structure of the modified chimeric antigen of FIG. 3 in its normal, assembled state as a dimer.

Disclosed herein are compositions and methods for eliciting immune responses against antigens. In particular embodiments, the compounds and methods elicit immune responses against antigens that are otherwise recognized by the host as "self" antigens. The immune response is enhanced by presenting the host immune system with a chimeric antigen comprising an immune response domain and a target binding domain, wherein the target binding domain comprises a xenotypic antibody fragment. By virtue of the target binding domain, antigen presenting cells take up, process and present the chimeric antigen, eliciting both a humoral and cellular immune response.

B. Definitions

Prior to describing the invention in further detail, the terms used in this application are defined as follows unless otherwise indicated.

"Antibody" refers to an immunoglobulin molecule produced by B lymphoid cells with a specific amino acid sequence evoked in humans or other animals by an antigen (immunogen). These molecules are characterized by reacting specifically with the antigen, each being defined in terms of the other.

"Antibody response" or "humoral response" refers to a type of immune response in which antibodies are produced by B lymphoid cells and are secreted into the blood and/or lymph in response to an antigenic stimulus. In a properly functioning immune response, the antibody binds specifically to antigens on the surface of cells (e.g., a pathogen), marking the cell for destruction by phagocytotic cells and/or complement-mediated mechanisms. Antibodies also circulate systemically and can bind to free virions. This antibody binding can neutralize the virion and prevent it from infecting a cell as well as marking the virion for elimination from circulation by phagocytosis or filtration in the kidneys.

"Antigen" refers to any substance that, as a result of coming in contact with appropriate cells, induces a state of sensitivity and/or immune responsiveness and that reacts in a demonstrable way with antibodies and/or immune cells of the sensitized subject in vivo or in vitro.

"Antigen-presenting cell" refers to the accessory cells of antigen-inductive events that function primarily by handling and presenting antigen to lymphocytes. The interaction of antigen presenting cells (APC) with antigens is an essential step in immune induction because it enables lymphocytes to encounter and recognize antigenic molecules and to become activated. Exemplary APCs include macrophages, Langerhans-dendritic cells, Follicular dendritic cells, and B cells.

"B cell" refers to a type of lymphocyte that produces immunoglobulins or antibodies that interact with antigens.

"$C_H1$ region" refers to a region of the heavy chain constant domain on the antigen binding fragment of an antibody.

"Cellular response" or "cellular host response" refers to a type of immune response mediated by specific helper and killer T cells capable of directly or indirectly eliminating virally infected or cancerous cells.

As used herein, the term "chimeric antigen" refers to a polypeptide comprising an immune response domain and a target binding domain. The immune response domain and target binding domains may be directly or indirectly linked by covalent or non-covalent means.

"Complex" or "antigen-antibody complex" refers to the product of the reaction between an antibody and an antigen. Complexes formed with polyvalent antigens tend to be insoluble in aqueous systems.

"Cytotoxic T-lymphocyte" is a specialized type of lymphocyte capable of destroying foreign cells and host cells infected with the infectious agents that produce viral antigens.

"Epitope" refers to the simplest form of an antigenic determinant, on a complex antigen molecule; this is the specific portion of an antigen that is recognized by an immunoglobulin or T cell receptor.

"Fusion protein" refers to a protein formed by expression of a hybrid gene made by combining two or more gene sequences.

"Hinge region" refers to the portion of an antibody that connects the Fab fragment to the Fc fragment; the hinge region contains disulfide bonds that covalently link the two heavy chains.

The term "homolog" refers to a molecule which exhibits homology to another molecule, by for example, having sequences of chemical residues that are the same or similar at corresponding positions. The phrase "% homologous" or "% homology" refers to the percent of nucleotides or amino acids at the same position of homologous polynucleotides or polypeptides that are identical or similar. For example, if 75 of 80 residues in two proteins are identical, the two proteins are 93.75% homologous. Percent homology can be determined using various software programs known to one of skill in the art.

"Host" refers to a warm-blooded animal, including a human, which suffers from an immune-treatable condition, such as an infection or a cancer. As used herein, "host" also refers to a warm-blooded animal, including a human, to which a chimeric antigen is administered.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances. The terms "hybridize", "hybridizing", "hybridizes" and the like, used in the context of polynucleotides, are meant to refer to conventional hybridization conditions, preferably such as hybridization in 50% formamide/6×SSC/0.1% SDS/100

μg/ml mDNA, in which temperatures for hybridization are above 37° C. and temperatures for washing in 0.1×SSC/0.1% SDS are above 55° C.

"Immunity" or "immune response" refers to the body's response to an antigen. In particular embodiments, it refers to the ability of the body to resist or protect itself against infectious disease.

"Immune Response Domain (IRD)" refers to the variously configured antigenic portion of a bifunctional molecule. The IRD comprises one or more antigens or one or more recombinant antigens. Preferred viral antigens include, but are not limited to, HBV PreS1/S2 HBV PreS1/S2/S, HBV Core, HBV Core ctm (C-terminal modified), HBV e-antigen, HBV Polymerase, HCV Core, HCV E1-E2, HCV E1, HCV E2, HCV NS3-serine protease, HCV NS5A and NS4A, HIV gp120 and HSV Alkaline nuclease and HPV Antigens.

As used herein, the phrase "immune-treatable condition" refers to a condition or disease that can be prevented, inhibited or relieved by eliciting or modulating an immune response in the subject.

"Lymphocyte" refers to a subset of nucleated cells found in the blood, which mediate specific immune responses.

"Monoclonal antibody" or "mAb" refers to an antibody produced from a clone or genetically homogenous population of fused hybrid cells, i.e., a hybridoma cell. Hybrid cells are cloned to establish cells lines producing a specific monoclonal antibody that is chemically and immunologically homogenous, i.e., that recognizes only one type of antigen.

"Peptide linkage" or "peptide bond" refers to two or more amino acids covalently joined by a substituted amide linkage between the α-amino group of one amino acid and the α-carboxyl group of another amino acid.

"pharmaceutical excipient" comprises a material such as an adjuvant, a carrier, a pH-adjusting and buffering agent, a tonicity adjusting agent, a wetting agent, a preservative, and the like.

"Pharmaceutically acceptable" refers to a non-toxic composition that is physiologically compatible with humans or other animals.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Protease cleavage site" refers to a site where proteolytic enzymes hydrolize (break) polypeptide chains.

In the present invention, the phrase "stringent hybridization conditions" or "stringent conditions" refers to conditions under which a compound of the invention will hybridize to its target sequence, but to a minimal number of other sequences.

The term "subject" refers to any warm-blooded animal, preferably a human.

"Tag" refers to a marker or marker sequence used to isolate or purify a molecule containing the tag. An exemplary tag includes a 6×His tag.

"T cell" refers to a type of lymphocyte responsible for antigen-specific cellular interactions, and which mediates humoral and cellular immune responses.

"Target Binding Domain (TBD)" refers to a region of an immunoglobulin heavy chain constant region.

The phrase "therapeutically effective amount" refers to an amount of chimeric antigen, or polynucleotide encoding a chimeric antigen, sufficient to elicit an effective B cell, cytotoxic T lymphocyte (CTL) and/or helper T lymphocyte (Th) response to the antigen and to block or to cure or at least partially arrest or slow symptoms and/or complications of a disease or disorder.

The terms "treating" and "treatment" as used herein cover any treatment of a condition treatable by a chimeric antigen in an animal, particularly a human, and include: (i) preventing the condition from occurring in a subject which may be predisposed to the condition but has not yet been diagnosed as having it; (ii) inhibiting the condition, e.g., arresting or slowing its development; or (iii) relieving the condition, e.g., causing regression of the condition or its symptoms "Xenotypic" refers to originating from a different species other than the host. For example, a recombinantly expressed antibody cloned from a mouse genome would be xenotypic to a human but not to a mouse, regardless of whether that recombinantly expressed antibody was produced in a bacterial, insect or mouse cell.

C. Chimeric Antigens

A composition of the present invention includes a chimeric antigen comprising an immune response domain (IRD) and a target binding domain (TBD). In preferred embodiments of the invention, the protein portion is capable of inducing humoral and/or T cell responses, and the target binding portion is capable of binding an antigen presenting cell, such as a dendritic cell. The chimeric antigen of the present invention may also include one or more of the following: a hinge region of an immunoglobulin, a $C_H1$ region of an immunoglobulin, a peptide linker, a protease cleavage site, and a tag suitable for use with a purification protocol. A chimeric antigen of the present invention is capable of binding to and activating an antigen presenting cell.

In some embodiments of the invention, the IRD of the chimeric antigen includes one or more proteins selected from the group comprising: one or more HBV proteins, one or more recombinant HBV proteins, one or more HCV proteins, or one or more recombinant HCV proteins.

In yet another embodiment of the invention, the IRD of the chimeric antigen includes a 6×His-peptide fused to one or more HBV proteins, one or more recombinant HBV proteins, one or more HCV proteins, or one or more recombinant HCV proteins.

In preferred embodiments of the invention, the target binding domain of the chimeric antigen is an antibody fragment xenotypic to the host. For example, if the host is a human, an exemplary xenotypic antibody fragment is a non-human animal antibody fragment, such as from a mouse. In the preferred embodiments of the invention, the xenotypic antibody fragment comprises a murine Fc fragment. In the most preferred embodiments of the invention, the target binding domain comprises a xenotypic Fc fragment, a hinge region, a $C_H1$ region, and a peptide linkage suitable for linking the target binding domain to the IRD.

The present invention also comprises the use of linking molecules to join the IRD to the TBD. Exemplary linker molecules include leucine zippers, and biotin/avidin.

In one embodiment, the chimeric antigen of the present invention is a fusion protein having two portions, namely an IRD containing an antigenic sequence (such as a viral antigen(s)), and a TBD containing a xenotypic Fc fragment. The xenotypic murine Fc fragment with the hinge region present recruits the antigen-presenting cells, specifically dendritic cells, to take up the chimeric antigen. The binding region of the chimeric antigen thus targets antigen-presenting cells specifically. The internal machinery of the APC then processes the IRD to form an activated APC. The activated APC must then be capable of contacting and activating immune response cells for generating humoral and cellular immune responses to clear infected cells.

In a further embodiment, the chimeric antigen is a fusion protein having two portions, namely a modified viral antigen or antigens, antigenic protein fragments or peptides, or any of these with glycosylation at specific sites, and a xenotypic murine Fc fragment with the hinge region present, which can also be, optionally, glycosylated.

In yet another embodiment, the invention provides a further modified chimeric antigen, wherein the antigen is biotinylated and the Fc fragment is generated with streptavidin as a fusion protein to facilitate the production of a wide assortment of antigen-Fc conjugates.

In yet another embodiment, the invention provides an association between the antigen and the antibody Fc fragment through chemical conjugation.

An embodiment of the present invention includes the use of recombinant antigens of HBV, HCV, or DHBV fused to a xenotypic antibody fragment by molecular biological techniques, production of the fusion proteins in a baculovirus expression system and their use as therapeutic vaccines against chronic HBV and HCV infections. The present invention provides an efficient method to deliver a hitherto unrecognized antigen to APCs in vivo so as to generate a broad immune response, a Th1 response involving CTLs and a Th2 (antibody) response. The immunogenicity of the pre-selected viral antigen unrecognized by the host immune system is increased due to the presence of the xenotypic antibody fragment as well as by the presence of specific glycosylation introduced in the insect cell expression system. The antigen-antibody fragment fusion protein, due to the presence of the antibody component, will bind to specific receptors present on various immune cell types including dendritic cells, macrophages, B cells and granulocytes. The fusion proteins administered to either humans or animals will be taken up by the APCs, especially DCs, will be hydrolyzed to small peptides and presented on the cell surface, complexed with MHC Class I and/or MHC Class II, which can elicit a broad immune response and clear the viral infection.

As used herein, the term “Target Binding Domain (TBD)” refers to a region of an immunoglobulin heavy chain constant region, which is an antibody fragment capable of binding to an Fc receptor on an APC. In accordance with the present invention, the TBD is a protein capable of binding to an Fc receptor on an APC, particularly a dendritic cell, and is subsequently transported into the APC by receptor-mediated uptake. In accordance with the present invention, the presence of an Fc fragment augments the uptake of the chimeric antigen through the Fc receptor on antigen-presenting cells, specifically dendritic cells. By virtue of the specific uptake, the viral antigen is processed and presented as foreign; thus, an immune response is effectively elicited to the previously tolerated viral antigen.

Also, in accordance with the present invention, the chimeric antigen, preferably, is capable of binding to a macrophage mannose receptor. The macrophage mannose receptor (MMR), also known as CD206, is expressed on antigen presenting cells (APC) such as dendritic cells (DC). This molecule is a member of the C-type lectin family of endocytic receptors. Mannosylated chimeric antigen can be bound and internalized by CD206. In general, exogenous antigen is thought to be processed and presented primarily through the MHC class II pathway. However, in the case of targeting through CD206, there is evidence that both the MHC class I and class II pathways are involved (Apostolopoulos et al., *Eur. J. Immunol.* 30:1714 (2000); Apostolopoulos and McKenzie, *Curr. Mol. Med.* 1:469 (2001); Ramakrishna et al., *J. Immunol.* 172:2845-2852 (2004)). Thus, monocyte-derived dendritic cells loaded with chimeric antigen that specifically targeted CD206 will induce both a potent class I-dependent $CD8^+$ CTL response and a class II-dependent proliferative T helper response (Ramakrishna et al., supra (2004)).

An exemplary TBD is derived from Mouse anti-HBVsAg mAb (Hybridoma 2C12) as cloned in pFastBac HTa expression vector, and expressed in a High Five™ insect cell expression system (Invitrogen). This TBD consists of part of $C_H1$, and Hinge-$C_H2$-$C_H3$ from N-terminal to C-terminal of the mouse anti-HBVs Ag mAb. The constant region of the IgG1 molecule for the practice of the present invention contains a linker peptide, part of $C_H1$-hinge and the regions $C_H2$ and $C_H3$. The hinge region portion of the monomeric TBD can form disulphide bonds with a second TBD molecule. FIG. 5 illustrates a schematic representation of a TBD molecule. The protein is expressed as an N-terminal fusion protein with a 6×His tag, a seven amino acid rTEV (recombinant tobacco etch virus) protease cleavage site and the N-terminal fusion of the Target Binding Domain (TBD) of the xenotypic (murine) mAb raised against HBV sAg (Hybridoma 2C12). The exemplary TBD is a fragment of the constant chain of the IgG1 mAb from 2C12 with the sequence of amino acids comprising the 8 amino acid peptide linker, five amino acids of the $C_H1$ region, the hinge sequences, $C_H2$ and $C_H3$ region sequences (FIG. 5) and ten additional amino acids from the expression vector. The exemplary TBD fragment defined herein forms the parent molecule for the generation of fusion proteins with antigens derived from viruses or other infectious agents. FIG. 1*b* depicts the formation of dimeric chimeric antigen molecule formed via intermolecular disulphide bonds. FIG. 6 shows the nucleotide sequence of the Open Reading Frame (ORF) encoding the exemplary TBD protein and the deduced amino acid sequence as defined in FIG. 5.

FIG. 7 shows a schematic representation of an exemplary chimeric antigen vaccine molecule, as produced in the insect cell expression system. This molecule is a fusion protein of N-terminal 6×His tag, rTEV protease cleavage site, HBV S1/S2 antigen, linker peptide, a part of the $C_H1$ as well as $C_H2$ and $C_H3$ domains of the mouse monoclonal antibody from 2C12 plus eight additional amino acids introduced as a cloning artifact. Cleavage and purification will result in the generation of HBV S1/S2-TBD molecule. FIG. 8 shows the nucleotide and amino acid sequences of the HBV S1/S2-TBD chimeric antigen molecule. FIG. 9 shows the nucleotide and the deduced amino acid sequences of the expressed HBV S1/S2 protein.

FIG. 10 shows a schematic representation of the fusion protein of HBV S1/S2/S-TBD. This molecule is a fusion protein of N-terminal 6×His tag, rTEV protease cleavage site, HBV S1/S2/S antigen, linker peptide, a part of the $C_H1$ as well as $C_H2$ and $C_H3$ domains of the mouse monoclonal antibody from 2C12 plus eight additional amino acids introduced as a cloning artifact. FIG. 11 shows the nucleotide and deduced amino acid sequences of the ORF of the fusion protein. FIG. 12 shows the nucleotide and deduced amino acid sequences of the HBV S1/S2/S protein.

Figure 13:
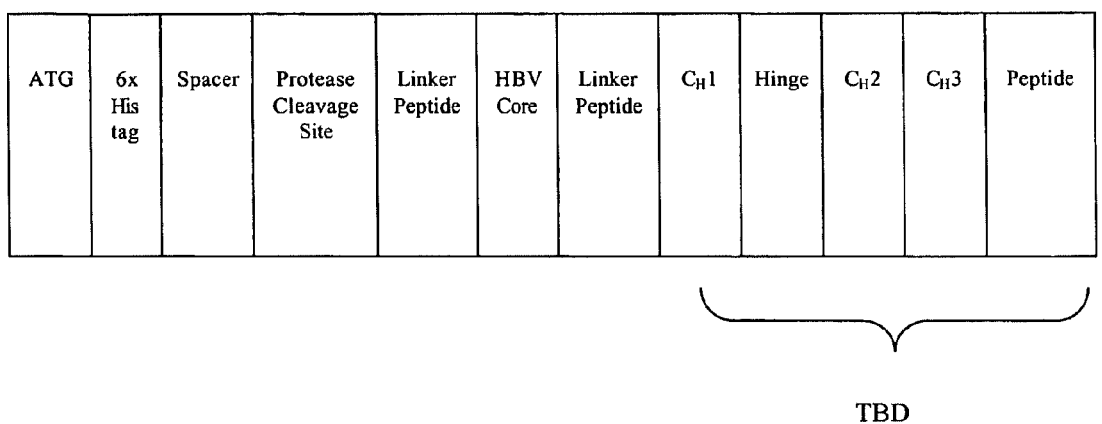
FIG. 13 is a schematic embodiment of an exemplary chimeric antigen of the present invention, illustrating an exemplary IRD of the present invention.
Figure 16:
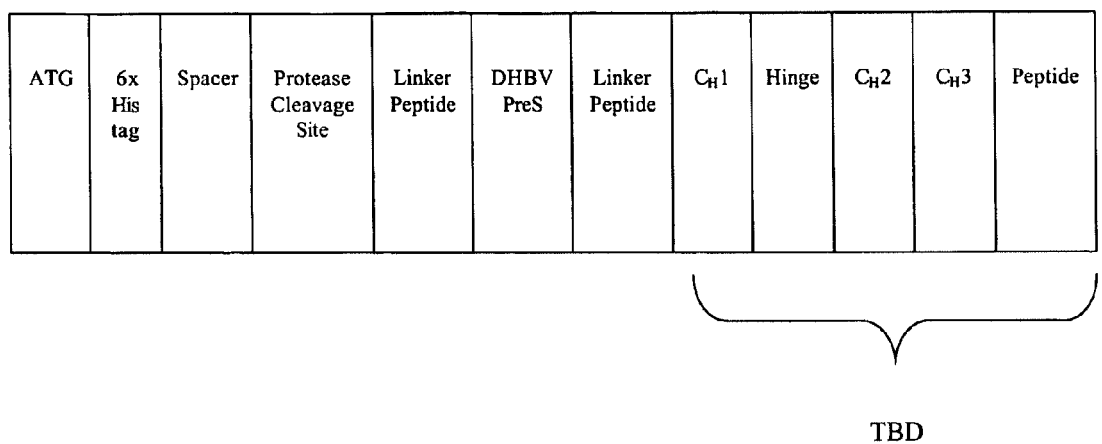
FIG. 16 is a schematic embodiment of an exemplary chimeric antigen of the present invention, illustrating an exemplary IRD of the present invention.

FIG. 13 illustrates the fusion protein of HBV Core-TBD molecule as expressed in the insect cells. This molecule is a fusion protein of N-terminal 6×His tag, rTEV protease cleavage site, HBV S1/S2 Core, linker peptide, a part of the $C_H1$ as well as $C_H2$ and $C_H3$ domains of the mouse monoclonal antibody from 2C12 plus eight additional amino acids introduced as a cloning artifact. FIG. 14 shows the nucleotide and amino acid sequences in the ORF of the fusion protein. FIG. 15 shows the nucleotide and deduced amino acid sequences of the HBV Core protein.

Another embodiment of the present invention involves the production and use of fusion proteins generated from Duck Hepatitis B Virus (DHBV) antigens and murine TBD. DHBV has been used as a very versatile animal model for the development of therapies for HBV, its human counterpart. DHBV genome encodes Surface antigens (PreS/S), the Core protein (Core), which form capsids, and the polymerase enzyme, which serves multiple functions.

FIG. 16 depicts a schematic representation of the fusion protein of DHBV PreS-TBD, as produced in High Five™ (Invitrogen) insect cell expression system. This is a fusion protein of N-terminal 6×His tag, rTEV protease cleavage site, DHBV PreS, linker peptide, a part of the $C_H1$ as well as $C_H2$ and $C_H3$ domains of the mouse monoclonal antibody from 2C12 plus eight additional amino acids introduced as a cloning artifact. The nucleotide and deduced amino acid sequences of the ORF of the fusion protein as cloned in the plasmid pFastBac HTa are shown in FIG. 17. The nucleotide and deduced amino acid sequences of the DHBV PreS protein are shown in FIG. 18.

FIG. 19 shows schematically, another embodiment of the present invention viz. DHBV PreS/S-TBD. This molecule is a fusion protein of N-terminal 6×His tag, rTEV protease cleavage site, DHBV PreS/S, linker peptide, a part of the $C_H1$ as well as $C_H2$ and $C_H3$ domains of the mouse monoclonal antibody from 2C12 plus eight additional amino acids introduced as a cloning artifact. The nucleotide and amino acid sequences are presented in FIG. 20. The nucleotide and deduced amino acid sequences of PreS/S are presented in FIG. 21.

FIG. 22 shows a schematic representation of the fusion protein of DHBV Core-TBD. This molecule is a fusion protein of N-terminal 6×His tag, rTEV protease cleavage site, DHBV Core, linker peptide, a part of the $C_H1$ as well as $C_H2$ and $C_H3$ domains of the mouse monoclonal antibody from 2C12 plus eight additional amino acids introduced as a cloning artifact. FIG. 23 shows the nucleotide and deduced amino acid sequences of the DHBV Core-TBD fusion protein. The nucleotide and deduced amino acid sequences of DHBV Core protein are shown in FIG. 24.

D. Novel Polynucleotides

Another aspect of the invention provides polynucleotides encoding a chimeric antigen comprising a first polynucleotide portion encoding an immune response domain and a second polynucleotide portion encoding a target binding domain. The first and second polynucleotide portions may be located on the same or different nucleotide chains.

The invention provides polynucleotides corresponding or complementary to genes encoding chimeric antigens, mRNAs, and/or coding sequences, preferably in isolated form, including polynucleotides encoding chimeric antigen variant proteins; DNA, RNA, DNA/RNA hybrids, and related molecules, polynucleotides or oligonucleotides complementary or having at least a 90% homology to the genes encoding a chimeric antigen or mRNA sequences or parts thereof; and polynucleotides or oligonucleotides that hybridize to the genes encoding a chimeric antigen, mRNAs, or to chimeric antigen-encoding polynucleotides.

Additionally, the invention includes analogs of the genes encoding a chimeric antigen specifically disclosed herein. Analogs include, e.g., mutants, that retain the ability to elicit an immune response, and preferably have a homology of at least 80%, more preferably 90%, and most preferably 95% to any of polynucleotides encoding a chimeric antigen, as specifically described by SEQ ID NOs: 31, 35, 39, 43, 47, 51, 57, 61, 65, 69, 73 and 77. Typically, such analogs differ by only 1 to 10 codon changes. Examples include polypeptides with minor amino acid variations from the natural amino acid sequence of a viral antigen or of an antibody fragment; in particular, conservative amino acid replacements. Conservative replacements are those that take place within a family of amino acids that are related in their side chains. Genetically-encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on biological activity. Polypeptide molecules having substantially the same amino acid sequence as any of the polypeptides disclosed in any one of SEQ ID NOs: 32, 36, 40, 44, 48, 52, 58, 62, 66, 70, 74 and 78 but possessing minor amino acid substitutions that do not substantially affect the ability of the chimeric antigens to elicit an immune response, are within the definition of a chimeric antigen. Derivatives include aggregative conjugates with other chimeric antigen molecules and covalent conjugates with unrelated chemical moieties. Covalent derivatives are prepared by linkage of functionalities to groups that are found in chimeric antigen amino acid chains or at the N- or C-terminal residues by means known in the art.

Amino acid abbreviations are provided in Table 1.

TABLE 1

| Amino Acid Abbreviations | | |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |

TABLE 1-continued Amino Acid Abbreviations

| Tryptophan | Trp | W |
| Tyrosine | Tyr | Y |
| Valine | Val | V |

Conservative amino acid substitutions can be made in a protein without altering either the conformation or the function of the protein. Proteins of the invention can comprise 1 to 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid is its charge and the differing pK's of these two amino acid residues are not significant Still other changes can be considered "conservative" in particular environments (see, e.g. *Biochemistry* 4$^{th}$ *Ed.*, Lubert Stryer ed. (W.H. Freeman and Co.), pages 18-23; Henikoff and Henikoff, *Proc Nat'l Acad Sci USA* 89:10915-10919 (1992); Lei et al., *J Biol Chem* 270(20):11882-6 (1995)).

The invention also includes polynucleotides that selectively hybridize to polynucleotides that encode chimeric antigens. Preferably a polynucleotide of the invention will hybridize under stringent conditions to a sequence selected from SEQ ID NOs: 31, 35, 39, 43, 47, 51, 57, 61, 65, 69, 73 and 77. Stringency of hybridization reactions is readily determinable by one of ordinary skill in the art and generally is an empirical calculation dependent upon probe length, washing temperature, and salt concentration. In general longer probes require higher temperatures for proper annealing, while shorter probes need lower temperatures. Hybridization generally depends on the ability of denatured nucleic acid sequences to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see, e.g., Ausubel et al., *Current Protocols in Molecular Biology*, Wiley Interscience Publishers, (©1995, as Supplemented April 2004, Supplement 66) at pages 2.9.1-2.10.8 and 4.9.1-4.9.13.

"Stringent conditions" or "high stringency conditions", as defined herein, are identified by, but not limited to, those that (1) employ low ionic strength and high temperature for washing, for example 0.015 M sodium chloride/0.0015 M sodium citrate/0.1% sodium dodecyl sulfate at 50° C.; (2) employ, during hybridization, a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., *Molecular Cloning: A Laboratory Manual*, 2$^{nd}$ *Ed.*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Embodiments of a polynucleotide of the invention include: a polynucleotide encoding a chimeric antigen having a sequence selected from any of the sequences shown in FIGS. 32, 36, 40, 44, 48 and 52, a nucleotide sequence of chimeric antigen selected from any of the sequences shown in FIGS. 31, 35, 39, 43, 47 and 51, wherein T may be U. For example, embodiments of chimeric antigen nucleotides comprise, without limitation:

(a) polynucleotide comprising or consisting of a sequence as shown in FIGS. 8*a*, 11*a*, 14*a*, 17*a*, 20*a*, 23*a*, 46*a*, 48*a*, 50*a*, 52*a*, 54*a* or 56*a* (SEQ ID NOs: 31, 35, 39, 43, 47, 51, 57, 61, 65, 69, 73 or 77), wherein T can also be U;

(b) a polynucleotide whose sequence is at least 80% homologous to a sequence shown in FIGS. 8*a*, 11*a*, 41*a*, 17*a*, 20*a*, 23*a*, 46*a*, 48*a*, 50*a*, 52*a*, 54*a* or 56*a* (SEQ ID NOs: 31, 35, 39, 43, 47, 51, 57, 61, 65, 69, 73 or 77);

(c) a polynucleotide that encodes a chimeric antigen whose sequence encoded by a DNA contained in one of the plasmids designated pFastBacHTa HBV S1/S2-TBD, pFastBacHTa HBV cor-TBD, pFastBacHTa HCV core (1-177)-TBD, pFastBacHTa HCV NS5A-TBD, and pFastBacHTa HCV E2-TBD deposited with the International Depository Authority of Canada (Bureau of Microbiology at Health Canada) as Accession Nos. 080504-03, 080504-04, 080504-05, 080504-02 and 080504-01 respectively;

(d) a polynucleotide that encodes a chimeric antigen whose sequence is shown in FIGS. 8*b*, 11*b*, 14*b*, 20*b*, 23*b*, 46*b*, 48*b*, 50*b*, 52*b*, 54*b* or 56*b* (SEQ ID NOS: 32, 36, 40, 44, 48, 52, 58, 62, 66, 70, 74 or 78);

(e) a polynucleotide that encodes a chimeric antigen-related protein that is at least 90% identical to an entire amino acid sequence shown in FIGS. 8*b*, 11*b*, 14*b*, 20*b*, 23*b*, 46*b*, 48*b*, 50*b*, 52*b*, 54*b* or 56*b* (SEQ ID NOs: 32, 36, 40, 44, 48, 52, 58, 62, 66, 70, 74 or 78);

(f) a polynucleotide that is fully complementary to a polynucleotide of any one of (a)-(e); and (g) a polynucleotide that selectively hybridizes under stringent conditions to a polynucleotide of (a)-(f).

The invention also provides recombinant DNA or RNA molecules containing a chimeric antigen polynucleotide, an analog or homologue thereof, including but not limited to phages, plasmids, phagemids, cosmids, YACs (yeast artificial chromosomes), BACs (bacterial artificial chromosomes), as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a chimeric antigen polynucleotide, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9, Sf21, Drosophila S2 or High Five™ cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of chimeric antigen or a fragment, analog or homolog thereof can be used to generate chimeric antigen thereof using any number of host-vector systems routinely used and widely known in the art.

A wide range of host-vector systems suitable for the expression of chimeric antigens thereof are available, see for example, Sambrook et al., 1989, supra; Ausubel, Current Protocols in Molecular Biology, 1995, supra). Preferred vectors for insect cell expression include, but are not limited to, pFastBac HTa (Invitrogen). Using such expression vectors, chimeric antigens can be expressed in several insect cell lines, including for example Sf9, Sf21, Drosophila S2 or High Five™. Alternatively, preferred yeast expression systems include Saccharomyces cerevisiae, Schizosaccharomyces pombe, Pichia pastoris, and Pichia august. The host-vector systems of the invention are useful for the production of a chimeric antigen.

A chimeric antigen or an analog or homolog thereof can be produced by cells transfected with a construct encoding a chimeric antigen. For example, Sf9 cells can be transfected with an expression plasmid encoding a chimeric antigen or analog or homolog thereof, the chimeric antigen or related protein is expressed in the Sf9 cells, and the chimeric antigen is isolated using standard purification methods. Various other expression systems well known in the art can also be employed. Expression constructs encoding a leader peptide joined in frame to the chimeric antigen coding sequence can be used for the generation of a secreted form of chimeric antigen.

As discussed herein, redundancy in the genetic code permits variation in chimeric antigen gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at world wide web URL www.kazusa.or.jp/codon.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to predicted hairpin secondary mRNA structures. Other useful modifications include the addition of a translational initiation consensus sequence at the start of the open reading frame, as described in Kozak, Mol. Cell. Biol. 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7):2662-2666 (1995) and Kozak Nucl Acids Res 15(20):8125-8148 (1987)).

E. Pharmaceutical Compositions of the Invention

One aspect of the invention relates to pharmaceutical compositions comprising a pharmaceutically acceptable excipient and a chimeric antigen comprising an immune response domain and a target binding domain, wherein the target binding domain comprises a xenotypic antibody fragment. In therapeutic applications, the pharmaceutical compositions can be administered to a subject in an amount sufficient to elicit an effective B cell, cytotoxic T lymphocyte (CTL) and/or helper T lymphocyte (Th) response to the antigen and to prevent infection or to cure or at least partially arrest or slow symptoms and/or complications. Amounts effective for this use will depend on, e.g., the particular composition administered, the manner of administration, the stage and severity of the disease being treated, the weight and general state of health of the subject, and the judgment of the prescribing physician.

The dosage for an initial therapeutic immunization (with chimeric antigen) generally occurs in a unit dosage range where the lower value is about 1, 5, 50, 500, or 1,000 ng and the higher value is about 10,000; 20,000; 30,000; or 50,000 μg. Dosage values for a human typically range from about 500 ng to about 50,000 μg per 70 kilogram subject. Boosting dosages of between about 1.0 ng to about 50,000 μg of chimeric antigen pursuant to a boosting regimen over weeks to months may be administered depending upon the subject's response and condition. Administration should continue until at least clinical symptoms or laboratory tests indicate that the condition has been prevented, arrested, slowed or eliminated and for a period thereafter. The dosages, routes of administration, and dose schedules are adjusted in accordance with methodologies known in the art.

A human unit dose form of a chimeric antigen is typically included in a pharmaceutical composition that comprises a human unit dose of an acceptable carrier, in one embodiment an aqueous carrier, and is administered in a volume/quantity that is known by those of skill in the art to be useful for administration of such polypeptides to humans (see, e.g., Remington: The Science and Practice of Pharmacy, 20$^{th}$ Edition, A. Gennaro, Editor, Lippincott Williams & Wilkins, Baltimore, Md., 2000). As appreciated by those of skill in the art, various factors can influence the ideal dose in a particular case. Such factors include, for example, half life of the chimeric antigen, the binding affinity of the chimeric antigen, the immunogenicity of the composition, the desired steady-state concentration level, route of administration, frequency of treatment, and the influence of other agents used in combination with the treatment method of the invention, as well as the health status of a particular subject.

In certain embodiments, the compositions of the present invention are employed in serious disease states, that is, life-threatening or potentially life-threatening situations. In such cases, as a result of the relative nontoxic nature of the chimeric antigen in preferred compositions of the invention, it is possible and may be felt desirable by the treating physician to administer substantial excesses of these chimeric antigens relative to these stated dosage amounts.

The concentration of chimeric antigen of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered by parenteral routes, such as subcutaneous or intradermal administration.

The pharmaceutical compositions can be prepared by mixing the desired chimeric antigens with an appropriate vehicle suitable for the intended route of administration. In making the pharmaceutical compositions of this invention, the chimeric antigen is usually mixed with an excipient, diluted by an excipient or enclosed within a carrier that can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the chimeric antigen, soft and hard gelatin capsules, suppositories, sterile injectable solutions, and sterile packaged powders.

Some examples of suitable excipients include, but are not limited to, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the chimeric antigen after administration to the subject by employing procedures known in the art. See, e.g., Remington, supra, at pages 903-92 and pages 1015-1050.

For preparing solid compositions such as tablets, the chimeric antigen is mixed with a pharmaceutical excipient to form a solid preformulation composition containing a homogeneous mixture of a chimeric antigen of the present invention. When referring to these preformulation compositions as homogeneous, it is meant that the chimeric antigen is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

In preparing a composition for parenteral administration strict attention must be paid to tonicity adjustment to reduce irritation. A reconstitutable composition is a sterile solid packaged in a dry form. A reconstitutable composition is preferred because it is more stable when stored as a dry solid rather than in a solution ready for immediate administration. The dry solid is usually packaged in a sterile container with a butyl rubber closure to ensure the solid is kept at an optimal moisture range. A reconstitutable dry solid is formed by dry fill, spray drying, or freeze-drying methods. Descriptions of these methods may be found, e.g., in Remington, supra, at pages 681-685 and 802-803.

Compositions for parenteral injection are generally dilute, and the component present in the higher proportion is the vehicle. The vehicle normally has no therapeutic activity and is nontoxic, but presents the chimeric antigen to the body tissues in a form appropriate for absorption. Absorption normally will occur most rapidly and completely when the chimeric antigen is presented as an aqueous solution. However, modification of the vehicle with water-miscible liquids or substitution with water-immiscible liquids can affect the rate of absorption. Preferably, the vehicle of greatest value for this composition is isotonic saline. In preparing the compositions that are suitable for injection, one can use aqueous vehicles, water-miscible vehicles, and nonaqueous vehicles Additional substances may be included in the injectable compositions of this invention to improve or safeguard the quality of the composition. Thus, an added substance may affect solubility, provide for subject comfort, enhance the chemical stability, or protect the preparation against the growth of microorganisms. Thus, the composition may include an appropriate solubilizer, substances to act as antioxidants, and substances that act as a preservative to prevent the growth of microorganisms. These substances will be present in an amount that is appropriate for their function, but will not adversely affect the action of the composition. Examples of appropriate antimicrobial agents include thimerosal, benzethonium chloride, benzalkonium chloride, phenol, methyl p-hydroxybenzoate, and propyl p-hyrodxybenzoate. Appropriate antioxidants may be found in Remington, supra, at p. 1015-1017.

In certain embodiments, liposomes, nanocapsules, microparticles, lipid particles, vesicles, and the like, are used for the administration of the chimeric antigens of the present invention. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

Compositions administered via liposomes may also serve: 1) to target the chimeric antigen to a particular tissue, such as lymphoid tissue; 2) to target selectively to antigen presenting cells; or, 3) to increase the half-life of the peptide composition. Liposomes include emulsions, foams, micelles, insoluble monolayers, liquid crystals, phospholipid dispersions, lamellar layers and the like. In these preparations, the chimeric antigen to be delivered is incorporated as part of a liposome, alone or in conjunction with a molecule that binds to a receptor prevalent among lymphoid cells, such as monoclonal antibodies that bind to the CD45 antigen, or with other therapeutic or immunogenic compositions. Thus, liposomes either filled or decorated with a desired chimeric antigen of the invention can be directed to the site of lymphoid cells, where the liposomes then deliver the chimeric antigens. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467-508 (1980), and U.S. Pat. Nos. 4,235,871, 4,501,728, 4,837,028, and 5,019,369. A liposome suspension containing a chimeric antigen may be administered intravenously, locally, topically, etc. in a dose which varies according to, inter alia, the manner of the chimeric antigen being delivered, and the stage of the disease being treated.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the chimeric antigen of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Additionally, it may be advantageous to include at least one antiviral therapeutic or chemotherapeutic in addition to the chimeric antigen and pharmaceutical excipient. Antiviral therapeutics include, but are not limited to, peptidomimetics (such as amprenavir, indinavir, lopinavir, nelfinavir, ritonavir, and saquinavir), polynucleotides (such as ampligen and fomivirsen), purine/pyrimidinones (such as abacavir, acyclovir, adefovir, cidofovir, cytarabine, didanosine, dideoxyadenosine, dipivoxil, edoxudine, emtricitabine, entecovir, famciclovir, ganciclovir, idoxuridine, inosine pranobex, lamivudine, MADU, penciclovir, sorivudine, stavudine, tenofovir, trifluridine, valacyclovir, valganciclovir, vidarabine, zalcitabine, and zidovudine), sialic acid analogs (such as oseltamivir and zanamivir), acemannan, acetylleucine monoethanolamine, amantadine, amidinomycin, ateviridine, capravirine, delavirdine, n-docosanol, efavirenz, foscarnet sodium, interferon-$\alpha$, interferon-$\beta$, interferon-$\gamma$, kethoxal, lysozyme, methisazone, moroxydine, nevirapine, pentafuside, pleconaril, podophyllotoxin, ribavirin, rimantidine, stallimycin, statolon, termacamra, and traomantadine. Other appropriate antiviral agents are discussed in Remington: supra, at Chapter 87: Anti-Infectives, pp. 1507-1561, particularly pp. 1555-1560. Preferred antiviral therapeutics for inclusion in the pharmaceutical compositions of the present invention include adefovir, dipivoxil, entecovir, lamivudine and ribavirin.

In some embodiments it may be desirable to include in the pharmaceutical compositions of the invention at least one component which primes B-Lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561 (1989)). Chimeric antigens of the invention can be coupled to $P_3CSS$, for example, and the lipopeptide administered to an individual to specifically prime an immune response to the target antigen.

While the compositions of the present invention should not require the use of adjuvants, adjuvant can be used. Various adjuvants may be used to increase the immunological response, depending on the host species, and including but not limited to Freund's (complete and incomplete), mineral gels such as aluminum hydroxide, surface active substances such as lysolecithin, detergents, pluronic polyols, polyanions, peptides, oil emulsions, keyhole limpet hemocyanins, dinitrophenol, immunostimulatory polynucleotide sequences, and potentially useful human adjuvants such as BCG (bacille Calmette-Guerin) and *corynebacterium parvum*. Additional adjuvants are also well known in the art.

F. Methods of using Chimeric Antigens

Another aspect of the invention provides methods of enhancing antigen presentation in antigen presenting cells, said method comprising administering, to the antigen presenting cells, a chimeric antigen that comprises an immune response domain and a target binding domain, wherein the target binding domain comprises a xenotypic antibody fragment. In a preferred embodiment, the antigen presenting cells are dendritic cells.

An aspect of the invention relates to methods of activating antigen presenting cells comprising contacting the antigen presenting cell with a chimeric antigen that comprises an immune response domain and a target binding domain, wherein the target binding domain comprises a xenotypic antibody fragment. In a preferred embodiment, the antigen presenting cell is contacted with the chimeric antigen in vivo. In another preferred embodiment, the contacting takes place in a human.

Yet another aspect of the invention provides methods of eliciting an immune response, said method comprising administering to an animal a chimeric antigen that comprises an immune response domain and a target binding domain, wherein the target binding domain comprises a xenotypic antibody fragment. The immune response can be a humoral and/or cellular immune response. In a preferred embodiment, the cellular immune response is both a Th1 and a Th2 response.

Another aspect of the invention provides methods of treating immune-treatable conditions comprising administering, to an animal in need thereof, a chimeric antigen that comprises an immune response domain and a target binding domain, wherein the target binding domain comprises a xenotypic antibody fragment. Preferably, the immune-treatable condition is a viral infection or cancer. More preferably, the immune-treatable condition is a chronic viral infection. Most preferably, the immune-treatable condition is a chronic hepatitis B viral infection or a chronic hepatitis C viral infection. For the treatment of HBV, preferably the immune response domain comprises a protein selected from the group consisting of a HBV Core protein, a HBV S protein, a HBV S1 protein, a HBV S2 protein, and combinations thereof. For the treatment of HCV, preferably the immune response domain comprises a protein selected from the group consisting of a HCV Core (1-191) protein, a HCV Core (1-177) protein, a HCV E1 protein, a HCV E2 protein, a HCV E1-E2 protein, a HCV NS3A protein, a HCV NS5A protein, and combinations thereof.

Another aspect of the invention provides methods of vaccinating an animal against a viral infection comprising administering to the animal a chimeric antigen that comprises an immune response domain and a target binding domain, wherein the target binding domain comprises a xenotypic antibody fragment. The method of the invention can prophylactically or therapeutically vaccinate the animal against the viral infection.

The present invention also comprises methods of using the compositions of the present invention to bind and activate antigen presenting cells, such as dendritic cells. The present invention also comprises methods of using the compositions of the present invention to activate T cells. The present invention also comprises a method of delivering an antigen to an immune system cell, such as an antigen presenting cell. The present invention also comprises compositions and methods for activating a humoral and/or cellular immune response in an animal or human, said method comprising administering one or more chimeric antigens of the present invention.

Following cloning and expression, the chimeric antigen is evaluated for its efficacy in generating an immune response. Evaluation involves presenting the chimeric antigen to dendritic cells ex vivo or in vivo. The dendritic cells are presented to T-lymphocytes and evaluated for the production of interferon-γ as a marker of T cell response. Specifically, in the ex vivo situation, naive dendritic cells are isolated from peripheral blood. Dendritic cells process and present antigen to naive T-lymphocytes. The chimeric antigen is then presented to naive dendritic cells for processing. These stimulated dendritic cells are in turn presented to a naive T cells, which cause their activation into effector cells, e.g. helper T cells or cytotoxic T-lymphocytes. Activation of the T cells by the dendritic cells is then evaluated by measuring markers, e.g. interferon-γ levels, by a known procedure (Berlyn, et al., *Clin. Immunol* 101(3):276-283 (2001)). An increase in the percentage of T cells that secrete interferon-γ by at least 50% over background predicts efficacy in vivo. In preferred embodiments, the percentage increase is at least 55%, 60%, 65%, 70%, 75%, 80%, 90% or 100%. In the case of the in vivo situation, the chimeric antigen is directly introduced parenterally in the host, where available dendritic and other antigen-processing cells have the capacity to interact with all antigens and process them accordingly.

G. Combination Therapy

Another aspect of the invention provides compositions for treating viral infections comprising a chimeric antigen and an antiviral agent. The invention also provides methods of treating viral infections comprising administering a chimeric antigen and an antiviral agent, either concurrently or sequentially.

Chimeric antigens have been shown to induce specific anti-HBV S1/S2 cytotoxic T cell functions ex vivo, to induce anti-HBV S1/S2 humoral responses in mice, and transiently reduce the viral load in ducks infected with the hepatitis B duck virus (DHBV). The use of a chimeric antigen in combination with an antiviral agent, such as a nucleoside analogue, may prove to be highly efficacious in inducing sustained responses in the treatment of subjects suffering from chronic hepatitis B. The mechanisms of action of the two agents used in combination may produce synergistic effects in treatment of hepatitis B subjects. While not being limited to a particular therapy, a nucleoside analogue, for example, would reduce the number of viral particles circulating in the blood and hence reduce the antigenic load that the immune system must eliminate, and the chimeric antigen would induce a highly specific cellular immune response that would eliminate cells that harbor virus, viral antigens and viral DNA/RNA. In addition, the chimeric antigen would induce a humoral immune response that would neutralize and remove circulating viral particles. Furthermore, the immune mechanism of action of the chimeric antigen could also minimize the toxicity of antiviral agents by permitting lower doses of the antiviral agent to be administered over a shorter period of time. A reduction in the length of time to achieve a sustained response may reduce the chances of development of drug-resistant viral mutants normally induced by antiviral agents, especially nucleoside analogue antiviral agents, when used alone in long-term therapy.

In brief, combination therapy with the hepatitis B chimeric antigen (e.g. S1/S2-TBD) and a nucleoside analogue in the treatment of hepatitis B has the potential to effect a complete cure of chronic HBV infection. Likewise, a combination of an HCV antiviral such as ribavirin along with the HCV chimeric antigens described herein will produce antigen-specific cellular as well as humoral immune response and thus clear HCV infection in chronically infected subjects.

H. Methods of Preparation

One aspect of the invention provides methods for producing a chimeric antigen comprising (a) providing a microorganism or cell line, preferably a eukaryotic, more preferably, a non-mammalian microorganism or cell line, that comprises a polynucleotide encoding a chimeric antigen; and (b) culturing said microorganism or cell line under conditions whereby the chimeric antigen is expressed. Preferably, the microorganism or cell line is a yeast, a plant cell line or an insect cell line. More preferably, the cell line is an insect cell line selected from the group consisting of Sf9, Sf21, *Drosophila* S2, and High Five™.

The present invention uses established recombinant DNA technology for producing the fusion proteins of selected antigen(s) and the TBD that are necessary in the practice of the invention. Fusion protein constructs are generated at the DNA level incorporating specific restriction enzyme sites, which are exploited in incorporating the desired DNA fragment into expression vectors, and used to express the desired fusion proteins in a heterologous expression system. As used herein, the term "vector" denotes plasmids that are capable of carrying the DNA, which encode the desired protein(s). The plasmid vectors used in the present invention include, but are not limited to, pFastBac HTa and the corresponding recombinant "BACMIDS" generated in DH10Bac™ *E. coli* (Invitrogen). It is possible to mobilize the ORF of the desired proteins and produce other recombinant plasmids for expression of the proteins in other systems, (bacterial or mammalian), in addition to the Bac-To-Bac™ baculovirus expression system (Invitrogen), employed in the present invention. The term "expression" is used to mean the transcription of the DNA sequence into mRNA, the translation of the mRNA transcript into the fusion protein.

This is achieved by the transposition of the gene of interest into the bacmids, transfected into Sf9 insect cells and recombinant baculovirus produced. These are used to infect Sf9 or High Five™ insect cells, which produce the protein of interest. All the recombinant proteins produced have an N-terminal 6×His tag, which is exploited in the purification of the proteins by using Ni-NTA Agarose (Qiagen). The proteins also have an N-terminal rTEV protease cleavage site cloned in. The Ni-purified protein is subjected to digestion with rTEV protease (Invitrogen), which also has an N-terminal 6×His tag. Following the protease digestion, the mixture can be loaded on to a Ni-NTA agarose column and the pure protein can be eluted out, while the 6×His tagged fragments will be bound to the column. This method of purification is standard procedure and one skilled in the art would be able to understand the methodology without further explanation.

Cloning and expression of the DNA sequences which encode the viral antigen and the Fc fragment of the murine monoclonal antibody to generate the chimeric antigen can be achieved through two approaches. The first approach involves cloning the two proteins as a fusion protein, while the second approach involves incorporating specific "bio-linkers" such as biotin or streptavidin in either of the molecules, purifying them separately and generating the chimeric antigen.

In an exemplary embodiment, a monoclonal antibody (2C12) was generated against the Hepatitis B virus surface antigen, and the hybridoma, which produced this monoclonal antibody, was used to isolate the total RNA for the murine immunoglobulin G. Total RNA was isolated and used to clone the murine Fc fragment. Specifically, the total RNA from a hybridoma cell that expresses murine IgG is isolated using Trizol® reagent (Invitrogen/Gibco BRL, product catalog number 10551-018, 10298-016; a monophasic solution of phenol and guanidine isothiocyante, as described in U.S. Pat. No. 5,346,994). The mRNA was purified from total RNA by affinity chromatography on an oligo-dT column (Invitrogen/Gibco BRL, product catalog number 15939-010). A complementary DNA (cDNA) was produced using reverse transcriptase in a polymerase chain reaction. The oligonucleotide primers were designed to add unique restriction enzyme recognition sites to facilitate cloning. This cDNA was cloned using the Bac-To-Bac™ baculovirus expression system (Invitrogen/Gibco BRL, product catalog number 15939-010).

Figure 4:
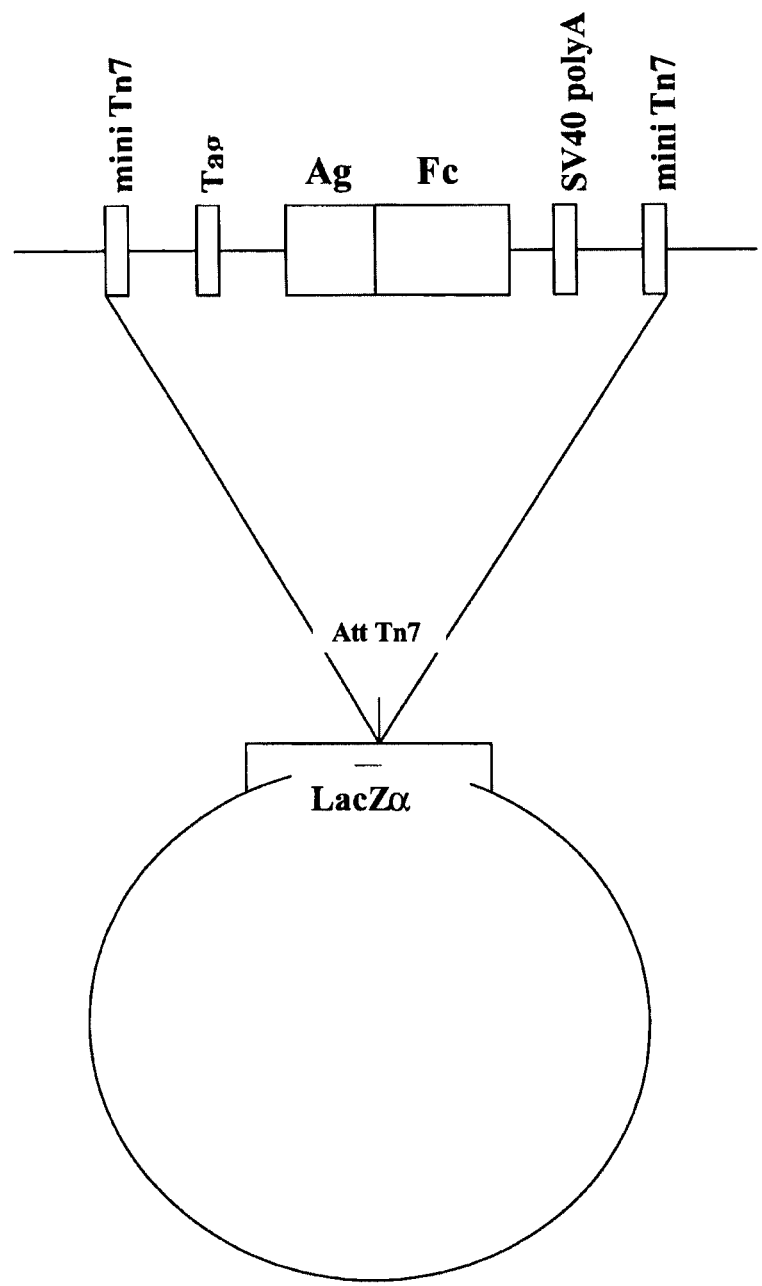
FIG. 4 is a schematic diagram illustrating a recombinant bacmid, capable of expressing a chimeric antigen.
Figure 5:
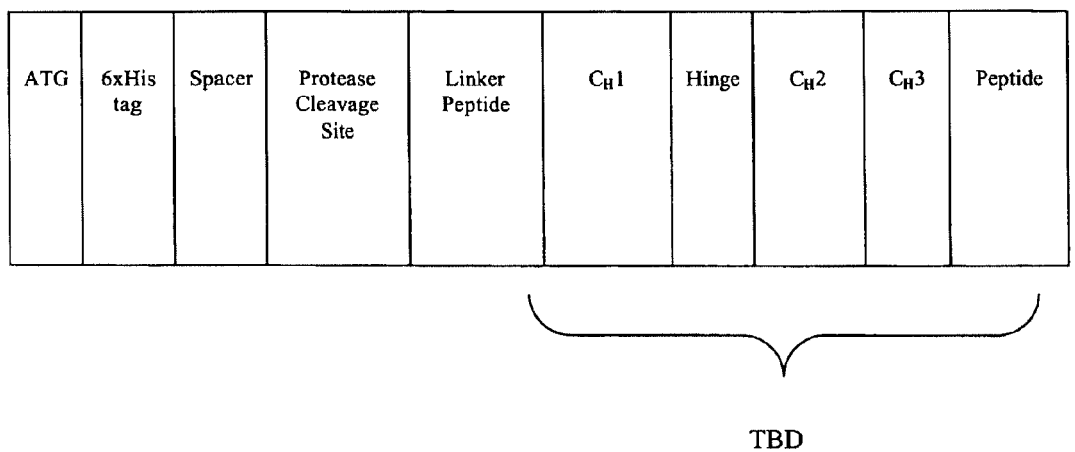
FIG. 5 is a schematic embodiment of TBD of the present invention.
Figure 7:
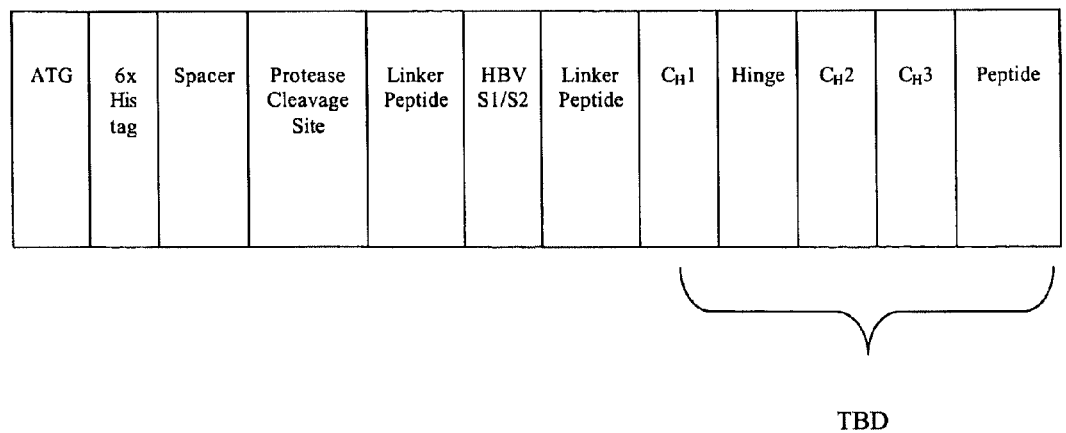
FIG. 7 provides a schematic embodiment of an exemplary chimeric antigen of the present invention, suitable for use with an insect cell expression system.
Figure 10:
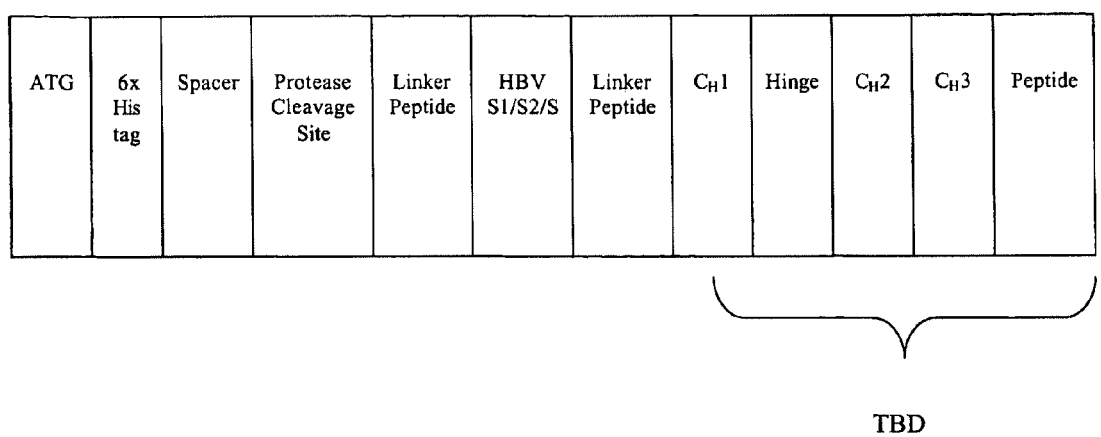
FIG. 10 provides a schematic embodiment of an exemplary chimeric antigen of the present invention, illustrating an exemplary IRD of the present invention.

The baculovirus system, preferentially, is used because not only are large amounts of heterologous proteins are produced, but also because post-translational modifications, such as phosphorylation and glycosylation, of eukaryotic proteins occur within the infected insect cell. In this expression system, the DNA can be cloned into vectors called pFastBac™ as illustrated schematically in FIG. 4 (Invitrogen/Gibco BRL, product catalog number 15939-010). In the Bac-To-Bac™ system, the generation of recombinants is based on site-specific transposition with the bacterial transposon Tn7. The gene of interest is cloned into pFastBac™, which has mini-Tn7 elements flanking the cloning sites. The plasmid is transformed into *Escherichia coli* strain DH10Bac™ (Invitrogen/Gibco BRL, product catalog number 10361-012), which has a baculovirus shuttle plasmid (bacmid) containing the attachment site of Tn7 within a LacZ gene. Transposition disrupts the LacZ gene so that only recombinants produce white colonies and are easily selected for. The advantage of using transposition in *E. coli* is that single colonies contain only recombinants so that plaque purification and screening are not required. The recombinant bacmids are transfected in insect cells to generate baculoviruses that express recombinant proteins.

The Bac-To-Bac™ baculovirus expression system is commercially available from Invitrogen and the procedures used were as described in the company protocols, available, for example, at www.invitrogen.com. The gene of interest is cloned into pFastBac HTa donor plasmid and the production of recombinant proteins is based upon the Bac-To-Bac™ baculovirus expression system (Invitrogen).

In the next step, the pFastBac HTa donor plasmid containing the gene of interest is used in a site-specific transposition in order to transfer the cloned gene into a baculovirus shuttle vector (bacmid). This is accomplished in *E. coli* strain DH10Bac™. The DH10Bac™ cells contain the bacmid, which confers kanamycin resistance and a helper plasmid, which encodes the transposase and confers resistance to tetracycline. The recombinant pFastBac HTa plasmids with the gene of interest are transformed into DH10Bac™ cells for the transposition to generate recombinant bacmids. A 100 μm aliquot of competent DH10Bac™ cells is thawed on ice, the pFastBac HTa based plasmids are added and the mixture is incubated on ice for 30 minutes. The mixture is given a heat shock for 45 seconds at 42° C. and then chilled on ice for 2 minutes. The mixture is then added to 900 μL of LB media and incubated for 4 hours at 37° C. The transformed cells are serially diluted with LB to $10^{-1}$ and $10^{-2}$ and 100 μl of each dilution is plated on Luria broth (LB) agar plates (supplemented with 50 μg/ml kanamycin, 7 μg/ml gentamicin, 10 μg/ml tetracycline, 100 μg/ml X-gal, and 40 μg/ml IPTG) and incubated for at least 36 hours at 37° C. The gentamicin resistance is conferred by the pFastBac HTa and the X-gal and IPTG are used to differentiate between white colonies (recombinant bacmids) from blue colonies (non recombinant). The white colonies are picked and inoculated into 2 ml of LB (supplemented with 50 μg/ml kanamycin, 7 μg/ml gentamicin and 10 μg/ml tetracycline) and incubated overnight at 37° C., with shaking. A sterile loop is used to sample a small amount of the overnight culture and the sample is streaked onto a fresh LB agar plate (supplemented with 50 μg/ml kanamycin, 7 μg/ml gentamicin, 10 μg/ml tetracycline, 100 μg/ml X-gal, and 40 μg/ml isopropylthio-β-D-galactoside (IPTG)) and incubated for at least 36 hours at 37° C. to confirm a white phenotype.

Recombinant bacmids were isolated by standard protocols (Sambrook, supra); the DNA sample was dissolved in 40 μl of TE (10 mM Tris-HCl pH 8, 1 mM EDTA (ethylenediaminetetraacetic acid)) and used for transfections.

In order to produce baculoviruses, the bacmid is transfected into Sf9 insect cells. Sf9 cells ($9 \times 10^5$) were seeded into each well of a 6-well cell culture dish (35 mm wells) in 2 ml of ESF 921 (Expression Systems) and allowed to attach for at least 1 hour at 27° C. Transfections were carried out using Cellfectin® Reagent (Invitrogen, Cat. No. 10362-010; a 1:1.5 (M/M) liposome formulation of the cationic lipid N, $N^I$, $N^{II}$, $N^{III}$-Tetramethyl-N, $N^I$, $N^{II}$, $N^{III}$-tetrapalmitylspermine and dioleoyl phosphatidylethanolammine in membrane filtered water) as per the protocols provided by the supplier of the Sf9 cells. Following transfection, the cells were incubated at 27°

C. for 72 hours. The medium containing baculovirus was collected and stored at 4° C. in the dark.

The efficiency of the transfection was verified by checking for production of baculoviral DNA. The isolated baculovirus DNA is subjected to PCR to screen for the inserted gene of interest. The primers used are pFastBac HTa 5' (sense) TAT-TCCGGATTATTCATACCG (SEQ ID NO: 3) and pFastBac HTa 3' (antisense) 5' CTCTACAAATGTGGTATGGC (SEQ ID NO: 4). Amplified products were separated on an agarose gel (0.8%). The expression of the heterologous protein in the cells was verified by SDS polyacrylamide gel electrophoresis (SDS-PAGE) and Western blots using the 6×His tag monoclonal antibody (Clontech) as the probe.

Once production of baculovirus and the expression of protein have been confirmed, the virus stock is amplified to produce a concentrated stock of the baculovirus that carry the gene of interest. It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect insect cells and the optimum time point for the production of the desired protein was also established.

The DNA encoding proteins of interest are generated by PCR with oligonucleotide primers bearing unique restriction enzyme sites from plasmids that contain a copy of the entire viral genome and cloned with the Fc DNA as a fusion protein. This chimeric protein is purified by protein A or G affinity chromatography using techniques known to those skilled in the art.

The second approach for linking the IRD and TBD involves incorporating specific "bio-linkers" such as biotin or streptavidin in either of the molecules, purifying them separately and generating the chimeric antigen. The viral antigens of interest are cloned into plasmids that control the expression of proteins by the bacteriophage T7 promoter. The recombinant plasmid is then transformed into an E. coli strain, e.g. BL21(DE3) Codon Plus™ RIL cells (Stratagene, product catalog number 230245), which has production of T7 RNA polymerase regulated by the lac repressor. The T7 RNA polymerase is highly specific for T7 promoters and is much more processive (~8 fold faster) than the E. coli host's RNA polymerase. When production of T7 RNA polymerase is induced by isopropylthio-β-D-galactoside (IPTG), the specificity and processivity of T7 RNA polymerase results in a high level of transcription of genes under control of the T7 promoter. In order to couple two proteins together, the tight binding between biotin and streptavidin is exploited. In E. coli, the BirA enzyme catalyzes the covalent linkage of biotin to a defined lysine residue in a specific recognition sequence. The murine Fc fragment is expressed in the baculovirus system, as described above, as a fusion protein with streptavidin. These two proteins can be mixed to form a dimeric protein complex by biotin-streptavidin binding.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, supra; and Ausubel, supra.

I. Article of Manufacture

Another aspect of this invention provides an article of manufacture that comprises a container holding a composition, comprising a chimeric antigen, that is suitable for injection or reconstitution for injection in combination with printed labeling instructions providing a discussion of how to administer the composition parenterally, e.g. subcutaneously, intramuscularly, intradermally, nasally or intravascularly. The composition will be contained in any suitable container that will not significantly interact with the composition and will be labeled with the appropriate labeling that indicates it will be for parenteral use. Associated with the container will be the labeling instructions consistent with the method of treatment as described hereinbefore. The container that holds the composition of this invention may be a container having a liquid composition suitable for injection that has an appropriate needle for injection and a syringe so that the patient, doctor, nurse, or other practitioner can administer the chimeric antigen. Alternatively, the composition may be a dry or concentrated composition containing a soluble version of the chimeric antigen, to be combined or diluted with an aqueous or nonaqueous vehicle to dissolve or suspend the composition. Alternatively, the container may have a suspension in a liquid or may be an insoluble version of the salt for combination with a vehicle in which the insoluble version will be suspended. Appropriate containers are discussed in Remington, supra, pages 788-789, 805, 850-851 and 1005-1014

The kit of the invention will typically comprise the container described above and one or more other containers comprising materials desirable from a commercial and user standpoint, including buffers, diluents, filters, needles, syringes, and package inserts with instructions for use. A label can be present on the container to indicate that the composition is used for a specific therapy or non-therapeutic application, and can also indicate directions for either in vivo or ex vivo use, such as those described above. Directions and or other information can also be included on an insert which is included with the kit

EXAMPLES

The following non-limiting examples provide further illustration of the invention.

Example 1

Construction of Murine TBD Protein Expression Vector

The mouse IgG1 DNA sequences encoding amino acids of a portion of $C_H1$-Hinge-$C_H2$-$C_H3$ region was generated from mRNA isolated from the hybridoma (2C12), which produces mAb against HBV surface antigen (sAg). Total RNA was isolated from 2C12 using Trizol® reagent (Gibco BRL cat. No. 15596-026) and the DNA of the TBD was generated by RT-PCR using Superscript First-strand Synthesis (Invitrogen Cat. No. 11904-018). The PCR primers contained linker sequences encoding the linker peptide -SRPQGGGS- (SEQ ID NO: 28) at the 5' terminus, a unique Not I site at the 5' and a unique Hind III restriction site at the 3' end. The resulting cDNA contains (5' Not I)-linker sequence-$C_H1$ (VDKKI)-$C_H2$-$C_H3$-(3' Hind III). Following digestion with the respective enzymes, the fragment is ligated with pFastBac HTa expression vector plasmid (Invitrogen) using the same restriction enzyme sites. The 5' primer used for PCR amplification was (Sense) 5' TGTCATTCTGCGGCCGCAAG-GCGGCGGATCCGTGGACAAGAAAATTGTGCCC AGG (SEQ ID NO: 1) and the 3' primer was (antisense) 5' ACGAATCAAGCTTTGCAGCCCAG-GAGAGTGGGAGAG (SEQ ID NO: 2), which contained the Not I and Hind III sites, respectively. The following protocol was used for directional cloning. The generated fragment was digested with the respective enzymes, purified on agarose gel and cloned into the vector plasmid. The DNA sequence and the correctness of the ORF were verified by standard sequencing methods.

Following the cloning of the gene of interest (e.g. TBD) into the pFastBac HTa donor plasmid, the production of recombinant proteins was based upon the Bac-To-Bac™ baculovirus expression system (Invitrogen). The next step was site-specific transposition of the cloned gene into a baculovirus shuttle vector (Bacmid). This was accomplished in a strain of E. coli called DH10Bac™. The DH10Bac™ cells contain the bacmid, which confers kanamycin resistance and a helper plasmid, which encodes the transposase and confers resistance to tetracycline. The recombinant pFastBac HTa plasmids with the gene of interest (TBD) were transformed into DH10Bac™ cells for the transposition to generate recombinant bacmids. A 100 μl aliquot of competent DH10Bac™ cells was thawed on ice, the pFastBac HTa based plasmids were added and the mixture was incubated on ice for 30 minutes. The mixture was given a heat shock for 45 seconds at 42° C. and then chilled on ice for 2 minutes. The mixture was then added to 900 μL of LB media and incubated for 4 hours at 37° C. The transformed cells were serially diluted with LB to $10^{-1}$ and $10^{-2}$ and 100 μl of each dilution was plated on LB agar plates supplemented with 50 μg/ml kanamycin, 7 μg/ml gentamicin, 10 μg/ml tetracycline, 100 μg/ml X-gal, and 40 μg/ml IPTG and incubated for at least 36 hours at 37° C. The gentamicin resistance was conferred by the pFastBac HTa and the X-gal and IPTG were used to differentiate between white colonies (recombinant bacmids) from blue colonies (non recombinant). The white colonies were picked and inoculated into 2 ml of LB supplemented with 50 μg/ml kanamycin, 7 μg/ml gentamicin and 10 μg/ml tetracycline and incubated overnight at 37° C., with shaking. A sterile loop was used to sample a small amount of the overnight culture and the sample was streaked onto a fresh LB agar plate supplemented with 50 μg/ml kanamycin, 7 μg/ml gentamicin, 10 μg/ml tetracycline, 100 μg/ml X-gal, and 40 μg/ml IPTG and incubated for at least 36 hours at 37° C. to confirm a white phenotype.

Recombinant bacmids were isolated by standard protocols (Sambrook, supra). The DNA sample was dissolved in 40 μl of TE (10 mM Tris-HCl pH 8, 1 mM EDTA) and used for transfections.

In order to produce baculoviruses, the bacmid was transfected into Sf9 insect cells. Sf9 cells ($9 \times 10^5$) were seeded into each well of a 6-well cell culture dish (35 mm wells) in 2 ml of ESF 921 (Expression Systems) and allowed to attach for at least 1 hour at 27° C. Transfections were carried out using Cellfectin® Reagent (Invitrogen, Cat. No. 10362-010) as per the protocols provided by the supplier of the Sf9 cells. Following transfection, the cells were incubated at 27° C. for 72 hours. The medium containing baculovirus was collected and stored at 4° C. in the dark.

The efficiency of the transfection was verified by checking for production of baculoviral DNA. The isolated baculovirus DNA was subjected to PCR to screen for the inserted gene of interest (TBD). The primers used are pFastBac HTa 5' (sense) TATTCCGGATTATTCATACCG (SEQ ID NO: 3) and pFastBac HTa 3' (antisense) 5' CTCTACAAATGTGGTATGGC (SEQ ID NO: 4). Amplified products were visualized on an agarose gel (0.8%). The expression of the heterologous protein in the cells was verified by SDS polyacrylamide gel electrophoresis (SDS-PAGE) and Western blots using the 6×His tag monoclonal antibody (Clonetech) as the probe.

Once production of baculovirus and the expression of protein had been confirmed, the virus production was amplified to produce a concentrated stock of the baculovirus that carry the gene of interest (e.g. TBD). It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect Sf9 and High Five™ cells and the optimum time point for the production of the desired protein was established as well.

Example 2

Construction of HBV Surface Antigen S1/S2 and HBV S1/S2-TBD Fusion Protein Expression Vectors The DNA encoding the HBV sAg fragment S1/S2 was generated from the plasmid pRSetB HBV S1/S2 template using PCR methodology. The primers used were: (sense) 5' GGATCTGTACGACGATGACG (SEQ ID NO: 5) and the 3' primer (antisense) 5' AGTCATTCTGCGGCCGCGAGTTCGTCACAGGGTCCCCGG (SEQ ID NO: 6) containing the restriction enzyme site Not I. The 5' end contained a unique Bam HI site derived from the parent plasmid that was used for ligations. Amplified DNA was digested with Bam HI/Not I and ligated with pFastBac HTa expression vector to generate the expression plasmid for HBV S1/S2 protein. The fragment was ligated with the plasmid pFastBac HTa-TBD (described in example 1) following the digestion with the respective enzymes. This produced the expression plasmid pFastBac HTa HBV S1/S2-TBD. This plasmid was used to produce recombinant baculovirus (described in example 1), which expressed the chimeric antigen-TBD fusion protein: 6×His tag-rTEV protease cleavage site-HBV S1/S2-TBD (See FIGS. 7-9).

Example 3

Construction of HBV Surface Antigen S1/S2/S and HBV S1/S2/S-TBD Fusion Protein Expression Vectors The DNA encoding the HBV sAg fragment S1/S2/S was generated from the plasmid pAlt HBV 991 (University of Alberta) template using PCR methodology. The 5' primer used for the PCR was (sense) 5' GATAAGGATCCTATGGGAGGTTGGTCATCAAAAC (SEQ ID NO: 7), containing the restriction enzyme Bam HI site. The PCR primer for 3' terminus was (antisense) 5' GTCATACTGCGGCCGCGAAATGTATACCCAGAGACAAAAG (SEQ ID NO: 8), containing the restriction enzyme Not I site. Amplified DNA was digested with the respective enzymes and ligated with pFastBac HTa expression vector to generate either the expression plasmid for HBV S1/S2/S or the expression plasmid pFastBac HTa HBV S1/S2/S-TBD for the fusion protein (see FIGS. 10-11).

Example 4

Construction of HBV Core Antigen and HBV Core-TBD Fusion Protein Expression Vectors HBV produces the Core proteins (Core) to encapsidate the replicating genome of the virus. There are two forms of the Core one secreted into circulation, also known as the "e" antigen and the capsid forming Core protein. The present invention also relates to the generation of expression plasmids to produce the Core protein as well as the Core antigen-TBD fusion protein, in insect cells. The DNA encoding the HBV Core protein was generated from the plasmid pAlt HBV 991 template using PCR technique. The 5' primer used for the PCR was (sense) 5' TGCGCTACCATGGACATTGACCCT-TATAAAG (SEQ ID NO: 9), which contains the restriction enzyme Nco I site and the 3' primer used was (anti sense) 5' TGTCATTCTGCGGCCGCGAACAT-TGAGATTCCCGAGATTGAG (SEQ ID NO: 10), containing the restriction enzyme Not I site. The PCR-amplified DNA was digested with the respective enzymes and ligated with pFastBac HTa expression vector to generate either the expression plasmid for HBV Core protein or the expression plasmid pFastBac HTa HBV Core-TBD for the fusion protein (see FIGS. 13-14).

Example 5

Construction of DHBV Surface Antigen Fragment PreS and DHBV PreS-TBD Fusion Protein Expression Vectors DHBV has served as a powerful animal model in the development of antiviral therapy for HBV. Pekin ducks, congenitally infected with DHBV have been used to study the mechanism of replication of the virus and for the screening of antiviral compounds. The present invention also describes the chimeric DHBV antigen-TBD molecules that could be used as therapeutic vaccines in DHBV-infected ducks, thus providing a viable animal model for the feasibility studies for HBV therapeutic vaccines.

The DNA encoding DHBV PreS antigen was produced by PCR from a plasmid pFastBac Hta-DHBV PreS/S (University of Alberta). The 5' primer used for the PCR was (sense) 5' TATTCCGGATTATTCATACCG (SEQ ID NO: 11). The unique restriction enzyme site EcoRI, resident on the parent plasmid was used for directional cloning. The 3' primer used was (antisense) 5' TGTCATTCTGCGGCCGCGTTTTCT-TCTTCAAGGGGGGAGT (SEQ ID NO: 12), containing the restriction enzyme Not I site. Following PCR amplification, the fragment was digested with the restriction enzymes EcoRI and Not I and the DNA fragment was purified on a 1% agarose gel. The fragment was ligated with the expression plasmid pFastBac HTa at the respective sites to produce pFastBac HTa DHBV PreS, which expressed the PreS antigen. The same fragment was also used to ligate with pFastBac HTa-TBD to generate the expression plasmid pFastBac HTa DHBV PreS-TBD. The production of baculovirus stocks from these plasmids and the expression of the PreS and PreS-TBD in High Five™ insect cells were done as described in example 1.

Example 6

Construction of DHBV Surface Antigen Fragment PreS/S and DHBV PreS/S-TBD Fusion Protein Expression Vectors DHBV PreS/S DNA was produced by PCR methods using 5' primer (sense) 5' TATTCCGGATTATTCATACCG (SEQ ID NO: 11) and the 3' primer (antisense) 5' TGTCAT-TCAGCGGCCGCGAACTCTTGTAAAAAAGAGCAGA (SEQ ID NO: 13), containing restriction enzyme Not I site. The unique restriction enzyme site EcoRI, resident on the parent plasmid pFastBac HTa PreS/S (University of Alberta) was used for directional cloning. This plasmid also was the template for generating the required DNA by PCR. All other protocols for the production of either the DHBV PreS/S or the fusion protein PreS/S-TBD are the same as described in the example 5 above.

Example 7

Construction of DHBV Core Antigen and DHBV Core-TBD Fusion Protein Expression Vectors The DNA coding for DHBV Core was generated from pRSet B DHBV Core by PCR using the following primers. The 5' terminus primer used was (sense) 5' TGCGCTAC-CATGGATATCAATGCTTCTAGAGCC (SEQ ID NO: 14), containing the restriction enzyme Nco I site. The 3' terminus primer used was (antisense) 5' TGTCATTCTGCGGCCGC-GATTTCCTAGGCGAGGGAGATCTATG (SEQ ID NO: 15), containing the restriction enzyme Not I site. All other protocols for the production of either the DHBV Core or the fusion protein DHBV Core-TBD are the same as described in the example 5 above.

Example 8

Chemically Cross-Linked HBV sAg-Fc (Murine)

HBV sAg was cross linked using the bifunctional cross linking agent dimethyl suberimidate (DMS), a homobifunctional imidoester that reacts with amino groups on the proteins. The unreacted components were removed by gel filtration. The conjugate was characterized with respect to the stoichiometry of sAg/Fc in the conjugate and the fraction containing sAg:Fc at 1:1 ratio was chosen for antigen presentation assays using human monocyte-derived immature Dendritic cells (DCs). Immature DCs were cultured for four days with GM-CSF/IL4, incubated with the sAg-Fc conjugate and matured in the presence of TNFα/IFNα. Autologous CD3+ T cells were added to the mature DCs. Following three rounds of exposure to the mature DCs, T cell stimulation was quantitated by measuring the production of intracellular interferon-γ, using flow cytometry.

Materials:

HBV sAg (US Biologicals; Cat# H 1910-27)

Mouse Polyclonal IgG Fc fragment (Harlan Sera-Lab Ltd., Cat# PP-19-01)

DMS (Dimethyl suberimidate. 2HCl) (Pierce Cat #20700)

Cross-linking Buffer 0.1M HEPES pH 8.7

Stop Buffer 0.1 M Tris HCl pH 7.8

Elution Buffer Phosphate Buffered Saline (PBS) pH 8.3

Sephadex G 75 (Pharmacia)

Methods: Solutions of sAg (100 μg) and Mouse Fc fragment (100 μg), were dialyzed against the cross linking buffer overnight at 4° C. The protein solutions were mixed together, DMS reagent was added immediately to a final concentration of 10 mM, and the mixture was incubated at room temperature for 1 hr. The reaction was stopped by the addition of 0.1 M Tris HCl pH 7.8. The reaction mixture was loaded on a Sephadex G 75 column (0.7×12 cm), and fractions were eluted using elution buffer. 0.5 ml fractions were collected and the fractions containing sAg/Fc at a molar ratio of 1:1, as estimated by ELISA using the respective antibodies were pooled and used for Antigen Presentation Assays. (Berlyn, et al., supra (2001)).

Results: The levels of intracellular interferon-γ produced in T cells in the presence of conjugate was substantially higher than the sAg or the Fc fragment alone.

Example 9

Chimeric Antigens of Hepatitis C Virus (HCV)

HCV Core-TBD was cloned using the pFastBac HTa vector and the baculovirus system and expressed in Sf9 and High Five™ insect cells, similar to the HBV fusion proteins. This was done as follows. The DNA encoding the HCV Core fragment was generated from the plasmid pCV-H77c (NIH) template using PCR methodology.

The primers used were: (sense) 5' CGGAATTCATGAG-CACGAATCCTAAAC (SEQ ID NO: 16) containing the restriction enzyme site EcoRI and the 3' primer (antisense) 5' GGACTAGTCCGGCTGAAGCGGGCACAGT-CAGGCAAGAG (SEQ ID NO: 17) containing the restriction enzyme site Spe I. Amplified DNA was digested with EcoRI/Spe I and the fragment was ligated into the plasmid pFastBac HTa TBD (described in example 1) following the digestion with the respective enzymes. This produced the expression plasmid pFastBac HTa HCV Core-TBD. This plasmid was used to produce recombinant baculovirus (described in example 1), which expressed the chimeric antigen (HCV Core-TBD) fusion protein 6×His tag-rTEV protease cleavage site-HCV Core-TBD.

HCV Core Protein was cloned as follows. Amplified DNA was digested with EcoRI/Spe I and ligated with plasmid pFastBac HTa expression vector to generate the expression plasmid for HCV Core protein. This protein is expressed with N-terminal 6×His tag and rTEV protease cleavage site.

The following HCV antigens and their respective chimeric antigens (antigen-TBD) have been cloned and are ready for expression.
E1 & E1-TBD:
E2 & E2-TBD
E1 E2 & E1 E2-TBD
NS5A & NS5A-TBD Example 10

Cloning, Expression and Purification of Recombinant Proteins using a Baculovirus Expression System Bac-to-Bac™ Baculovirus Expression System is commercially available from Invitrogen and the procedures used were as described in the company protocols. The gene of interest was cloned into pFastBac HTa donor plasmid and the production of recombinant proteins was based upon the Bac-to-Bac™ baculovirus expression system (Invitrogen).

In the next step, the pFastBac HTa donor plasmid containing the gene of interest was used in a site-specific transposition in order to transfer the cloned gene into a baculovirus shuttle vector (bacmid). This was accomplished in *E. coli* strain DH10Bac™. The DH10Bac™ cells contain the bacmid, which conferred kanamycin resistance and a helper plasmid, which encoded the transposase and conferred resistance to tetracycline. The recombinant pFastBac HTa plasmids with the gene of interest were transformed into DH10Bac™ cells for the transposition to generate recombinant bacmids. A 100 µl aliquot of competent DH10Bac™ cells was thawed on ice, the pFastBac HTa based plasmids were added and the mixture was incubated on ice for 30 minutes. The mixture was given a heat shock for 45 seconds at 42° C. and then chilled on ice for 2 minutes. The mixture was then added to 900 µL of LB media and incubated for 4 hours at 37° C. The transformed cells were serially diluted with LB to $10^{-1}$ and $10^{-2}$ and 100 µl of each dilution was plated on Luria broth (LB) agar plates (supplemented with 50 µg/ml kanamycin, 7 µg/ml gentamicin, 10 µg/ml tetracycline, 100 µg/ml X-gal, and 40 µg/ml IPTG) and incubated for at least 36 hours at 37° C. The gentamicin resistance was conferred by the pFastBac HTa and the X-gal and IPTG were used to differentiate between white colonies (recombinant bacmids) from blue colonies (non recombinant). The white colonies were picked and inoculated into 2 ml of LB (supplemented with 50 µg/ml kanamycin, 7 µg/ml gentamicin and 10 µg/ml tetracycline) and incubated overnight at 37° C., with shaking. A sterile loop was used to sample a small amount of the overnight culture and the sample was streaked onto a fresh LB agar plate (supplemented with 50 µg/ml kanamycin, 7 µg/ml gentamicin, 10 µg/ml tetracycline, 100 µg/ml X-gal, and 40 µg/ml IPTG) and incubated for at least 36 hours at 37° C. to confirm a white phenotype.

Recombinant bacmids were isolated by standard protocols (Sambrook, supra); the DNA sample was dissolved in 40 µl of TE (10 mM Tris-HCl pH 8, 1 mM EDTA) and used for transfections.

In order to produce baculoviruses, the bacmid was transfected into Sf9 insect cells. Sf9 cells ($9 \times 10^5$) were seeded into each well of a 6-well cell culture dish (35 mm wells) in 2 ml of SFM 900 II and allowed to attach for at least 1 hour at 27° C. Transfections were carried out using Cellfectin® Reagent (Invitrogen, Cat. No. 10362-010) as per the protocols provided by the supplier of the Sf9 cells. Following transfection, the cells were incubated at 27° C. for 72 hours. The medium containing baculovirus was collected and stored at 4° C. in the dark.

The efficiency of the transfection was verified by checking for production of baculoviral DNA. The isolated baculovirus DNA is subjected to PCR to screen for the inserted gene of interest. The primers used are pFastBac HTa 5' (sense) TAT-TCCGGATTATTCATACCG (SEQ ID NO: 3) and pFastBac HTa 3' (antisense) 5' CTCTACAAATGTGGTATGGC (SEQ ID NO: 4). Amplified products were separated on an agarose gel (0.8%). The expression of the heterologous protein in the cells was verified by SDS polyacrylamide gel electrophoresis (SDS-PAGE) and Western blots using the 6×His tag monoclonal antibody (Clontech) as the probe.

Once production of baculovirus and the expression of protein were been confirmed, the virus stock was amplified to produce a concentrated stock of the baculovirus that carry the gene of interest. It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect insect cells and the optimum time point for the production of the desired protein was also established.

Example 11

Expression of the Recombinant Proteins

Recombinant baculovirus of standardized multiplicity of infection (MOI) were used to infect High Five™ insect cells. For suspension cultures, cells were seeded at a density of $3 \times 10^5$ cells/mL and incubated at 27.5° C. with shaking at 138 rpm until the cell density reached $2-3 \times 10^6$ cells/mL. Standardized amounts of the respective recombinant baculovirus was added to the cells. The incubation temperature was 27.5° C. and the appropriate infection period was standardized for individual protein expression. The cells were harvested by centrifugation at 2,500 rpm for 10 minutes at 4° C. and used for the purification of the recombinant proteins. Unused portions of cells were snap frozen in liquid nitrogen and stored at −70° C.

Example 12

Purification of Proteins

For purification under denaturing conditions, the cells were lysed in a buffer containing 6 M guanidinium-HCl in 100 mM $NaH_2PO_4$, 10 mM Tris, 300 mM NaCl, 10 mM Imidazole, pH 8.0 (lysis buffer). The suspension was sonicated on ice with 5 pulses of 1 minute per pulse at a power setting of 60 watts, and was mixed at room temperature for 1 hour. The lysate was centrifuged at 27,000×g for 30 min to remove unbroken cells and cell debris. The supernatant was loaded on to a Ni-NTA agarose (Qiagen) bead column (1×5 cm/100 mL cell lysate), pre-equilibrated with lysis buffer. Following loading, the column was washed with 20 column volumes of 6 M guanidinium-HCl in 100 mM $NaH_2PO_4$, 10 mM Tris, 300 mM NaCl, 40 mM Imidazole, pH 8.0 (wash buffer 1), followed by washes with 20 column volumes of 8 M urea in 100 mM $NaH_2PO_4$, 10 mM Tris, 300 mM NaCl, 40 mM imidazole, pH 8.0 (wash buffer 2). The bound protein was eluted with a buffer containing 8 M urea, 100 mM $NaH_2PO_4$, 10 mM Tris, 300 mM NaCl, 250 mM imidazole, pH 8 (Elution Buffer). The fractions containing the protein was pooled and dialyzed against PBS, (Overnight, 4° C.).

Examples 13-16

Use of Chimeric Antigens to Enhance Antigen Presentation by Human PBMC-Derived Dendritic Cells and to Elicit an Immune Response in T Lymphocytes Example 13

Human PBMC Monocyte Isolation and Differentiation to DCs

Peripheral blood mononuclear cells (PBMC) were obtained from Ficoll/Histopaque (Sigma) treatment of a leukapheresis cell preparation (Berlyn, et al., supra (2001)). Monocytes were separated from the PBMC population by negative selection using a monocyte isolation kit (Dynal) following the manufacturer's directions. The monocytes were greater than 95% pure as assessed by antibody analysis and flow cytometry ($CD3^-$, $CD19^-$, $CD16^-$, $CD11a^+$, $CD14^+$). Monocytes were washed twice with AIM V (Invitrogen) media containing L-glutamine, streptomycin sulfate (50 μg/mL) and gentamicin sulfate (10 μg/mL) with 1% donor matched sera (isolated as described in Berlyn, et al., supra (2001)). Next, the monocytes were cultured in AIM V media containing 2.5% donor matched sera and the cytokines GM-CSF and IL-4 to differentiate the cells toward the dendritic cell (DC) lineage. The cells were incubated in 12-well tissue culture plates at 37° C. under a 7% $CO_2$ atmosphere. The DCs were used for APAs and ligand binding and uptake studies.

The monocyte-derived DCs (mDC) were harvested on days 1 through 4. The cells were subsequently washed once with AIM V media with 0.1% BSA (Sigma), and twice with Dulbecco's phosphate buffered saline (Invitrogen) with 0.1% (w/v) BSA (PBSB). The mDC were used in 4° C. labeling or binding assays or in 37° C. binding/uptake assays.

Example 14

Human Dendritic Cell T Cell Stimulation Assay

Antigen presentation assays were performed using human PBMC-derived dendritic cells according to established protocols (Berlyn, et al., supra (2001)). Monocytes were generated from leukapheresis samples from healthy donors and were depleted of lymphocytes and granulocytes by incubation with anti-CD2, CD7, CD16, CD19, and CD56 antibodies. This was followed by incubation with magnetic bead conjugated anti-mouse IgG and separation on a magnet (Dynal). Negatively selected cells were greater than 95% pure monocytes as characterized by flow cytometry using a broad CD marker panel. Next, monocytes were incubated with IL-4 and GM-CSF (R&D Systems) for 4 days in AIM V plus 2.5% matched human serum to generate immature dendritic cells. Again, an aliquot of the cells was stained with a broad CD marker panel to ensure purity and identity of the cells. The cells then were loaded with various antigens for 2-4 hours at 37° C., and matured with interferon-α and TNF-α for 3 days. Dendritic cells were checked again using flow cytometry for an array of CD markers to ensure that cells had undergone proper maturation. The resulting mature, loaded dendritic cells were used for the T cell stimulation assay. A protocol summary for the T cell stimulation assay is presented in schematic form.

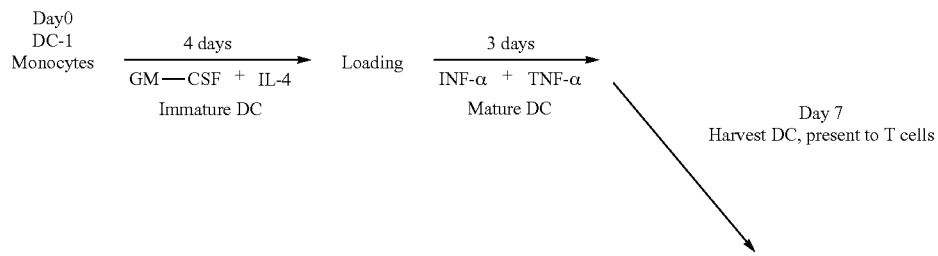

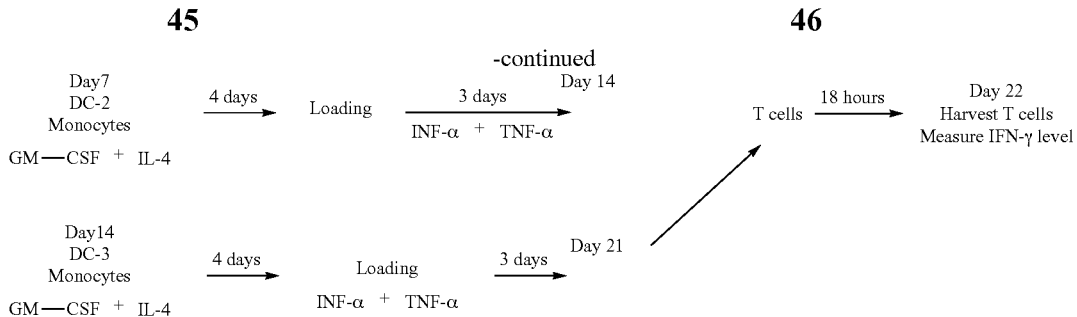

T cells were generated from the same monocytes as the dendritic cells by means of negative selection using a magnetic T cell isolation kit (Dynal) according to the manufacturer's directions. Mature, loaded dendritic cells (DC-1) were washed thoroughly and added to the T cells (Day 0). The T cells and dendritic cells were incubated for 7 days On Day 7, the T cells were re-stimulated with matured, loaded dendritic cells (DC-2). An aliquot of the cells was taken 2 hours later (the Day 7 aliquot). The Day 7 aliquot was incubated with Brefeldin A (GolgiPlug™, R&D Systems) for 18 hours. The cells of the Day 7 aliquot were then assayed for intracellular cytokine staining as described below.

The remaining cells were incubated for another 7 days. On Day 14, the remaining cells were stimulated with another batch of mature, loaded dendritic cells (DC-3). An aliquot of the cells was taken 2 hours later (the Day 14 aliquot). The Day 14 aliquot was incubated with Brefeldin A (GolgiPlug™, R&D Systems) for 18 hours. The cells of the Day 14 aliquot were then assayed for intracellular cytokine staining as described below.

After removal of the D14 aliquot, the remaining cells were incubated for three days and the supernatant was used for measuring the level of secreted interferon-γ by ELISA (Opt E1A ELISA kit, BD Biosciences).

For intracellular cytokine staining, cells were stained with anti-CD3-FITC and anti-CD8-Cy-Chrome for 30 minutes, washed, fixed, permeabilized, and then stained with anti-interferon-γ-PE for 30 minutes on ice. The cells were washed and analyzed by flow cytometry (FACScan, BD Biosciences).

Example 15

Expression of Fc-γ Receptors and CD206 on Maturing DC

There are several receptors on the APCs that bind and take up antigens. The abundance of these receptors on maturing dendritic cells was evaluated using fluorescent labeled receptor-specific antibodies. FACS analysis was used to estimate percentage of specific receptor positive cells in the total population of dendritic cells. The degree of receptor expression was assessed by determination of the relative mean fluorescent intensity and as a function of relative fluorescent intensity (FIG. 30). The expression of CD64 decreased with time in culture and at day 4 was almost negligible. In contrast, CD32, and to a lesser extent CD16, continued to be expressed after 4 days of DC culture. On day 0 of culture, there was essentially no CD206 expression, but expression was induced upon culture with IL-4 and GM-CSF, and by day 4 CD206 was expressed at very high levels. Thus at day 4, when antigen was loaded in the antigen presentation assays, the DCs possessed at least two potential receptors for the binding of chimeric antigens: CD32 and CD206. In addition, as shown in FIG. 31, they had the full complement of the co-stimulatory molecules. The expression of HLA-DR (Class II) and HLA-ABC (Class I) also increased with time in culture. Co-stimulatory molecules CD86 (B7.2) and CD80 (B7.1) were expressed throughout the period of the assay (FIG. 31). These results indicate that the monocyte-derived DCs were differentiating towards mature DCs and were capable of antigen processing and presentation to T cells. The cells were used to evaluate the binding and uptake of the chimeric antigens in comparison to relevant antibodies.

Example 16

Phenotypic Analysis, Binding and Uptake Assay

For the phenotypic analysis and binding assay, all procedures using incubations were performed at 4° C.; buffer solutions were also held at 4° C. The binding of antigens, chimeric antigens or antibodies was determined by incubating the cells with various of the agents for 60 minutes in Dulbecco's phosphate buffered saline with 0.1% (u/v) BSA (PBSB).

For phenotypic analysis, cells were incubated with the various conjugated mAbs at the concentrations recommended by the manufacturer for 20 minutes. Incubations were performed with $1\times10^5$ cells/well in 96-well v-bottom plates in a volume of 25 μL/well. Subsequently, the cells were washed twice with PBSB.

For binding analysis, the cells were treated with F(ab')$_2$ goat anti-mouse Alexa-488 (10 μg/mL) in PBSB for 20 minutes. The cells were washed twice with PBSB and either resuspended in PBSB with 2% PF and acquired by FACS or in PBSB and incubated with PE-conjugated CD32 or CD206 specific mAb for 20 minutes before washing twice with PBSB.

To determine the extent of uptake of chimeric antigens (e.g. HBV S1/S2-TBD) compared with IgG1 and IgG2a, cells were incubated with various concentrations of the antigen, IgG1 (2C12, the parent mAb from which TBD was produced) or IgG2a (G155-178) for 1 hour at 37° C. in AIM V media with 0.1% BSA. Cells were washed twice in PBSB and fixed with PBS with 2% PF overnight at 4° C. Subsequently, the cells were washed twice in PBSB and permeabilized with PBS containing 0.1% (w/v) saponin (Sigma) for 40 minutes at 20° C.

The cells were washed twice with PBSB and incubated with F(ab')$_2$ goat anti-mouse Alexa-488 (10 μg/mL) in PBSB with 0.1% (w/v) saponin for 20 minutes at 4° C. After washing twice in PBSB, the cells were resuspended in PBSB. A variant of this assay involved treating the cells as above with chimeric antigen, IgG1, or IgG2a for 10 minutes followed by the addition of F(ab')$_2$ goat anti-mouse Alexa-488 (10 μg/mL) for 50 minutes. Subsequently the cells were washed and resuspended in PBS with 2% PF. This procedure relied on the ability of the anti-mouse Alexa-488 Ab to directly bind the S1/S2-TBD, IgG1 or IgG2a molecules.

Cells were acquired by a Becton Dickinson (BD) FACScan fitted with Cellquest acquisition and analysis software (BD). A gate was made on the viable cell population as determined by the FSC and SSC scatter profile and ≧10,000 events were acquired. To determine the percentage of positive cells, a gate was set based on negative control treated cells (isotype control labeled or cells labeled with F(ab')$_2$ goat anti-mouse Alexa-488 alone).

The percent of specific positive cells was calculated as:

$$\frac{\% \text{ positive cells test sample} - \% \text{ positive cells control}}{100 - \% \text{ positive cells of control}} \times 100$$

The relative mean fluorescent intensity (MFI) was determined as the MFI of the test sample minus the MFI of the control sample.

Example 17

Construction of pFastBac HTa-TBD, TBD Protein Expression Vector

The mouse IgG1 DNA sequences encoding amino acids of $C_H1$-Hinge-$C_H2$-$C_H3$ region was generated from mRNA isolated from the hybridoma (2C12), which produces mAb against HBV surface antigen (sAg). Total mRNA was isolated using Trizol® reagent (Gibco BRL cat. No. 15596-026) and the cDNA of the TBD was generated by RT-PCR using Superscript First-strand Synthesis (Invitrogen Cat. No. 11904-018). The PCR primers contained linker sequences encoding the linker peptide -SRPQGGGS- (SEQ ID NO: 28) at the 5' terminus, a unique Not I site at the 5'-end and a unique Hind III restriction site at the 3' end. The resulting cDNA contains (5' Not I)-linker sequence-$C_H1$ (VDKKI)-$C_H2$-$C_H3$- (3' Hind III). Following digestion with the respective enzymes, the fragment is ligated with pFastBac HTa expression vector plasmid (Invitrogen) using the same restriction enzyme sites to generate pFastBac HTa-TBD. The 5' primer used for PCR amplification was (Sense) 5' TGTCATTCT-GCGGCCGCAAGGCGGCGGATCCGTGGA-CAAGAAAATTGTG CCCAGG (SEQ ID NO: 1) and the 3' primer was (antisense) 5' ACGAATCAAGCTTTGCAGC-CCAGGAGAGTGGGAGAG (SEQ ID NO: 2), which contained the Not I and Hind III sites, respectively. The following is the protocol used for directional cloning. The generated fragment was digested with the respective enzymes, purified on agarose gel and cloned into the vector plasmid. The DNA sequence and the correctness of the ORF were verified by standard sequencing methods. Nucleotide sequence of the ORF of TBD in the plasmid pFastBac HTa-TBD and the deduced amino acid sequences of the expressed TBD protein from the ORF are shown in FIG. 6.

Example 18

Expression and Purification of TBD Protein

Recombinant baculovirus of standardized multiplicity of infection (MOI) were used to infect High Five™ insect cells. For suspension cultures, cells were seeded at a density of 3×10$^5$ cells/mL and incubated at 27.5° C. with shaking at 138 rpm until the cell density reached 2–3×10$^6$ cells/mL. Recombinant baculovirus was added to the cells. For the expression of TBD the MOI used was 10 pfu/cell. The incubation at 27.5° C. was continued for 48 hrs. The cells were harvested by centrifugation at 2,500 rpm for 10 minutes at 4° C. and used for the purification of the recombinant proteins.

TBD protein was expressed in Express Five Insect cells, purified as described in Example 12. The protein was subjected to electrophoresis on a 12% polyacrylamide gel and the coomassie blue-stained band is shown.

Example 19

Construction of HBV Surface Antigen S1/S2 and HBV S1/S2-TBD Chimeric Fusion Protein Plasmids The DNA encoding the HBV sAg fragment S1/S2 was generated from the plasmid pRSetB HBV S1/S2 template using PCR methodology. The primers used were: (sense) 5' GGATCTGTACGACGATGACG (SEQ ID NO: 5) and the 3' primer (antisense) 5' AGTCATTCTGCGGCCGCGAGT-TCGTCACAGGGTCCCCGG (SEQ ID NO: 6) containing the restriction enzyme site Not I. The 5' end contained a unique Bam HI site derived from the parent plasmid that was used for ligations. Amplified DNA was digested with Bam HI/Not I and ligated with pFastBac HTa expression vector to generate the expression plasmid for HBV S1/S2 protein. The fragment was ligated with the plasmid pFastBac HTa-TBD (described in Example 1) following the digestion with the respective enzymes. This produced the expression plasmid pFastBac HTa HBV S1/S2-TBD. This plasmid was used to produce recombinant baculovirus (as described in Example 1), which expressed the chimeric antigen-TBD fusion protein: 6×His tag-rTEV protease cleavage site-HBV S1/S2-TBD. Nucleotide and deduced amino acid sequences from the ORFs of plasmid pFastBac HTa HBV S1/S2 are shown in FIG. 9. Nucleotide and deduced amino acid sequences from the ORFs of plasmid pFastBac HTa HBV S1/S2-TBD are shown in FIG. 8.

Example 20

Expression and Purification of HBV Surface Antigen S1/S2 and HBV S1/S2-TBD Chimeric Fusion Proteins Recombinant bacmids of standardized multiplicity of infection (MOI) were used to infect High Five™ insect cells. For suspension cultures, cells were seeded at a density of 3×10$^5$ cells/mL and incubated at 27.5° C. with shaking at 138 rpm until the cell density reached 2–3×10$^6$ cells/mL. Recombinant baculovirus was added to the cells. For the expression of the fusion protein HBV S1/S2-TBD, the MOI was 1 pfu/cell and for S1/S2, 2 pfu/cell was used. The incubation at 27.5° C. was continued for 48 hrs. The cells were harvested by centrifugation at 2,500 rpm for 10 minutes at 4° C. and used for the purification of the recombinant proteins.

Expression of S1/S2-TBD was performed in High Five™ cells (*Trichoplusia ni* BTI-Tn-5B1-4) grown in Express Five SFM media. The High Five™ cells were grown in a shaker culture at 27.5° C. until the cell density reached 2.5×10$^6$ cells/ml. Usually, a 250 ml culture is prepared. The culture was infected with HBV S1/S2-TBD baculovirus at a multiplicity of infection (MOI) of 1 pfu/cell and incubated at 27.5° C. for 48 hrs with shaking. Infected cells were harvested by centrifugation at 4000×g on a JA-10 (Beckman) rotor for 10 minutes. The cells were stored at −70° C. until purification were performed.

For purification, 40 ml of ice-cold lysis buffer (6M guanidine hydrochloride, 0.1 M NaH$_2$PO$_4$, 10 mM Tris, 500 mM NaCl, 10 mM imidazole, pH 8.0) was added to a frozen cell pellet. The cells were sonicated on ice for 5 pulses at 1 minute per pulse at 78-81 W and stirred at room temperature for 1 hour. The lysate was clarified by centrifugation at 27000×g on a JA-25.50 rotor (Beckman) for 30 min. Purification was performed on Ni-NTA Superflow. A 1.5×12 cm column was packed with 3 ml of Ni-NTA Superflow and equilibrated with 10 column volumes of lysis buffer. The clarified lysate was loaded onto the column. First, the column was washed with lysis buffer until the $OD_{280}$ was <0.01. Next, the column was washed with 6M guanidine hydrochloride, 0.1 M $NaH_2PO_4$, 10 mM Tris, 500 mM NaCl, 40 mM imidazole, pH 8.0 until the $OD_{280}$ is <0.01. Then the column was washed with 8 M urea, 0.1 M $NaH_2PO_4$, 10 mM Tris, 500 mM NaCl, 40 mM imidazole, pH 8.0 until the $OD_{280}$ was <0.01. Elution was performed with 8M urea, 0.1 M $NaH_2PO_4$, 10 mM Tris, 500 mM NaCl, 250 mM imidazole, pH 8.0 and 0.5 ml fractions were collected. The fractions were analyzed by $OD_{280}$ for protein. HBV S1/S2 and TBD protein fractions were dialyzed against 10 mM $NaH_2PO_4$, 0.3 M NaCl, pH 8.0.

S1/S2-TBD was dialyzed against 8M urea, 0.1 M $NaH_2PO_4$, 10 mM Tris, pH 8.0 with 3 changes and was subjected to further purification as follows. A 1 ml bed of DEAE Sepharose Fast Flow was equilibrated with 8M urea, 0.1 M $NaH_2PO_4$, 10 mM Tris, pH 8.0. The dialyzed S1/S2-TBD was added to the DEAE Sepharose Fast Flow and mixed together for 2 hours at room temperature. The mixture was centrifuged at 2500 rpm for 2 mM and the supernatant was collected.

Purified S1/S2-TBD was subjected to refolding. The DEAE purified S1/S2-TBD was reduced by adding 10 mM DTT and incubated for 30 minutes at room temperature. The reduced S1/S2-TBD was dialyzed against 4 M urea, 0.1 M $NaH_2PO_4$, 10 mM Tris, 150 mM NaCl, pH 8.0 at 4° C. for at least 6 hrs. The buffer was changed to 2M urea, 0.1 M $NaH_2PO_4$, 10 mM Tris, 150 mM NaCl, pH 8.0 and dialysis was continued at 4° C. After at least 6 hrs, the dialysis buffer was changed to 1 M urea, 0.1 M $NaH_2PO_4$, 10 mM Tris, 150 mM NaCl, 200 mM L-arginine, 0.5 mM oxidized glutathione (GSSG), pH 8.0 and dialysis was continued at 4° C. overnight. Following this, the buffer was changed to 0.5 M urea, 0.1 M $NaH_2PO_4$, 10 mM Tris, 150 mM NaCl, 200 mM L-arginine, 0.5 mM GSSG, pH 8.0 and dialysis was continued at 4° C. overnight. Finally, the sample was dialyzed against 10 mM $NaH_2PO_4$, 150 mM NaCl, pH 8.0 at 4° C. for at least 6 hrs. The last step was repeated 2 more times.

Example 21

Binding of Chimeric Antigens to Maturing DCs

The chimeric antigen S1/S2-TBD binds to maturing DCs with high efficiency (FIG. 32). The extent of binding of S1/S2-TBD relative to murine IgG1 and IgG2a to maturating DC was compared. DCs were isolated at various days of ex vivo culture (from day 0 to day 4) and treated with S1/S2-TBD (10 μg/mL) or with murine IgG1 (clone 2C12) or IgG2a (clone G155-178, 90 μg/mL) for 1 hour at 4° C. Subsequently, binding was detected with a $F(ab')_2$ anti-mouse IgG conjugated to Alexa 488 as described in Example 16. The binding of S1/S2-TBD relative to IgG1 and IgG2a on DC after 1 and 4 days of culture is shown in FIGS. 33 and 34. S1/S2-TBD binding was clearly much greater than the binding of either IgG1 or IgG2a with more S1/S2-TBD binding evident on day 1 than on day 4. These experiments clearly demonstrated that S1/S2-TBD was bound with high efficiency to the maturing DC.

Example 22

A High Proportion of Maturing DCs Bind Chimeric Antigen S1/S2-TBD

A large proportion of maturing DCs bind S1/S2-TBD. The binding of S1/S2-TBD in comparison to murine IgG2a and IgG1 was measured as a function of phenotypic changes on day 2 of the maturation of DCs as described in Example 16. DCs were isolated at various days of culture (from day 0 to day 4) and were treated with S1/S2-TBD (10 μg/mL), murine IgG1 (clone 2C12), or IgG2a (clone G155-178, 90 μg/rap for 1 hour at 4° C. Subsequently, binding was detected with a $F(ab')_2$ anti-mouse IgG conjugated to Alexa 488. The binding of S1/S2-TBD relative to IgG1 and IgG2a on DC after 1 and 4 days of culture is shown in FIGS. 33 and 34. S1/S2-TBD binding was clearly much greater than the binding of either IgG1 or IgG2a with more S1/S2-TBD binding evident on day 1 than day 4. Thus, these experiments demonstrated that a large proportion of maturing DCs bind S1/S2-TBD The proportion of DCs that bind S1/S2-TBD was much greater than either IgG2a or IgG1. Furthermore, the degree of binding of S1/S2-TBD was several orders of magnitude greater than that of the immunoglobulins.

The chimeric Antigen S1/S2-TBD binds to DCs more efficiently than IgG1 or IgG2a on days 1 and 4 of culture.

Example 23

Chimeric Antigen S1/S2-TBD is Taken up by DCs with High Efficiency

The uptake of S1/S2-TBD in comparison to murine IgG1 and IgG2a was estimated as a function of concentration on day 4 of DC maturation. The uptake was quantified at 37° C. for 1 hour and the results are shown in FIG. 35.

There was a linear increase in the uptake of S1/S2-TBD with concentration. IgG1 was taken up at a much lower level and there was very little uptake of IgG2a. Therefore, the chimeric antigen S1/S2-TBD is taken up by the DCs more efficiently than immunoglobulins.

Example 24

Correlation of CD32/CD206 Expression and S1/S2-TBD Binding to Maturing DCs

There is a direct correlation between the expression of CD32/CD206 receptors and S1/S2-TBD binding to maturing DCs. Since it was known that murine IgG1 binds to human CD32, it was expected that S1/S2-TBD, which contains the murine Fc component of IgG1, would also bind CD32. Furthermore, S1/S2-TBD by virtue of its high mannose glycosylation, would also be expected to bind to DC through the CD206 receptor.

The dot plots in FIG. 36 show S1/S2-TBD binding (10 μg/mL) and CD32 expression as well as S1/S2-TBD binding and CD206 expression. There was a direct correlation between the extent of S1/S2-TBD binding and the degree of CD32 expression, which was relatively heterogeneous, i.e., there was a broad degree of expression. These results demonstrate that S1/S2-TBD binds to CD32, and that the greater the expression of CD32, the greater was the degree of binding of the chimeric antigen S1/S2-TBD. The dot plot of S1/S2-TBD binding and CD206 expression shows that the vast majority of cells expressing CD206 also bound S1/S2-TBD A small percentage of the cell population was CD206 negative and was consequently negative for S1/S2-TBD binding. Therefore both CD32 and CD206 receptors correlate with the binding of S1/S2-TBD.

Example 25

The Binding and Uptake of S1/S2-TBD is Primarily Via CD32 with CD206 Involved to a Lesser Extent The uptake of S1/S2-TBD in comparison to murine IgG1 and IgG2a was estimated as a function of concentration on day 4 of DC maturation. The uptake was quantified at 37° C. for 1 hour in the presence and absence of inhibitors of CD32 and CD206 and the results are shown in FIG. 37. There was a progressive increase in the binding of the chimeric antigen with its concentration. Incubation of the cells with a high concentration of mouse Fcγ fragment abolished this binding, whereas mannan, an inhibitor of CD206 receptor binding, had only a marginal effect. Therefore, CD32 may be the primary receptor involved in the binding and uptake of the chimeric antigen.

Example 26

Glycosylated HBV S1/S2 Antigen Produced in Insect Cells Binds to DCs through CD206 Receptors The insect cell pathway of protein glycosylation is different from that of mammalian cells in that proteins synthesized in insect cells undergo glycosylation that results in high mannose content and a lack of terminal sialic acid residues in the secreted protein (Altman, et al., *Glycoconjug* 16:109-123 (1999)).

HBV S1/S2, the antigen component of the chimeric antigen was expressed in both *E. coli* (no glycosylation) and in High Five™ insect cells (high mannose glycosylation). These antigens were compared for their binding to DCs. Glycosylated protein showed better binding and uptake by DCs (FIG. 38).

Example 27

Chimeric Antigen S1/S2-TBD Elicited T Cell Responses as Measured by Interferon-γ Production The T cell response was greater with S1/S2-TBD treatment than with either of its two components measured individually. DCs were loaded with S1/S2 antigen, TBD, or S1/S2-TBD and presented to T cells in an antigen presentation assay as described in example 14. T cell stimulation was evaluated by measuring intracellular and secreted interferon-γ levels. The results are presented in FIGS. 39 and 40. The chimeric antigen S1/S2-TBD induced the production of higher interferon-γ levels compared to either the IRD or the TBD domain of the molecule when tested alone, at equivalent concentrations. It should be pointed out that 5 µg dose of S1/S2-TBD contains roughly 2.5 µg each of the components.

Example 28

Interferon-γ Production Following S1/S2-TBD Antigen Presentation by DCs

Interferon-γ production and secretion by CD3+ T cells increased in a concentration dependent manner following S1/S2-TBD antigen presentation by DCs. Purified S1/S2-TBD was used in antigen presentation assays using human PBMC-derived DCs, and the secreted and intracellular interferon-γ levels were measured in T cells following three rounds of antigen presentation. FIG. 41 presents intracellular levels and FIG. 42 shows the secreted levels. The results are the mean of three estimates.

concentrations of S1/S2-TBD were tested for the T cell response. The effect of S1/S2-TBD was greater than the tetanus toxoid treatment at similar concentrations. At concentrations lower than 5 µg/mL, the chimeric antigen elicited a concentration dependent increase in the production and secretion of interferon-γ. The positive response at low concentrations would be beneficial with respect to the dose necessary for vaccination and the cost of manufacturing of a vaccine.

Example 29

Glycosylation of HBV S1/S2 Antigen Imparts Immunogenicity to the Antigen and Generates Higher T Cell Responses Glycosylation of HBV S1/S2 elicits increased immunogenicity and T Cell responses. The insect cell pathway of protein glycosylation is different from that of mammalian cells in that proteins synthesized in insect cells undergo glycosylation that results in high mannose content and a lack of terminal sialic acid residues in the secreted protein (Altman, et al., supra).

HBV S1/S2, the antigen component of the chimeric antigen was expressed in both *E. coli* (no glycosylation) and in High Five™ insect cells (high mannose glycosylation). These antigens were compared for T cell responses when presented by DCs. Both intracellular and secreted interferon-γ levels were measured and the results are presented in FIGS. 43 and 44. HBV S1/S2 expressed in insect cells generated a higher level of both intracellular and secreted interferon, as compared to the unglycosylated protein expressed in E-coli.

Example 30

Construction of HBV Core Antigen and HBV Core-TBD Fusion Protein Expression Vectors HBV produces the Core proteins (Core) to encapsidate the replicating genome of the virus. There are two forms of the Core; one secreted into circulation, also known as the "e" antigen; and other is the capsid forming Core protein. The present invention also relates to the generation of expression plasmids to produce the Core protein as well as the Core antigen-TBD fusion protein in insect cells, similar to examples described in Example 19. The DNA encoding the HBV Core protein was generated from the plasmid pAlt HBV 991 template using PCR technique. The 5' primer used for the PCR was (sense) 5' TGCGCTACCATGGACATTGACCCT-TATAAAG (SEQ ID NO: 9) that contains the restriction enzyme Nco I site and the 3' primer used was (antisense) 5' TGTCATTCTGCGGCCGCGAACAT-TGAGATTCCCGAGATTGAG (SEQ ID NO: 10), containing the restriction enzyme Not I site. The PCR-amplified cDNA was digested with the respective enzymes and ligated with pFastBac HTa expression vector to generate either the expression plasmid for HBV Core protein or the expression plasmid pFastBac HTa HBV Core-TBD fusion protein. Nucleotide and deduced amino acid sequences from the ORFs of plasmid pFastBac HTa HBV Core are shown in FIG.

15. Nucleotide and deduced amino acid sequences from the ORFs of plasmid pFastBac HTa HBV Core-TBD are shown in FIG. 14.

Example 31

Construction of DHBV Surface Antigen PreS/S and DHBV PreS/S-TBD Fusion Protein Expression Vectors DHBV has served as a powerful animal model in the development of antiviral therapy for HBV. Pekin ducks, congenitally infected with DHBV have been used to study the mechanism of replication of the virus and for the screening of antiviral compounds. The present invention also describes the chimeric DHBV antigen-TBD molecules that could be used as therapeutic vaccines in DHBV-infected ducks, thus providing a viable animal model for the feasibility studies for a HBV therapeutic vaccines.

Figure 19:
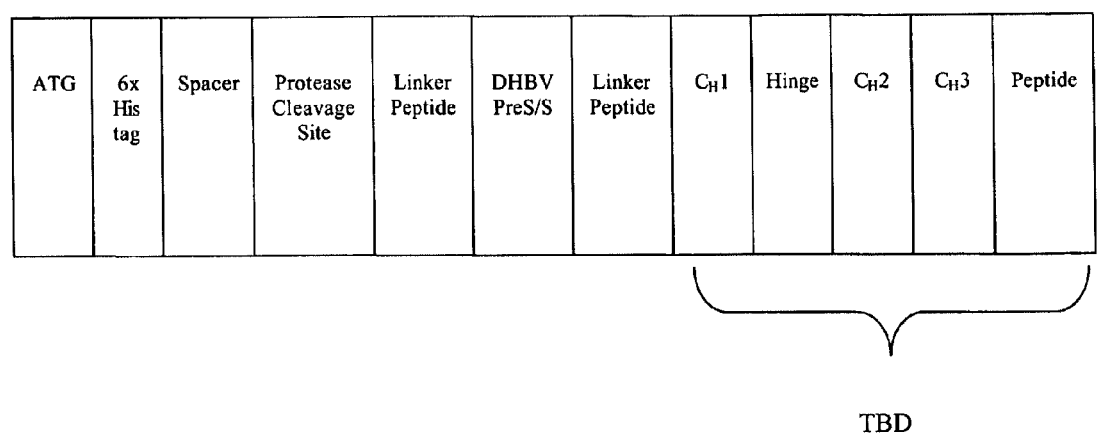
FIG. 19 is a schematic embodiment of an exemplary chimeric antigen of the present invention, illustrating an exemplary IRD of the present invention.
Figure 22:
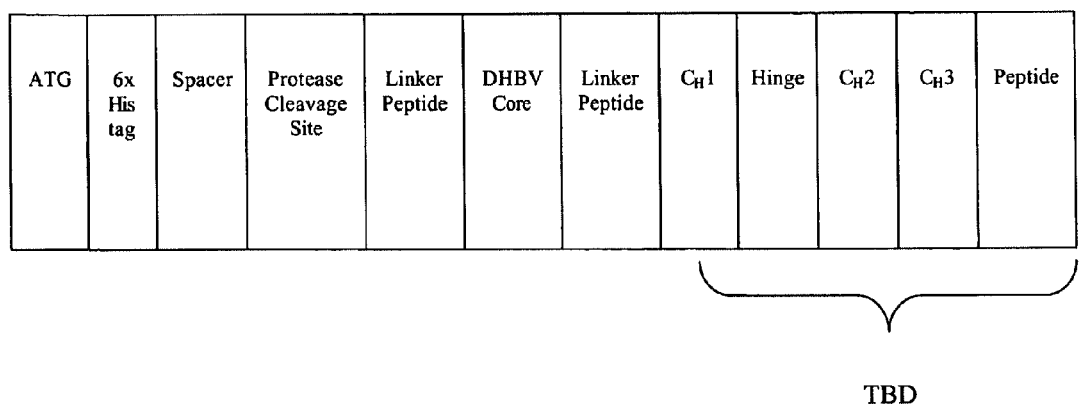
FIG. 22 is a schematic embodiment of an exemplary chimeric antigen of the present invention, illustrating an exemplary IRD of the present invention.

DNA encoding DHBV PreS/S was produced by PCR methods from template plasmid pFastBac HTa PreS/S (University of Alberta) using 5' primer (sense) 5' TATTCCGGATTATTCATACCG (SEQ ID NO: 11) and the 3' primer (antisense) 5' TGTCATTCAGCGGCCGCGAACTCTTG-TAAAAAAGAGCAGA (SEQ ID NO: 13), containing restriction enzyme Not I site. The unique restriction enzyme site EcoRI, resident on the parent plasmid pFastBac HTa PreS/S was used for directional cloning. All other protocols for the production of either the DHBV PreS/S or the fusion protein PreS/S-TBD are the same as described in Example 19. Nucleotide and deduced amino acid sequences from the ORFs of plasmid pFastBac HTa DHBV PreS/S are shown in FIG. 21. Nucleotide and deduced amino acid sequences from the ORFs of plasmid pFastBac HTa DHBV PreS/S-TBD are shown in FIG. 19.

Example 32

Construction of DHBV Core antigen and DHBV Core-TBD Fusion Protein Vector Plasmids The DNA coding for DHBV Core was generated by PCR using the following primers. The 5' terminus primer used was (sense) 5' TGCGCTACCATGGATATCATGCTTCTA-GAGCC (SEQ ID NO: 14), containing the restriction enzyme Nco I site. The 3' terminus primer used was (antisense) 5' TGTCATTCTGCGGCCGCGATTTCCTAG-GCGAGGGAGATCTATG (SEQ ID NO: 15), containing the restriction enzyme Not I site. All other protocols for the production of either the DHBV Core or the fusion protein DHBV Core-TBD are the same as described in the example 4 above. Nucleotide and deduced amino acid sequences from the ORFs of plasmid pFastBac HTa DHBV Core are shown in FIG. 24. Nucleotide and deduced amino acid sequences from the ORFs of plasmid pFastBac HTa DHBV Core-TBD are shown in FIG. 23.

Example 33

Construction of pFastBac HTa HCV Core (1-191) Antigen and the Chimeric Antigen pFastBac HTa HCV Core (1-191)-TBD Fusion Protein Vector Plasmids The DNA encoding the HCV Core was generated from the plasmid pCV-H77C template (University of Alberta) using PCR methodology. The primers used were: (sense) 5' CGGAATTCATGAGCACGAATCCTAAAC (SEQ ID NO: 16) containing the unique restriction enzyme site EcoRI and the 3' primer (antisense) 5' GGACTAGTCCGGCT-GAAGCGGGCACAGTCAGGCAAGAG (SEQ ID NO: 17) containing the unique restriction enzyme site Spe I. Amplified DNA was digested with EcoRI/Spe I and ligated with pFastBac HTa expression vector digested with the same two enzymes. The expression plasmid for HCV Core protein was generated with this method. The fragment was ligated with the plasmid pFastBac HTa (described in Example 19) following the digestion with the respective enzymes. This produced the expression plasmid pFastBac HTa HCV Core. This plasmid was used for the transposition in DH10Bac™ and the recombinant Bacmids used for Sf9 insect cell transfections. The resulting baculovirus carrying the gene of interest was optimized for MOI and the time for efficient protein expression (described in example 19). The generation of recombinant plasmid pFastBac HTa-HCV Core-TBD was achieved through similar protocols. The PCR-amplified DNA was digested with EcoRI/Spe I and the purified fragment was ligated with the plasmid pFastBac HTa-TBD (described in example 19) following the digestion with the respective enzymes. This produced the expression plasmid pFastBac HTa HCV Core-TBD. This plasmid was used to produce recombinant baculovirus that expressed the chimeric antigen-TBD fusion protein: 6×His tag-rTEV protease cleavage site-HCV Core-TBD. Nucleotide and deduced amino acid sequences from the ORFs of plasmid pFastBac HTa HCV Core (1-191) are shown in FIG. 45. Nucleotide and deduced amino acid sequences from the ORFs of plasmid pFastBac HTa HCV Core (1-191)-TBD are shown in FIG. 46. All other protocols are described in example 19.

Example 34

Expression and Purification of HCV Core Antigen and HCV Core-TBD Chimeric Fusion Protein Recombinant bacmids of standardized multiplicity of infection (MOI) were used to infect High Five™ insect cells. For suspension cultures, cells were seeded at a density of $3 \times 10^5$ cells/mL and incubated at 27.5° C. with shaking at 138 rpm until the cell density reached $2-3 \times 10^6$ cells/mL. Recombinant baculovirus was added to the cells. For HCV Core, infections of High Five™ cells were performed at an MOI of 1 pfu/cell. Cells in suspension were grown to mid-log phase and infected with the recombinant baculovirus at this MOI. These infected cultures were incubated for 48 hours and then the cells were harvested. For HCV Core-TBD, infections of High Five™ cells were done at an MOI of 1 pfu/cell and for 72 hours.

Purification of Proteins: The purification of HCV Core and HCV Core-TBD was done under denaturing conditions as follows. The cells were lysed in a buffer containing 6 M Guanidinium-HCl, 0.1 M $Na_2HPO_4$, 0.01 M Tris-HCl pH 8.0, 0.01 M Imidazole, (lysis buffer). The suspension was sonicated on ice with 5 pulses of 1 minute per pulse at a power setting of 60 watts, and was mixed at room temperature for 1 hour. The lysate was centrifuged at 27,000×g for 30 min to remove unbroken cells and cell debris. The supernatant was mixed for 1 hr with Ni-NTA agarose (Qiagen) beads (5 mL/100 mL cell lysate), pre-equilibrated with lysis buffer. Following the mixing step, the beads were loaded on to a column and was washed with a minimum of 20 column volumes of 8M Urea, 0.1 M $Na_2HPO_4$, 0.01 M Tris-HCl pH 8.0, 0.02M Imidazole (wash buffer), until the $OD_{280}$ was <0.01.

The bound protein was eluted in a buffer containing 8M Urea, 0.1 M Na$_2$HPO$_4$, 0.01 M Tris-HCl pH 8, 0.25 M imidazole.

HCV Core-TBD was separated from other proteins by gel filtration. The peak elution fractions from Ni-NTA agarose column were loaded on a Sephadex G100 (Pharmacia) gel filtration column and the column was eluted with 8M Urea, 0.1 M Na$_2$HPO$_4$, 0.01 M Tris-HCl, pH 8.0. The fractions containing HCV Core-TBD were pooled and dialyzed against PBS (phosphate buffered saline).

HCV Core antigen and the fusion protein HCV Core-TBD fusion protein were expressed in High Five™ insect cells, and purified; Coomassie blue-stained HCV Core was run on a 12% polyacrylamide gel. Core-TBD was purified and a Western blot using 6×His monoclonal antibody.

Example 35

Construction of pFastBac HTa HCV Core (1-177) Antigen and pFastBac HTa HCV Core (1-177)-TBD Fusion Protein Plasmid Vectors The DNA coding for HCV Core (1-177) was generated by PCR using the following primers. The 5' terminus primer used was (sense) 5' CGGAATTCATGAGCACGAATCCTAAAC (SEQ ID NO: 18), containing the restriction enzyme EcoRI site. The 3' terminus primer used was (antisense) 5' GGACTAGTCCGAAGATAGAGAAAGAGC (SEQ ID NO: 19), containing the restriction enzyme Spe I site. Following digestion with the two enzymes, the DNA fragment was ligated with plasmid pFastBac HTa to generate pFastBac HTa HCV (Core 1-177) and with pFastBac HTa-TBD to generate the expression plasmid pFastBac HTa HCV Core (1-177)-TBD. All other protocols for the production of either the HCV Core (1-177) antigen or the chimeric antigen fusion protein HCV Core (1-177)-TBD are the same as described in example 19. Nucleotide sequence and the deduced amino acid sequence of 6×His-rTEVprotease site-HCV Core (1-177) are shown in FIG. 47. Nucleotide sequence and the deduced amino acid sequence of 6×His-rTEVprotease site-HCV Core (1-177)-TBD are shown in FIG. 48.

Example 36

Construction of pFastBac HTa HCV NS5A Antigen and pFastBac HTa HCV NS5A-TBD Fusion Protein Expression Vector Plasmids The DNA encoding the HCV NS5A fragment was generated from the plasmid pCV-H77C (University of Alberta) template using PCR methodology. The 5' primer used form the PCR was (sense) 5' CCGGAATTCTCCGGTTCCTGGCTAAGG (SEQ ID NO: 20) containing the restriction enzyme EcoRI site. The PCR primer for 3' terminus was (antisense) 5' GGACTAGTCCGCACACGACATCTTCCGT (SEQ ID NO: 21) containing the restriction enzyme Spe I site. Amplified DNA was digested with the respective enzymes and ligated with pFastBac HTa expression vector to generate either the expression plasmid for HCV NS5A or it was ligated with the expression plasmid pFastBac HTa-TBD to generate the expression plasmid pFastBac HTa HCV NS5A-TBD fusion protein.

Nucleotide sequence and the deduced amino acid sequence of 6×His-rTEVprotease site-HCV NS5A are shown in FIG. 49. Nucleotide sequence and the deduced amino acid sequence of 6×His-rTEVprotease site-HCV NS5A-TBD are shown in FIG. 50.

Example 37

Construction of pFastBac HTa HCV E1 Antigen and pFastBac HTa HCV E1-TBD Fusion Protein Expression Vectors Plasmid pFastBac HTa HCV E1 and pFastBac HTa HCV E1-TBD, which are used to express HCV envelope protein E1 and the respective chimeric antigen E1-TBD fusion protein, were generated as follows. The DNA encoding the E1 protein was generated from the plasmid pCV-H77C template using PCR technique. The 5' primer used for the PCR was (sense) 5' CCGGAATTCTACCAAGTGCGCAATTCCT (SEQ ID NO: 22), which contains the restriction enzyme EcoRI site and the 3' primer used was (antisense) 5' GGACTAGTCCTTCCGCGTCGACGCCGGCAAAT (SEQ ID NO: 23), containing the restriction enzyme Spe I site. The PCR-amplified cDNA was digested with the respective enzymes and ligated with pFastBac HTa expression vector to generate the expression plasmid pFastBac HTa HCV E1 for the expression of HCV E1 protein. The digested DNA fragment was ligated with pFastBac HTa-TBD to generate the plasmid pFastBac HTa HCV E1-TBD, which was used to express HCV E1-TBD fusion protein.

FIG. 51 shows the nucleotide and the deduced amino acid sequences of 6×His-rTEVprotease site-HCV E1 in the open reading frame of the expression plasmid. FIG. 52 shows nucleotide and the deduced amino acid sequences of 6×His-rTEVprotease site-HCV E1-TBD chimeric antigen fusion protein.

Example 38

Construction of pFastBac HTa HCV E2 Antigen and pFastBac HTa HCV E2-TBD Fusion Protein Expression Vectors The DNA encoding HCV E2 antigen was produced by PCR from a plasmid pCV-H77C. The 5' primer used for the PCR was (sense) 5' GCGGAATTCACCCACGTCACCGGGGGAAATGC (SEQ ID NO: 24) containing a unique restriction enzyme site EcoRI that is used for directional cloning. The 3' primer used was (antisense) 5' GGACTAGTCCAGCCGCCTCCGCTTGGGATATGAGT (SEQ ID NO: 25) containing the restriction enzyme Spe I site. Following PCR amplification, the fragment was digested with the restriction enzymes EcoRI and Spe I an the DNA fragment was purified and ligated with the expression plasmid pFastBac HTa at the respective sites to produce pFastBac HTa HCV E2, which expressed the E2 antigen. The same fragment was also used to ligate with pFastBac HTa-TBD to generate the expression plasmid pFastBac HTa HCV E2-TBD, which expressed the chimeric antigen fusion protein HCV E2-TBD. The production of baculovirus stocks from these plasmids and the expression of the E2 and E2-TBD in High Five™ insect cells were done as described in previous examples.

FIG. 53 shows the nucleotide and the deduced amino acid sequences of 6×His-rTEVprotease site-HCV E2 in the open reading frame of the expression plasmid. FIG. 54 shows nucleotide and the deduced amino acid sequences of 6×His-rTEVprotease site-HCV E2-TBD chimeric antigen fusion protein.

DNA encoding HCV E1/E2 was produced by PCR methods from the plasmid pCV-H77C using 5' primer (sense) 5' CCGGAATTCTACCAAGTGCGCAATTCCT (SEQ ID NO: 26) containing the restriction enzyme site EcoRI and the 3' primer (antisense) 5' GGACTAGTCCAGCCGCCTCCGCT-TGGGATATGAGT (SEQ ID NO: 27) containing the restriction enzyme site Spe I. Restriction enzyme-digested DNA fragment was cloned into the respective sites of either pFastBac HTa to generate HTa HCV E1/E2 or pFastBac HTa-TBD to generate pFastBac HTa HCV E1/E2-TBD. All other protocols for the production of either the E1/E2 antigen or the fusion protein E1/E2-TBD are the same as described in the example above.

FIG. 55 shows the nucleotide and the deduced amino acid sequences of 6×His-rTEVprotease site-HCV E1/E2 in the open reading frame of the expression plasmid. FIG. 56 shows nucleotide and the deduced amino acid sequences of 6×His-rTEVprotease site-HCV E1/E2-TBD chimeric antigen fusion protein.

Conclusions from Examples 10-38

1. A new class of Chimeric Antigens is designed in order to incorporate antigen and antibody components in the molecule.
2. Antigen components can be derived from infectious agents or cancer antigen.
3. Antibody components are xenotypic, preferably of murine origin, in the case of chimeric antigens for administration to humans.
4. Chimeric antigen fusion proteins, TBD and the respective antigens have been produced by recombinant techniques.
5. Chimeric antigen fusion proteins, TBD and the respective antigens have been produced (expressed) in a heterologous expression system (insect cells).
6. By virtue of the expression in insect cells, the proteins have mannose glycosylation content.
7. Chimeric antigens include fusion proteins from HBV surface antigens (S1/S2), and/or HBV Core and TBD, derived from the murine mAb 2C12.
8. Chimeric antigens include fusion proteins of DHBV surface antigens PreS/S, Core and TBD.
9. The following antigens from HCV have been cloned and expressed in insect cell expression systems. HCV Core (1-191), HCV Core (1-177), HCV NS3, HCV NS5A, HCV E1, HCV E2, HCV E1/E2.
10. Chimeric antigen fusion proteins of HCV include HCV Core (1-191), HCV Core (1-177), HCV NS3, HCV NS5A, HCV E1, HCV E2, HCV E1/E2 and TBD.
11. Chimeric antigen fusion protein HCV Core (1-191)-TBD and HCV Core (1-191) have been expressed and purified.
12. Chimeric antigen fusion protein HBV surface antigen S1/S2-TBD and HBV surface antigen S1/S2 have been expressed and purified.
13. The fusion proteins bind to and are internalized by antigen presenting cells (Human PBMC-derived DCs).
14. Binding and uptake is via Fcγ receptors CD32 and possibly through CD64.
15. Binding and uptake can occur via CD206, the mannose macrophage receptor.
16. Mannose glycosylation augments the binding and uptake of the antigens via CD206.
17. Chimeric antigen fusion protein HBV surface antigen S1/S2-TBD enhances the antigen presentation by professional antigen presenting cells (DCs).
18. DCs loaded with the Chimeric antigen fusion protein HBV surface antigen S1/S2-TBD, on presentation to T cells, elicit an immune response.
19. The immune response can be measured as an increase in intracellular and secreted interferon-γ.

Example 39

Maturation and Loading of Dendritic Cells

Peripheral blood mononuclear cells (PBMCs) were thawed by the addition of AIM-V (ratio of 9 ml of AIM-V added to 1 ml of frozen cells). The cells were then centrifuged at 200×g for 5 min, the supernatant removed, and the cells resuspended in AIM-V/1% matched serum and added to either a 100 mm culture dish or a T-25 culture flask. The PBMCs were incubated for 1 hr at 37° C. in a humidified incubator under 7% $CO_2$. To remove non-adherent cells, the culture was triturated several times, the supernatant discarded, and the cells washed once with AIM-V medium. Monocytes were harvested with a cell scraper and centrifuged at 300×g for 5 min. The cell pellet was re-suspended in AIM-V/2.5% matched serum at $2×10^6$ cells/ml and seeded into a 24-well dish. Th IL-4 and GM-CSF (1000 IU/ml each) were added to drive the differentiation of monocytes into immature DCs. Antigen was added to immature DCs within 4 to 24 hr of isolation. After a further 24 hr, antigen loaded immature monocytes were induced to mature by culturing with PGE2 (1 μM), IL-1b (10 ng/ml), and TNF-a (10 ng/ml) for 24 hr.

Example 40

Combination Therapy using DHBV Core-TBD and Lamivudine in Pekin Ducks

Normal ducklings were infected with DHBV-containing duck serum a day after the ducklings were hatched. This is standard practice in the field of DHBV research. The presence of persistent viremia was verified using established techniques at week four before the start of the immunizations. Congenitally DHBV-infected animals at four weeks of age also were used for the experiments reported herein.

Congenitally DHBV-infected and post-hatch infected ducks were divided into three groups. A sample of blood (1.0 mL) was collected for reference of pre-immunization antibody levels and blood samples were collected every week before the vaccinations. The first experimental group received DHBV Core-TBD chimeric antigen fusion protein 40 μg/dose injected intramuscularly every other week on the same day until week 22. The second experimental group received DHBV Core protein 19.9 μg/dose injected intramuscularly every other week on the same day until week 22. The third (control) group received buffer (20 mM Sodium Phosphate pH 8.0, 300 mM NaCl) injected intramuscularly every other week on the same day until week 22. In addition, each group also received 20 mg/kg lamivudine injected intramuscularly b.i.d. until week 12, at which point the lamivudine dose was increased to 40 mg/kg injected intramuscularly b.i.d.

No observable local reaction to the injections of the DHBV core-chimeric antigen vaccine. No other adverse reaction was noticed. Lamivudine alone (control) decreased serum viremia in both congenitally and post-hatch DHBV infected ducks.

In the control group of ducks, the viremia rebounded at an earlier time point compared to the vaccinated group, i.e., ducks receiving DHBV Core-TBD. Thus a trend towards increased viral suppression exists in response to vaccination with the chimerica antigen, although a complete elimination of the viremia was not seen in any of the experimental animals. A trend towards increased inflammatory response also was observed in the group receiving DHBV Core-TBD compared to the control group (lamibviudine alone). Such a trend indicates that the DHBV Core-chimeric antigen induces immune responses in the duck animal model.

In post-hatch DHBV-infected ducks, there was an elevation of serum anti-core antibody levels in core-chimeric antigen treated group compared to the control groups. This suggests a humoral response to the vaccination with the chimeric antigen in a chronic virus-infected animal model.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

SEQUENCE LISTING

<160> NUMBER OF SEQ ID NOS: 79

<210> SEQ ID NO 1
<211> LENGTH: 55
<212> TYPE: DNA
<213> ORGANISM: artificial sequence
<220> FEATURE:
<223> OTHER INFORMATION: primer sequence

<400> SEQUENCE: 1
tgtcattctg cggccgcaag gcggcggatc cgtggacaag aaaattgtgc ccagg 55

<210> SEQ ID NO 2
<211> LENGTH: 36
<212> TYPE: DNA
<213> ORGANISM: artificial sequence
<220> FEATURE:
<223> OTHER INFORMATION: primer sequence

<400> SEQUENCE: 2
acgaatcaag ctttgcagcc caggagagtg ggagag 36

<210> SEQ ID NO 3
<211> LENGTH: 21
<212> TYPE: DNA
<213> ORGANISM: artificial sequence
<220> FEATURE:
<223> OTHER INFORMATION: primer sequence

<400> SEQUENCE: 3
tattccggat tattcatacc g 21

<210> SEQ ID NO 4
<211> LENGTH: 20
<212> TYPE: DNA
<213> ORGANISM: artificial sequence
<220> FEATURE:
<223> OTHER INFORMATION: primer sequence

<400> SEQUENCE: 4
ctctacaaat gtggtatggc 20

<210> SEQ ID NO 5
<211> LENGTH: 20
<212> TYPE: DNA
<213> ORGANISM: artificial sequence
<220> FEATURE:
<223> OTHER INFORMATION: primer sequence

<400> SEQUENCE: 5
ggatctgtac gacgatgacg 20

<210> SEQ ID NO 6

```
<211> LENGTH: 39
<212> TYPE: DNA
<213> ORGANISM: artificial sequence
<220> FEATURE:
<223> OTHER INFORMATION: primer sequence

<400> SEQUENCE: 6
agtcattctg cggccgcgag ttcgtcacag ggtccccgg                              39

<210> SEQ ID NO 7
<211> LENGTH: 34
<212> TYPE: DNA
<213> ORGANISM: artificial sequence
<220> FEATURE:
<223> OTHER INFORMATION: primer sequence

<400> SEQUENCE: 7
gataaggatc ctatgggagg ttggtcatca aaac                                  34

<210> SEQ ID NO 8
<211> LENGTH: 40
<212> TYPE: DNA
<213> ORGANISM: artificial sequence
<220> FEATURE:
<223> OTHER INFORMATION: primer sequence

<400> SEQUENCE: 8
gtcatactgc ggccgcgaaa tgtatacccca gagacaaaag                           40

<210> SEQ ID NO 9
<211> LENGTH: 31
<212> TYPE: DNA
<213> ORGANISM: artificial sequence
<220> FEATURE:
<223> OTHER INFORMATION: primer sequence

<400> SEQUENCE: 9
tgcgctacca tggacattga cccttataaa g                                     31

<210> SEQ ID NO 10
<211> LENGTH: 42
<212> TYPE: DNA
<213> ORGANISM: artificial sequence
<220> FEATURE:
<223> OTHER INFORMATION: primer sequence

<400> SEQUENCE: 10
tgtcattctg cggccgcgaa cattgagatt cccgagattg ag                         42

<210> SEQ ID NO 11
<211> LENGTH: 21
<212> TYPE: DNA
<213> ORGANISM: artificial sequence
<220> FEATURE:
<223> OTHER INFORMATION: primer sequence

<400> SEQUENCE: 11
tattccggat tattcatacc g                                                21

<210> SEQ ID NO 12
<211> LENGTH: 40
<212> TYPE: DNA
<213> ORGANISM: artificial sequence
<220> FEATURE:
<223> OTHER INFORMATION: primer sequence

<400> SEQUENCE: 12
```
tgtcattctg cggccgcgtt ttcttcttca agggggagt                    40

<210> SEQ ID NO 13
<211> LENGTH: 40
<212> TYPE: DNA
<213> ORGANISM: artificial sequence
<220> FEATURE:
<223> OTHER INFORMATION: primer sequence

<400> SEQUENCE: 13
tgtcattcag cggccgcgaa ctcttgtaaa aaagagcaga                    40

<210> SEQ ID NO 14
<211> LENGTH: 33
<212> TYPE: DNA
<213> ORGANISM: artificial sequence
<220> FEATURE:
<223> OTHER INFORMATION: primer sequence

<400> SEQUENCE: 14
tgcgctacca tggatatcaa tgcttctaga gcc                           33

<210> SEQ ID NO 15
<211> LENGTH: 43
<212> TYPE: DNA
<213> ORGANISM: artificial sequence
<220> FEATURE:
<223> OTHER INFORMATION: primer sequence

<400> SEQUENCE: 15
tgtcattctg cggccgcgat ttcctaggcg agggagatct atg                43

<210> SEQ ID NO 16
<211> LENGTH: 27
<212> TYPE: DNA
<213> ORGANISM: artificial sequence
<220> FEATURE:
<223> OTHER INFORMATION: primer sequence

<400> SEQUENCE: 16
cggaattcat gagcacgaat cctaaac                                  27

<210> SEQ ID NO 17
<211> LENGTH: 38
<212> TYPE: DNA
<213> ORGANISM: artificial sequence
<220> FEATURE:
<223> OTHER INFORMATION: primer sequence

<400> SEQUENCE: 17
ggactagtcc ggctgaagcg ggcacagtca ggcaagag                      38

<210> SEQ ID NO 18
<211> LENGTH: 27
<212> TYPE: DNA
<213> ORGANISM: artificial sequence
<220> FEATURE:
<223> OTHER INFORMATION: primer sequence

<400> SEQUENCE: 18
cggaattcat gagcacgaat cctaaac                                  27

<210> SEQ ID NO 19
<211> LENGTH: 27
<212> TYPE: DNA
<213> ORGANISM: artificial sequence
<220> FEATURE:

```
<223> OTHER INFORMATION: primer sequence

<400> SEQUENCE: 19
ggactagtcc gaagatagag aaagagc                                        27

<210> SEQ ID NO 20
<211> LENGTH: 27
<212> TYPE: DNA
<213> ORGANISM: artificial sequence
<220> FEATURE:
<223> OTHER INFORMATION: primer sequence

<400> SEQUENCE: 20
ccggaattct ccggttcctg gctaagg                                        27

<210> SEQ ID NO 21
<211> LENGTH: 28
<212> TYPE: DNA
<213> ORGANISM: artificial sequence
<220> FEATURE:
<223> OTHER INFORMATION: primer sequence

<400> SEQUENCE: 21
ggactagtcc gcacacgaca tcttccgt                                       28

<210> SEQ ID NO 22
<211> LENGTH: 28
<212> TYPE: DNA
<213> ORGANISM: artificial sequence
<220> FEATURE:
<223> OTHER INFORMATION: primer sequence

<400> SEQUENCE: 22
ccggaattct accaagtgcg caattcct                                       28

<210> SEQ ID NO 23
<211> LENGTH: 32
<212> TYPE: DNA
<213> ORGANISM: artificial sequence
<220> FEATURE:
<223> OTHER INFORMATION: primer sequence

<400> SEQUENCE: 23
ggactagtcc ttccgcgtcg acgccggcaa at                                  32

<210> SEQ ID NO 24
<211> LENGTH: 32
<212> TYPE: DNA
<213> ORGANISM: artificial sequence
<220> FEATURE:
<223> OTHER INFORMATION: primer sequence

<400> SEQUENCE: 24
gcggaattca cccacgtcac cgggggaaat gc                                  32

<210> SEQ ID NO 25
<211> LENGTH: 35
<212> TYPE: DNA
<213> ORGANISM: artificial sequence
<220> FEATURE:
<223> OTHER INFORMATION: primer sequence

<400> SEQUENCE: 25
ggactagtcc agccgcctcc gcttgggata tgagt                               35

<210> SEQ ID NO 26
```

```
<210> SEQ ID NO 26
<211> LENGTH: 28
<212> TYPE: DNA
<213> ORGANISM: artificial sequence
<220> FEATURE:
<223> OTHER INFORMATION: HCV E2 antigen primer

<400> SEQUENCE: 26
ccggaattct accaagtgcg caattcct                                        28

<210> SEQ ID NO 27
<211> LENGTH: 35
<212> TYPE: DNA
<213> ORGANISM: Artificial
<220> FEATURE:
<223> OTHER INFORMATION: HCV E1/E2 3' primer

<400> SEQUENCE: 27
ggactagtcc agccgcctcc gcttgggata tgagt                                35

<210> SEQ ID NO 28
<211> LENGTH: 8
<212> TYPE: PRT
<213> ORGANISM: Artificial
<220> FEATURE:
<223> OTHER INFORMATION: linker peptide
<220> FEATURE:
<221> NAME/KEY: misc_feature
<222> LOCATION: (1)..(1)
<223> OTHER INFORMATION: Xaa can be Val or Ser

<400> SEQUENCE: 28

Xaa Arg Pro Gln Gly Gly Gly Ser
 1               5

<210> SEQ ID NO 29
<211> LENGTH: 870
<212> TYPE: DNA
<213> ORGANISM: Mus musculus
<220> FEATURE:
<221> NAME/KEY: CDS
<222> LOCATION: (1)..(870)

<400> SEQUENCE: 29 atg tcg tac tac cat cac cat cac cat cac gat tac gat atc cca acg    48
Met Ser Tyr Tyr His His His His His His Asp Tyr Asp Ile Pro Thr
 1               5                  10                  15 acc gaa aac ctg tat ttt cag ggc gcc atg gat ccg gaa ttc aaa ggc    96
Thr Glu Asn Leu Tyr Phe Gln Gly Ala Met Asp Pro Glu Phe Lys Gly
             20                  25                  30 cta cgt cga cga gct caa cta gtg cgg ccg caa ggc ggc gga tcc gtg   144
Leu Arg Arg Arg Ala Gln Leu Val Arg Pro Gln Gly Gly Gly Ser Val
         35                  40                  45 gac aag aaa att gtg ccc agg gat tgt ggt tgt aag cct tgc ata tgt   192
Asp Lys Lys Ile Val Pro Arg Asp Cys Gly Cys Lys Pro Cys Ile Cys
     50                  55                  60 aca gtc cca gaa gta tca tct gtc ttc atc ttc ccc cca aag ccc aag   240
Thr Val Pro Glu Val Ser Ser Val Phe Ile Phe Pro Pro Lys Pro Lys
 65                  70                  75                  80 gat gtg ctc acc att act ctg act cct aag gtc acg tgt gtt gtg gta   288
Asp Val Leu Thr Ile Thr Leu Thr Pro Lys Val Thr Cys Val Val Val
                 85                  90                  95 gac atc agc aag gat gat ccc gag gtc cag ttc agc tgg ttt gta gat   336
Asp Ile Ser Lys Asp Asp Pro Glu Val Gln Phe Ser Trp Phe Val Asp
            100                 105                 110 gat gtg gag gtg cac aca gct cag acg caa ccc cgg gag gag cag ttc   384
Asp Val Glu Val His Thr Ala Gln Thr Gln Pro Arg Glu Glu Gln Phe
```

```
                    115                 120                 125
aac agc act ttc cgc tca gtc agt gaa ctt ccc atc atg cac cag gac        432
Asn Ser Thr Phe Arg Ser Val Ser Glu Leu Pro Ile Met His Gln Asp
    130                 135                 140 tgg ctc aat ggc aag gag ttc aaa tgc agg gtc aac agt gca gct ttc        480
Trp Leu Asn Gly Lys Glu Phe Lys Cys Arg Val Asn Ser Ala Ala Phe
145                 150                 155                 160 cct gcc ccc atc gag aaa acc atc tcc aaa acc aaa ggc aga ccg aag        528
Pro Ala Pro Ile Glu Lys Thr Ile Ser Lys Thr Lys Gly Arg Pro Lys
                165                 170                 175 gct cca cag gtg tac acc att cca cct ccc aag gag cag atg gcc aag        576
Ala Pro Gln Val Tyr Thr Ile Pro Pro Pro Lys Glu Gln Met Ala Lys
            180                 185                 190 gat aaa gtc agt ctg acc tgc atg ata aca gac ttc ttc cct gaa gac        624
Asp Lys Val Ser Leu Thr Cys Met Ile Thr Asp Phe Phe Pro Glu Asp
        195                 200                 205 att act gtg gag tgg cag tgg aat ggg cag cca gcg gag aac tac aag        672
Ile Thr Val Glu Trp Gln Trp Asn Gly Gln Pro Ala Glu Asn Tyr Lys
    210                 215                 220 aac act cag ccc atc atg gac aca gat ggc tct tac ttc gtc tac agc        720
Asn Thr Gln Pro Ile Met Asp Thr Asp Gly Ser Tyr Phe Val Tyr Ser
225                 230                 235                 240 aag ctc aat gtg cag aag agc aac tgg gag gca gga aat act ttc acc        768
Lys Leu Asn Val Gln Lys Ser Asn Trp Glu Ala Gly Asn Thr Phe Thr
                245                 250                 255 tgc tct gtg tta cat gag ggc ctg cac aac cac cat act gag aag agc        816
Cys Ser Val Leu His Glu Gly Leu His Asn His His Thr Glu Lys Ser
            260                 265                 270 ctc tcc cac tct cct ggg ctg caa agc ttg tcg aga agt act aga gga        864
Leu Ser His Ser Pro Gly Leu Gln Ser Leu Ser Arg Ser Thr Arg Gly
        275                 280                 285 tca taa                                                                870
Ser

<210> SEQ ID NO 30
<211> LENGTH: 289
<212> TYPE: PRT
<213> ORGANISM: Mus musculus

<400> SEQUENCE: 30

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val Arg Pro Gln Gly Gly Gly Ser Val
            35                  40                  45

Asp Lys Lys Ile Val Pro Arg Asp Cys Gly Cys Lys Pro Cys Ile Cys
        50                  55                  60

Thr Val Pro Glu Val Ser Ser Val Phe Ile Phe Pro Lys Pro Lys
65                  70                  75                  80

Asp Val Leu Thr Ile Thr Leu Thr Pro Lys Val Thr Cys Val Val
                85                  90                  95

Asp Ile Ser Lys Asp Asp Pro Glu Val Gln Phe Ser Trp Phe Val Asp
            100                 105                 110

Asp Val Glu Val His Thr Ala Gln Thr Gln Pro Arg Glu Glu Gln Phe
        115                 120                 125

Asn Ser Thr Phe Arg Ser Val Ser Glu Leu Pro Ile Met His Gln Asp
    130                 135                 140
```

-continued

```
Trp Leu Asn Gly Lys Glu Phe Lys Cys Arg Val Asn Ser Ala Ala Phe
145                 150                 155                 160

Pro Ala Pro Ile Glu Lys Thr Ile Ser Lys Thr Lys Gly Arg Pro Lys
                165                 170                 175

Ala Pro Gln Val Tyr Thr Ile Pro Pro Lys Glu Gln Met Ala Lys
            180                 185                 190

Asp Lys Val Ser Leu Thr Cys Met Ile Thr Asp Phe Phe Pro Glu Asp
        195                 200                 205

Ile Thr Val Glu Trp Gln Trp Asn Gly Gln Pro Ala Glu Asn Tyr Lys
    210                 215                 220

Asn Thr Gln Pro Ile Met Asp Thr Asp Gly Ser Tyr Phe Val Tyr Ser
225                 230                 235                 240

Lys Leu Asn Val Gln Lys Ser Asn Trp Glu Ala Gly Asn Thr Phe Thr
                245                 250                 255

Cys Ser Val Leu His Glu Gly Leu His Asn His His Thr Glu Lys Ser
            260                 265                 270

Leu Ser His Ser Pro Gly Leu Gln Ser Leu Ser Arg Ser Thr Arg Gly
        275                 280                 285

Ser
```

<210> SEQ ID NO 31
<211> LENGTH: 1359
<212> TYPE: DNA
<213> ORGANISM: Artificial
<220> FEATURE:
<223> OTHER INFORMATION: HBV plus TBD
<220> FEATURE:
<221> NAME/KEY: CDS
<222> LOCATION: (1)..(1359)

<400> SEQUENCE: 31

```
atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gat cct atg aaa aaa tgg        96
Thr Glu Asn Leu Tyr Phe Gln Gly Ala Met Asp Pro Met Lys Lys Trp
            20                  25                  30 tca tca aaa cct cgc aaa ggc atg ggg acg aat ctt tct gtt ccc aac       144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc       192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg       240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc       288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg       336
Pro Pro His Gly Gly Val Leu Gly Trp Ser Pro Gln Ala Gln Gly Met
            100                 105                 110 ttg acc cca gtg tca aca att cct cct cct gcc tcc gcc aat cgg cag       384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat       432
Ser Gly Arg Gln Pro Thr Pro Ile Ser Pro Pro Leu Arg Asp Ser His
    130                 135                 140 cct cag gcc atg cag tgg aat tcc act gcc ttc cac caa gct ctg caa       480
Pro Gln Ala Met Gln Trp Asn Ser Thr Ala Phe His Gln Ala Leu Gln
```

-continued

| | | | | | | | | | | | | |
|---|---|---|---|---|---|---|---|---|---|---|---|---|
| | 145 | | | | 150 | | | | 155 | | | 160 |
| gac | ccc | aga | gtc | agg | ggt | ctg | tat | ttt | cct | gct | ggt | ggc | tcc | agt | tca | 528 |
| Asp | Pro | Arg | Val | Arg | Gly | Leu | Tyr | Phe | Pro | Ala | Gly | Gly | Ser | Ser | Ser | |
| | | | | 165 | | | | | 170 | | | | | 175 | | |
| gga | aca | gta | aac | cct | gct | ccg | aat | att | gcc | tct | cac | atc | tcg | tca | atc | 576 |
| Gly | Thr | Val | Asn | Pro | Ala | Pro | Asn | Ile | Ala | Ser | His | Ile | Ser | Ser | Ile | |
| | | | 180 | | | | | 185 | | | | | 190 | | | |
| tcc | gcg | agg | acc | ggg | gac | cct | gtg | acg | aac | tcg | cgg | ccg | caa | ggc | ggc | 624 |
| Ser | Ala | Arg | Thr | Gly | Asp | Pro | Val | Thr | Asn | Ser | Arg | Pro | Gln | Gly | Gly | |
| | | 195 | | | | | 200 | | | | | 205 | | | | |
| gga | tcc | gtg | gac | aag | aaa | att | gtg | ccc | agg | gat | tgt | ggt | tgt | aag | cct | 672 |
| Gly | Ser | Val | Asp | Lys | Lys | Ile | Val | Pro | Arg | Asp | Cys | Gly | Cys | Lys | Pro | |
| | 210 | | | | | 215 | | | | | 220 | | | | | |
| tgc | ata | tgt | aca | gtc | cca | gaa | gta | tca | tct | gtc | ttc | atc | ttc | ccc | cca | 720 |
| Cys | Ile | Cys | Thr | Val | Pro | Glu | Val | Ser | Ser | Val | Phe | Ile | Phe | Pro | Pro | |
| 225 | | | | | 230 | | | | | 235 | | | | | 240 | |
| aag | ccc | aag | gat | gtg | ctc | acc | att | act | ctg | act | cct | aag | gtc | acg | tgt | 768 |
| Lys | Pro | Lys | Asp | Val | Leu | Thr | Ile | Thr | Leu | Thr | Pro | Lys | Val | Thr | Cys | |
| | | | | 245 | | | | | 250 | | | | | 255 | | |
| gtt | gtg | gta | gac | atc | agc | aag | gat | gat | ccc | gag | gtc | cag | ttc | agc | tgg | 816 |
| Val | Val | Val | Asp | Ile | Ser | Lys | Asp | Asp | Pro | Glu | Val | Gln | Phe | Ser | Trp | |
| | | | 260 | | | | | 265 | | | | | 270 | | | |
| ttt | gta | gat | gat | gtg | gag | gtg | cac | aca | gct | cag | acg | caa | ccc | cgg | gag | 864 |
| Phe | Val | Asp | Asp | Val | Glu | Val | His | Thr | Ala | Gln | Thr | Gln | Pro | Arg | Glu | |
| | | 275 | | | | | 280 | | | | | 285 | | | | |
| gag | cag | ttc | aac | agc | act | ttc | cgc | tca | gtc | agt | gaa | ctt | ccc | atc | atg | 912 |
| Glu | Gln | Phe | Asn | Ser | Thr | Phe | Arg | Ser | Val | Ser | Glu | Leu | Pro | Ile | Met | |
| | 290 | | | | | 295 | | | | | 300 | | | | | |
| cac | cag | gac | tgg | ctc | aat | ggc | aag | gag | ttc | aaa | tgc | agg | gtc | aac | agt | 960 |
| His | Gln | Asp | Trp | Leu | Asn | Gly | Lys | Glu | Phe | Lys | Cys | Arg | Val | Asn | Ser | |
| 305 | | | | | 310 | | | | | 315 | | | | | 320 | |
| gca | gct | ttc | cct | gcc | ccc | atc | gag | aaa | acc | atc | tcc | aaa | acc | aaa | ggc | 1008 |
| Ala | Ala | Phe | Pro | Ala | Pro | Ile | Glu | Lys | Thr | Ile | Ser | Lys | Thr | Lys | Gly | |
| | | | | 325 | | | | | 330 | | | | | 335 | | |
| aga | ccg | aag | gct | cca | cag | gtg | tac | acc | att | cca | cct | ccc | aag | gag | cag | 1056 |
| Arg | Pro | Lys | Ala | Pro | Gln | Val | Tyr | Thr | Ile | Pro | Pro | Pro | Lys | Glu | Gln | |
| | | | 340 | | | | | 345 | | | | | 350 | | | |
| atg | gcc | aag | gat | aaa | gtc | agt | ctg | acc | tgc | atg | ata | aca | gac | ttc | ttc | 1104 |
| Met | Ala | Lys | Asp | Lys | Val | Ser | Leu | Thr | Cys | Met | Ile | Thr | Asp | Phe | Phe | |
| | | 355 | | | | | 360 | | | | | 365 | | | | |
| cct | gaa | gac | att | act | gtg | gag | tgg | cag | tgg | aat | ggg | cag | cca | gcg | gag | 1152 |
| Pro | Glu | Asp | Ile | Thr | Val | Glu | Trp | Gln | Trp | Asn | Gly | Gln | Pro | Ala | Glu | |
| | 370 | | | | | 375 | | | | | 380 | | | | | |
| aac | tac | aag | aac | act | cag | ccc | atc | atg | gac | aca | gat | ggc | tct | tac | ttc | 1200 |
| Asn | Tyr | Lys | Asn | Thr | Gln | Pro | Ile | Met | Asp | Thr | Asp | Gly | Ser | Tyr | Phe | |
| 385 | | | | | 390 | | | | | 395 | | | | | 400 | |
| gtc | tac | agc | aag | ctc | aat | gtg | cag | aag | agc | aac | tgg | gag | gca | gga | aat | 1248 |
| Val | Tyr | Ser | Lys | Leu | Asn | Val | Gln | Lys | Ser | Asn | Trp | Glu | Ala | Gly | Asn | |
| | | | | 405 | | | | | 410 | | | | | 415 | | |
| act | ttc | acc | tgc | tct | gtg | tta | cat | gag | ggc | ctg | cac | aac | cac | cat | act | 1296 |
| Thr | Phe | Thr | Cys | Ser | Val | Leu | His | Glu | Gly | Leu | His | Asn | His | His | Thr | |
| | | | 420 | | | | | 425 | | | | | 430 | | | |
| gag | aag | agc | ctc | tcc | cac | tct | cct | ggg | ctg | caa | agc | ttg | tcg | aga | agt | 1344 |
| Glu | Lys | Ser | Leu | Ser | His | Ser | Pro | Gly | Leu | Gln | Ser | Leu | Ser | Arg | Ser | |
| | | 435 | | | | | 440 | | | | | 445 | | | | |
| act | aga | gga | tca | taa | | | | | | | | | | | | 1359 |
| Thr | Arg | Gly | Ser | | | | | | | | | | | | | |
| | 450 | | | | | | | | | | | | | | | |

<210> SEQ ID NO 32

<211> LENGTH: 452
<212> TYPE: PRT
<213> ORGANISM: Artificial
<220> FEATURE:
<223> OTHER INFORMATION: Synthetic Construct

<400> SEQUENCE: 32

```
Met Ser Tyr Tyr His His His His His His Asp Tyr Asp Ile Pro Thr
1               5                   10                  15

Thr Glu Asn Leu Tyr Phe Gln Gly Ala Met Asp Pro Met Lys Lys Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Ser Arg Pro Gln Gly Gly
        195                 200                 205

Gly Ser Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380
```

```
Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Leu Gln Ser Leu Ser Arg Ser
        435                 440                 445

Thr Arg Gly Ser
    450

<210> SEQ ID NO 33
<211> LENGTH: 687
<212> TYPE: DNA
<213> ORGANISM: Hepatitis B virus
<220> FEATURE:
<221> NAME/KEY: CDS
<222> LOCATION: (1)..(687)

<400> SEQUENCE: 33 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat cct atg aaa aaa tgg    96
Thr Glu Asn Leu Tyr Phe Gln Gly Ala Met Asp Pro Met Lys Lys Trp
            20                  25                  30 tca tca aaa cct cgc aaa ggc atg ggg acg aat ctt tct gtt ccc aac   144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc   192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg   240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc   288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg   336
Pro Pro His Gly Gly Val Leu Gly Trp Ser Pro Gln Ala Gln Gly Met
            100                 105                 110 ttg acc cca gtg tca aca att cct cct cct gcc tcc gcc aat cgg cag   384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat   432
Ser Gly Arg Gln Pro Thr Pro Ile Ser Pro Pro Leu Arg Asp Ser His
    130                 135                 140 cct cag gcc atg cag tgg aat tcc act gcc ttc cac caa gct ctg caa   480
Pro Gln Ala Met Gln Trp Asn Ser Thr Ala Phe His Gln Ala Leu Gln
145                 150                 155                 160 gac ccc aga gtc agg ggt ctg tat ttt cct gct ggt ggc tcc agt tca   528
Asp Pro Arg Val Arg Gly Leu Tyr Phe Pro Ala Gly Gly Ser Ser Ser
                165                 170                 175 gga aca gta aac cct gct ccg aat att gcc tct cac atc tcg tca atc   576
Gly Thr Val Asn Pro Ala Pro Asn Ile Ala Ser His Ile Ser Ser Ile
            180                 185                 190 tcc gcg agg acc ggg gac cct gtg acg aac tcg cgg ccg ctt tcg aat   624
Ser Ala Arg Thr Gly Asp Pro Val Thr Asn Ser Arg Pro Leu Ser Asn
        195                 200                 205 cta gag cct gca gtc tcg agg cat gcg gta cca agc ttg tcg aga agt   672
Leu Glu Pro Ala Val Ser Arg His Ala Val Pro Ser Leu Ser Arg Ser
```

```
                        210                 215                 220
act aga gga tca taa                                                          687
Thr Arg Gly Ser
225

<210> SEQ ID NO 34
<211> LENGTH: 228
<212> TYPE: PRT
<213> ORGANISM: Hepatitis B virus

<400> SEQUENCE: 34

Met Ser Tyr Tyr His His His His His His Asp Tyr Asp Ile Pro Thr
1               5                   10                  15

Thr Glu Asn Leu Tyr Phe Gln Gly Ala Met Asp Pro Met Lys Lys Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Ser Arg Pro Leu Ser Asn
        195                 200                 205

Leu Glu Pro Ala Val Ser Arg His Ala Val Pro Ser Leu Ser Arg Ser
    210                 215                 220

Thr Arg Gly Ser
225

<210> SEQ ID NO 35
<211> LENGTH: 2037
<212> TYPE: DNA
<213> ORGANISM: Artificial
<220> FEATURE:
<223> OTHER INFORMATION: Hepatitis B Virus plus murine
<220> FEATURE:
<221> NAME/KEY: CDS
<222> LOCATION: (1)..(2037)

<400> SEQUENCE: 35 atg tcg tac tac cat cac cat cac cat cac gat tac gat atc cca acg         48
Met Ser Tyr Tyr His His His His His His Asp Tyr Asp Ile Pro Thr
1               5                   10                  15 acc gaa aac ctg tat ttt cag ggc gcc atg gat cct atg gga ggt tgg         96
Thr Glu Asn Leu Tyr Phe Gln Gly Ala Met Asp Pro Met Gly Gly Trp
            20                  25                  30
```

| | | |
|---|---|---|
| tca tca aaa cct cgc aaa ggc atg ggg acg aat ctt tct gtt ccc aac<br>Ser Ser Lys Pro Arg Lys Gly Met Gly Thr Asn Leu Ser Val Pro Asn<br>35                                 40                          45 | | 144 |
| cct ctg gga ttc ttt ccc gat cat cag ttg gac cct gta ttc gga gcc<br>Pro Leu Gly Phe Phe Pro Asp His Gln Leu Asp Pro Val Phe Gly Ala<br>50                                 55                          60 | | 192 |
| aac tca aac aat cca gat tgg gac ttc aac ccc atc aag gac cac tgg<br>Asn Ser Asn Asn Pro Asp Trp Asp Phe Asn Pro Ile Lys Asp His Trp<br>65                                 70                          75                        80 | | 240 |
| cca gca gcc aac cag gta gga gtg gga gca ttc ggg cca ggg ttc acc<br>Pro Ala Ala Asn Gln Val Gly Val Gly Ala Phe Gly Pro Gly Phe Thr<br>                           85                          90                          95 | | 288 |
| cct cca cac ggc ggt gtt ttg ggg tgg agc cct cag gct cag ggc atg<br>Pro Pro His Gly Gly Val Leu Gly Trp Ser Pro Gln Ala Gln Gly Met<br>                 100                        105                       110 | | 336 |
| ttg acc cca gtg tca aca att cct cct cct gcc tcc gcc aat cgg cag<br>Leu Thr Pro Val Ser Thr Ile Pro Pro Pro Ala Ser Ala Asn Arg Gln<br>             115                        120                       125 | | 384 |
| tca gga agg cag cct act ccc atc tct cca cct cta aga gac agt cat<br>Ser Gly Arg Gln Pro Thr Pro Ile Ser Pro Pro Leu Arg Asp Ser His<br>130                             135                         140 | | 432 |
| cct cag gcc atg cag tgg aat tcc act gcc ttc cac caa gct ctg caa<br>Pro Gln Ala Met Gln Trp Asn Ser Thr Ala Phe His Gln Ala Leu Gln<br>145                             150                         155                    160 | | 480 |
| gac ccc aga gtc agg ggt ctg tat ttt cct gct ggt ggc tcc agt tca<br>Asp Pro Arg Val Arg Gly Leu Tyr Phe Pro Ala Gly Gly Ser Ser Ser<br>                         165                         170                       175 | | 528 |
| gga aca gta aac cct gct ccg aat att gcc tct cac atc tcg tca atc<br>Gly Thr Val Asn Pro Ala Pro Asn Ile Ala Ser His Ile Ser Ser Ile<br>             180                        185                       190 | | 576 |
| tcc gcg agg act ggg gac cct gtg acg aac atg gag aac atc aca tca<br>Ser Ala Arg Thr Gly Asp Pro Val Thr Asn Met Glu Asn Ile Thr Ser<br>195                           200                         205 | | 624 |
| gga ttc cta gga ccc ctg ctc gtg tta cag gcg ggg ttt ttc ttg ttg<br>Gly Phe Leu Gly Pro Leu Leu Val Leu Gln Ala Gly Phe Phe Leu Leu<br>210                           215                         220 | | 672 |
| aca aga atc ctc aca ata ccg cag agt cta gac tcg tgg tgg act tct<br>Thr Arg Ile Leu Thr Ile Pro Gln Ser Leu Asp Ser Trp Trp Thr Ser<br>225                           230                         235                   240 | | 720 |
| ctc aat ttt cta ggg gga tca ccc gtg tgt ctt ggc caa aat tcg cag<br>Leu Asn Phe Leu Gly Gly Ser Pro Val Cys Leu Gly Gln Asn Ser Gln<br>                         245                         250                       255 | | 768 |
| tcc cca acc tcc aat cac tca cca acc tcc tgt cct cca att tgt cct<br>Ser Pro Thr Ser Asn His Ser Pro Thr Ser Cys Pro Pro Ile Cys Pro<br>                         260                         265                       270 | | 816 |
| ggt tat cgc tgg atg tgt ctg cgg cgt ttt atc ata ttc ctc ttc atc<br>Gly Tyr Arg Trp Met Cys Leu Arg Arg Phe Ile Ile Phe Leu Phe Ile<br>275                           280                         285 | | 864 |
| ctg ctg cta tgc ctc atc ttc tta ttg gtt ctt ctg gat tat caa ggt<br>Leu Leu Leu Cys Leu Ile Phe Leu Leu Val Leu Leu Asp Tyr Gln Gly<br>             290                        295                       300 | | 912 |
| atg ttg ccc gtt tgt cct cta att cca gga tca aca aca acc agt acg<br>Met Leu Pro Val Cys Pro Leu Ile Pro Gly Ser Thr Thr Thr Ser Thr<br>305                           310                         315                   320 | | 960 |
| gga cca tgc aaa acc tgc acg act cct gct caa ggc aac tct atg ttt<br>Gly Pro Cys Lys Thr Cys Thr Thr Pro Ala Gln Gly Asn Ser Met Phe<br>                         325                         330                       335 | | 1008 |
| ccc tca tgt tgc tgt aca aaa cct acg gat gga aat tgc acc tgt att<br>Pro Ser Cys Cys Cys Thr Lys Pro Thr Asp Gly Asn Cys Thr Cys Ile<br>                         340                         345                       350 | | 1056 |

-continued

| | | |
|---|---|---|
| ccc atc cca tcg tct tgg gct ttc gca aaa tac cta tgg gag tgg gcc<br>Pro Ile Pro Ser Ser Trp Ala Phe Ala Lys Tyr Leu Trp Glu Trp Ala<br>355                           360                         365 | 1104 |
| tca gtc cgt ttc tct tgg ctc agt tta cta gtg cca ttt gtt cag tgg<br>Ser Val Arg Phe Ser Trp Leu Ser Leu Leu Val Pro Phe Val Gln Trp<br>    370                         375                        380 | 1152 |
| ttc gta ggg ctt tcc ccc act gtt tgg ctt tca gct ata tgg atg atg<br>Phe Val Gly Leu Ser Pro Thr Val Trp Leu Ser Ala Ile Trp Met Met<br>385                         390                        395                400 | 1200 |
| tgg tat tgg ggg cca agt ctg tac agc atc gtg agt ccc ttt ata ccg<br>Trp Tyr Trp Gly Pro Ser Leu Tyr Ser Ile Val Ser Pro Phe Ile Pro<br>                  405                        410                        415 | 1248 |
| ctg tta cca att ttc ttt tgt ctc tgg gta tac att tcg cgg ccg caa<br>Leu Leu Pro Ile Phe Phe Cys Leu Trp Val Tyr Ile Ser Arg Pro Gln<br>              420                        425                        430 | 1296 |
| ggc ggc gga tcc gtg gac aag aaa att gtg ccc agg gat tgt ggt tgt<br>Gly Gly Gly Ser Val Asp Lys Lys Ile Val Pro Arg Asp Cys Gly Cys<br>435                           440                        445 | 1344 |
| aag cct tgc ata tgt aca gtc cca gaa gta tca tct gtc ttc atc ttc<br>Lys Pro Cys Ile Cys Thr Val Pro Glu Val Ser Ser Val Phe Ile Phe<br>    450                         455                        460 | 1392 |
| ccc cca aag ccc aag gat gtg ctc acc att act ctg act cct aag gtc<br>Pro Pro Lys Pro Lys Asp Val Leu Thr Ile Thr Leu Thr Pro Lys Val<br>465                           470                        475                480 | 1440 |
| acg tgt gtt gtg gta gac atc agc aag gat gat ccc gag gtc cag ttc<br>Thr Cys Val Val Val Asp Ile Ser Lys Asp Asp Pro Glu Val Gln Phe<br>                  485                        490                        495 | 1488 |
| agc tgg ttt gta gat gat gtg gag gtg cac aca gct cag acg caa ccc<br>Ser Trp Phe Val Asp Asp Val Glu Val His Thr Ala Gln Thr Gln Pro<br>              500                        505                        510 | 1536 |
| cgg gag gag cag ttc aac agc act ttc cgc tca gtc agt gaa ctt ccc<br>Arg Glu Glu Gln Phe Asn Ser Thr Phe Arg Ser Val Ser Glu Leu Pro<br>515                           520                        525 | 1584 |
| atc atg cac cag gac tgg ctc aat ggc aag gag ttc aaa tgc agg gtc<br>Ile Met His Gln Asp Trp Leu Asn Gly Lys Glu Phe Lys Cys Arg Val<br>    530                         535                        540 | 1632 |
| aac agt gca gct ttc cct gcc ccc atc gag aaa acc atc tcc aaa acc<br>Asn Ser Ala Ala Phe Pro Ala Pro Ile Glu Lys Thr Ile Ser Lys Thr<br>545                           550                        555                560 | 1680 |
| aaa ggc aga ccg aag gct cca cag gtg tac acc att cca cct ccc aag<br>Lys Gly Arg Pro Lys Ala Pro Gln Val Tyr Thr Ile Pro Pro Pro Lys<br>                  565                        570                        575 | 1728 |
| gag cag atg gcc aag gat aaa gtc agt ctg acc tgc atg ata aca gac<br>Glu Gln Met Ala Lys Asp Lys Val Ser Leu Thr Cys Met Ile Thr Asp<br>              580                        585                        590 | 1776 |
| ttc ttc cct gaa gac att act gtg gag tgg cag tgg aat ggg cag cca<br>Phe Phe Pro Glu Asp Ile Thr Val Glu Trp Gln Trp Asn Gly Gln Pro<br>         595                        600                        605 | 1824 |
| gcg gag aac tac aag aac act cag ccc atc atg gac aca gat ggc tct<br>Ala Glu Asn Tyr Lys Asn Thr Gln Pro Ile Met Asp Thr Asp Gly Ser<br>610                           615                        620 | 1872 |
| tac ttc gtc tac agc aag ctc aat gtg cag aag agc aac tgg gag gca<br>Tyr Phe Val Tyr Ser Lys Leu Asn Val Gln Lys Ser Asn Trp Glu Ala<br>625                           630                        635                640 | 1920 |
| gga aat act ttc acc tgc tct gtg tta cat gag ggc ctg cac aac cac<br>Gly Asn Thr Phe Thr Cys Ser Val Leu His Glu Gly Leu His Asn His<br>                  645                        650                        655 | 1968 |
| cat act gag aag agc ctc tcc cac tct cct ggg ctg caa agc ttg tcg<br>His Thr Glu Lys Ser Leu Ser His Ser Pro Gly Leu Gln Ser Leu Ser<br>              660                        665                        670 | 2016 |

```
aga agt act aga gga tca taa                                              2037
Arg Ser Thr Arg Gly Ser
        675
```

<210> SEQ ID NO 36
<211> LENGTH: 678
<212> TYPE: PRT
<213> ORGANISM: Artificial
<220> FEATURE:
<223> OTHER INFORMATION: Synthetic Construct

<400> SEQUENCE: 36

```
Met Ser Tyr Tyr His His His His His His Asp Tyr Asp Ile Pro Thr
1               5                   10                  15

Thr Glu Asn Leu Tyr Phe Gln Gly Ala Met Asp Pro Met Gly Gly Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Met Glu Asn Ile Thr Ser
        195                 200                 205

Gly Phe Leu Gly Pro Leu Leu Val Leu Gln Ala Gly Phe Phe Leu Leu
    210                 215                 220

Thr Arg Ile Leu Thr Ile Pro Gln Ser Leu Asp Ser Trp Trp Thr Ser
225                 230                 235                 240

Leu Asn Phe Leu Gly Gly Ser Pro Val Cys Leu Gly Gln Asn Ser Gln
                245                 250                 255

Ser Pro Thr Ser Asn His Ser Pro Thr Ser Cys Pro Pro Ile Cys Pro
            260                 265                 270

Gly Tyr Arg Trp Met Cys Leu Arg Arg Phe Ile Ile Phe Leu Phe Ile
        275                 280                 285

Leu Leu Leu Cys Leu Ile Phe Leu Leu Val Leu Leu Asp Tyr Gln Gly
    290                 295                 300

Met Leu Pro Val Cys Pro Leu Ile Pro Gly Ser Thr Thr Ser Thr
305                 310                 315                 320

Gly Pro Cys Lys Thr Cys Thr Thr Pro Ala Gln Gly Asn Ser Met Phe
                325                 330                 335

Pro Ser Cys Cys Cys Thr Lys Pro Thr Asp Gly Asn Cys Thr Cys Ile
            340                 345                 350
```

```
Pro Ile Pro Ser Ser Trp Ala Phe Ala Lys Tyr Leu Trp Glu Trp Ala
        355                 360                 365

Ser Val Arg Phe Ser Trp Leu Ser Leu Leu Val Pro Phe Val Gln Trp
    370                 375                 380

Phe Val Gly Leu Ser Pro Thr Val Trp Leu Ser Ala Ile Trp Met Met
385                 390                 395                 400

Trp Tyr Trp Gly Pro Ser Leu Tyr Ser Ile Val Ser Pro Phe Ile Pro
                405                 410                 415

Leu Leu Pro Ile Phe Phe Cys Leu Trp Val Tyr Ile Ser Arg Pro Gln
            420                 425                 430

Gly Gly Gly Ser Val Asp Lys Lys Ile Val Pro Arg Asp Cys Gly Cys
        435                 440                 445

Lys Pro Cys Ile Cys Thr Val Pro Glu Val Ser Ser Val Phe Ile Phe
450                 455                 460

Pro Pro Lys Pro Lys Asp Val Leu Thr Ile Thr Leu Thr Pro Lys Val
465                 470                 475                 480

Thr Cys Val Val Val Asp Ile Ser Lys Asp Asp Pro Glu Val Gln Phe
                485                 490                 495

Ser Trp Phe Val Asp Asp Val Glu Val His Thr Ala Gln Thr Gln Pro
                500                 505                 510

Arg Glu Glu Gln Phe Asn Ser Thr Phe Arg Ser Val Ser Glu Leu Pro
    515                 520                 525

Ile Met His Gln Asp Trp Leu Asn Gly Lys Glu Phe Lys Cys Arg Val
    530                 535                 540

Asn Ser Ala Ala Phe Pro Ala Pro Ile Glu Lys Thr Ile Ser Lys Thr
545                 550                 555                 560

Lys Gly Arg Pro Lys Ala Pro Gln Val Tyr Thr Ile Pro Pro Pro Lys
                565                 570                 575

Glu Gln Met Ala Lys Asp Lys Val Ser Leu Thr Cys Met Ile Thr Asp
            580                 585                 590

Phe Phe Pro Glu Asp Ile Thr Val Glu Trp Gln Trp Asn Gly Gln Pro
        595                 600                 605

Ala Glu Asn Tyr Lys Asn Thr Gln Pro Ile Met Asp Thr Asp Gly Ser
    610                 615                 620

Tyr Phe Val Tyr Ser Lys Leu Asn Val Gln Lys Ser Asn Trp Glu Ala
625                 630                 635                 640

Gly Asn Thr Phe Thr Cys Ser Val Leu His Glu Gly Leu His Asn His
                645                 650                 655

His Thr Glu Lys Ser Leu Ser His Ser Pro Gly Leu Gln Ser Leu Ser
            660                 665                 670

Arg Ser Thr Arg Gly Ser
        675

<210> SEQ ID NO 37
<211> LENGTH: 1365
<212> TYPE: DNA
<213> ORGANISM: Hepatitis B virus
<220> FEATURE:
<221> NAME/KEY: CDS
<222> LOCATION: (1)..(1365)

<400> SEQUENCE: 37 atg tcg tac tac cat cac cat cac cat cac gat tac gat atc cca acg    48
Met Ser Tyr Tyr His His His His His His Asp Tyr Asp Ile Pro Thr
 1               5                  10                  15 acc gaa aac ctg tat ttt cag ggc gcc atg gat cct atg gga ggt tgg    96
Thr Glu Asn Leu Tyr Phe Gln Gly Ala Met Asp Pro Met Gly Gly Trp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 20  |     |     |     |     | 25  |     |     |     |     | 30  |     |     |     |      |
| tca | tca | aaa | cct | cgc | aaa | ggc | atg | ggg | acg | aat | ctt | tct | gtt | ccc | aac | 144  |
| Ser | Ser | Lys | Pro | Arg | Lys | Gly | Met | Gly | Thr | Asn | Leu | Ser | Val | Pro | Asn |      |
|     |     | 35  |     |     |     | 40  |     |     |     |     | 45  |     |     |     |     |      |
| cct | ctg | gga | ttc | ttt | ccc | gat | cat | cag | ttg | gac | cct | gta | ttc | gga | gcc | 192  |
| Pro | Leu | Gly | Phe | Phe | Pro | Asp | His | Gln | Leu | Asp | Pro | Val | Phe | Gly | Ala |      |
| 50  |     |     |     |     | 55  |     |     |     |     | 60  |     |     |     |     |     |      |
| aac | tca | aac | aat | cca | gat | tgg | gac | ttc | aac | ccc | atc | aag | gac | cac | tgg | 240  |
| Asn | Ser | Asn | Asn | Pro | Asp | Trp | Asp | Phe | Asn | Pro | Ile | Lys | Asp | His | Trp |      |
| 65  |     |     |     | 70  |     |     |     |     | 75  |     |     |     |     | 80  |     |      |
| cca | gca | gcc | aac | cag | gta | gga | gtg | gga | gca | ttc | ggg | cca | ggg | ttc | acc | 288  |
| Pro | Ala | Ala | Asn | Gln | Val | Gly | Val | Gly | Ala | Phe | Gly | Pro | Gly | Phe | Thr |      |
|     |     |     | 85  |     |     |     |     | 90  |     |     |     |     | 95  |     |     |      |
| cct | cca | cac | ggc | ggt | gtt | ttg | ggg | tgg | agc | cct | cag | gct | cag | ggc | atg | 336  |
| Pro | Pro | His | Gly | Gly | Val | Leu | Gly | Trp | Ser | Pro | Gln | Ala | Gln | Gly | Met |      |
|     |     | 100 |     |     |     |     | 105 |     |     |     |     | 110 |     |     |     |      |
| ttg | acc | cca | gtg | tca | aca | att | cct | cct | cct | gcc | tcc | gcc | aat | cgg | cag | 384  |
| Leu | Thr | Pro | Val | Ser | Thr | Ile | Pro | Pro | Pro | Ala | Ser | Ala | Asn | Arg | Gln |      |
| 115 |     |     |     |     | 120 |     |     |     |     | 125 |     |     |     |     |     |      |
| tca | gga | agg | cag | cct | act | ccc | atc | tct | cca | cct | cta | aga | gac | agt | cat | 432  |
| Ser | Gly | Arg | Gln | Pro | Thr | Pro | Ile | Ser | Pro | Pro | Leu | Arg | Asp | Ser | His |      |
|     | 130 |     |     |     |     | 135 |     |     |     |     | 140 |     |     |     |     |      |
| cct | cag | gcc | atg | cag | tgg | aat | tcc | act | gcc | ttc | cac | caa | gct | ctg | caa | 480  |
| Pro | Gln | Ala | Met | Gln | Trp | Asn | Ser | Thr | Ala | Phe | His | Gln | Ala | Leu | Gln |      |
| 145 |     |     |     |     | 150 |     |     |     |     | 155 |     |     |     |     | 160 |      |
| gac | ccc | aga | gtc | agg | ggt | ctg | tat | ttt | cct | gct | ggt | ggc | tcc | agt | tca | 528  |
| Asp | Pro | Arg | Val | Arg | Gly | Leu | Tyr | Phe | Pro | Ala | Gly | Gly | Ser | Ser | Ser |      |
|     |     |     |     | 165 |     |     |     |     | 170 |     |     |     |     | 175 |     |      |
| gga | aca | gta | aac | cct | gct | ccg | aat | att | gcc | tct | cac | atc | tcg | tca | atc | 576  |
| Gly | Thr | Val | Asn | Pro | Ala | Pro | Asn | Ile | Ala | Ser | His | Ile | Ser | Ser | Ile |      |
|     |     |     | 180 |     |     |     |     | 185 |     |     |     |     | 190 |     |     |      |
| tcc | gcg | agg | act | ggg | gac | cct | gtg | acg | aac | atg | gag | aac | atc | aca | tca | 624  |
| Ser | Ala | Arg | Thr | Gly | Asp | Pro | Val | Thr | Asn | Met | Glu | Asn | Ile | Thr | Ser |      |
|     |     | 195 |     |     |     |     | 200 |     |     |     |     | 205 |     |     |     |      |
| gga | ttc | cta | gga | ccc | ctg | ctc | gtg | tta | cag | gcg | ggg | ttt | ttc | ttg | ttg | 672  |
| Gly | Phe | Leu | Gly | Pro | Leu | Leu | Val | Leu | Gln | Ala | Gly | Phe | Phe | Leu | Leu |      |
|     | 210 |     |     |     |     | 215 |     |     |     |     | 220 |     |     |     |     |      |
| aca | aga | atc | ctc | aca | ata | ccg | cag | agt | cta | gac | tcg | tgg | tgg | act | tct | 720  |
| Thr | Arg | Ile | Leu | Thr | Ile | Pro | Gln | Ser | Leu | Asp | Ser | Trp | Trp | Thr | Ser |      |
| 225 |     |     |     |     | 230 |     |     |     |     | 235 |     |     |     |     | 240 |      |
| ctc | aat | ttt | cta | ggg | gga | tca | ccc | gtg | tgt | ctt | ggc | caa | aat | tcg | cag | 768  |
| Leu | Asn | Phe | Leu | Gly | Gly | Ser | Pro | Val | Cys | Leu | Gly | Gln | Asn | Ser | Gln |      |
|     |     |     |     | 245 |     |     |     |     | 250 |     |     |     |     | 255 |     |      |
| tcc | cca | acc | tcc | aat | cac | tca | cca | acc | tcc | tgt | cct | cca | att | tgt | cct | 816  |
| Ser | Pro | Thr | Ser | Asn | His | Ser | Pro | Thr | Ser | Cys | Pro | Pro | Ile | Cys | Pro |      |
|     |     |     | 260 |     |     |     |     | 265 |     |     |     |     | 270 |     |     |      |
| ggt | tat | cgc | tgg | atg | tgt | ctg | cgg | cgt | ttt | atc | ata | ttc | ctc | ttc | atc | 864  |
| Gly | Tyr | Arg | Trp | Met | Cys | Leu | Arg | Arg | Phe | Ile | Ile | Phe | Leu | Phe | Ile |      |
|     |     | 275 |     |     |     |     | 280 |     |     |     |     | 285 |     |     |     |      |
| ctg | ctg | cta | tgc | ctc | atc | ttc | tta | ttg | gtt | ctt | ctg | gat | tat | caa | ggt | 912  |
| Leu | Leu | Leu | Cys | Leu | Ile | Phe | Leu | Leu | Val | Leu | Leu | Asp | Tyr | Gln | Gly |      |
|     | 290 |     |     |     |     | 295 |     |     |     |     | 300 |     |     |     |     |      |
| atg | ttg | ccc | gtt | tgt | cct | cta | att | cca | gga | tca | aca | aca | acc | agt | acg | 960  |
| Met | Leu | Pro | Val | Cys | Pro | Leu | Ile | Pro | Gly | Ser | Thr | Thr | Thr | Ser | Thr |      |
| 305 |     |     |     |     | 310 |     |     |     |     | 315 |     |     |     |     | 320 |      |
| gga | cca | tgc | aaa | acc | tgc | acg | act | cct | gct | caa | ggc | aac | tct | atg | ttt | 1008 |
| Gly | Pro | Cys | Lys | Thr | Cys | Thr | Thr | Pro | Ala | Gln | Gly | Asn | Ser | Met | Phe |      |
|     |     |     |     | 325 |     |     |     |     | 330 |     |     |     |     | 335 |     |      |
| ccc | tca | tgt | tgc | tgt | aca | aaa | cct | acg | gat | gga | aat | tgc | acc | tgt | att | 1056 |
| Pro | Ser | Cys | Cys | Cys | Thr | Lys | Pro | Thr | Asp | Gly | Asn | Cys | Thr | Cys | Ile |      |

```
                          340                 345                 350
ccc atc cca tcg tct tgg gct ttc gca aaa tac cta tgg gag tgg gcc      1104
Pro Ile Pro Ser Ser Trp Ala Phe Ala Lys Tyr Leu Trp Glu Trp Ala
        355                 360                 365 tca gtc cgt ttc tct tgg ctc agt tta cta gtg cca ttt gtt cag tgg      1152
Ser Val Arg Phe Ser Trp Leu Ser Leu Leu Val Pro Phe Val Gln Trp
370                 375                 380 ttc gta ggg ctt tcc ccc act gtt tgg ctt tca gct ata tgg atg atg      1200
Phe Val Gly Leu Ser Pro Thr Val Trp Leu Ser Ala Ile Trp Met Met
385                 390                 395                 400 tgg tat tgg ggg cca agt ctg tac agc atc gtg agt ccc ttt ata ccg      1248
Trp Tyr Trp Gly Pro Ser Leu Tyr Ser Ile Val Ser Pro Phe Ile Pro
                405                 410                 415 ctg tta cca att ttc ttt tgt ctc tgg gta tac att tcg cgg ccg ctt      1296
Leu Leu Pro Ile Phe Phe Cys Leu Trp Val Tyr Ile Ser Arg Pro Leu
            420                 425                 430 tcg aat cta gag cct gca gtc tcg agg cat gcg gta cca agc ttg tcg      1344
Ser Asn Leu Glu Pro Ala Val Ser Arg His Ala Val Pro Ser Leu Ser
        435                 440                 445 aga agt act aga gga tca taa                                          1365
Arg Ser Thr Arg Gly Ser
    450

<210> SEQ ID NO 38
<211> LENGTH: 454
<212> TYPE: PRT
<213> ORGANISM: Hepatitis B virus

<400> SEQUENCE: 38

Met Ser Tyr Tyr His His His His His Asp Tyr Asp Ile Pro Thr
1               5                   10                  15

Thr Glu Asn Leu Tyr Phe Gln Gly Ala Met Asp Pro Met Gly Gly Trp
                20                  25                  30

Ser Ser Lys Pro Arg Lys Gly Met Gly Thr Asn Leu Ser Val Pro Asn
            35                  40                  45

Pro Leu Gly Phe Phe Pro Asp His Gln Leu Asp Pro Val Phe Gly Ala
50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Met Glu Asn Ile Thr Ser
        195                 200                 205

Gly Phe Leu Gly Pro Leu Leu Val Leu Gln Ala Gly Phe Phe Leu Leu
210                 215                 220
```

```
Thr Arg Ile Leu Thr Ile Pro Gln Ser Leu Asp Ser Trp Trp Thr Ser
225                 230                 235                 240

Leu Asn Phe Leu Gly Ser Pro Val Cys Leu Gly Gln Asn Ser Gln
            245                 250                 255

Ser Pro Thr Ser Asn His Ser Pro Thr Ser Cys Pro Pro Ile Cys Pro
            260                 265                 270

Gly Tyr Arg Trp Met Cys Leu Arg Arg Phe Ile Ile Phe Leu Phe Ile
            275                 280                 285

Leu Leu Leu Cys Leu Ile Phe Leu Leu Val Leu Leu Asp Tyr Gln Gly
            290                 295                 300

Met Leu Pro Val Cys Pro Leu Ile Pro Gly Ser Thr Thr Thr Ser Thr
305                 310                 315                 320

Gly Pro Cys Lys Thr Cys Thr Thr Pro Ala Gln Gly Asn Ser Met Phe
            325                 330                 335

Pro Ser Cys Cys Cys Thr Lys Pro Thr Asp Gly Asn Cys Thr Cys Ile
            340                 345                 350

Pro Ile Pro Ser Ser Trp Ala Phe Ala Lys Tyr Leu Trp Glu Trp Ala
            355                 360                 365

Ser Val Arg Phe Ser Trp Leu Ser Leu Leu Val Pro Phe Val Gln Trp
    370                 375                 380

Phe Val Gly Leu Ser Pro Thr Val Trp Leu Ser Ala Ile Trp Met Met
385                 390                 395                 400

Trp Tyr Trp Gly Pro Ser Leu Tyr Ser Ile Val Ser Pro Phe Ile Pro
            405                 410                 415

Leu Leu Pro Ile Phe Phe Cys Leu Trp Val Tyr Ile Ser Arg Pro Leu
            420                 425                 430

Ser Asn Leu Glu Pro Ala Val Ser Arg His Ala Val Pro Ser Leu Ser
            435                 440                 445

Arg Ser Thr Arg Gly Ser
    450

<210> SEQ ID NO 39
<211> LENGTH: 1383
<212> TYPE: DNA
<213> ORGANISM: Artificial
<220> FEATURE:
<223> OTHER INFORMATION: Hepatitis B virus plus murine
<220> FEATURE:
<221> NAME/KEY: CDS
<222> LOCATION: (1)..(1383)

<400> SEQUENCE: 39 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gac att gac cct tat aaa    96
Thr Glu Asn Leu Tyr Phe Gln Gly Ala Met Asp Ile Asp Pro Tyr Lys
            20                  25                  30 gaa ttt gga gct act gtg gag tta ctc tcg ttt ttg cct tct gac ttc   144
Glu Phe Gly Ala Thr Val Glu Leu Leu Ser Phe Leu Pro Ser Asp Phe
        35                  40                  45 ttt cct tcc gtc aga gat ctc cta gac acc gcc tcg gct ctg tat cgg   192
Phe Pro Ser Val Arg Asp Leu Leu Asp Thr Ala Ser Ala Leu Tyr Arg
    50                  55                  60 gaa gcc tta gag tct cct gag cat tgc tca cct cac cat acc gca ctc   240
Glu Ala Leu Glu Ser Pro Glu His Cys Ser Pro His His Thr Ala Leu
65                  70                  75                  80 agg caa gca att ctc tgc tgg ggg gaa ttg atg act cta gct acc tgg   288
Arg Gln Ala Ile Leu Cys Trp Gly Glu Leu Met Thr Leu Ala Thr Trp
```

```
                            85                  90                  95 gtg ggt aat aat ttg gaa gat cca gca tcc agg gat cta gta gtc aat      336
Val Gly Asn Asn Leu Glu Asp Pro Ala Ser Arg Asp Leu Val Val Asn
                100                 105                 110 tat gtt aat act aac atg gga tta aag atc agg caa ctc ttg tgg ttt      384
Tyr Val Asn Thr Asn Met Gly Leu Lys Ile Arg Gln Leu Leu Trp Phe
            115                 120                 125 cat atc tct tgc ctt act ttt gga aga gaa act gta ctt gaa tat ttg      432
His Ile Ser Cys Leu Thr Phe Gly Arg Glu Thr Val Leu Glu Tyr Leu
        130                 135                 140 gtc tct ttc gga gtg tgg att cgc act cct cca gcc tat aga cca cca      480
Val Ser Phe Gly Val Trp Ile Arg Thr Pro Pro Ala Tyr Arg Pro Pro
145                 150                 155                 160 aat gcc cct atc tta tca aca ctt ccg gaa act act gtt gtt aga cga      528
Asn Ala Pro Ile Leu Ser Thr Leu Pro Glu Thr Thr Val Val Arg Arg
                165                 170                 175 cgg gac cga ggc agg tcc cct aga aga aga act ccc tcg cct cgc aga      576
Arg Asp Arg Gly Arg Ser Pro Arg Arg Arg Thr Pro Ser Pro Arg Arg
            180                 185                 190 cgc aga tct caa tcg ccg cgt cgc aga aga tct caa tct cgg gaa tct      624
Arg Arg Ser Gln Ser Pro Arg Arg Arg Ser Gln Ser Arg Glu Ser
        195                 200                 205 caa tgt tcg cgg ccg caa ggc ggc gga tcc gtg gac aag aaa att gtg      672
Gln Cys Ser Arg Pro Gln Gly Gly Gly Ser Val Asp Lys Lys Ile Val
210                 215                 220 ccc agg gat tgt ggt tgt aag cct tgc ata tgt aca gtc cca gaa gta      720
Pro Arg Asp Cys Gly Cys Lys Pro Cys Ile Cys Thr Val Pro Glu Val
225                 230                 235                 240 tca tct gtc ttc atc ttc ccc cca aag ccc aag gat gtg ctc acc att      768
Ser Ser Val Phe Ile Phe Pro Pro Lys Pro Lys Asp Val Leu Thr Ile
                245                 250                 255 act ctg act cct aag gtc acg tgt gtt gtg gta gac atc agc aag gat      816
Thr Leu Thr Pro Lys Val Thr Cys Val Val Val Asp Ile Ser Lys Asp
            260                 265                 270 gat ccc gag gtc cag ttc agc tgg ttt gta gat gat gtg gag gtg cac      864
Asp Pro Glu Val Gln Phe Ser Trp Phe Val Asp Asp Val Glu Val His
        275                 280                 285 aca gct cag acg caa ccc cgg gag gag cag ttc aac agc act ttc cgc      912
Thr Ala Gln Thr Gln Pro Arg Glu Glu Gln Phe Asn Ser Thr Phe Arg
    290                 295                 300 tca gtc agt gaa ctt ccc atc atg cac cag gac tgg ctc aat ggc aag      960
Ser Val Ser Glu Leu Pro Ile Met His Gln Asp Trp Leu Asn Gly Lys
305                 310                 315                 320 gag ttc aaa tgc agg gtc aac agt gca gct ttc cct gcc ccc atc gag     1008
Glu Phe Lys Cys Arg Val Asn Ser Ala Ala Phe Pro Ala Pro Ile Glu
                325                 330                 335 aaa acc atc tcc aaa acc aaa ggc aga ccg aag gct cca cag gtg tac     1056
Lys Thr Ile Ser Lys Thr Lys Gly Arg Pro Lys Ala Pro Gln Val Tyr
            340                 345                 350 acc att cca cct ccc aag gag cag atg gcc aag gat aaa gtc agt ctg     1104
Thr Ile Pro Pro Pro Lys Glu Gln Met Ala Lys Asp Lys Val Ser Leu
        355                 360                 365 acc tgc atg ata aca gac ttc ttc cct gaa gac att act gtg gag tgg     1152
Thr Cys Met Ile Thr Asp Phe Phe Pro Glu Asp Ile Thr Val Glu Trp
    370                 375                 380 cag tgg aat ggg cag cca gcg gag aac tac aag aac act cag ccc atc     1200
Gln Trp Asn Gly Gln Pro Ala Glu Asn Tyr Lys Asn Thr Gln Pro Ile
385                 390                 395                 400 atg gac aca gat ggc tct tac ttc gtc tac agc aag ctc aat gtg cag     1248
Met Asp Thr Asp Gly Ser Tyr Phe Val Tyr Ser Lys Leu Asn Val Gln
```

```
                405                 410                 415
aag agc aac tgg gag gca gga aat act ttc acc tgc tct gtg tta cat       1296
Lys Ser Asn Trp Glu Ala Gly Asn Thr Phe Thr Cys Ser Val Leu His
        420                 425                 430 gag ggc ctg cac aac cac cat act gag aag agc ctc tcc cac tct cct       1344
Glu Gly Leu His Asn His His Thr Glu Lys Ser Leu Ser His Ser Pro
        435                 440                 445 ggg ctg caa agc ttg tcg aga agt act aga gga tca taa                   1383
Gly Leu Gln Ser Leu Ser Arg Ser Thr Arg Gly Ser
        450                 455                 460

<210> SEQ ID NO 40
<211> LENGTH: 460
<212> TYPE: PRT
<213> ORGANISM: Artificial
<220> FEATURE:
<223> OTHER INFORMATION: Synthetic Construct

<400> SEQUENCE: 40

Met Ser Tyr Tyr His His His His Asp Tyr Asp Ile Pro Thr
 1               5                  10                  15

Thr Glu Asn Leu Tyr Phe Gln Gly Ala Met Asp Ile Asp Pro Tyr Lys
            20                  25                  30

Glu Phe Gly Ala Thr Val Glu Leu Leu Ser Phe Leu Pro Ser Asp Phe
        35                  40                  45

Phe Pro Ser Val Arg Asp Leu Leu Asp Thr Ala Ser Ala Leu Tyr Arg
    50                  55                  60

Glu Ala Leu Glu Ser Pro Glu His Cys Ser Pro His His Thr Ala Leu
65                  70                  75                  80

Arg Gln Ala Ile Leu Cys Trp Gly Glu Leu Met Thr Leu Ala Thr Trp
                85                  90                  95

Val Gly Asn Asn Leu Glu Asp Pro Ala Ser Arg Asp Leu Val Val Asn
            100                 105                 110

Tyr Val Asn Thr Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val Arg Arg
                165                 170                 175

Arg Asp Arg Gly Arg Ser Pro Arg Arg Thr Pro Ser Pro Arg Arg
            180                 185                 190

Arg Arg Ser Gln Ser Pro Arg Arg Arg Ser Gln Ser Arg Glu Ser
        195                 200                 205

Gln Cys Ser Arg Pro Gln Gly Gly Ser Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270

Asp Pro Glu Val Gln Phe Ser Trp Phe Val Asp Val Glu Val His
        275                 280                 285

Thr Ala Gln Thr Gln Pro Arg Glu Glu Gln Phe Asn Ser Thr Phe Arg
    290                 295                 300
```

```
Ser Val Ser Glu Leu Pro Ile Met His Gln Asp Trp Leu Asn Gly Lys
305                 310                 315                 320

Glu Phe Lys Cys Arg Val Asn Ser Ala Ala Phe Pro Ala Pro Ile Glu
                325                 330                 335

Lys Thr Ile Ser Lys Thr Lys Gly Arg Pro Lys Ala Pro Gln Val Tyr
            340                 345                 350

Thr Ile Pro Pro Lys Glu Gln Met Ala Lys Asp Lys Val Ser Leu
        355                 360                 365

Thr Cys Met Ile Thr Asp Phe Phe Pro Glu Asp Ile Thr Val Glu Trp
    370                 375                 380

Gln Trp Asn Gly Gln Pro Ala Glu Asn Tyr Lys Thr Gln Pro Ile
385                 390                 395                 400

Met Asp Thr Asp Gly Ser Tyr Phe Val Tyr Ser Lys Leu Asn Val Gln
                405                 410                 415

Lys Ser Asn Trp Glu Ala Gly Asn Thr Phe Thr Cys Ser Val Leu His
                420                 425                 430

Glu Gly Leu His Asn His His Thr Glu Lys Ser Leu Ser His Ser Pro
            435                 440                 445

Gly Leu Gln Ser Leu Ser Arg Ser Thr Arg Gly Ser
    450                 455                 460

<210> SEQ ID NO 41
<211> LENGTH: 711
<212> TYPE: DNA
<213> ORGANISM: Hepatitis B virus
<220> FEATURE:
<221> NAME/KEY: CDS
<222> LOCATION: (1)..(711)

<400> SEQUENCE: 41 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gac att gac cct tat aaa      96
Thr Glu Asn Leu Tyr Phe Gln Gly Ala Met Asp Ile Asp Pro Tyr Lys
            20                  25                  30 gaa ttt gga gct act gtg gag tta ctc tcg ttt ttg cct tct gac ttc     144
Glu Phe Gly Ala Thr Val Glu Leu Leu Ser Phe Leu Pro Ser Asp Phe
        35                  40                  45 ttt cct tcc gtc aga gat ctc cta gac acc gcc tcg gct ctg tat cgg    192
Phe Pro Ser Val Arg Asp Leu Leu Asp Thr Ala Ser Ala Leu Tyr Arg
    50                  55                  60 gaa gcc tta gag tct cct gag cat tgc tca cct cac cat acc gca ctc    240
Glu Ala Leu Glu Ser Pro Glu His Cys Ser Pro His His Thr Ala Leu
65                  70                  75                  80 agg caa gcc att ctc tgc tgg ggg gaa ttg atg act cta gct acc tgg    288
Arg Gln Ala Ile Leu Cys Trp Gly Glu Leu Met Thr Leu Ala Thr Trp
                85                  90                  95 gtg ggt aat aat ttg gaa gat cca gca tcc agg gat cta gta gtc aat    336
Val Gly Asn Asn Leu Glu Asp Pro Ala Ser Arg Asp Leu Val Val Asn
            100                 105                 110 tat gtt aat act aac atg gga tta aag atc agg caa ctc ttg tgg ttt    384
Tyr Val Asn Thr Asn Met Gly Leu Lys Ile Arg Gln Leu Leu Trp Phe
        115                 120                 125 cat atc tct tgc ctt act ttt gga aga gaa act gta ctt gaa tat ttg    432
His Ile Ser Cys Leu Thr Phe Gly Arg Glu Thr Val Leu Glu Tyr Leu
    130                 135                 140 gtc tct ttc gga gtg tgg att cgc act cct cca gcc tat aga cca cca    480
Val Ser Phe Gly Val Trp Ile Arg Thr Pro Pro Ala Tyr Arg Pro Pro
```

```
                    145                 150                 155                 160
aat gcc cct atc tta tca aca ctt ccg gaa act act gtt gtt aga cga    528
Asn Ala Pro Ile Leu Ser Thr Leu Pro Glu Thr Thr Val Val Arg Arg
                165                 170                 175 cgg gac cga ggc agg tcc cct aga aga aga act ccc tcg cct cgc aga    576
Arg Asp Arg Gly Arg Ser Pro Arg Arg Arg Thr Pro Ser Pro Arg Arg
            180                 185                 190 cgc aga tct caa tcg ccg cgt cgc aga aga tct caa tct cgg gaa tct    624
Arg Arg Ser Gln Ser Pro Arg Arg Arg Ser Gln Ser Arg Glu Ser
        195                 200                 205 caa tgt tcg cgg ccg ctt tcg aat cta gag cct gca gtc tcg agg cat    672
Gln Cys Ser Arg Pro Leu Ser Asn Leu Glu Pro Ala Val Ser Arg His
    210                 215                 220 gcg gta cca agc ttg tcg aga agt act aga gga tca taa                711
Ala Val Pro Ser Leu Ser Arg Ser Thr Arg Gly Ser
225                 230                 235

<210> SEQ ID NO 42
<211> LENGTH: 236
<212> TYPE: PRT
<213> ORGANISM: Hepatitis B virus

<400> SEQUENCE: 42

Met Ser Tyr Tyr His His His His His Asp Tyr Asp Ile Pro Thr
1               5                   10                  15

Thr Glu Asn Leu Tyr Phe Gln Gly Ala Met Asp Ile Asp Pro Tyr Lys
            20                  25                  30

Glu Phe Gly Ala Thr Val Glu Leu Leu Ser Phe Leu Pro Ser Asp Phe
        35                  40                  45

Phe Pro Ser Val Arg Asp Leu Leu Asp Thr Ala Ser Ala Leu Tyr Arg
    50                  55                  60

Glu Ala Leu Glu Ser Pro Glu His Cys Ser Pro His His Thr Ala Leu
65                  70                  75                  80

Arg Gln Ala Ile Leu Cys Trp Gly Glu Leu Met Thr Leu Ala Thr Trp
                85                  90                  95

Val Gly Asn Asn Leu Glu Asp Pro Ala Ser Arg Asp Leu Val Val Asn
            100                 105                 110

Tyr Val Asn Thr Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val Arg Arg
                165                 170                 175

Arg Asp Arg Gly Arg Ser Pro Arg Arg Arg Thr Pro Ser Pro Arg Arg
            180                 185                 190

Arg Arg Ser Gln Ser Pro Arg Arg Arg Ser Gln Ser Arg Glu Ser
        195                 200                 205

Gln Cys Ser Arg Pro Leu Ser Asn Leu Glu Pro Ala Val Ser Arg His
    210                 215                 220

Ala Val Pro Ser Leu Ser Arg Ser Thr Arg Gly Ser
225                 230                 235

<210> SEQ ID NO 43
<211> LENGTH: 1326
<212> TYPE: DNA
<213> ORGANISM: Artificial
```

<220> FEATURE:
<223> OTHER INFORMATION: Duck hepatitis B virus plus murine
<220> FEATURE:
<221> NAME/KEY: CDS
<222> LOCATION: (1)..(1326)

<400> SEQUENCE: 43

```
atg tcg tac tac cat cac cat cac cat cac gat tac gat atc cca acg      48
Met Ser Tyr Tyr His His His His His His Asp Tyr Asp Ile Pro Thr
1               5                  10                  15 acc gaa aac ctg tat ttt cag ggc gcc atg gat ccg gaa ttc atg ggg      96
Thr Glu Asn Leu Tyr Phe Gln Gly Ala Met Asp Pro Glu Phe Met Gly
                20                  25                  30 caa cat cca gca aaa tca atg gac gtc aga cgg ata gaa gga gga gaa    144
Gln His Pro Ala Lys Ser Met Asp Val Arg Arg Ile Glu Gly Gly Glu
            35                  40                  45 ata ctg tta aac caa ctt gcc gga agg atg atc cca aaa ggg act ttg    192
Ile Leu Leu Asn Gln Leu Ala Gly Arg Met Ile Pro Lys Gly Thr Leu
        50                  55                  60 aca tgg tca ggc aag ttt cca aca cta gat cac gtg tta gac cat gtg    240
Thr Trp Ser Gly Lys Phe Pro Thr Leu Asp His Val Leu Asp His Val
65                  70                  75                  80 caa aca atg gag gag ata aac acc ctc cag aat cag gga gct tgg cct    288
Gln Thr Met Glu Glu Ile Asn Thr Leu Gln Asn Gln Gly Ala Trp Pro
                85                  90                  95 gct ggg gcg gga agg aga gta gga tta tca aat ccg act cct caa gag    336
Ala Gly Ala Gly Arg Arg Val Gly Leu Ser Asn Pro Thr Pro Gln Glu
            100                 105                 110 att cct cag ccc cag tgg act ccc gag gaa gac caa aaa gca cgc gaa    384
Ile Pro Gln Pro Gln Trp Thr Pro Glu Glu Asp Gln Lys Ala Arg Glu
        115                 120                 125 gct ttt cgc cgt tat caa gaa gaa aga cca ccg gaa acc acc acc att    432
Ala Phe Arg Arg Tyr Gln Glu Glu Arg Pro Pro Glu Thr Thr Thr Ile
130                 135                 140 cct ccg tct tcc cct cct cag tgg aag cta caa ccc ggg gac gat cca    480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca    528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa acg    576
Glu Pro Ala Val Pro Val Ile Lys Thr Pro Pro Leu Lys Lys Lys Thr
            180                 185                 190 cgg ccg caa ggc ggc gga tcc gtg gac aag aaa att gtg ccc agg gat    624
Arg Pro Gln Gly Gly Gly Ser Val Asp Lys Lys Ile Val Pro Arg Asp
        195                 200                 205 tgt ggt tgt aag cct tgc ata tgt aca gtc cca gaa gta tca tct gtc    672
Cys Gly Cys Lys Pro Cys Ile Cys Thr Val Pro Glu Val Ser Ser Val
210                 215                 220 ttc atc ttc ccc cca aag ccc aag gat gtg ctc acc att act ctg act    720
Phe Ile Phe Pro Pro Lys Pro Lys Asp Val Leu Thr Ile Thr Leu Thr
225                 230                 235                 240 cct aag gtc acg tgt gtt gtg gta gac atc agc aag gat gat ccc gag    768
Pro Lys Val Thr Cys Val Val Val Asp Ile Ser Lys Asp Asp Pro Glu
                245                 250                 255 gtc cag ttc agc tgg ttt gta gat gat gtg gag gtg cac aca gct cag    816
Val Gln Phe Ser Trp Phe Val Asp Asp Val Glu Val His Thr Ala Gln
            260                 265                 270 acg caa ccc cgg gag gag cag ttc aac agc act ttc cgc tca gtc agt    864
Thr Gln Pro Arg Glu Glu Gln Phe Asn Ser Thr Phe Arg Ser Val Ser
        275                 280                 285
```

```
gaa ctt ccc atc atg cac cag gac tgg ctc aat ggc aag gag ttc aaa       912
Glu Leu Pro Ile Met His Gln Asp Trp Leu Asn Gly Lys Glu Phe Lys
    290                 295                 300 tgc agg gtc aac agt gca gct ttc cct gcc ccc atc gag aaa acc atc       960
Cys Arg Val Asn Ser Ala Ala Phe Pro Ala Pro Ile Glu Lys Thr Ile
305                 310                 315                 320 tcc aaa acc aaa ggc aga ccg aag gct cca cag gtg tac acc att cca      1008
Ser Lys Thr Lys Gly Arg Pro Lys Ala Pro Gln Val Tyr Thr Ile Pro
                325                 330                 335 cct ccc aag gag cag atg gcc aag gat aaa gtc agt ctg acc tgc atg      1056
Pro Pro Lys Glu Gln Met Ala Lys Asp Lys Val Ser Leu Thr Cys Met
            340                 345                 350 ata aca gac ttc ttc cct gaa gac att act gtg gag tgg cag tgg aat      1104
Ile Thr Asp Phe Phe Pro Glu Asp Ile Thr Val Glu Trp Gln Trp Asn
        355                 360                 365 ggg cag cca gcg gag aac tac aag aac act cag ccc atc atg gac aca      1152
Gly Gln Pro Ala Glu Asn Tyr Lys Asn Thr Gln Pro Ile Met Asp Thr
    370                 375                 380 gat ggc tct tac ttc gtc tac agc aag ctc aat gtg cag aag agc aac      1200
Asp Gly Ser Tyr Phe Val Tyr Ser Lys Leu Asn Val Gln Lys Ser Asn
385                 390                 395                 400 tgg gag gca gga aat act ttc acc tgc tct gtg tta cat gag ggc ctg      1248
Trp Glu Ala Gly Asn Thr Phe Thr Cys Ser Val Leu His Glu Gly Leu
                405                 410                 415 cac aac cac cat act gag aag agc ctc tcc cac tct cct ggg ctg caa      1296
His Asn His His Thr Glu Lys Ser Leu Ser His Ser Pro Gly Leu Gln
            420                 425                 430 agc ttg tcg aga agt act aga gga tca taa                              1326
Ser Leu Ser Arg Ser Thr Arg Gly Ser
        435                 440

<210> SEQ ID NO 44
<211> LENGTH: 441
<212> TYPE: PRT
<213> ORGANISM: Artificial
<220> FEATURE:
<223> OTHER INFORMATION: Synthetic Construct

<400> SEQUENCE: 44

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Gly
                20                  25                  30

Gln His Pro Ala Lys Ser Met Asp Val Arg Arg Ile Glu Gly Gly Glu
            35                  40                  45

Ile Leu Leu Asn Gln Leu Ala Gly Arg Met Ile Pro Lys Gly Thr Leu
        50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Glu Thr Thr Thr Ile
130                 135                 140

Pro Pro Ser Ser Pro Gln Trp Lys Leu Gln Pro Gly Asp Asp Pro
145                 150                 155                 160
```

```
Leu Leu Gly Asn Gln Ser Leu Leu Glu Thr His Pro Leu Tyr Gln Ser
            165                 170                 175

Glu Pro Ala Val Pro Val Ile Lys Thr Pro Pro Leu Lys Lys Lys Thr
        180                 185                 190

Arg Pro Gln Gly Gly Ser Val Asp Lys Lys Ile Val Pro Arg Asp
    195                 200                 205

Cys Gly Cys Lys Pro Cys Ile Cys Thr Val Pro Glu Val Ser Ser Val
210                 215                 220

Phe Ile Phe Pro Pro Lys Pro Lys Asp Val Leu Thr Ile Thr Leu Thr
225                 230                 235                 240

Pro Lys Val Thr Cys Val Val Asp Ile Ser Lys Asp Asp Pro Glu
            245                 250                 255

Val Gln Phe Ser Trp Phe Val Asp Val Glu Val His Thr Ala Gln
        260                 265                 270

Thr Gln Pro Arg Glu Glu Gln Phe Asn Ser Thr Phe Arg Ser Val Ser
    275                 280                 285

Glu Leu Pro Ile Met His Gln Asp Trp Leu Asn Gly Lys Glu Phe Lys
290                 295                 300

Cys Arg Val Asn Ser Ala Ala Phe Pro Ala Pro Ile Glu Lys Thr Ile
305                 310                 315                 320

Ser Lys Thr Lys Gly Arg Pro Lys Ala Pro Gln Val Tyr Thr Ile Pro
            325                 330                 335

Pro Pro Lys Glu Gln Met Ala Lys Asp Lys Val Ser Leu Thr Cys Met
        340                 345                 350

Ile Thr Asp Phe Phe Pro Glu Asp Ile Thr Val Glu Trp Gln Trp Asn
    355                 360                 365

Gly Gln Pro Ala Glu Asn Tyr Lys Asn Thr Gln Pro Ile Met Asp Thr
370                 375                 380

Asp Gly Ser Tyr Phe Val Tyr Ser Lys Leu Asn Val Gln Lys Ser Asn
385                 390                 395                 400

Trp Glu Ala Gly Asn Thr Phe Thr Cys Ser Val Leu His Glu Gly Leu
            405                 410                 415

His Asn His His Thr Glu Lys Ser Leu Ser His Ser Pro Gly Leu Gln
        420                 425                 430

Ser Leu Ser Arg Ser Thr Arg Gly Ser
    435                 440

<210> SEQ ID NO 45
<211> LENGTH: 654
<212> TYPE: DNA
<213> ORGANISM: Duck hepatitis B virus
<220> FEATURE:
<221> NAME/KEY: CDS
<222> LOCATION: (1)..(654)

<400> SEQUENCE: 45 atg tcg tac tac cat cac cat cac cat gat tac gat atc cca acg       48
Met Ser Tyr Tyr His His His His His Asp Tyr Asp Ile Pro Thr
1               5                   10                  15 acc gaa aac ctg tat ttt cag ggc gcc atg gat ccg gaa ttc atg ggg    96
Thr Glu Asn Leu Tyr Phe Gln Gly Ala Met Asp Pro Glu Phe Met Gly
            20                  25                  30 caa cat cca gca aaa tca atg gac gtc aga cgg ata gaa gga gga gaa  144
Gln His Pro Ala Lys Ser Met Asp Val Arg Arg Ile Glu Gly Gly Glu
        35                  40                  45 ata ctg tta aac caa ctt gcc gga agg atg atc cca aaa ggg act ttg  192
Ile Leu Leu Asn Gln Leu Ala Gly Arg Met Ile Pro Lys Gly Thr Leu
    50                  55                  60
```

```
aca tgg tca ggc aag ttt cca aca cta gat cac gtg tta gac cat gtg    240
Thr Trp Ser Gly Lys Phe Pro Thr Leu Asp His Val Leu Asp His Val
 65                  70                  75                  80 caa aca atg gag gag ata aac acc ctc cag aat cag gga gct tgg cct    288
Gln Thr Met Glu Glu Ile Asn Thr Leu Gln Asn Gln Gly Ala Trp Pro
                 85                  90                  95 gct ggg gcg gga agg aga gta gga tta tca aat ccg act cct caa gag    336
Ala Gly Ala Gly Arg Arg Val Gly Leu Ser Asn Pro Thr Pro Gln Glu
            100                 105                 110 att cct cag ccc cag tgg act ccc gag gaa gac caa aaa gca cgc gaa    384
Ile Pro Gln Pro Gln Trp Thr Pro Glu Glu Asp Gln Lys Ala Arg Glu
        115                 120                 125 gct ttt cgc cgt tat caa gaa gaa aga cca ccg gaa acc acc acc att    432
Ala Phe Arg Arg Tyr Gln Glu Glu Arg Pro Pro Glu Thr Thr Thr Ile
    130                 135                 140 cct ccg tct tcc cct cct cag tgg aag cta caa ccc ggg gac gat cca    480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca    528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa acg    576
Glu Pro Ala Val Pro Val Ile Lys Thr Pro Pro Leu Lys Lys Lys Thr
            180                 185                 190 cgg ccg ctt tcg aat cta gag cct gca gtc tcg agg cat gcg gta cca    624
Arg Pro Leu Ser Asn Leu Glu Pro Ala Val Ser Arg His Ala Val Pro
        195                 200                 205 agc ttg tcg aga agt act aga gga tca taa                            654
Ser Leu Ser Arg Ser Thr Arg Gly Ser
    210                 215

<210> SEQ ID NO 46
<211> LENGTH: 217
<212> TYPE: PRT
<213> ORGANISM: Duck hepatitis B virus

<400> SEQUENCE: 46

Met Ser Tyr Tyr His His His His His Asp Tyr Asp Ile Pro Thr
  1               5                  10                  15

Thr Glu Asn Leu Tyr Phe Gln Gly Ala Met Asp Pro Glu Phe Met Gly
             20                  25                  30

Gln His Pro Ala Lys Ser Met Asp Val Arg Arg Ile Glu Gly Gly Glu
         35                  40                  45

Ile Leu Leu Asn Gln Leu Ala Gly Arg Met Ile Pro Lys Gly Thr Leu
     50                  55                  60

Thr Trp Ser Gly Lys Phe Pro Thr Leu Asp His Val Leu Asp His Val
 65                  70                  75                  80

Gln Thr Met Glu Glu Ile Asn Thr Leu Gln Asn Gln Gly Ala Trp Pro
                 85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
```

```
                    165                 170                 175
Glu Pro Ala Val Pro Val Ile Lys Thr Pro Pro Leu Lys Lys Lys Thr
        180                 185                 190
Arg Pro Leu Ser Asn Leu Glu Pro Ala Val Ser Arg His Ala Val Pro
            195                 200                 205
Ser Leu Ser Arg Ser Thr Arg Gly Ser
        210                 215

<210> SEQ ID NO 47
<211> LENGTH: 1827
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1824)

<400> SEQUENCE: 47 atg tcg tac tac cat cac cat cac cat cac gat tac gat atc cca acg       48
Met Ser Tyr Tyr His His His His His His Asp Tyr Asp Ile Pro Thr
1               5                   10                  15 acc gaa aac ctg tat ttt cag ggc gcc atg gat ccg gaa ttc atg ggg       96
Thr Glu Asn Leu Tyr Phe Gln Gly Ala Met Asp Pro Glu Phe Met Gly
                20                  25                  30 caa cat cca gca aaa tca atg gac gtc aga cgg ata gaa gga gga gaa      144
Gln His Pro Ala Lys Ser Met Asp Val Arg Arg Ile Glu Gly Gly Glu
            35                  40                  45 ata ctg tta aac caa ctt gcc gga agg atg atc cca aaa ggg act ttg      192
Ile Leu Leu Asn Gln Leu Ala Gly Arg Met Ile Pro Lys Gly Thr Leu
        50                  55                  60 aca tgg tca ggc aag ttt cca aca cta gat cac gtg tta gac cat gtg      240
Thr Trp Ser Gly Lys Phe Pro Thr Leu Asp His Val Leu Asp His Val
65                  70                  75                  80 caa aca atg gag gag ata aac acc ctc cag aat cag gga gct tgg cct      288
Gln Thr Met Glu Glu Ile Asn Thr Leu Gln Asn Gln Gly Ala Trp Pro
                85                  90                  95 gct ggg gcg gga agg aga gta gga tta tca aat ccg act cct caa gag      336
Ala Gly Ala Gly Arg Arg Val Gly Leu Ser Asn Pro Thr Pro Gln Glu
            100                 105                 110 att cct cag ccc cag tgg act ccc gag gaa gac caa aaa gca cgc gaa      384
Ile Pro Gln Pro Gln Trp Thr Pro Glu Glu Asp Gln Lys Ala Arg Glu
        115                 120                 125 gct ttt cgc cgt tat caa gaa gaa aga cca ccg gaa acc acc acc att      432
Ala Phe Arg Arg Tyr Gln Glu Glu Arg Pro Pro Glu Thr Thr Thr Ile
130                 135                 140 cct ccg tct tcc cct cct cag tgg aag cta caa ccc ggg gac gat cca      480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca      528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa atg      576
Glu Pro Ala Val Pro Val Ile Lys Thr Pro Pro Leu Lys Lys Lys Met
            180                 185                 190 tct ggt acc ttc ggg gga ata cta gct ggc cta atc gga tta ctg gta      624
Ser Gly Thr Phe Gly Gly Ile Leu Ala Gly Leu Ile Gly Leu Leu Val
        195                 200                 205 agc ttt ttc ttg ttg ata aaa att cta gaa ata ctg agg agg cta gat      672
Ser Phe Phe Leu Leu Ile Lys Ile Leu Glu Ile Leu Arg Arg Leu Asp
210                 215                 220
```

```
tgg tgg tgg att tct ctc agt tct cca aag gga aaa atg caa tgc gct    720
Trp Trp Trp Ile Ser Leu Ser Ser Pro Lys Gly Lys Met Gln Cys Ala
225                 230                 235                 240 ttc caa gat act gga gcc caa atc tct cca cat tac gta gga tct tgc    768
Phe Gln Asp Thr Gly Ala Gln Ile Ser Pro His Tyr Val Gly Ser Cys
                245                 250                 255 ccg tgg gga tgc cca gga ttt ctt tgg acc tat ctc agg ctt ttt atc    816
Pro Trp Gly Cys Pro Gly Phe Leu Trp Thr Tyr Leu Arg Leu Phe Ile
            260                 265                 270 atc ttc ctc tta atc ctg cta gta gca gca ggc ttg ctg tat ctg acg    864
Ile Phe Leu Leu Ile Leu Leu Val Ala Ala Gly Leu Leu Tyr Leu Thr
        275                 280                 285 gac aac ggg tct act att tta gga aag ctc caa tgg gcg tcg gtc tca    912
Asp Asn Gly Ser Thr Ile Leu Gly Lys Leu Gln Trp Ala Ser Val Ser
290                 295                 300 gcc ctt ttc tcc tcc atc tct tca cta ctg ccc tcg gat ccg aaa tct    960
Ala Leu Phe Ser Ser Ile Ser Ser Leu Leu Pro Ser Asp Pro Lys Ser
305                 310                 315                 320 ctc gtc gct tta acg ttt gga ctt tca ctt ata tgg atg act tcc tcc   1008
Leu Val Ala Leu Thr Phe Gly Leu Ser Leu Ile Trp Met Thr Ser Ser
                325                 330                 335 tct gcc acc caa acg ctc gtc acc tta acg caa tta gcc acg ctg tct   1056
Ser Ala Thr Gln Thr Leu Val Thr Leu Thr Gln Leu Ala Thr Leu Ser
            340                 345                 350 gct ctt ttt tac aag agt tcg cgg ccg caa ggc ggc gga tcc gtg gac   1104
Ala Leu Phe Tyr Lys Ser Ser Arg Pro Gln Gly Gly Gly Ser Val Asp
        355                 360                 365 aag aaa att gtg ccc agg gat tgt ggt tgt aag cct tgc ata tgt aca   1152
Lys Lys Ile Val Pro Arg Asp Cys Gly Cys Lys Pro Cys Ile Cys Thr
370                 375                 380 gtc cca gaa gta tca tct gtc ttc atc ttc ccc cca aag ccc aag gat   1200
Val Pro Glu Val Ser Ser Val Phe Ile Phe Pro Pro Lys Pro Lys Asp
385                 390                 395                 400 gtg ctc acc att act ctg act cct aag gtc acg tgt gtt gtg gta gac   1248
Val Leu Thr Ile Thr Leu Thr Pro Lys Val Thr Cys Val Val Val Asp
                405                 410                 415 atc agc aag gat gat ccc gag gtc cag ttc agc tgg ttt gta gat gat   1296
Ile Ser Lys Asp Asp Pro Glu Val Gln Phe Ser Trp Phe Val Asp Asp
            420                 425                 430 gtg gag gtg cac aca gct cag acg caa ccc cgg gag gag cag ttc aac   1344
Val Glu Val His Thr Ala Gln Thr Gln Pro Arg Glu Glu Gln Phe Asn
        435                 440                 445 agc act ttc cgc tca gtc agt gaa ctt ccc atc atg cac cag gac tgg   1392
Ser Thr Phe Arg Ser Val Ser Glu Leu Pro Ile Met His Gln Asp Trp
450                 455                 460 ctc aat ggc aag gag ttc aaa tgc agg gtc aac agt gca gct ttc cct   1440
Leu Asn Gly Lys Glu Phe Lys Cys Arg Val Asn Ser Ala Ala Phe Pro
465                 470                 475                 480 gcc ccc atc gag aaa acc atc tcc aaa acc aaa ggc aga ccg aag gct   1488
Ala Pro Ile Glu Lys Thr Ile Ser Lys Thr Lys Gly Arg Pro Lys Ala
                485                 490                 495 cca cag gtg tac acc att cca cct ccc aag gag cag atg gcc aag gat   1536
Pro Gln Val Tyr Thr Ile Pro Pro Pro Lys Glu Gln Met Ala Lys Asp
            500                 505                 510 aaa gtc agt ctg acc tgc atg ata aca gac ttc ttc cct gaa gac att   1584
Lys Val Ser Leu Thr Cys Met Ile Thr Asp Phe Phe Pro Glu Asp Ile
        515                 520                 525 act gtg gag tgg cag tgg aat ggg cag cca gcg gag aac tac aag aac   1632
Thr Val Glu Trp Gln Trp Asn Gly Gln Pro Ala Glu Asn Tyr Lys Asn
530                 535                 540
```

-continued

| | | | | | | | | | | | | | | |
|---|---|---|---|---|---|---|---|---|---|---|---|---|---|---|
| act | cag | ccc | atc | atg | gac | aca | gat | ggc | tct | tac | ttc | gtc | tac | agc | aag | 1680 |
| Thr | Gln | Pro | Ile | Met | Asp | Thr | Asp | Gly | Ser | Tyr | Phe | Val | Tyr | Ser | Lys | |
| 545 | | | | 550 | | | | | 555 | | | | | 560 | | |

| ctc | aat | gtg | cag | aag | agc | aac | tgg | gag | gca | gga | aat | act | ttc | acc | tgc | 1728 |
| Leu | Asn | Val | Gln | Lys | Ser | Asn | Trp | Glu | Ala | Gly | Asn | Thr | Phe | Thr | Cys | |
| | | | | 565 | | | | | 570 | | | | | 575 | | |

| tct | gtg | tta | cat | gag | ggc | ctg | cac | aac | cac | cat | act | gag | aag | agc | ctc | 1776 |
| Ser | Val | Leu | His | Glu | Gly | Leu | His | Asn | His | His | Thr | Glu | Lys | Ser | Leu | |
| | | | | 580 | | | | | 585 | | | | | 590 | | |

| tcc | cac | tct | cct | ggg | ctg | caa | agc | ttg | tcg | aga | agt | act | aga | gga | tca | 1824 |
| Ser | His | Ser | Pro | Gly | Leu | Gln | Ser | Leu | Ser | Arg | Ser | Thr | Arg | Gly | Ser | |
| | | | 595 | | | | | 600 | | | | | 605 | | | |

| taa | | | | | | | | | | | | | | | | 1827 |

<210> SEQ ID NO 48
<211> LENGTH: 608
<212> TYPE: PRT
<213> ORGANISM: Artificial
<220> FEATURE:
<223> OTHER INFORMATION: Synthetic Construct

<400> SEQUENCE: 48

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Gly
            20                  25                  30

Gln His Pro Ala Lys Ser Met Asp Val Arg Arg Ile Glu Gly Gly Glu
        35                  40                  45

Ile Leu Leu Asn Gln Leu Ala Gly Arg Met Ile Pro Lys Gly Thr Leu
    50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Met
            180                 185                 190

Ser Gly Thr Phe Gly Gly Ile Leu Ala Gly Leu Ile Gly Leu Leu Val
        195                 200                 205

Ser Phe Phe Leu Leu Ile Lys Ile Leu Glu Ile Leu Arg Arg Leu Asp
    210                 215                 220

Trp Trp Trp Ile Ser Leu Ser Ser Pro Lys Gly Lys Met Gln Cys Ala
225                 230                 235                 240

Phe Gln Asp Thr Gly Ala Gln Ile Ser Pro His Tyr Val Gly Ser Cys
                245                 250                 255

Pro Trp Gly Cys Pro Gly Phe Leu Trp Thr Tyr Leu Arg Leu Phe Ile
            260                 265                 270

Ile Phe Leu Leu Ile Leu Leu Val Ala Ala Gly Leu Leu Tyr Leu Thr

```
                    275                 280                 285
Asp Asn Gly Ser Thr Ile Leu Gly Lys Leu Gln Trp Ala Ser Val Ser
290                 295                 300

Ala Leu Phe Ser Ser Ile Ser Ser Leu Leu Pro Ser Asp Pro Lys Ser
305                 310                 315                 320

Leu Val Ala Leu Thr Phe Gly Leu Ser Leu Ile Trp Met Thr Ser Ser
            325                 330                 335

Ser Ala Thr Gln Thr Leu Val Thr Leu Thr Gln Leu Ala Thr Leu Ser
            340                 345                 350

Ala Leu Phe Tyr Lys Ser Ser Arg Pro Gln Gly Gly Gly Ser Val Asp
        355                 360                 365

Lys Lys Ile Val Pro Arg Asp Cys Gly Cys Lys Pro Cys Ile Cys Thr
370                 375                 380

Val Pro Glu Val Ser Ser Val Phe Ile Phe Pro Pro Lys Pro Lys Asp
385                 390                 395                 400

Val Leu Thr Ile Thr Leu Thr Pro Lys Val Thr Cys Val Val Val Asp
            405                 410                 415

Ile Ser Lys Asp Asp Pro Glu Val Gln Phe Ser Trp Phe Val Asp Asp
            420                 425                 430

Val Glu Val His Thr Ala Gln Thr Gln Pro Arg Glu Glu Gln Phe Asn
        435                 440                 445

Ser Thr Phe Arg Ser Val Ser Glu Leu Pro Ile Met His Gln Asp Trp
        450                 455                 460

Leu Asn Gly Lys Glu Phe Lys Cys Arg Val Asn Ser Ala Ala Phe Pro
465                 470                 475                 480

Ala Pro Ile Glu Lys Thr Ile Ser Lys Thr Lys Gly Arg Pro Lys Ala
            485                 490                 495

Pro Gln Val Tyr Thr Ile Pro Pro Lys Glu Gln Met Ala Lys Asp
        500                 505                 510

Lys Val Ser Leu Thr Cys Met Ile Thr Asp Phe Phe Pro Glu Asp Ile
515                 520                 525

Thr Val Glu Trp Gln Trp Asn Gly Gln Pro Ala Glu Asn Tyr Lys Asn
530                 535                 540

Thr Gln Pro Ile Met Asp Thr Asp Gly Ser Tyr Phe Val Tyr Ser Lys
545                 550                 555                 560

Leu Asn Val Gln Lys Ser Asn Trp Glu Ala Gly Asn Thr Phe Thr Cys
            565                 570                 575

Ser Val Leu His Glu Gly Leu His Asn His Thr Glu Lys Ser Leu
            580                 585                 590

Ser His Ser Pro Gly Leu Gln Ser Leu Ser Arg Ser Thr Arg Gly Ser
        595                 600                 605

<210> SEQ ID NO 49
<211> LENGTH: 1155
<212> TYPE: DNA
<213> ORGANISM: Duck hepatitis B virus
<220> FEATURE:
<221> NAME/KEY: CDS
<222> LOCATION: (1)..(1155)

<400> SEQUENCE: 49 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc atg ggg    96
Thr Glu Asn Leu Tyr Phe Gln Gly Ala Met Asp Pro Glu Phe Met Gly
            20                  25                  30
```

```
caa cat cca gca aaa tca atg gac gtc aga cgg ata gaa gga gaa      144
Gln His Pro Ala Lys Ser Met Asp Val Arg Arg Ile Glu Gly Glu
        35                  40                  45 ata ctg tta aac caa ctt gcc gga agg atg atc cca aaa ggg act ttg  192
Ile Leu Leu Asn Gln Leu Ala Gly Arg Met Ile Pro Lys Gly Thr Leu
 50                  55                  60 aca tgg tca ggc aag ttt cca aca cta gat cac gtg tta gac cat gtg  240
Thr Trp Ser Gly Lys Phe Pro Thr Leu Asp His Val Leu Asp His Val
 65                  70                  75                  80 caa aca atg gag gag ata aac acc ctc cag aat cag gga gct tgg cct  288
Gln Thr Met Glu Glu Ile Asn Thr Leu Gln Asn Gln Gly Ala Trp Pro
                 85                  90                  95 gct ggg gcg gga agg aga gta gga tta tca aat ccg act cct caa gag  336
Ala Gly Ala Gly Arg Arg Val Gly Leu Ser Asn Pro Thr Pro Gln Glu
            100                 105                 110 att cct cag ccc cag tgg act ccc gag gaa gac caa aaa gca cgc gaa  384
Ile Pro Gln Pro Gln Trp Thr Pro Glu Glu Asp Gln Lys Ala Arg Glu
        115                 120                 125 gct ttt cgc cgt tat caa gaa gaa aga cca ccg gaa acc acc acc att  432
Ala Phe Arg Arg Tyr Gln Glu Glu Arg Pro Pro Glu Thr Thr Thr Ile
130                 135                 140 cct ccg tct tcc cct cct cag tgg aag cta caa ccc ggg gac gat cca  480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca  528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa atg  576
Glu Pro Ala Val Pro Val Ile Lys Thr Pro Pro Leu Lys Lys Lys Met
            180                 185                 190 tct ggt acc ttc ggg gga ata cta gct ggc cta atc gga tta ctg gta  624
Ser Gly Thr Phe Gly Gly Ile Leu Ala Gly Leu Ile Gly Leu Leu Val
        195                 200                 205 agc ttt ttc ttg ttg ata aaa att cta gaa ata ctg agg agg cta gat  672
Ser Phe Phe Leu Leu Ile Lys Ile Leu Glu Ile Leu Arg Arg Leu Asp
210                 215                 220 tgg tgg tgg att tct ctc agt tct cca aag gga aaa atg caa tgc gct  720
Trp Trp Trp Ile Ser Leu Ser Ser Pro Lys Gly Lys Met Gln Cys Ala
225                 230                 235                 240 ttc caa gat act gga gcc caa atc tct cca cat tac gta gga tct tgc  768
Phe Gln Asp Thr Gly Ala Gln Ile Ser Pro His Tyr Val Gly Ser Cys
                245                 250                 255 ccg tgg gga tgc cca gga ttt ctt tgg acc tat ctc agg ctt ttt atc  816
Pro Trp Gly Cys Pro Gly Phe Leu Trp Thr Tyr Leu Arg Leu Phe Ile
            260                 265                 270 atc ttc ctc tta atc ctg cta gta gca gca ggc ttg ctg tat ctg acg  864
Ile Phe Leu Leu Ile Leu Leu Val Ala Ala Gly Leu Leu Tyr Leu Thr
        275                 280                 285 gac aac ggg tct act att tta gga aag ctc caa tgg gcg tcg gtc tca  912
Asp Asn Gly Ser Thr Ile Leu Gly Lys Leu Gln Trp Ala Ser Val Ser
290                 295                 300 gcc ctt ttc tcc tcc atc tct tca cta ctg ccc tcg gat ccg aaa tct  960
Ala Leu Phe Ser Ser Ile Ser Ser Leu Leu Pro Ser Asp Pro Lys Ser
305                 310                 315                 320 ctc gtc gct tta acg ttt gga ctt tca ctt ata tgg atg act tcc tcc  1008
Leu Val Ala Leu Thr Phe Gly Leu Ser Leu Ile Trp Met Thr Ser Ser
                325                 330                 335 tct gcc acc caa acg ctc gtc acc tta acg caa tta gcc acg ctg tct  1056
Ser Ala Thr Gln Thr Leu Val Thr Leu Thr Gln Leu Ala Thr Leu Ser
            340                 345                 350
```

```
gct ctt ttt tac aag agt tcg cgg ccg ctt tcg aat cta gag cct gca    1104
Ala Leu Phe Tyr Lys Ser Ser Arg Pro Leu Ser Asn Leu Glu Pro Ala
            355                 360                 365 gtc tcg agg cat gcg gta cca agc ttg tcg aga agt act aga gga tca    1152
Val Ser Arg His Ala Val Pro Ser Leu Ser Arg Ser Thr Arg Gly Ser
    370                 375                 380 taa                                                                1155

<210> SEQ ID NO 50
<211> LENGTH: 384
<212> TYPE: PRT
<213> ORGANISM: Duck hepatitis B virus

<400> SEQUENCE: 50

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Gly
                20                  25                  30

Gln His Pro Ala Lys Ser Met Asp Val Arg Arg Ile Glu Gly Gly Glu
            35                  40                  45

Ile Leu Leu Asn Gln Leu Ala Gly Arg Met Ile Pro Lys Gly Thr Leu
50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Leu Lys Lys Lys Met
            180                 185                 190

Ser Gly Thr Phe Gly Gly Ile Leu Ala Gly Leu Ile Gly Leu Leu Val
        195                 200                 205

Ser Phe Phe Leu Leu Ile Lys Ile Leu Glu Ile Leu Arg Arg Leu Asp
    210                 215                 220

Trp Trp Trp Ile Ser Leu Ser Ser Pro Lys Gly Lys Met Gln Cys Ala
225                 230                 235                 240

Phe Gln Asp Thr Gly Ala Gln Ile Ser Pro His Tyr Val Gly Ser Cys
                245                 250                 255

Pro Trp Gly Cys Pro Gly Phe Leu Trp Thr Tyr Leu Arg Leu Phe Ile
            260                 265                 270

Ile Phe Leu Leu Ile Leu Leu Val Ala Ala Gly Leu Leu Tyr Leu Thr
        275                 280                 285

Asp Asn Gly Ser Thr Ile Leu Gly Lys Leu Gln Trp Ala Ser Val Ser
    290                 295                 300

Ala Leu Phe Ser Ser Ile Ser Ser Leu Leu Pro Ser Asp Pro Lys Ser
305                 310                 315                 320

Leu Val Ala Leu Thr Phe Gly Leu Ser Leu Ile Trp Met Thr Ser Ser
```

|  |  |  |  |  | 325 |  |  |  |  | 330 |  |  |  |  | 335 |  |
|---|---|---|---|---|---|---|---|---|---|---|---|---|---|---|---|---|
| Ser | Ala | Thr | Gln | Thr | Leu | Val | Thr | Leu | Thr | Gln | Leu | Ala | Thr | Leu | Ser |  |
|  |  |  | 340 |  |  |  |  | 345 |  |  |  |  | 350 |  |  |  |

Ala Leu Phe Tyr Lys Ser Ser Arg Pro Leu Ser Asn Leu Glu Pro Ala
        355                 360                 365

Val Ser Arg His Ala Val Pro Ser Leu Ser Arg Ser Thr Arg Gly Ser
370                 375                 380

```
<210> SEQ ID NO 51
<211> LENGTH: 1614
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1614)

<400> SEQUENCE: 51
```

| atg | tcg | tac | tac | cat | cac | cat | cac | cat | cac | gat | tac | gat | atc | cca | acg | 48 |
|---|---|---|---|---|---|---|---|---|---|---|---|---|---|---|---|---|
| Met | Ser | Tyr | Tyr | His | His | His | His | His | His | Asp | Tyr | Asp | Ile | Pro | Thr |  |
| 1 |  |  |  | 5 |  |  |  |  | 10 |  |  |  |  | 15 |  |  |

| acc | gaa | aac | ctg | tat | ttt | cag | ggc | gcc | atg | gat | atc | aat | gct | tct | aga | 96 |
|---|---|---|---|---|---|---|---|---|---|---|---|---|---|---|---|---|
| Thr | Glu | Asn | Leu | Tyr | Phe | Gln | Gly | Ala | Met | Asp | Ile | Asn | Ala | Ser | Arg |  |
|  |  |  | 20 |  |  |  |  | 25 |  |  |  |  | 30 |  |  |  |

| gcc | tta | gcc | aat | gtg | tat | gat | cta | cca | gat | gat | ttc | ttt | cca | aaa | ata | 144 |
|---|---|---|---|---|---|---|---|---|---|---|---|---|---|---|---|---|
| Ala | Leu | Ala | Asn | Val | Tyr | Asp | Leu | Pro | Asp | Asp | Phe | Phe | Pro | Lys | Ile |  |
|  |  | 35 |  |  |  |  | 40 |  |  |  |  | 45 |  |  |  |  |

| gat | gat | ctt | gtt | aga | gat | gct | aaa | gac | gct | tta | gag | cct | tat | tgg | aaa | 192 |
|---|---|---|---|---|---|---|---|---|---|---|---|---|---|---|---|---|
| Asp | Asp | Leu | Val | Arg | Asp | Ala | Lys | Asp | Ala | Leu | Glu | Pro | Tyr | Trp | Lys |  |
|  | 50 |  |  |  |  | 55 |  |  |  |  | 60 |  |  |  |  |  |

| tca | gat | tca | ata | aag | aaa | cat | gtt | ttg | att | gca | act | cac | ttt | gtg | gat | 240 |
|---|---|---|---|---|---|---|---|---|---|---|---|---|---|---|---|---|
| Ser | Asp | Ser | Ile | Lys | Lys | His | Val | Leu | Ile | Ala | Thr | His | Phe | Val | Asp |  |
| 65 |  |  |  |  | 70 |  |  |  |  | 75 |  |  |  |  | 80 |  |

| ctc | att | gaa | gac | ttc | tgg | cag | act | aca | cag | ggc | atg | cat | gaa | ata | gcc | 288 |
|---|---|---|---|---|---|---|---|---|---|---|---|---|---|---|---|---|
| Leu | Ile | Glu | Asp | Phe | Trp | Gln | Thr | Thr | Gln | Gly | Met | His | Glu | Ile | Ala |  |
|  |  |  |  | 85 |  |  |  |  | 90 |  |  |  |  | 95 |  |  |

| gaa | tca | tta | aga | gct | gtt | ata | cct | ccc | act | act | act | cct | gtt | cca | ccg | 336 |
|---|---|---|---|---|---|---|---|---|---|---|---|---|---|---|---|---|
| Glu | Ser | Leu | Arg | Ala | Val | Ile | Pro | Pro | Thr | Thr | Thr | Pro | Val | Pro | Pro |  |
|  |  |  | 100 |  |  |  |  | 105 |  |  |  |  | 110 |  |  |  |

| ggt | tat | ctt | att | cag | cac | gag | gaa | gct | gaa | gag | ata | cct | ttg | gga | gat | 384 |
|---|---|---|---|---|---|---|---|---|---|---|---|---|---|---|---|---|
| Gly | Tyr | Leu | Ile | Gln | His | Glu | Glu | Ala | Glu | Glu | Ile | Pro | Leu | Gly | Asp |  |
|  |  |  | 115 |  |  |  |  | 120 |  |  |  |  | 125 |  |  |  |

| tta | ttt | aaa | cac | caa | gaa | gaa | agg | ata | gta | agt | ttc | caa | ccc | gac | tat | 432 |
|---|---|---|---|---|---|---|---|---|---|---|---|---|---|---|---|---|
| Leu | Phe | Lys | His | Gln | Glu | Glu | Arg | Ile | Val | Ser | Phe | Gln | Pro | Asp | Tyr |  |
|  | 130 |  |  |  |  | 135 |  |  |  |  | 140 |  |  |  |  |  |

| ccg | att | acg | gct | aga | att | cat | gct | cat | ttg | aaa | gct | tat | gca | aaa | att | 480 |
|---|---|---|---|---|---|---|---|---|---|---|---|---|---|---|---|---|
| Pro | Ile | Thr | Ala | Arg | Ile | His | Ala | His | Leu | Lys | Ala | Tyr | Ala | Lys | Ile |  |
| 145 |  |  |  |  | 150 |  |  |  |  | 155 |  |  |  |  | 160 |  |

| aac | gag | gaa | tca | ctg | gat | agg | gct | agg | aga | ttg | ctt | tgg | tgg | cat | tac | 528 |
|---|---|---|---|---|---|---|---|---|---|---|---|---|---|---|---|---|
| Asn | Glu | Glu | Ser | Leu | Asp | Arg | Ala | Arg | Arg | Leu | Leu | Trp | Trp | His | Tyr |  |
|  |  |  |  | 165 |  |  |  |  | 170 |  |  |  |  | 175 |  |  |

| aac | tgt | tta | ctg | tgg | gga | gaa | gct | caa | gtt | act | aac | tat | att | tct | cgt | 576 |
|---|---|---|---|---|---|---|---|---|---|---|---|---|---|---|---|---|
| Asn | Cys | Leu | Leu | Trp | Gly | Glu | Ala | Gln | Val | Thr | Asn | Tyr | Ile | Ser | Arg |  |
|  |  |  | 180 |  |  |  |  | 185 |  |  |  |  | 190 |  |  |  |

| ttg | cgt | act | tgg | ttg | tca | act | cct | gag | aaa | tat | aga | ggt | aga | gat | gcc | 624 |
|---|---|---|---|---|---|---|---|---|---|---|---|---|---|---|---|---|
| Leu | Arg | Thr | Trp | Leu | Ser | Thr | Pro | Glu | Lys | Tyr | Arg | Gly | Arg | Asp | Ala |  |
|  |  | 195 |  |  |  |  | 200 |  |  |  |  | 205 |  |  |  |  |

| ccg | acc | att | gaa | gca | atc | act | aga | cca | atc | cag | gtg | gct | cag | gga | ggc | 672 |
|---|---|---|---|---|---|---|---|---|---|---|---|---|---|---|---|---|
| Pro | Thr | Ile | Glu | Ala | Ile | Thr | Arg | Pro | Ile | Gln | Val | Ala | Gln | Gly | Gly |  |
|  | 210 |  |  |  |  | 215 |  |  |  |  | 220 |  |  |  |  |  |

```
            -continued
aga aaa aca act acg ggt act aga aaa cct cgt gga ctc gaa cct aga       720
Arg Lys Thr Thr Thr Gly Thr Arg Lys Pro Arg Gly Leu Glu Pro Arg
225                 230                 235                 240 aga aga aaa gtt aaa acc aca gtt gtc tat ggg aga aga cgt tca aag       768
Arg Arg Lys Val Lys Thr Thr Val Val Tyr Gly Arg Arg Arg Ser Lys
                245                 250                 255 tcc cgg gaa agg aga gcc cct aca ccc caa cgt gcg ggc tcc cct ctc       816
Ser Arg Glu Arg Arg Ala Pro Thr Pro Gln Arg Ala Gly Ser Pro Leu
            260                 265                 270 cca cgt agt tcg agc agc cac cat aga tct ccc tcg cct agg aaa tcg       864
Pro Arg Ser Ser Ser Ser His His Arg Ser Pro Ser Pro Arg Lys Ser
        275                 280                 285 cgg ccg caa ggc ggc gga tcc gtg gac aag aaa att gtg ccc agg gat       912
Arg Pro Gln Gly Gly Gly Ser Val Asp Lys Lys Ile Val Pro Arg Asp
    290                 295                 300 tgt ggt tgt aag cct tgc ata tgt aca gtc cca gaa gta tca tct gtc       960
Cys Gly Cys Lys Pro Cys Ile Cys Thr Val Pro Glu Val Ser Ser Val
305                 310                 315                 320 ttc atc ttc ccc cca aag ccc aag gat gtg ctc acc att act ctg act      1008
Phe Ile Phe Pro Pro Lys Pro Lys Asp Val Leu Thr Ile Thr Leu Thr
                325                 330                 335 cct aag gtc acg tgt gtt gtg gta gac atc agc aag gat gat ccc gag      1056
Pro Lys Val Thr Cys Val Val Val Asp Ile Ser Lys Asp Asp Pro Glu
            340                 345                 350 gtc cag ttc agc tgg ttt gta gat gat gtg gag gtg cac aca gct cag      1104
Val Gln Phe Ser Trp Phe Val Asp Asp Val Glu Val His Thr Ala Gln
        355                 360                 365 acg caa ccc cgg gag gag cag ttc aac agc act ttc cgc tca gtc agt      1152
Thr Gln Pro Arg Glu Glu Gln Phe Asn Ser Thr Phe Arg Ser Val Ser
    370                 375                 380 gaa ctt ccc atc atg cac cag gac tgg ctc aat ggc aag gag ttc aaa      1200
Glu Leu Pro Ile Met His Gln Asp Trp Leu Asn Gly Lys Glu Phe Lys
385                 390                 395                 400 tgc agg gtc aac agt gca gct ttc cct gcc ccc atc gag aaa acc atc      1248
Cys Arg Val Asn Ser Ala Ala Phe Pro Ala Pro Ile Glu Lys Thr Ile
                405                 410                 415 tcc aaa acc aaa ggc aga ccg aag gct cca cag gtg tac acc att cca      1296
Ser Lys Thr Lys Gly Arg Pro Lys Ala Pro Gln Val Tyr Thr Ile Pro
            420                 425                 430 cct ccc aag gag cag atg gcc aag gat aaa gtc agt ctg acc tgc atg      1344
Pro Pro Lys Glu Gln Met Ala Lys Asp Lys Val Ser Leu Thr Cys Met
        435                 440                 445 ata aca gac ttc ttc cct gaa gac att act gtg gag tgg cag tgg aat      1392
Ile Thr Asp Phe Phe Pro Glu Asp Ile Thr Val Glu Trp Gln Trp Asn
    450                 455                 460 ggg cag cca gcg gag aac tac aag aac act cag ccc atc atg gac aca      1440
Gly Gln Pro Ala Glu Asn Tyr Lys Asn Thr Gln Pro Ile Met Asp Thr
465                 470                 475                 480 gat ggc tct tac ttc gtc tac agc aag ctc aat gtg cag aag agc aac      1488
Asp Gly Ser Tyr Phe Val Tyr Ser Lys Leu Asn Val Gln Lys Ser Asn
                485                 490                 495 tgg gag gca gga aat act ttc acc tgc tct gtg tta cat gag ggc ctg      1536
Trp Glu Ala Gly Asn Thr Phe Thr Cys Ser Val Leu His Glu Gly Leu
            500                 505                 510 cac aac cac cat act gag aag agc ctc tcc cac tct cct ggg ctg caa      1584
His Asn His His Thr Glu Lys Ser Leu Ser His Ser Pro Gly Leu Gln
        515                 520                 525 agc ttg tcg aga agt act aga gga tca taa                              1614
Ser Leu Ser Arg Ser Thr Arg Gly Ser
    530                 535
```

```
<210> SEQ ID NO 52
<211> LENGTH: 537
<212> TYPE: PRT
<213> ORGANISM: Artificial
<220> FEATURE:
<223> OTHER INFORMATION: Synthetic Construct

<400> SEQUENCE: 52
```

| | | | | | | | | | | | | | | |
|---|---|---|---|---|---|---|---|---|---|---|---|---|---|---|
|Met|Ser|Tyr|Tyr|His|His|His|His|His|Asp|Tyr|Asp|Ile|Pro|Thr|
|1| | | |5| | | | |10| | | |15| |
|Thr|Glu|Asn|Leu|Tyr|Phe|Gln|Gly|Ala|Met|Asp|Ile|Asn|Ala|Ser|Arg|
| | | |20| | | |25| | | |30| | | |
|Ala|Leu|Ala|Asn|Val|Tyr|Asp|Leu|Pro|Asp|Asp|Phe|Phe|Pro|Lys|Ile|
| | |35| | | |40| | | |45| | | | |
|Asp|Asp|Leu|Val|Arg|Asp|Ala|Lys|Asp|Ala|Leu|Glu|Pro|Tyr|Trp|Lys|
| |50| | | |55| | | |60| | | | | |
|Ser|Asp|Ser|Ile|Lys|Lys|His|Val|Leu|Ile|Ala|Thr|His|Phe|Val|Asp|
|65| | | |70| | | |75| | | |80| | | |
|Leu|Ile|Glu|Asp|Phe|Trp|Gln|Thr|Thr|Gln|Gly|Met|His|Glu|Ile|Ala|
| | | |85| | | |90| | | |95| | | |
|Glu|Ser|Leu|Arg|Ala|Val|Ile|Pro|Thr|Thr|Thr|Pro|Val|Pro|Pro|
| | | |100| | | |105| | | |110| | | |
|Gly|Tyr|Leu|Ile|Gln|His|Glu|Glu|Ala|Glu|Ile|Pro|Leu|Gly|Asp|
| | |115| | | |120| | | |125| | | |
|Leu|Phe|Lys|His|Gln|Glu|Glu|Arg|Ile|Val|Ser|Phe|Gln|Pro|Asp|Tyr|
| |130| | | |135| | | |140| | | | | |
|Pro|Ile|Thr|Ala|Arg|Ile|His|Ala|His|Leu|Lys|Ala|Tyr|Ala|Lys|Ile|
|145| | | |150| | | |155| | | |160| | | |
|Asn|Glu|Glu|Ser|Leu|Asp|Arg|Ala|Arg|Arg|Leu|Leu|Trp|Trp|His|Tyr|
| | | |165| | | |170| | | |175| | | |
|Asn|Cys|Leu|Leu|Trp|Gly|Glu|Ala|Gln|Val|Thr|Asn|Tyr|Ile|Ser|Arg|
| | |180| | | |185| | | |190| | | | |
|Leu|Arg|Thr|Trp|Leu|Ser|Thr|Pro|Glu|Lys|Tyr|Arg|Gly|Arg|Asp|Ala|
| |195| | | |200| | | |205| | | | | |
|Pro|Thr|Ile|Glu|Ala|Ile|Thr|Arg|Pro|Ile|Gln|Val|Ala|Gln|Gly|Gly|
|210| | | |215| | | |220| | | | | | | |
|Arg|Lys|Thr|Thr|Thr|Gly|Thr|Lys|Pro|Arg|Gly|Leu|Glu|Pro|Arg|
|225| | | |230| | | |235| | | |240| | | |
|Arg|Arg|Lys|Val|Lys|Thr|Thr|Val|Val|Tyr|Gly|Arg|Arg|Ser|Lys|
| | | |245| | | |250| | | |255| | | |
|Ser|Arg|Glu|Arg|Arg|Ala|Pro|Thr|Pro|Gln|Arg|Ala|Gly|Ser|Pro|Leu|
| | | |260| | | |265| | | |270| | | | |
|Pro|Arg|Ser|Ser|Ser|His|His|Arg|Ser|Pro|Ser|Pro|Arg|Lys|Ser|
| |275| | | |280| | | |285| | | | | |
|Arg|Pro|Gln|Gly|Gly|Gly|Ser|Val|Asp|Lys|Lys|Ile|Val|Pro|Arg|Asp|
| |290| | | |295| | | |300| | | | | |
|Cys|Gly|Cys|Lys|Pro|Cys|Ile|Cys|Thr|Val|Pro|Glu|Val|Ser|Ser|Val|
|305| | | |310| | | |315| | | |320| | | |
|Phe|Ile|Phe|Pro|Pro|Lys|Pro|Lys|Asp|Val|Leu|Thr|Ile|Thr|Leu|Thr|
| | | |325| | | |330| | | |335| | | |
|Pro|Lys|Val|Thr|Cys|Val|Val|Asp|Ile|Ser|Lys|Asp|Asp|Pro|Glu|
| | |340| | | |345| | | |350| | | | |
|Val|Gln|Phe|Ser|Trp|Phe|Val|Asp|Asp|Val|Glu|Val|His|Thr|Ala|Gln|
| | |355| | | |360| | | |365| | | | |
|Thr|Gln|Pro|Arg|Glu|Glu|Gln|Phe|Asn|Ser|Thr|Phe|Arg|Ser|Val|Ser|

```
                370               375               380
Glu Leu Pro Ile Met His Gln Asp Trp Leu Asn Gly Lys Glu Phe Lys
385                 390                 395                 400

Cys Arg Val Asn Ser Ala Ala Phe Pro Ala Pro Ile Glu Lys Thr Ile
                405                 410                 415

Ser Lys Thr Lys Gly Arg Pro Lys Ala Pro Gln Val Tyr Thr Ile Pro
                420                 425                 430

Pro Pro Lys Glu Gln Met Ala Lys Asp Lys Val Ser Leu Thr Cys Met
                435                 440                 445

Ile Thr Asp Phe Phe Pro Glu Asp Ile Thr Val Glu Trp Gln Trp Asn
450                 455                 460

Gly Gln Pro Ala Glu Asn Tyr Lys Asn Thr Gln Pro Ile Met Asp Thr
465                 470                 475                 480

Asp Gly Ser Tyr Phe Val Tyr Ser Lys Leu Asn Val Gln Lys Ser Asn
                485                 490                 495

Trp Glu Ala Gly Asn Thr Phe Thr Cys Ser Val Leu His Glu Gly Leu
                500                 505                 510

His Asn His His Thr Glu Lys Ser Leu Ser His Ser Pro Gly Leu Gln
                515                 520                 525

Ser Leu Ser Arg Ser Thr Arg Gly Ser
530                 535

<210> SEQ ID NO 53
<211> LENGTH: 942
<212> TYPE: DNA
<213> ORGANISM: Duck hepatitis B virus
<220> FEATURE:
<221> NAME/KEY: CDS
<222> LOCATION: (1)..(942)

<400> SEQUENCE: 53 atg tcg tac tac cat cac cat cac cat cac gat tac gat atc cca acg     48
Met Ser Tyr Tyr His His His His His His Asp Tyr Asp Ile Pro Thr
1               5                   10                  15 acc gaa aac ctg tat ttt cag ggc gcc atg gat atc aat gct tct aga     96
Thr Glu Asn Leu Tyr Phe Gln Gly Ala Met Asp Ile Asn Ala Ser Arg
            20                  25                  30 gcc tta gcc aat gtg tat gat cta cca gat gat ttc ttt cca aaa ata    144
Ala Leu Ala Asn Val Tyr Asp Leu Pro Asp Asp Phe Phe Pro Lys Ile
        35                  40                  45 gat gat ctt gtt aga gat gct aaa gac gct tta gag cct tat tgg aaa    192
Asp Asp Leu Val Arg Asp Ala Lys Asp Ala Leu Glu Pro Tyr Trp Lys
    50                  55                  60 tca gat tca ata aag aaa cat gtt ttg att gca act cac ttt gtg gat    240
Ser Asp Ser Ile Lys Lys His Val Leu Ile Ala Thr His Phe Val Asp
65                  70                  75                  80 ctc att gaa gac ttc tgg cag act aca cag ggc atg cat gaa ata gcc    288
Leu Ile Glu Asp Phe Trp Gln Thr Thr Gln Gly Met His Glu Ile Ala
                85                  90                  95 gaa tca tta aga gct gtt ata cct ccc act act act cct gtt cca ccg    336
Glu Ser Leu Arg Ala Val Ile Pro Pro Thr Thr Thr Pro Val Pro Pro
            100                 105                 110 ggt tat ctt att cag cac gag gaa gct gaa gag ata cct ttg gga gat    384
Gly Tyr Leu Ile Gln His Glu Glu Ala Glu Glu Ile Pro Leu Gly Asp
        115                 120                 125 tta ttt aaa cac caa gaa gaa agg ata gta agt ttc caa ccc gac tat    432
Leu Phe Lys His Gln Glu Glu Arg Ile Val Ser Phe Gln Pro Asp Tyr
    130                 135                 140 ccg att acg gct aga att cat gct cat ttg aaa gct tat gca aaa att    480
Pro Ile Thr Ala Arg Ile His Ala His Leu Lys Ala Tyr Ala Lys Ile
```

```
Pro Ile Thr Ala Arg Ile His Ala His Leu Lys Ala Tyr Ala Lys Ile
145                 150                 155                 160 aac gag gaa tca ctg gat agg gct agg aga ttg ctt tgg tgg cat tac    528
Asn Glu Glu Ser Leu Asp Arg Ala Arg Arg Leu Leu Trp Trp His Tyr
                165                 170                 175 aac tgt tta ctg tgg gga gaa gct caa gtt act aac tat att tct cgt    576
Asn Cys Leu Leu Trp Gly Glu Ala Gln Val Thr Asn Tyr Ile Ser Arg
            180                 185                 190 ttg cgt act tgg ttg tca act cct gag aaa tat aga ggt aga gat gcc    624
Leu Arg Thr Trp Leu Ser Thr Pro Glu Lys Tyr Arg Gly Arg Asp Ala
        195                 200                 205 ccg acc att gaa gca atc act aga cca atc cag gtg gct cag gga ggc    672
Pro Thr Ile Glu Ala Ile Thr Arg Pro Ile Gln Val Ala Gln Gly Gly
    210                 215                 220 aga aaa aca act acg ggt act aga aaa cct cgt gga ctc gaa cct aga    720
Arg Lys Thr Thr Thr Gly Thr Arg Lys Pro Arg Gly Leu Glu Pro Arg
225                 230                 235                 240 aga aga aaa gtt aaa acc aca gtt gtc tat ggg aga aga cgt tca aag    768
Arg Arg Lys Val Lys Thr Thr Val Val Tyr Gly Arg Arg Arg Ser Lys
                245                 250                 255 tcc cgg gaa agg aga gcc cct aca ccc caa cgt gcg ggc tcc cct ctc    816
Ser Arg Glu Arg Arg Ala Pro Thr Pro Gln Arg Ala Gly Ser Pro Leu
            260                 265                 270 cca cgt agt tcg agc agc cac cat aga tct ccc tcg cct agg aaa tcg    864
Pro Arg Ser Ser Ser Ser His His Arg Ser Pro Ser Pro Arg Lys Ser
        275                 280                 285 cgg ccg ctt tcg aat cta gag cct gca gtc tcg agg cat gcg gta cca    912
Arg Pro Leu Ser Asn Leu Glu Pro Ala Val Ser Arg His Ala Val Pro
    290                 295                 300 agc ttg tcg aga agt act aga gga tca taa                            942
Ser Leu Ser Arg Ser Thr Arg Gly Ser
305                 310

<210> SEQ ID NO 54
<211> LENGTH: 313
<212> TYPE: PRT
<213> ORGANISM: Duck hepatitis B virus

<400> SEQUENCE: 54

Met Ser Tyr Tyr His His His His His Asp Tyr Asp Ile Pro Thr
1               5                   10                  15

Thr Glu Asn Leu Tyr Phe Gln Gly Ala Met Asp Ile Asn Ala Ser Arg
                20                  25                  30

Ala Leu Ala Asn Val Tyr Asp Leu Pro Asp Asp Phe Phe Pro Lys Ile
            35                  40                  45

Asp Asp Leu Val Arg Asp Ala Lys Asp Ala Leu Glu Pro Tyr Trp Lys
        50                  55                  60

Ser Asp Ser Ile Lys Lys His Val Leu Ile Ala Thr His Phe Val Asp
65                  70                  75                  80

Leu Ile Glu Asp Phe Trp Gln Thr Thr Gln Gly Met His Glu Ile Ala
                85                  90                  95

Glu Ser Leu Arg Ala Val Ile Pro Pro Thr Thr Thr Pro Val Pro Pro
            100                 105                 110

Gly Tyr Leu Ile Gln His Glu Glu Ala Glu Glu Ile Pro Leu Gly Asp
        115                 120                 125

Leu Phe Lys His Gln Glu Glu Arg Ile Val Ser Phe Gln Pro Asp Tyr
    130                 135                 140

Pro Ile Thr Ala Arg Ile His Ala His Leu Lys Ala Tyr Ala Lys Ile
145                 150                 155                 160
```

```
Asn Glu Glu Ser Leu Asp Arg Ala Arg Arg Leu Leu Trp Trp His Tyr
            165                 170                 175

Asn Cys Leu Leu Trp Gly Glu Ala Gln Val Thr Asn Tyr Ile Ser Arg
            180                 185                 190

Leu Arg Thr Trp Leu Ser Thr Pro Glu Lys Tyr Arg Gly Arg Asp Ala
            195                 200                 205

Pro Thr Ile Glu Ala Ile Thr Arg Pro Ile Gln Val Ala Gln Gly Gly
            210                 215                 220

Arg Lys Thr Thr Thr Gly Thr Arg Lys Pro Arg Gly Leu Glu Pro Arg
225                 230                 235                 240

Arg Arg Lys Val Lys Thr Thr Val Val Tyr Gly Arg Arg Ser Lys
                245                 250                 255

Ser Arg Glu Arg Arg Ala Pro Thr Pro Gln Arg Ala Gly Ser Pro Leu
            260                 265                 270

Pro Arg Ser Ser Ser Ser His His Arg Ser Pro Ser Pro Arg Lys Ser
            275                 280                 285

Arg Pro Leu Ser Asn Leu Glu Pro Ala Val Ser Arg His Ala Val Pro
            290                 295                 300

Ser Leu Ser Arg Ser Thr Arg Gly Ser
305                 310

<210> SEQ ID NO 55
<211> LENGTH: 750
<212> TYPE: DNA
<213> ORGANISM: Hepatitis C virus
<220> FEATURE:
<221> NAME/KEY: CDS
<222> LOCATION: (1)..(750)

<400> SEQUENCE: 55 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc      96
Thr Glu Asn Leu Tyr Phe Gln Gly Ala Met Asp Pro Glu Phe Met Ser
                20                  25                  30 acg aat cct aaa cct caa aga aaa acc aaa cgt aac acc aac cgt cgc     144
Thr Asn Pro Lys Pro Gln Arg Lys Thr Lys Arg Asn Thr Asn Arg Arg
            35                  40                  45 cca cag gac gtc aag ttc ccg ggt ggc ggt cag atc gtt ggt gga gtt     192
Pro Gln Asp Val Lys Phe Pro Gly Gly Gly Gln Ile Val Gly Gly Val
        50                  55                  60 tac ttg ttg ccg cgc agg ggc cct aga ttg ggt gtg cgc gcg acg agg     240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc     288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct     336
Lys Ala Arg Arg Pro Glu Gly Arg Thr Trp Ala Gln Pro Gly Tyr Pro
            100                 105                 110 tgg ccc ctc tat ggc aat gag ggt tgc ggg tgg gcg gga tgg ctc ctg     384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt     432
Ser Pro Arg Gly Ser Arg Pro Ser Trp Gly Pro Thr Asp Pro Arg Arg
130                 135                 140 agg tcg cgc aat ttg ggt aag gtc atc gat acc ctt acg tgc ggc ttc     480
Arg Ser Arg Asn Leu Gly Lys Val Ile Asp Thr Leu Thr Cys Gly Phe
```

```
                     145                 150                 155                 160
gcc gac ctc atg ggg tac ata ccg ctc gtc ggc gcc cct ctt gga ggc                528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg                576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc ctt                624
Asn Tyr Ala Thr Gly Asn Leu Pro Gly Cys Ser Phe Ser Ile Phe Leu
        195                 200                 205 ctg gcc ctg ctc tct tgc ctg act gtg ccc gct tca gcc gga cta gtg                672
Leu Ala Leu Leu Ser Cys Leu Thr Val Pro Ala Ser Ala Gly Leu Val
    210                 215                 220 cgg ccg ctt tcg aat cta gag cct gca gtc tcg agg cat gcg gta cca                720
Arg Pro Leu Ser Asn Leu Glu Pro Ala Val Ser Arg His Ala Val Pro
225                 230                 235                 240 agc ttg tcg aga agt act aga gga tca taa                                        750
Ser Leu Ser Arg Ser Thr Arg Gly Ser
                245

<210> SEQ ID NO 56
<211> LENGTH: 249
<212> TYPE: PRT
<213> ORGANISM: Hepatitis C virus

<400> SEQUENCE: 56

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Leu
        195                 200                 205

Leu Ala Leu Leu Ser Cys Leu Thr Val Pro Ala Ser Ala Gly Leu Val
    210                 215                 220

Arg Pro Leu Ser Asn Leu Glu Pro Ala Val Ser Arg His Ala Val Pro
225                 230                 235                 240

Ser Leu Ser Arg Ser Thr Arg Gly Ser
```

<210> SEQ ID NO 57
<211> LENGTH: 1422
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1422)

<400> SEQUENCE: 57

| | | | | | | | | | | | | | | | | |
|---|---|---|---|---|---|---|---|---|---|---|---|---|---|---|---|---|
| atg | tcg | tac | tac | cat | cac | cat | cac | cat | cac | gat | tac | gat | atc | cca | acg | 48 |
| Met | Ser | Tyr | Tyr | His | His | His | His | His | His | Asp | Tyr | Asp | Ile | Pro | Thr | |
| 1 | | | | 5 | | | | | 10 | | | | | 15 | | |

| acc | gaa | aac | ctg | tat | ttt | cag | ggc | gcc | atg | gat | ccg | gaa | ttc | atg | agc | 96 |
|---|---|---|---|---|---|---|---|---|---|---|---|---|---|---|---|---|
| Thr | Glu | Asn | Leu | Tyr | Phe | Gln | Gly | Ala | Met | Asp | Pro | Glu | Phe | Met | Ser | |
| | | | 20 | | | | | 25 | | | | | 30 | | | |

| acg | aat | cct | aaa | cct | caa | aga | aaa | acc | aaa | cgt | aac | acc | aac | cgt | cgc | 144 |
|---|---|---|---|---|---|---|---|---|---|---|---|---|---|---|---|---|
| Thr | Asn | Pro | Lys | Pro | Gln | Arg | Lys | Thr | Lys | Arg | Asn | Thr | Asn | Arg | Arg | |
| | | 35 | | | | | 40 | | | | | 45 | | | | |

| cca | cag | gac | gtc | aag | ttc | ccg | ggt | ggc | ggt | cag | atc | gtt | ggt | gga | gtt | 192 |
|---|---|---|---|---|---|---|---|---|---|---|---|---|---|---|---|---|
| Pro | Gln | Asp | Val | Lys | Phe | Pro | Gly | Gly | Gly | Gln | Ile | Val | Gly | Gly | Val | |
| 50 | | | | | 55 | | | | | 60 | | | | | | |

| tac | ttg | ttg | ccg | cgc | agg | ggc | cct | aga | ttg | ggt | gtg | cgc | gcg | acg | agg | 240 |
|---|---|---|---|---|---|---|---|---|---|---|---|---|---|---|---|---|
| Tyr | Leu | Leu | Pro | Arg | Arg | Gly | Pro | Arg | Leu | Gly | Val | Arg | Ala | Thr | Arg | |
| 65 | | | | | 70 | | | | | 75 | | | | | 80 | |

| aag | act | tcc | gag | cgg | tcg | caa | cct | cga | ggt | aga | cgt | cag | cct | atc | ccc | 288 |
|---|---|---|---|---|---|---|---|---|---|---|---|---|---|---|---|---|
| Lys | Thr | Ser | Glu | Arg | Ser | Gln | Pro | Arg | Gly | Arg | Arg | Gln | Pro | Ile | Pro | |
| | | | | 85 | | | | | 90 | | | | | 95 | | |

| aag | gca | cgt | cgg | ccc | gag | ggc | agg | acc | tgg | gct | cag | ccc | ggg | tac | cct | 336 |
|---|---|---|---|---|---|---|---|---|---|---|---|---|---|---|---|---|
| Lys | Ala | Arg | Arg | Pro | Glu | Gly | Arg | Thr | Trp | Ala | Gln | Pro | Gly | Tyr | Pro | |
| | | | 100 | | | | | 105 | | | | | 110 | | | |

| tgg | ccc | ctc | tat | ggc | aat | gag | ggt | tgc | ggg | tgg | gcg | gga | tgg | ctc | ctg | 384 |
|---|---|---|---|---|---|---|---|---|---|---|---|---|---|---|---|---|
| Trp | Pro | Leu | Tyr | Gly | Asn | Glu | Gly | Cys | Gly | Trp | Ala | Gly | Trp | Leu | Leu | |
| | | 115 | | | | | 120 | | | | | 125 | | | | |

| tct | ccc | cgt | ggc | tct | cgg | cct | agc | tgg | ggc | ccc | aca | gac | ccc | cgg | cgt | 432 |
|---|---|---|---|---|---|---|---|---|---|---|---|---|---|---|---|---|
| Ser | Pro | Arg | Gly | Ser | Arg | Pro | Ser | Trp | Gly | Pro | Thr | Asp | Pro | Arg | Arg | |
| | 130 | | | | | 135 | | | | | 140 | | | | | |

| agg | tcg | cgc | aat | ttg | ggt | aag | gtc | atc | gat | acc | ctt | acg | tgc | ggc | ttc | 480 |
|---|---|---|---|---|---|---|---|---|---|---|---|---|---|---|---|---|
| Arg | Ser | Arg | Asn | Leu | Gly | Lys | Val | Ile | Asp | Thr | Leu | Thr | Cys | Gly | Phe | |
| 145 | | | | | 150 | | | | | 155 | | | | | 160 | |

| gcc | gac | ctc | atg | ggg | tac | ata | ccg | ctc | gtc | ggc | gcc | cct | ctt | gga | ggc | 528 |
|---|---|---|---|---|---|---|---|---|---|---|---|---|---|---|---|---|
| Ala | Asp | Leu | Met | Gly | Tyr | Ile | Pro | Leu | Val | Gly | Ala | Pro | Leu | Gly | Gly | |
| | | | | 165 | | | | | 170 | | | | | 175 | | |

| gct | gcc | agg | gcc | ctg | gcg | cat | ggc | gtc | cgg | gtt | ctg | gaa | gac | ggc | gtg | 576 |
|---|---|---|---|---|---|---|---|---|---|---|---|---|---|---|---|---|
| Ala | Ala | Arg | Ala | Leu | Ala | His | Gly | Val | Arg | Val | Leu | Glu | Asp | Gly | Val | |
| | | | 180 | | | | | 185 | | | | | 190 | | | |

| aac | tat | gca | aca | ggg | aac | ctt | cct | ggt | tgc | tct | ttc | tct | atc | ttc | ctt | 624 |
|---|---|---|---|---|---|---|---|---|---|---|---|---|---|---|---|---|
| Asn | Tyr | Ala | Thr | Gly | Asn | Leu | Pro | Gly | Cys | Ser | Phe | Ser | Ile | Phe | Leu | |
| | | 195 | | | | | 200 | | | | | 205 | | | | |

| ctg | gcc | ctg | ctc | tct | tgc | ctg | act | gtg | ccc | gct | tca | gcc | gga | cta | gtg | 672 |
|---|---|---|---|---|---|---|---|---|---|---|---|---|---|---|---|---|
| Leu | Ala | Leu | Leu | Ser | Cys | Leu | Thr | Val | Pro | Ala | Ser | Ala | Gly | Leu | Val | |
| | 210 | | | | | 215 | | | | | 220 | | | | | |

| cgg | ccg | caa | ggc | ggc | gga | tcc | gtg | gac | aag | aaa | att | gtg | ccc | agg | gat | 720 |
|---|---|---|---|---|---|---|---|---|---|---|---|---|---|---|---|---|
| Arg | Pro | Gln | Gly | Gly | Gly | Ser | Val | Asp | Lys | Lys | Ile | Val | Pro | Arg | Asp | |
| 225 | | | | | 230 | | | | | 235 | | | | | 240 | |

| tgt | ggt | tgt | aag | cct | tgc | ata | tgt | aca | gtc | cca | gaa | gta | tca | tct | gtc | 768 |
|---|---|---|---|---|---|---|---|---|---|---|---|---|---|---|---|---|
| Cys | Gly | Cys | Lys | Pro | Cys | Ile | Cys | Thr | Val | Pro | Glu | Val | Ser | Ser | Val | |
| | | | | 245 | | | | | 250 | | | | | 255 | | |

| ttc | atc | ttc | ccc | cca | aag | ccc | aag | gat | gtg | ctc | acc | att | act | ctg | act | 816 |

```
                Phe Ile Phe Pro Pro Lys Pro Lys Asp Val Leu Thr Ile Thr Leu Thr
                                260                 265                 270 cct aag gtc acg tgt gtt gtg gta gac atc agc aag gat gat ccc gag            864
Pro Lys Val Thr Cys Val Val Val Asp Ile Ser Lys Asp Asp Pro Glu
        275                 280                 285 gtc cag ttc agc tgg ttt gta gat gat gtg gag gtg cac aca gct cag            912
Val Gln Phe Ser Trp Phe Val Asp Asp Val Glu Val His Thr Ala Gln
    290                 295                 300 acg caa ccc cgg gag gag cag ttc aac agc act ttc cgc tca gtc agt            960
Thr Gln Pro Arg Glu Glu Gln Phe Asn Ser Thr Phe Arg Ser Val Ser
305                 310                 315                 320 gaa ctt ccc atc atg cac cag gac tgg ctc aat ggc aag gag ttc aaa           1008
Glu Leu Pro Ile Met His Gln Asp Trp Leu Asn Gly Lys Glu Phe Lys
                325                 330                 335 tgc agg gtc aac agt gca gct ttc cct gcc ccc atc gag aaa acc atc           1056
Cys Arg Val Asn Ser Ala Ala Phe Pro Ala Pro Ile Glu Lys Thr Ile
            340                 345                 350 tcc aaa acc aaa ggc aga ccg aag gct cca cag gtg tac acc att cca           1104
Ser Lys Thr Lys Gly Arg Pro Lys Ala Pro Gln Val Tyr Thr Ile Pro
        355                 360                 365 cct ccc aag gag cag atg gcc aag gat aaa gtc agt ctg acc tgc atg           1152
Pro Pro Lys Glu Gln Met Ala Lys Asp Lys Val Ser Leu Thr Cys Met
370                 375                 380 ata aca gac ttc ttc cct gaa gac att act gtg gag tgg cag tgg aat           1200
Ile Thr Asp Phe Phe Pro Glu Asp Ile Thr Val Glu Trp Gln Trp Asn
385                 390                 395                 400 ggg cag cca gcg gag aac tac aag aac act cag ccc atc atg gac aca           1248
Gly Gln Pro Ala Glu Asn Tyr Lys Asn Thr Gln Pro Ile Met Asp Thr
                405                 410                 415 gat ggc tct tac ttc gtc tac agc aag ctc aat gtg cag aag agc aac           1296
Asp Gly Ser Tyr Phe Val Tyr Ser Lys Leu Asn Val Gln Lys Ser Asn
            420                 425                 430 tgg gag gca gga aat act ttc acc tgc tct gtg tta cat gag ggc ctg           1344
Trp Glu Ala Gly Asn Thr Phe Thr Cys Ser Val Leu His Glu Gly Leu
        435                 440                 445 cac aac cac cat act gag aag agc ctc tcc cac tct cct ggg ctg caa           1392
His Asn His His Thr Glu Lys Ser Leu Ser His Ser Pro Gly Leu Gln
    450                 455                 460 agc ttg tcg aga agt act aga gga tca taa                                    1422
Ser Leu Ser Arg Ser Thr Arg Gly Ser
465                 470

<210> SEQ ID NO 58
<211> LENGTH: 473
<212> TYPE: PRT
<213> ORGANISM: Artificial
<220> FEATURE:
<223> OTHER INFORMATION: Synthetic Construct

<400> SEQUENCE: 58

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80
```

```
Lys Thr Ser Glu Arg Ser Gln Pro Arg Gly Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Leu
        195                 200                 205

Leu Ala Leu Leu Ser Cys Leu Thr Val Pro Ala Ser Ala Gly Leu Val
    210                 215                 220

Arg Pro Gln Gly Gly Gly Ser Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Asp Ile Ser Lys Asp Asp Pro Glu
        275                 280                 285

Val Gln Phe Ser Trp Phe Val Asp Asp Val Glu Val His Thr Ala Gln
    290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
        355                 360                 365

Pro Pro Lys Glu Gln Met Ala Lys Asp Lys Val Ser Leu Thr Cys Met
    370                 375                 380

Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
            420                 425                 430

Trp Glu Ala Gly Asn Thr Phe Thr Cys Ser Val Leu His Glu Gly Leu
        435                 440                 445

His Asn His His Thr Glu Lys Ser Leu Ser His Ser Pro Gly Leu Gln
    450                 455                 460

Ser Leu Ser Arg Ser Thr Arg Gly Ser
465                 470

<210> SEQ ID NO 59
<211> LENGTH: 708
<212> TYPE: DNA
<213> ORGANISM: Hepatitis C virus
```

<220> FEATURE:
<221> NAME/KEY: CDS
<222> LOCATION: (1)..(708)

<400> SEQUENCE: 59

```
atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc        96
Thr Glu Asn Leu Tyr Phe Gln Gly Ala Met Asp Pro Glu Phe Met Ser
            20                  25                  30 acg aat cct aaa cct caa aga aaa acc aaa cgt aac acc aac cgt cgc       144
Thr Asn Pro Lys Pro Gln Arg Lys Thr Lys Arg Asn Thr Asn Arg Arg
        35                  40                  45 cca cag gac gtc aag ttc ccg ggt ggc ggt cag atc gtt ggt gga gtt       192
Pro Gln Asp Val Lys Phe Pro Gly Gly Gly Gln Ile Val Gly Gly Val
    50                  55                  60 tac ttg ttg ccg cgc agg ggc cct aga ttg ggt gtg cgc gcg acg agg       240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc       288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct       336
Lys Ala Arg Arg Pro Glu Gly Arg Thr Trp Ala Gln Pro Gly Tyr Pro
            100                 105                 110 tgg ccc ctc tat ggc aat gag ggt tgc ggg tgg gcg gga tgg ctc ctg       384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt       432
Ser Pro Arg Gly Ser Arg Pro Ser Trp Gly Pro Thr Asp Pro Arg Arg
    130                 135                 140 agg tcg cgc aat ttg ggt aag gtc atc gat acc ctt acg tgc ggc ttc       480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc       528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg       576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc gga       624
Asn Tyr Ala Thr Gly Asn Leu Pro Gly Cys Ser Phe Ser Ile Phe Gly
        195                 200                 205 cta gtg cgg ccg ctt tcg aat cta gag cct gca gtc tcg agg cat gcg       672
Leu Val Arg Pro Leu Ser Asn Leu Glu Pro Ala Val Ser Arg His Ala
    210                 215                 220 gta cca agc ttg tcg aga agt act aga gga tca taa                       708
Val Pro Ser Leu Ser Arg Ser Thr Arg Gly Ser
225                 230                 235
```

<210> SEQ ID NO 60
<211> LENGTH: 235
<212> TYPE: PRT
<213> ORGANISM: Hepatitis C virus

<400> SEQUENCE: 60

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30
```

```
Thr Asn Pro Lys Pro Gln Arg Lys Thr Lys Arg Asn Thr Asn Arg Arg
            35                  40                  45

Pro Gln Asp Val Lys Phe Pro Gly Gly Gly Gln Ile Val Gly Gly Val
 50                  55                  60

Tyr Leu Leu Pro Arg Arg Gly Pro Arg Leu Gly Val Arg Ala Thr Arg
 65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
               100                 105                 110

Trp Pro Leu Tyr Gly Asn Glu Gly Cys Gly Trp Ala Gly Trp Leu Leu
               115                 120                 125

Ser Pro Arg Gly Ser Arg Pro Ser Trp Gly Pro Thr Asp Pro Arg Arg
130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
           180                 185                 190

Asn Tyr Ala Thr Gly Asn Leu Pro Gly Cys Ser Phe Ser Ile Phe Gly
               195                 200                 205

Leu Val Arg Pro Leu Ser Arg Ser Leu Glu Pro Ala Val Ser Arg His Ala
           210                 215                 220

Val Pro Ser Leu Ser Arg Ser Thr Arg Gly Ser
225                 230                 235

<210> SEQ ID NO 61
<211> LENGTH: 1380
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1380)

<400> SEQUENCE: 61 atg tcg tac tac cat cac cat cac cat cac gat tac gat atc cca acg      48
Met Ser Tyr Tyr His His His His His His Asp Tyr Asp Ile Pro Thr
 1               5                  10                  15 acc gaa aac ctg tat ttt cag ggc gcc atg gat ccg gaa ttc atg agc      96
Thr Glu Asn Leu Tyr Phe Gln Gly Ala Met Asp Pro Glu Phe Met Ser
                20                  25                  30 acg aat cct aaa cct caa aga aaa acc aaa cgt aac acc aac cgt cgc     144
Thr Asn Pro Lys Pro Gln Arg Lys Thr Lys Arg Asn Thr Asn Arg Arg
            35                  40                  45 cca cag gac gtc aag ttc ccg ggt ggc ggt cag atc gtt ggt gga gtt     192
Pro Gln Asp Val Lys Phe Pro Gly Gly Gly Gln Ile Val Gly Gly Val
 50                  55                  60 tac ttg ttg ccg cgc agg ggc cct aga ttg ggt gtg cgc gcg acg agg     240
Tyr Leu Leu Pro Arg Arg Gly Pro Arg Leu Gly Val Arg Ala Thr Arg
 65                  70                  75                  80 aag act tcc gag cgg tcg caa cct cga ggt aga cgt cag cct atc ccc     288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct     336
Lys Ala Arg Arg Pro Glu Gly Arg Thr Trp Ala Gln Pro Gly Tyr Pro
               100                 105                 110
```

```
tgg ccc ctc tat ggc aat gag ggt tgc ggg tgg gcg gga tgg ctc ctg      384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt      432
Ser Pro Arg Gly Ser Arg Pro Ser Trp Gly Pro Thr Asp Pro Arg Arg
130                 135                 140 agg tcg cgc aat ttg ggt aag gtc atc gat acc ctt acg tgc ggc ttc      480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc      528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg      576
Ala Ala Arg Ala Leu Ala His Gly Val Arg Val Leu Glu Asp Gly Val
        180                 185                 190 aac tat gca aca ggg aac ctt cct ggt tgc tct ttc tct atc ttc gga      624
Asn Tyr Ala Thr Gly Asn Leu Pro Gly Cys Ser Phe Ser Ile Phe Gly
            195                 200                 205 cta gtg cgg ccg caa ggc ggc gga tcc gtg gac aag aaa att gtg ccc      672
Leu Val Arg Pro Gln Gly Gly Gly Ser Val Asp Lys Lys Ile Val Pro
210                 215                 220 agg gat tgt ggt tgt aag cct tgc ata tgt aca gtc cca gaa gta tca      720
Arg Asp Cys Gly Cys Lys Pro Cys Ile Cys Thr Val Pro Glu Val Ser
225                 230                 235                 240 tct gtc ttc atc ttc ccc cca aag ccc aag gat gtg ctc acc att act      768
Ser Val Phe Ile Phe Pro Pro Lys Pro Lys Asp Val Leu Thr Ile Thr
                245                 250                 255 ctg act cct aag gtc acg tgt gtt gtg gta gac atc agc aag gat gat      816
Leu Thr Pro Lys Val Thr Cys Val Val Val Asp Ile Ser Lys Asp Asp
            260                 265                 270 ccc gag gtc cag ttc agc tgg ttt gta gat gat gtg gag gtg cac aca      864
Pro Glu Val Gln Phe Ser Trp Phe Val Asp Asp Val Glu Val His Thr
        275                 280                 285 gct cag acg caa ccc cgg gag gag cag ttc aac agc act ttc cgc tca      912
Ala Gln Thr Gln Pro Arg Glu Glu Gln Phe Asn Ser Thr Phe Arg Ser
290                 295                 300 gtc agt gaa ctt ccc atc atg cac cag gac tgg ctc aat ggc aag gag      960
Val Ser Glu Leu Pro Ile Met His Gln Asp Trp Leu Asn Gly Lys Glu
305                 310                 315                 320 ttc aaa tgc agg gtc aac agt gca gct ttc cct gcc ccc atc gag aaa     1008
Phe Lys Cys Arg Val Asn Ser Ala Ala Phe Pro Ala Pro Ile Glu Lys
                325                 330                 335 acc atc tcc aaa acc aaa ggc aga ccg aag gct cca cag gtg tac acc     1056
Thr Ile Ser Lys Thr Lys Gly Arg Pro Lys Ala Pro Gln Val Tyr Thr
            340                 345                 350 att cca cct ccc aag gag cag atg gcc aag gat aaa gtc agt ctg acc     1104
Ile Pro Pro Pro Lys Glu Gln Met Ala Lys Asp Lys Val Ser Leu Thr
        355                 360                 365 tgc atg ata aca gac ttc ttc cct gaa gac att act gtg gag tgg cag     1152
Cys Met Ile Thr Asp Phe Phe Pro Glu Asp Ile Thr Val Glu Trp Gln
370                 375                 380 tgg aat ggg cag cca gcg gag aac tac aag aac act cag ccc atc atg     1200
Trp Asn Gly Gln Pro Ala Glu Asn Tyr Lys Asn Thr Gln Pro Ile Met
385                 390                 395                 400 gac aca gat ggc tct tac ttc gtc tac agc aag ctc aat gtg cag aag     1248
Asp Thr Asp Gly Ser Tyr Phe Val Tyr Ser Lys Leu Asn Val Gln Lys
                405                 410                 415 agc aac tgg gag gca gga aat act ttc acc tgc tct gtg tta cat gag     1296
Ser Asn Trp Glu Ala Gly Asn Thr Phe Thr Cys Ser Val Leu His Glu
            420                 425                 430
```

```
ggc ctg cac aac cac cat act gag aag agc ctc tcc cac tct cct ggg    1344
Gly Leu His Asn His His Thr Glu Lys Ser Leu Ser His Ser Pro Gly
        435                 440                 445 ctg caa agc ttg tcg aga agt act aga gga tca taa                    1380
Leu Gln Ser Leu Ser Arg Ser Thr Arg Gly Ser
    450                 455
```

<210> SEQ ID NO 62
<211> LENGTH: 459
<212> TYPE: PRT
<213> ORGANISM: Artificial
<220> FEATURE:
<223> OTHER INFORMATION: Synthetic Construct

<400> SEQUENCE: 62

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Gly
        195                 200                 205

Leu Val Arg Pro Gln Gly Gly Gly Ser Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335
```

```
Thr Ile Ser Lys Thr Lys Gly Arg Pro Lys Ala Pro Gln Val Tyr Thr
            340                 345                 350

Ile Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
370                 375                 380

Trp Asn Gly Gln Pro Ala Glu Asn Tyr Lys Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
            435                 440                 445

Leu Gln Ser Leu Ser Arg Ser Thr Arg Gly Ser
        450                 455

<210> SEQ ID NO 63
<211> LENGTH: 1518
<212> TYPE: DNA
<213> ORGANISM: Hepatitis C virus
<220> FEATURE:
<221> NAME/KEY: CDS
<222> LOCATION: (1)..(1518)

<400> SEQUENCE: 63 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tcc ggt      96
Thr Glu Asn Leu Tyr Phe Gln Gly Ala Met Asp Pro Glu Phe Ser Gly
            20                  25                  30 tcc tgg cta agg gac atc tgg gac tgg ata tgc gag gtg ctg agc gac     144
Ser Trp Leu Arg Asp Ile Trp Asp Trp Ile Cys Glu Val Leu Ser Asp
        35                  40                  45 ttt aag acc tgg ctg aaa gcc aag ctc atg cca caa ctg cct ggg att     192
Phe Lys Thr Trp Leu Lys Ala Lys Leu Met Pro Gln Leu Pro Gly Ile
    50                  55                  60 ccc ttt gtg tcc tgc cag cgc ggg tat agg ggg gtc tgg cga gga gac     240
Pro Phe Val Ser Cys Gln Arg Gly Tyr Arg Gly Val Trp Arg Gly Asp
65                  70                  75                  80 ggc att atg cac act cgc tgc cac tgt gga gct gag atc act gga cat     288
Gly Ile Met His Thr Arg Cys His Cys Gly Ala Glu Ile Thr Gly His
                85                  90                  95 gtc aaa aac ggg acg atg agg atc gtc ggt cct agg acc tgc agg aac     336
Val Lys Asn Gly Thr Met Arg Ile Val Gly Pro Arg Thr Cys Arg Asn
            100                 105                 110 atg tgg agt ggg acg ttc ccc att aac gcc tac acc acg ggc ccc tgt     384
Met Trp Ser Gly Thr Phe Pro Ile Asn Ala Tyr Thr Thr Gly Pro Cys
        115                 120                 125 act ccc ctt cct gcg ccg aac tat aag ttc gcg ctg tgg agg gtg tct     432
Thr Pro Leu Pro Ala Pro Asn Tyr Lys Phe Ala Leu Trp Arg Val Ser
    130                 135                 140 gca gag gaa tac gtg gag ata agg cgg gtg ggg gac ttc cac tac gta     480
Ala Glu Glu Tyr Val Glu Ile Arg Arg Val Gly Asp Phe His Tyr Val
145                 150                 155                 160 tcg ggt atg act act gac aat ctt aaa tgc ccg tgc cag atc cca tcg     528
Ser Gly Met Thr Thr Asp Asn Leu Lys Cys Pro Cys Gln Ile Pro Ser
                165                 170                 175
```

| | | |
|---|---|---|
| ccc gaa ttt ttc aca gaa ttg gac ggg gtg cgc cta cac agg ttt gcg<br>Pro Glu Phe Phe Thr Glu Leu Asp Gly Val Arg Leu His Arg Phe Ala<br>180 185 190 | 576 | |
| ccc cct tgc aag ccc ttg ctg cgg gag gag gta tca ttc aga gta gga<br>Pro Pro Cys Lys Pro Leu Leu Arg Glu Glu Val Ser Phe Arg Val Gly<br>195 200 205 | 624 | |
| ctc cac gag tac ccg gtg ggg tcg caa tta cct tgc gag ccc gaa ccg<br>Leu His Glu Tyr Pro Val Gly Ser Gln Leu Pro Cys Glu Pro Glu Pro<br>210 215 220 | 672 | |
| gac gta gcc gtg ttg acg tcc atg ctc act gat ccc tcc cat ata aca<br>Asp Val Ala Val Leu Thr Ser Met Leu Thr Asp Pro Ser His Ile Thr<br>225 230 235 240 | 720 | |
| gca gag gcg gcc ggg aga agg ttg gcg aga ggg tca ccc cct tct atg<br>Ala Glu Ala Ala Gly Arg Arg Leu Ala Arg Gly Ser Pro Pro Ser Met<br>245 250 255 | 768 | |
| gcc agc tcc tcg gct agc cag ctg tcc gct cca tct ctc aag gca act<br>Ala Ser Ser Ser Ala Ser Gln Leu Ser Ala Pro Ser Leu Lys Ala Thr<br>260 265 270 | 816 | |
| tgc acc gcc aac cat gac tcc cct gac gcc gag ctc ata gag gct aac<br>Cys Thr Ala Asn His Asp Ser Pro Asp Ala Glu Leu Ile Glu Ala Asn<br>275 280 285 | 864 | |
| ctc ctg tgg agg cag gag atg ggc ggc aac atc acc agg gtt gag tca<br>Leu Leu Trp Arg Gln Glu Met Gly Gly Asn Ile Thr Arg Val Glu Ser<br>290 295 300 | 912 | |
| gag aac aaa gtg gtg att ctg gac tcc ttc gat ccg ctt gtg gca gag<br>Glu Asn Lys Val Val Ile Leu Asp Ser Phe Asp Pro Leu Val Ala Glu<br>305 310 315 320 | 960 | |
| gag gat gag cgg gag gtc tcc gta cct gca gaa att ctg cgg aag tct<br>Glu Asp Glu Arg Glu Val Ser Val Pro Ala Glu Ile Leu Arg Lys Ser<br>325 330 335 | 1008 | |
| cgg aga ttc gcc cgg gcc ctg ccc gtc tgg gcg cgg ccg gac tac aac<br>Arg Arg Phe Ala Arg Ala Leu Pro Val Trp Ala Arg Pro Asp Tyr Asn<br>340 345 350 | 1056 | |
| ccc ccg cta gta gag acg tgg aaa aag cct gac tac gaa cca cct gtg<br>Pro Pro Leu Val Glu Thr Trp Lys Lys Pro Asp Tyr Glu Pro Pro Val<br>355 360 365 | 1104 | |
| gtc cat ggc tgc ccg cta cca cct cca cgg tcc cct cct gtg cct ccg<br>Val His Gly Cys Pro Leu Pro Pro Pro Arg Ser Pro Pro Val Pro Pro<br>370 375 380 | 1152 | |
| cct cgg aaa aag cgt acg gtg gtc ctc acc gaa tca acc cta tct act<br>Pro Arg Lys Lys Arg Thr Val Val Leu Thr Glu Ser Thr Leu Ser Thr<br>385 390 395 400 | 1200 | |
| gcc ttg gcc gag ctt gcc acc aaa agt ttt ggc agc tcc tca act tcc<br>Ala Leu Ala Glu Leu Ala Thr Lys Ser Phe Gly Ser Ser Ser Thr Ser<br>405 410 415 | 1248 | |
| ggc att acg ggc gac aat acg aca aca tcc tct gag ccc gcc cct tct<br>Gly Ile Thr Gly Asp Asn Thr Thr Thr Ser Ser Glu Pro Ala Pro Ser<br>420 425 430 | 1296 | |
| ggc tgc ccc ccc gac tcc gac gtt gag tcc tat tct tcc atg ccc ccc<br>Gly Cys Pro Pro Asp Ser Asp Val Glu Ser Tyr Ser Ser Met Pro Pro<br>435 440 445 | 1344 | |
| ctg gag ggg gag cct ggg gat ccg gat ctc agc gac ggg tca tgg tcg<br>Leu Glu Gly Glu Pro Gly Asp Pro Asp Leu Ser Asp Gly Ser Trp Ser<br>450 455 460 | 1392 | |
| acg gtc agt agt ggg gcc gac acg gaa gat gtc gtg tgc gga cta gtg<br>Thr Val Ser Ser Gly Ala Asp Thr Glu Asp Val Val Cys Gly Leu Val<br>465 470 475 480 | 1440 | |
| cgg ccg ctt tcg aat cta gag cct gca gtc tcg agg cat gcg gta cca<br>Arg Pro Leu Ser Asn Leu Glu Pro Ala Val Ser Arg His Ala Val Pro<br>485 490 495 | 1488 | |

```
agc ttg tcg aga agt act aga gga tca taa                                    1518
Ser Leu Ser Arg Ser Thr Arg Gly Ser
            500                 505
```

<210> SEQ ID NO 64
<211> LENGTH: 505
<212> TYPE: PRT
<213> ORGANISM: Hepatitis C virus

<400> SEQUENCE: 64

```
Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Ser Gly
                20                  25                  30

Ser Trp Leu Arg Asp Ile Trp Asp Trp Ile Cys Glu Val Leu Ser Asp
            35                  40                  45

Phe Lys Thr Trp Leu Lys Ala Lys Leu Met Pro Gln Leu Pro Gly Ile
        50                  55                  60

Pro Phe Val Ser Cys Gln Arg Gly Tyr Arg Gly Val Trp Arg Gly Asp
65                  70                  75                  80

Gly Ile Met His Thr Arg Cys His Cys Gly Ala Glu Ile Thr Gly His
                85                  90                  95

Val Lys Asn Gly Thr Met Arg Ile Val Gly Pro Arg Thr Cys Arg Asn
            100                 105                 110

Met Trp Ser Gly Thr Phe Pro Ile Asn Ala Tyr Thr Thr Gly Pro Cys
        115                 120                 125

Thr Pro Leu Pro Ala Pro Asn Tyr Lys Phe Ala Leu Trp Arg Val Ser
130                 135                 140

Ala Glu Glu Tyr Val Glu Ile Arg Arg Val Gly Asp Phe His Tyr Val
145                 150                 155                 160

Ser Gly Met Thr Thr Asp Asn Leu Lys Cys Pro Cys Gln Ile Pro Ser
                165                 170                 175

Pro Glu Phe Phe Thr Glu Leu Asp Gly Val Arg Leu His Arg Phe Ala
            180                 185                 190

Pro Pro Cys Lys Pro Leu Leu Arg Glu Glu Val Ser Phe Arg Val Gly
        195                 200                 205

Leu His Glu Tyr Pro Val Gly Ser Gln Leu Pro Cys Glu Pro Glu Pro
210                 215                 220

Asp Val Ala Val Leu Thr Ser Met Leu Thr Asp Pro Ser His Ile Thr
225                 230                 235                 240

Ala Glu Ala Ala Gly Arg Arg Leu Ala Arg Gly Ser Pro Pro Ser Met
                245                 250                 255

Ala Ser Ser Ser Ala Ser Gln Leu Ser Ala Pro Ser Leu Lys Ala Thr
            260                 265                 270

Cys Thr Ala Asn His Asp Ser Pro Asp Ala Glu Leu Ile Glu Ala Asn
        275                 280                 285

Leu Leu Trp Arg Gln Glu Met Gly Gly Asn Ile Thr Arg Val Glu Ser
290                 295                 300

Glu Asn Lys Val Val Ile Leu Asp Ser Phe Asp Pro Leu Val Ala Glu
305                 310                 315                 320

Glu Asp Glu Arg Glu Val Ser Val Pro Ala Glu Ile Leu Arg Lys Ser
                325                 330                 335

Arg Arg Phe Ala Arg Ala Leu Pro Val Trp Ala Arg Pro Asp Tyr Asn
            340                 345                 350

Pro Pro Leu Val Glu Thr Trp Lys Lys Pro Asp Tyr Glu Pro Pro Val
        355                 360                 365
```

-continued

```
Val His Gly Cys Pro Leu Pro Pro Pro Arg Ser Pro Pro Val Pro Pro
    370                 375                 380

Pro Arg Lys Lys Arg Thr Val Val Leu Thr Glu Ser Thr Leu Ser Thr
385                 390                 395                 400

Ala Leu Ala Glu Leu Ala Thr Lys Ser Phe Gly Ser Ser Ser Thr Ser
                405                 410                 415

Gly Ile Thr Gly Asp Asn Thr Thr Thr Ser Ser Glu Pro Ala Pro Ser
            420                 425                 430

Gly Cys Pro Pro Asp Ser Asp Val Glu Ser Tyr Ser Ser Met Pro Pro
        435                 440                 445

Leu Glu Gly Glu Pro Gly Asp Pro Asp Leu Ser Asp Gly Ser Trp Ser
    450                 455                 460

Thr Val Ser Ser Gly Ala Asp Thr Glu Asp Val Val Cys Gly Leu Val
465                 470                 475                 480

Arg Pro Leu Ser Asn Leu Glu Pro Ala Val Ser Arg His Ala Val Pro
                485                 490                 495

Ser Leu Ser Arg Ser Thr Arg Gly Ser
            500                 505

<210> SEQ ID NO 65
<211> LENGTH: 2190
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2190)

<400> SEQUENCE: 65 atg tcg tac tac cat cac cat cac cat cac gat tac gat atc cca acg      48
Met Ser Tyr Tyr His His His His His His Asp Tyr Asp Ile Pro Thr
1               5                  10                  15 acc gaa aac ctg tat ttt cag ggc gcc atg gat ccg gaa ttc tcc ggt      96
Thr Glu Asn Leu Tyr Phe Gln Gly Ala Met Asp Pro Glu Phe Ser Gly
            20                  25                  30 tcc tgg cta agg gac atc tgg gac tgg ata tgc gag gtg ctg agc gac    144
Ser Trp Leu Arg Asp Ile Trp Asp Trp Ile Cys Glu Val Leu Ser Asp
        35                  40                  45 ttt aag acc tgg ctg aaa gcc aag ctc atg cca caa ctg cct ggg att    192
Phe Lys Thr Trp Leu Lys Ala Lys Leu Met Pro Gln Leu Pro Gly Ile
    50                  55                  60 ccc ttt gtg tcc tgc cag cgc ggg tat agg ggg gtc tgg cga gga gac    240
Pro Phe Val Ser Cys Gln Arg Gly Tyr Arg Gly Val Trp Arg Gly Asp
65                  70                  75                  80 ggc att atg cac act cgc tgc cac tgt gga gct gag atc act gga cat    288
Gly Ile Met His Thr Arg Cys His Cys Gly Ala Glu Ile Thr Gly His
                85                  90                  95 gtc aaa aac ggg acg atg agg atc gtc ggt cct agg acc tgc agg aac    336
Val Lys Asn Gly Thr Met Arg Ile Val Gly Pro Arg Thr Cys Arg Asn
            100                 105                 110 atg tgg agt ggg acg ttc ccc att aac gcc tac acc acg ggc ccc tgt    384
Met Trp Ser Gly Thr Phe Pro Ile Asn Ala Tyr Thr Thr Gly Pro Cys
        115                 120                 125 act ccc ctt cct gcg ccg aac tat aag ttc gcg ctg tgg agg gtg tct    432
Thr Pro Leu Pro Ala Pro Asn Tyr Lys Phe Ala Leu Trp Arg Val Ser
    130                 135                 140 gca gag gaa tac gtg gag ata agg cgg gtg ggg gac ttc cac tac gta    480
Ala Glu Glu Tyr Val Glu Ile Arg Arg Val Gly Asp Phe His Tyr Val
145                 150                 155                 160
```

```
tcg ggt atg act act gac aat ctt aaa tgc ccg tgc cag atc cca tcg      528
Ser Gly Met Thr Thr Asp Asn Leu Lys Cys Pro Cys Gln Ile Pro Ser
            165                 170                 175 ccc gaa ttt ttc aca gaa ttg gac ggg gtg cgc cta cac agg ttt gcg      576
Pro Glu Phe Phe Thr Glu Leu Asp Gly Val Arg Leu His Arg Phe Ala
        180                 185                 190 ccc cct tgc aag ccc ttg ctg cgg gag gag gta tca ttc aga gta gga      624
Pro Pro Cys Lys Pro Leu Leu Arg Glu Glu Val Ser Phe Arg Val Gly
    195                 200                 205 ctc cac gag tac ccg gtg ggg tcg caa tta cct tgc gag ccc gaa ccg      672
Leu His Glu Tyr Pro Val Gly Ser Gln Leu Pro Cys Glu Pro Glu Pro
210                 215                 220 gac gta gcc gtg ttg acg tcc atg ctc act gat ccc tcc cat ata aca      720
Asp Val Ala Val Leu Thr Ser Met Leu Thr Asp Pro Ser His Ile Thr
225                 230                 235                 240 gca gag gcg gcc ggg aga agg ttg gcg aga ggg tca ccc cct tct atg      768
Ala Glu Ala Ala Gly Arg Arg Leu Ala Arg Gly Ser Pro Pro Ser Met
                245                 250                 255 gcc agc tcc tcg gct agc cag ctg tcc gct cca tct ctc aag gca act      816
Ala Ser Ser Ser Ala Ser Gln Leu Ser Ala Pro Ser Leu Lys Ala Thr
            260                 265                 270 tgc acc gcc aac cat gac tcc cct gac gcc gag ctc ata gag gct aac      864
Cys Thr Ala Asn His Asp Ser Pro Asp Ala Glu Leu Ile Glu Ala Asn
        275                 280                 285 ctc ctg tgg agg cag gag atg ggc ggc aac atc acc agg gtt gag tca      912
Leu Leu Trp Arg Gln Glu Met Gly Gly Asn Ile Thr Arg Val Glu Ser
    290                 295                 300 gag aac aaa gtg gtg att ctg gac tcc ttc gat ccg ctt gtg gca gag      960
Glu Asn Lys Val Val Ile Leu Asp Ser Phe Asp Pro Leu Val Ala Glu
305                 310                 315                 320 gag gat gag cgg gag gtc tcc gta cct gca gaa att ctg cgg aag tct     1008
Glu Asp Glu Arg Glu Val Ser Val Pro Ala Glu Ile Leu Arg Lys Ser
                325                 330                 335 cgg aga ttc gcc cgg gcc ctg ccc gtc tgg gcg cgg ccg gac tac aac     1056
Arg Arg Phe Ala Arg Ala Leu Pro Val Trp Ala Arg Pro Asp Tyr Asn
            340                 345                 350 ccc ccg cta gta gag acg tgg aaa aag cct gac tac gaa cca cct gtg     1104
Pro Pro Leu Val Glu Thr Trp Lys Lys Pro Asp Tyr Glu Pro Pro Val
        355                 360                 365 gtc cat ggc tgc ccg cta cca cct cca cgg tcc cct cct gtg cct ccg     1152
Val His Gly Cys Pro Leu Pro Pro Pro Arg Ser Pro Pro Val Pro Pro
    370                 375                 380 cct cgg aaa aag cgt acg gtg gtc ctc acc gaa tca acc cta tct act     1200
Pro Arg Lys Lys Arg Thr Val Val Leu Thr Glu Ser Thr Leu Ser Thr
385                 390                 395                 400 gcc ttg gcc gag ctt gcc acc aaa agt ttt ggc agc tcc tca act tcc     1248
Ala Leu Ala Glu Leu Ala Thr Lys Ser Phe Gly Ser Ser Ser Thr Ser
                405                 410                 415 ggc att acg ggc gac aat acg aca aca tcc tct gag ccc gcc cct tct     1296
Gly Ile Thr Gly Asp Asn Thr Thr Thr Ser Ser Glu Pro Ala Pro Ser
            420                 425                 430 ggc tgc ccc ccc gac tcc gac gtt gag tcc tat tct tcc atg ccc ccc     1344
Gly Cys Pro Pro Asp Ser Asp Val Glu Ser Tyr Ser Ser Met Pro Pro
        435                 440                 445 ctg gag ggg gag cct ggg gat ccg gat ctc agc gac ggg tca tgg tcg     1392
Leu Glu Gly Glu Pro Gly Asp Pro Asp Leu Ser Asp Gly Ser Trp Ser
    450                 455                 460 acg gtc agt agt ggg gcc gac acg gaa gat gtc gtg tgc gga cta gtg     1440
Thr Val Ser Ser Gly Ala Asp Thr Glu Asp Val Val Cys Gly Leu Val
465                 470                 475                 480
```

```
cgg ccg caa ggc ggc gga tcc gtg gac aag aaa att gtg ccc agg gat     1488
Arg Pro Gln Gly Gly Gly Ser Val Asp Lys Lys Ile Val Pro Arg Asp
                485                 490                 495 tgt ggt tgt aag cct tgc ata tgt aca gtc cca gaa gta tca tct gtc     1536
Cys Gly Cys Lys Pro Cys Ile Cys Thr Val Pro Glu Val Ser Ser Val
            500                 505                 510 ttc atc ttc ccc cca aag ccc aag gat gtg ctc acc att act ctg act     1584
Phe Ile Phe Pro Pro Lys Pro Lys Asp Val Leu Thr Ile Thr Leu Thr
        515                 520                 525 cct aag gtc acg tgt gtt gtg gta gac atc agc aag gat gat ccc gag     1632
Pro Lys Val Thr Cys Val Val Val Asp Ile Ser Lys Asp Asp Pro Glu
    530                 535                 540 gtc cag ttc agc tgg ttt gta gat gat gtg gag gtg cac aca gct cag     1680
Val Gln Phe Ser Trp Phe Val Asp Asp Val Glu Val His Thr Ala Gln
545                 550                 555                 560 acg caa ccc cgg gag gag cag ttc aac agc act ttc cgc tca gtc agt     1728
Thr Gln Pro Arg Glu Glu Gln Phe Asn Ser Thr Phe Arg Ser Val Ser
                565                 570                 575 gaa ctt ccc atc atg cac cag gac tgg ctc aat ggc aag gag ttc aaa     1776
Glu Leu Pro Ile Met His Gln Asp Trp Leu Asn Gly Lys Glu Phe Lys
            580                 585                 590 tgc agg gtc aac agt gca gct ttc cct gcc ccc atc gag aaa acc atc     1824
Cys Arg Val Asn Ser Ala Ala Phe Pro Ala Pro Ile Glu Lys Thr Ile
        595                 600                 605 tcc aaa acc aaa ggc aga ccg aag gct cca cag gtg tac acc att cca     1872
Ser Lys Thr Lys Gly Arg Pro Lys Ala Pro Gln Val Tyr Thr Ile Pro
    610                 615                 620 cct ccc aag gag cag atg gcc aag gat aaa gtc agt ctg acc tgc atg     1920
Pro Pro Lys Glu Gln Met Ala Lys Asp Lys Val Ser Leu Thr Cys Met
625                 630                 635                 640 ata aca gac ttc ttc cct gaa gac att act gtg gag tgg cag tgg aat     1968
Ile Thr Asp Phe Phe Pro Glu Asp Ile Thr Val Glu Trp Gln Trp Asn
                645                 650                 655 ggg cag cca gcg gag aac tac aag aac act cag ccc atc atg gac aca     2016
Gly Gln Pro Ala Glu Asn Tyr Lys Asn Thr Gln Pro Ile Met Asp Thr
            660                 665                 670 gat ggc tct tac ttc gtc tac agc aag ctc aat gtg cag aag agc aac     2064
Asp Gly Ser Tyr Phe Val Tyr Ser Lys Leu Asn Val Gln Lys Ser Asn
        675                 680                 685 tgg gag gca gga aat act ttc acc tgc tct gtg tta cat gag ggc ctg     2112
Trp Glu Ala Gly Asn Thr Phe Thr Cys Ser Val Leu His Glu Gly Leu
    690                 695                 700 cac aac cac cat act gag aag agc ctc tcc cac tct cct ggg ctg caa     2160
His Asn His His Thr Glu Lys Ser Leu Ser His Ser Pro Gly Leu Gln
705                 710                 715                 720 agc ttg tcg aga agt act aga gga tca taa                             2190
Ser Leu Ser Arg Ser Thr Arg Gly Ser
                725

<210> SEQ ID NO 66
<211> LENGTH: 729
<212> TYPE: PRT
<213> ORGANISM: Artificial
<220> FEATURE:
<223> OTHER INFORMATION: Synthetic Construct

<400> SEQUENCE: 66

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Ser Gly
            20                  25                  30
```

```
Ser Trp Leu Arg Asp Ile Trp Asp Trp Ile Cys Glu Val Leu Ser Asp
        35                  40                  45

Phe Lys Thr Trp Leu Lys Ala Lys Leu Met Pro Gln Leu Pro Gly Ile
 50                  55                  60

Pro Phe Val Ser Cys Gln Arg Gly Tyr Arg Gly Val Trp Arg Gly Asp
 65                  70                  75                  80

Gly Ile Met His Thr Arg Cys His Cys Gly Ala Glu Ile Thr Gly His
                 85                  90                  95

Val Lys Asn Gly Thr Met Arg Ile Val Gly Pro Arg Thr Cys Arg Asn
            100                 105                 110

Met Trp Ser Gly Thr Phe Pro Ile Asn Ala Tyr Thr Thr Gly Pro Cys
        115                 120                 125

Thr Pro Leu Pro Ala Pro Asn Tyr Lys Phe Ala Leu Trp Arg Val Ser
        130                 135                 140

Ala Glu Glu Tyr Val Glu Ile Arg Arg Val Gly Asp Phe His Tyr Val
145                 150                 155                 160

Ser Gly Met Thr Thr Asp Asn Leu Lys Cys Pro Cys Gln Ile Pro Ser
            165                 170                 175

Pro Glu Phe Phe Thr Glu Leu Asp Gly Val Arg Leu His Arg Phe Ala
            180                 185                 190

Pro Pro Cys Lys Pro Leu Leu Arg Glu Glu Val Ser Phe Arg Val Gly
            195                 200                 205

Leu His Glu Tyr Pro Val Gly Ser Gln Leu Pro Cys Glu Pro Glu Pro
            210                 215                 220

Asp Val Ala Val Leu Thr Ser Met Leu Thr Asp Pro Ser His Ile Thr
225                 230                 235                 240

Ala Glu Ala Ala Gly Arg Arg Leu Ala Arg Gly Ser Pro Pro Ser Met
                245                 250                 255

Ala Ser Ser Ser Ala Ser Gln Leu Ser Ala Pro Ser Leu Lys Ala Thr
            260                 265                 270

Cys Thr Ala Asn His Asp Ser Pro Asp Ala Glu Leu Ile Glu Ala Asn
            275                 280                 285

Leu Leu Trp Arg Gln Glu Met Gly Gly Asn Ile Thr Arg Val Glu Ser
        290                 295                 300

Glu Asn Lys Val Val Ile Leu Asp Ser Phe Asp Pro Leu Val Ala Glu
305                 310                 315                 320

Glu Asp Glu Arg Glu Val Ser Val Pro Ala Glu Ile Leu Arg Lys Ser
                325                 330                 335

Arg Arg Phe Ala Arg Ala Leu Pro Val Trp Ala Arg Pro Asp Tyr Asn
            340                 345                 350

Pro Pro Leu Val Glu Thr Trp Lys Lys Pro Asp Tyr Glu Pro Pro Val
            355                 360                 365

Val His Gly Cys Pro Leu Pro Pro Arg Ser Pro Pro Val Pro Pro Pro
        370                 375                 380

Pro Arg Lys Lys Arg Thr Val Val Leu Thr Glu Ser Thr Leu Ser Thr
385                 390                 395                 400

Ala Leu Ala Glu Leu Ala Thr Lys Ser Phe Gly Ser Ser Ser Thr Ser
                405                 410                 415

Gly Ile Thr Gly Asp Asn Thr Thr Thr Ser Ser Glu Pro Ala Pro Ser
            420                 425                 430

Gly Cys Pro Pro Asp Ser Asp Val Glu Ser Tyr Ser Ser Met Pro Pro
        435                 440                 445

Leu Glu Gly Glu Pro Gly Asp Pro Asp Leu Ser Asp Gly Ser Trp Ser
```

```
                450             455             460
Thr Val Ser Ser Gly Ala Asp Thr Glu Asp Val Val Cys Gly Leu Val
465                 470                 475                 480

Arg Pro Gln Gly Gly Gly Ser Val Asp Lys Lys Ile Val Pro Arg Asp
                485                 490                 495

Cys Gly Cys Lys Pro Cys Ile Cys Thr Val Pro Glu Val Ser Ser Val
                500                 505                 510

Phe Ile Phe Pro Pro Lys Pro Lys Asp Val Leu Thr Ile Thr Leu Thr
                515                 520                 525

Pro Lys Val Thr Cys Val Val Val Asp Ile Ser Lys Asp Asp Pro Glu
530                 535                 540

Val Gln Phe Ser Trp Phe Val Asp Asp Val Glu Val His Thr Ala Gln
545                 550                 555                 560

Thr Gln Pro Arg Glu Glu Gln Phe Asn Ser Thr Phe Arg Ser Val Ser
                565                 570                 575

Glu Leu Pro Ile Met His Gln Asp Trp Leu Asn Gly Lys Glu Phe Lys
                580                 585                 590

Cys Arg Val Asn Ser Ala Ala Phe Pro Ala Pro Ile Glu Lys Thr Ile
                595                 600                 605

Ser Lys Thr Lys Gly Arg Pro Lys Ala Pro Gln Val Tyr Thr Ile Pro
610                 615                 620

Pro Pro Lys Glu Gln Met Ala Lys Asp Lys Val Ser Leu Thr Cys Met
625                 630                 635                 640

Ile Thr Asp Phe Phe Pro Glu Asp Ile Thr Val Glu Trp Gln Trp Asn
                645                 650                 655

Gly Gln Pro Ala Glu Asn Tyr Lys Asn Thr Gln Pro Ile Met Asp Thr
                660                 665                 670

Asp Gly Ser Tyr Phe Val Tyr Ser Lys Leu Asn Val Gln Lys Ser Asn
                675                 680                 685

Trp Glu Ala Gly Asn Thr Phe Thr Cys Ser Val Leu His Glu Gly Leu
                690                 695                 700

His Asn His His Thr Glu Lys Ser Leu Ser His Ser Pro Gly Leu Gln
705                 710                 715                 720

Ser Leu Ser Arg Ser Thr Arg Gly Ser
                725

<210> SEQ ID NO 67
<211> LENGTH: 756
<212> TYPE: DNA
<213> ORGANISM: Hepatitis C virus
<220> FEATURE:
<221> NAME/KEY: CDS
<222> LOCATION: (1)..(756)

<400> SEQUENCE: 67 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa    96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac   144
Val Arg Asn Ser Ser Gly Leu Tyr His Val Thr Asn Asp Cys Pro Asn
        35                  40                  45 tcg agt att gtg tac gag gcg gcc gat gcc atc ctg cac act ccg ggg   192
Ser Ser Ile Val Tyr Glu Ala Ala Asp Ala Ile Leu His Thr Pro Gly
    50                  55                  60
```

```
tgt gtc cct tgc gtt cgc gag ggt aac gcc tcg agg tgt tgg gtg gcg      240
Cys Val Pro Cys Val Arg Glu Gly Asn Ala Ser Arg Cys Trp Val Ala
 65                  70                  75                  80 gtg acc ccc acg gtg gcc acc agg gac ggc aaa ctc ccc aca acg cag      288
Val Thr Pro Thr Val Ala Thr Arg Asp Gly Lys Leu Pro Thr Thr Gln
                 85                  90                  95 ctt cga cgt cat atc gat ctg ctt gtc ggg agc gcc acc ctc tgc tcg      336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa      384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat      432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat      480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg      528
Met Met Met Asn Trp Ser Pro Thr Ala Ala Leu Val Val Ala Gln Leu
                165                 170                 175 ctc cgg atc cca caa gcc atc atg gac atg atc gct ggt gct cac tgg      576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg      624
Gly Val Leu Ala Gly Ile Ala Tyr Phe Ser Met Val Gly Asn Trp Ala
        195                 200                 205 aag gtc ctg gta gtg ctg ctg cta ttt gcc ggc gtc gac gcg gaa gga      672
Lys Val Leu Val Val Leu Leu Leu Phe Ala Gly Val Asp Ala Glu Gly
    210                 215                 220 cta gtg cgg ccg ctt tcg aat cta gag cct gca gtc tcg agg cat gcg      720
Leu Val Arg Pro Leu Ser Asn Leu Glu Pro Ala Val Ser Arg His Ala
225                 230                 235                 240 gta cca agc ttg tcg aga agt act aga gga tca taa                      756
Val Pro Ser Leu Ser Arg Ser Thr Arg Gly Ser
                245                 250
```

<210> SEQ ID NO 68
<211> LENGTH: 251
<212> TYPE: PRT
<213> ORGANISM: Hepatitis C virus

<400> SEQUENCE: 68

```
Met Ser Tyr Tyr His His His His His Asp Tyr Asp Ile Pro Thr
 1               5                  10                  15

Thr Glu Asn Leu Tyr Phe Gln Gly Ala Met Asp Pro Glu Phe Tyr Gln
                 20                  25                  30

Val Arg Asn Ser Ser Gly Leu Tyr His Val Thr Asn Asp Cys Pro Asn
            35                  40                  45

Ser Ser Ile Val Tyr Glu Ala Ala Asp Ala Ile Leu His Thr Pro Gly
        50                  55                  60

Cys Val Pro Cys Val Arg Glu Gly Asn Ala Ser Arg Cys Trp Val Ala
 65                  70                  75                  80

Val Thr Pro Thr Val Ala Thr Arg Asp Gly Lys Leu Pro Thr Thr Gln
                 85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125
```

| | | | | | | | | | | | | |
|---|---|---|---|---|---|---|---|---|---|---|---|---|
|Leu|Phe|Thr|Phe|Ser|Pro|Arg|Arg|His|Trp|Thr|Thr|Gln|Asp|Cys|Asn|
| |130| | | |135| | | |140| | | | | | |

| Cys | Ser | Ile | Tyr | Pro | Gly | His | Ile | Thr | Gly | His | Arg | Met | Ala | Trp | Asp |
|---|---|---|---|---|---|---|---|---|---|---|---|---|---|---|---|
| 145 | | | | | 150 | | | | | 155 | | | | | 160 |

| Met | Met | Met | Asn | Trp | Ser | Pro | Thr | Ala | Ala | Leu | Val | Val | Ala | Gln | Leu |
|---|---|---|---|---|---|---|---|---|---|---|---|---|---|---|---|
| | | | | 165 | | | | | 170 | | | | | 175 | |

| Leu | Arg | Ile | Pro | Gln | Ala | Ile | Met | Asp | Met | Ile | Ala | Gly | Ala | His | Trp |
|---|---|---|---|---|---|---|---|---|---|---|---|---|---|---|---|
| | | | 180 | | | | | 185 | | | | | 190 | | |

| Gly | Val | Leu | Ala | Gly | Ile | Ala | Tyr | Phe | Ser | Met | Val | Gly | Asn | Trp | Ala |
|---|---|---|---|---|---|---|---|---|---|---|---|---|---|---|---|
| | | 195 | | | | | 200 | | | | | 205 | | | |

| Lys | Val | Leu | Val | Val | Leu | Leu | Leu | Phe | Ala | Gly | Val | Asp | Ala | Glu | Gly |
|---|---|---|---|---|---|---|---|---|---|---|---|---|---|---|---|
| | 210 | | | | | 215 | | | | | 220 | | | | |

| Leu | Val | Arg | Pro | Leu | Ser | Asn | Leu | Glu | Pro | Ala | Val | Ser | Arg | His | Ala |
|---|---|---|---|---|---|---|---|---|---|---|---|---|---|---|---|
| 225 | | | | | 230 | | | | | 235 | | | | | 240 |

| Val | Pro | Ser | Leu | Ser | Arg | Ser | Thr | Arg | Gly | Ser |
|---|---|---|---|---|---|---|---|---|---|---|
| | | | | 245 | | | | | 250 | |

```
<210> SEQ ID NO 69
<211> LENGTH: 1428
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1428)

<400> SEQUENCE: 69
```

| atg | tcg | tac | tac | cat | cac | cat | cac | cat | cac | gat | tac | gat | atc | cca | acg | 48 |
|---|---|---|---|---|---|---|---|---|---|---|---|---|---|---|---|---|
| Met | Ser | Tyr | Tyr | His | His | His | His | His | His | Asp | Tyr | Asp | Ile | Pro | Thr | |
| 1 | | | | 5 | | | | | 10 | | | | | 15 | | |

| acc | gaa | aac | ctg | tat | ttt | cag | ggc | gcc | atg | gat | ccg | gaa | ttc | tac | caa | 96 |
|---|---|---|---|---|---|---|---|---|---|---|---|---|---|---|---|---|
| Thr | Glu | Asn | Leu | Tyr | Phe | Gln | Gly | Ala | Met | Asp | Pro | Glu | Phe | Tyr | Gln | |
| | | | 20 | | | | | 25 | | | | | 30 | | | |

| gtg | cgc | aat | tcc | tcg | ggg | ctt | tac | cat | gtc | acc | aat | gat | tgc | cct | aac | 144 |
|---|---|---|---|---|---|---|---|---|---|---|---|---|---|---|---|---|
| Val | Arg | Asn | Ser | Ser | Gly | Leu | Tyr | His | Val | Thr | Asn | Asp | Cys | Pro | Asn | |
| | | 35 | | | | | 40 | | | | | 45 | | | | |

| tcg | agt | att | gtg | tac | gag | gcg | gcc | gat | gcc | atc | ctg | cac | act | ccg | ggg | 192 |
|---|---|---|---|---|---|---|---|---|---|---|---|---|---|---|---|---|
| Ser | Ser | Ile | Val | Tyr | Glu | Ala | Ala | Asp | Ala | Ile | Leu | His | Thr | Pro | Gly | |
| 50 | | | | | 55 | | | | | 60 | | | | | | |

| tgt | gtc | cct | tgc | gtt | cgc | gag | ggt | aac | gcc | tcg | agg | tgt | tgg | gtg | gcg | 240 |
|---|---|---|---|---|---|---|---|---|---|---|---|---|---|---|---|---|
| Cys | Val | Pro | Cys | Val | Arg | Glu | Gly | Asn | Ala | Ser | Arg | Cys | Trp | Val | Ala | |
| 65 | | | | 70 | | | | | 75 | | | | | 80 | | |

| gtg | acc | ccc | acg | gtg | gcc | acc | agg | gac | ggc | aaa | ctc | ccc | aca | acg | cag | 288 |
|---|---|---|---|---|---|---|---|---|---|---|---|---|---|---|---|---|
| Val | Thr | Pro | Thr | Val | Ala | Thr | Arg | Asp | Gly | Lys | Leu | Pro | Thr | Thr | Gln | |
| | | | 85 | | | | | 90 | | | | | 95 | | | |

| ctt | cga | cgt | cat | atc | gat | ctg | ctt | gtc | ggg | agc | gcc | acc | ctc | tgc | tcg | 336 |
|---|---|---|---|---|---|---|---|---|---|---|---|---|---|---|---|---|
| Leu | Arg | Arg | His | Ile | Asp | Leu | Leu | Val | Gly | Ser | Ala | Thr | Leu | Cys | Ser | |
| | | 100 | | | | | 105 | | | | | 110 | | | | |

| gcc | ctc | tac | gtg | ggg | gac | ctg | tgc | ggg | tct | gtc | ttt | ctt | gtt | ggt | caa | 384 |
|---|---|---|---|---|---|---|---|---|---|---|---|---|---|---|---|---|
| Ala | Leu | Tyr | Val | Gly | Asp | Leu | Cys | Gly | Ser | Val | Phe | Leu | Val | Gly | Gln | |
| | 115 | | | | | 120 | | | | | 125 | | | | | |

| ctg | ttt | acc | ttc | tct | ccc | agg | cgc | cac | tgg | acg | acg | caa | gac | tgc | aat | 432 |
|---|---|---|---|---|---|---|---|---|---|---|---|---|---|---|---|---|
| Leu | Phe | Thr | Phe | Ser | Pro | Arg | Arg | His | Trp | Thr | Thr | Gln | Asp | Cys | Asn | |
| 130 | | | | | 135 | | | | | 140 | | | | | | |

| tgt | tct | atc | tat | ccc | ggc | cat | ata | acg | ggt | cat | cgc | atg | gca | tgg | gat | 480 |
|---|---|---|---|---|---|---|---|---|---|---|---|---|---|---|---|---|
| Cys | Ser | Ile | Tyr | Pro | Gly | His | Ile | Thr | Gly | His | Arg | Met | Ala | Trp | Asp | |
| 145 | | | | 150 | | | | | 155 | | | | | 160 | | |

| atg | atg | atg | aac | tgg | tcc | cct | acg | gca | gcg | ttg | gtg | gta | gct | cag | ctg | 528 |
|---|---|---|---|---|---|---|---|---|---|---|---|---|---|---|---|---|
| Met | Met | Met | Asn | Trp | Ser | Pro | Thr | Ala | Ala | Leu | Val | Val | Ala | Gln | Leu | |
| | | | | 165 | | | | | 170 | | | | | 175 | | |

```
ctc cgg atc cca caa gcc atc atg gac atg atc gct ggt gct cac tgg      576
Leu Arg Ile Pro Gln Ala Ile Met Asp Met Ile Ala Gly Ala His Trp
        180                 185                 190 gga gtc ctg gcg ggc ata gcg tat ttc tcc atg gtg ggg aac tgg gcg      624
Gly Val Leu Ala Gly Ile Ala Tyr Phe Ser Met Val Gly Asn Trp Ala
            195                 200                 205 aag gtc ctg gta gtg ctg ctg cta ttt gcc ggc gtc gac gcg gaa gga      672
Lys Val Leu Val Val Leu Leu Leu Phe Ala Gly Val Asp Ala Glu Gly
    210                 215                 220 cta gtg cgg ccg caa ggc ggc gga tcc gtg gac aag aaa att gtg ccc      720
Leu Val Arg Pro Gln Gly Gly Gly Ser Val Asp Lys Lys Ile Val Pro
225                 230                 235                 240 agg gat tgt ggt tgt aag cct tgc ata tgt aca gtc cca gaa gta tca      768
Arg Asp Cys Gly Cys Lys Pro Cys Ile Cys Thr Val Pro Glu Val Ser
                245                 250                 255 tct gtc ttc atc ttc ccc cca aag ccc aag gat gtg ctc acc att act      816
Ser Val Phe Ile Phe Pro Pro Lys Pro Lys Asp Val Leu Thr Ile Thr
            260                 265                 270 ctg act cct aag gtc acg tgt gtt gtg gta gac atc agc aag gat gat      864
Leu Thr Pro Lys Val Thr Cys Val Val Val Asp Ile Ser Lys Asp Asp
        275                 280                 285 ccc gag gtc cag ttc agc tgg ttt gta gat gat gtg gag gtg cac aca      912
Pro Glu Val Gln Phe Ser Trp Phe Val Asp Asp Val Glu Val His Thr
    290                 295                 300 gct cag acg caa ccc cgg gag gag cag ttc aac agc act ttc cgc tca      960
Ala Gln Thr Gln Pro Arg Glu Glu Gln Phe Asn Ser Thr Phe Arg Ser
305                 310                 315                 320 gtc agt gaa ctt ccc atc atg cac cag gac tgg ctc aat ggc aag gag     1008
Val Ser Glu Leu Pro Ile Met His Gln Asp Trp Leu Asn Gly Lys Glu
                325                 330                 335 ttc aaa tgc agg gtc aac agt gca gct ttc cct gcc ccc atc gag aaa     1056
Phe Lys Cys Arg Val Asn Ser Ala Ala Phe Pro Ala Pro Ile Glu Lys
            340                 345                 350 acc atc tcc aaa acc aaa ggc aga ccg aag gct cca cag gtg tac acc     1104
Thr Ile Ser Lys Thr Lys Gly Arg Pro Lys Ala Pro Gln Val Tyr Thr
        355                 360                 365 att cca cct ccc aag gag cag atg gcc aag gat aaa gtc agt ctg acc     1152
Ile Pro Pro Pro Lys Glu Gln Met Ala Lys Asp Lys Val Ser Leu Thr
    370                 375                 380 tgc atg ata aca gac ttc ttc cct gaa gac att act gtg gag tgg cag     1200
Cys Met Ile Thr Asp Phe Phe Pro Glu Asp Ile Thr Val Glu Trp Gln
385                 390                 395                 400 tgg aat ggg cag cca gcg gag aac tac aag aac act cag ccc atc atg     1248
Trp Asn Gly Gln Pro Ala Glu Asn Tyr Lys Asn Thr Gln Pro Ile Met
                405                 410                 415 gac aca gat ggc tct tac ttc gtc tac agc aag ctc aat gtg cag aag     1296
Asp Thr Asp Gly Ser Tyr Phe Val Tyr Ser Lys Leu Asn Val Gln Lys
            420                 425                 430 agc aac tgg gag gca gga aat act ttc acc tgc tct gtg tta cat gag     1344
Ser Asn Trp Glu Ala Gly Asn Thr Phe Thr Cys Ser Val Leu His Glu
        435                 440                 445 ggc ctg cac aac cac cat act gag aag agc ctc tcc cac tct cct ggg     1392
Gly Leu His Asn His His Thr Glu Lys Ser Leu Ser His Ser Pro Gly
    450                 455                 460 ctg caa agc ttg tcg aga agt act aga gga tca taa                      1428
Leu Gln Ser Leu Ser Arg Ser Thr Arg Gly Ser
465                 470                 475
```

<210> SEQ ID NO 70
<211> LENGTH: 475

<210> TYPE: PRT
<213> ORGANISM: Artificial
<220> FEATURE:
<223> OTHER INFORMATION: Synthetic Construct

<400> SEQUENCE: 70

```
Met Ser Tyr Tyr His His His His His His Asp Tyr Asp Ile Pro Thr
1               5                   10                  15
Thr Glu Asn Leu Tyr Phe Gln Gly Ala Met Asp Pro Glu Phe Tyr Gln
            20                  25                  30
Val Arg Asn Ser Ser Gly Leu Tyr His Val Thr Asn Asp Cys Pro Asn
        35                  40                  45
Ser Ser Ile Val Tyr Glu Ala Ala Asp Ala Ile Leu His Thr Pro Gly
    50                  55                  60
Cys Val Pro Cys Val Arg Glu Gly Asn Ala Ser Arg Cys Trp Val Ala
65                  70                  75                  80
Val Thr Pro Thr Val Ala Thr Arg Asp Gly Lys Leu Pro Thr Thr Gln
            85                  90                  95
Leu Arg Arg His Ile Asp Leu Leu Val Gly Ser Ala Thr Leu Cys Ser
        100                 105                 110
Ala Leu Tyr Val Gly Asp Leu Cys Gly Ser Val Phe Leu Val Gly Gln
    115                 120                 125
Leu Phe Thr Phe Ser Pro Arg Arg His Trp Thr Thr Gln Asp Cys Asn
130                 135                 140
Cys Ser Ile Tyr Pro Gly His Ile Thr Gly His Arg Met Ala Trp Asp
145                 150                 155                 160
Met Met Met Asn Trp Ser Pro Thr Ala Ala Leu Val Val Ala Gln Leu
                165                 170                 175
Leu Arg Ile Pro Gln Ala Ile Met Asp Met Ile Ala Gly Ala His Trp
            180                 185                 190
Gly Val Leu Ala Gly Ile Ala Tyr Phe Ser Met Val Gly Asn Trp Ala
        195                 200                 205
Lys Val Leu Val Val Leu Leu Leu Phe Ala Gly Val Asp Ala Glu Gly
    210                 215                 220
Leu Val Arg Pro Gln Gly Gly Gly Ser Val Asp Lys Lys Ile Val Pro
225                 230                 235                 240
Arg Asp Cys Gly Cys Lys Pro Cys Ile Cys Thr Val Pro Glu Val Ser
                245                 250                 255
Ser Val Phe Ile Phe Pro Pro Lys Pro Lys Asp Val Leu Thr Ile Thr
            260                 265                 270
Leu Thr Pro Lys Val Thr Cys Val Val Val Asp Ile Ser Lys Asp Asp
        275                 280                 285
Pro Glu Val Gln Phe Ser Trp Phe Val Asp Asp Val Glu Val His Thr
    290                 295                 300
Ala Gln Thr Gln Pro Arg Glu Glu Gln Phe Asn Ser Thr Phe Arg Ser
305                 310                 315                 320
Val Ser Glu Leu Pro Ile Met His Gln Asp Trp Leu Asn Gly Lys Glu
                325                 330                 335
Phe Lys Cys Arg Val Asn Ser Ala Ala Phe Pro Ala Pro Ile Glu Lys
            340                 345                 350
Thr Ile Ser Lys Thr Lys Gly Arg Pro Lys Ala Pro Gln Val Tyr Thr
        355                 360                 365
Ile Pro Pro Pro Lys Glu Gln Met Ala Lys Asp Lys Val Ser Leu Thr
    370                 375                 380
Cys Met Ile Thr Asp Phe Phe Pro Glu Asp Ile Thr Val Glu Trp Gln
```

```
                    385                 390                 395                 400
Trp Asn Gly Gln Pro Ala Glu Asn Tyr Lys Asn Thr Gln Pro Ile Met
                405                 410                 415

Asp Thr Asp Gly Ser Tyr Phe Val Tyr Ser Lys Leu Asn Val Gln Lys
                420                 425                 430

Ser Asn Trp Glu Ala Gly Asn Thr Phe Thr Cys Ser Val Leu His Glu
                435                 440                 445

Gly Leu His Asn His His Thr Glu Lys Ser Leu Ser Ser Pro Gly
                450                 455                 460

Leu Gln Ser Leu Ser Arg Ser Thr Arg Gly Ser
465                 470                 475

<210> SEQ ID NO 71
<211> LENGTH: 1266
<212> TYPE: DNA
<213> ORGANISM: Hepatitis C virus
<220> FEATURE:
<221> NAME/KEY: CDS
<222> LOCATION: (1)..(1266)

<400> SEQUENCE: 71 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc acc cac      96
Thr Glu Asn Leu Tyr Phe Gln Gly Ala Met Asp Pro Glu Phe Thr His
            20                  25                  30 gtc acc ggg gga aat gcc ggc cgc acc acg gct ggg ctt gtt ggt ctc      144
Val Thr Gly Gly Asn Ala Gly Arg Thr Thr Ala Gly Leu Val Gly Leu
        35                  40                  45 ctt aca cca ggc gcc aag cag aac atc caa ctg atc aac acc aac ggc      192
Leu Thr Pro Gly Ala Lys Gln Asn Ile Gln Leu Ile Asn Thr Asn Gly
    50                  55                  60 agt tgg cac atc aat agc acg gcc ttg aat tgc aat gaa agc ctt aac      240
Ser Trp His Ile Asn Ser Thr Ala Leu Asn Cys Asn Glu Ser Leu Asn
65                  70                  75                  80 acc ggc tgg tta gca ggg ctc ttc tat caa cac aaa ttc aac tct tca      288
Thr Gly Trp Leu Ala Gly Leu Phe Tyr Gln His Lys Phe Asn Ser Ser
                85                  90                  95 ggc tgt cct gag agg ttg gcc agc tgc cga cgc ctt acc gat ttt gcc      336
Gly Cys Pro Glu Arg Leu Ala Ser Cys Arg Arg Leu Thr Asp Phe Ala
            100                 105                 110 cag ggc tgg ggt cct atc agt tat gcc aac gga agc ggc ctc gac gaa      384
Gln Gly Trp Gly Pro Ile Ser Tyr Ala Asn Gly Ser Gly Leu Asp Glu
        115                 120                 125 cgc ccc tac tgc tgg cac tac cct cca aga cct tgt ggc att gtg ccc      432
Arg Pro Tyr Cys Trp His Tyr Pro Pro Arg Pro Cys Gly Ile Val Pro
    130                 135                 140 gca aag agc gtg tgt ggc ccg gta tat tgc ttc act ccc agc ccc gtg      480
Ala Lys Ser Val Cys Gly Pro Val Tyr Cys Phe Thr Pro Ser Pro Val
145                 150                 155                 160 gtg gtg gga acg acc gac agg tcg ggc gcg cct acc tac agc tgg ggt      528
Val Val Gly Thr Thr Asp Arg Ser Gly Ala Pro Thr Tyr Ser Trp Gly
                165                 170                 175 gca aat gat acg gat gtc ttc gtc ctt aac aac acc agg cca ccg ctg      576
Ala Asn Asp Thr Asp Val Phe Val Leu Asn Asn Thr Arg Pro Pro Leu
            180                 185                 190 ggc aat tgg ttc ggt tgt acc tgg atg aac tca act gga ttc acc aaa      624
Gly Asn Trp Phe Gly Cys Thr Trp Met Asn Ser Thr Gly Phe Thr Lys
        195                 200                 205
```

```
gtg tgc gga gcg ccc cct tgt gtc atc gga ggg gtg ggc aac aac acc      672
Val Cys Gly Ala Pro Pro Cys Val Ile Gly Gly Val Gly Asn Asn Thr
210             215                 220 ttg ctc tgc ccc act gat tgc ttc cgc aaa cat ccg gaa gcc aca tac      720
Leu Leu Cys Pro Thr Asp Cys Phe Arg Lys His Pro Glu Ala Thr Tyr
225             230                 235                 240 tct cgg tgc ggc tcc ggt ccc tgg att aca ccc agg tgc atg gtc gac      768
Ser Arg Cys Gly Ser Gly Pro Trp Ile Thr Pro Arg Cys Met Val Asp
                245                 250                 255 tac ccg tat agg ctt tgg cac tat cct tgt acc atc aat tac acc ata      816
Tyr Pro Tyr Arg Leu Trp His Tyr Pro Cys Thr Ile Asn Tyr Thr Ile
        260                 265                 270 ttc aaa gtc agg atg tac gtg gga ggg gtc gag cac agg ctg gaa gcg      864
Phe Lys Val Arg Met Tyr Val Gly Gly Val Glu His Arg Leu Glu Ala
275             280                 285 gcc tgc aac tgg acg cgg ggc gaa cgc tgt gat ctg gaa gac agg gac      912
Ala Cys Asn Trp Thr Arg Gly Glu Arg Cys Asp Leu Glu Asp Arg Asp
290             295                 300 agg tcc gag ctc agc ccg ttg ctg ctg tcc acc aca cag tgg cag gtc      960
Arg Ser Glu Leu Ser Pro Leu Leu Leu Ser Thr Thr Gln Trp Gln Val
305             310                 315                 320 ctt ccg tgt tct ttc acg acc ctg cca gcc ttg tcc acc ggc ctc atc     1008
Leu Pro Cys Ser Phe Thr Thr Leu Pro Ala Leu Ser Thr Gly Leu Ile
                325                 330                 335 cac ctc cac cag aac att gtg gac gtg cag tac ttg tac ggg gta ggg     1056
His Leu His Gln Asn Ile Val Asp Val Gln Tyr Leu Tyr Gly Val Gly
        340                 345                 350 tca agc atc gcg tcc tgg gcc att aag tgg gag tac gtc gtt ctc ctg     1104
Ser Ser Ile Ala Ser Trp Ala Ile Lys Trp Glu Tyr Val Val Leu Leu
355             360                 365 ttc ctt ctg ctt gca gac gcg cgc gtc tgc tcc tgc ttg tgg atg atg     1152
Phe Leu Leu Leu Ala Asp Ala Arg Val Cys Ser Cys Leu Trp Met Met
370             375                 380 tta ctc ata tcc caa gcg gag gcg gct gga cta gtg cgg ccg ctt tcg     1200
Leu Leu Ile Ser Gln Ala Glu Ala Ala Gly Leu Val Arg Pro Leu Ser
385             390                 395                 400 aat cta gag cct gca gtc tcg agg cat gcg gta cca agc ttg tcg aga     1248
Asn Leu Glu Pro Ala Val Ser Arg His Ala Val Pro Ser Leu Ser Arg
                405                 410                 415 agt act aga gga tca taa                                             1266
Ser Thr Arg Gly Ser
                420

<210> SEQ ID NO 72
<211> LENGTH: 421
<212> TYPE: PRT
<213> ORGANISM: Hepatitis C virus

<400> SEQUENCE: 72

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Thr His
                20                  25                  30

Val Thr Gly Gly Asn Ala Gly Arg Thr Thr Ala Gly Leu Val Gly Leu
        35                  40                  45

Leu Thr Pro Gly Ala Lys Gln Asn Ile Gln Leu Ile Asn Thr Asn Gly
    50                  55                  60

Ser Trp His Ile Asn Ser Thr Ala Leu Asn Cys Asn Glu Ser Leu Asn
65                  70                  75                  80

Thr Gly Trp Leu Ala Gly Leu Phe Tyr Gln His Lys Phe Asn Ser Ser
```

```
                    85                  90                  95
Gly Cys Pro Glu Arg Leu Ala Ser Cys Arg Arg Leu Thr Asp Phe Ala
                100                 105                 110
Gln Gly Trp Gly Pro Ile Ser Tyr Ala Asn Gly Ser Gly Leu Asp Glu
                115                 120                 125
Arg Pro Tyr Cys Trp His Tyr Pro Arg Pro Cys Gly Ile Val Pro
            130                 135                 140
Ala Lys Ser Val Cys Gly Pro Val Tyr Cys Phe Thr Pro Ser Pro Val
145                 150                 155                 160
Val Val Gly Thr Thr Asp Arg Ser Gly Ala Pro Thr Tyr Ser Trp Gly
                165                 170                 175
Ala Asn Asp Thr Asp Val Phe Val Leu Asn Asn Thr Arg Pro Pro Leu
                180                 185                 190
Gly Asn Trp Phe Gly Cys Thr Trp Met Asn Ser Thr Gly Phe Thr Lys
                195                 200                 205
Val Cys Gly Ala Pro Pro Cys Val Ile Gly Gly Val Gly Asn Asn Thr
            210                 215                 220
Leu Leu Cys Pro Thr Asp Cys Phe Arg Lys His Pro Glu Ala Thr Tyr
225                 230                 235                 240
Ser Arg Cys Gly Ser Gly Pro Trp Ile Thr Pro Arg Cys Met Val Asp
                245                 250                 255
Tyr Pro Tyr Arg Leu Trp His Tyr Pro Cys Thr Ile Asn Tyr Thr Ile
                260                 265                 270
Phe Lys Val Arg Met Tyr Val Gly Gly Val Glu His Arg Leu Glu Ala
                275                 280                 285
Ala Cys Asn Trp Thr Arg Gly Glu Arg Cys Asp Leu Glu Asp Arg Asp
            290                 295                 300
Arg Ser Glu Leu Ser Pro Leu Leu Leu Ser Thr Thr Gln Trp Gln Val
305                 310                 315                 320
Leu Pro Cys Ser Phe Thr Thr Leu Pro Ala Leu Ser Thr Gly Leu Ile
                325                 330                 335
His Leu His Gln Asn Ile Val Asp Val Gln Tyr Leu Tyr Gly Val Gly
                340                 345                 350
Ser Ser Ile Ala Ser Trp Ala Ile Lys Trp Glu Tyr Val Val Leu Leu
                355                 360                 365
Phe Leu Leu Leu Ala Asp Ala Arg Val Cys Ser Cys Leu Trp Met Met
            370                 375                 380
Leu Leu Ile Ser Gln Ala Glu Ala Ala Gly Leu Val Arg Pro Leu Ser
385                 390                 395                 400
Asn Leu Glu Pro Ala Val Ser Arg His Ala Val Pro Ser Leu Ser Arg
                405                 410                 415
Ser Thr Arg Gly Ser
            420

<210> SEQ ID NO 73
<211> LENGTH: 1938
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1938)

<400> SEQUENCE: 73 atg tcg tac tac cat cac cat cac cat cac gat tac gat atc cca acg      48
Met Ser Tyr Tyr His His His His His His Asp Tyr Asp Ile Pro Thr
```

```
 1               5                  10                 15
acc gaa aac ctg tat ttt cag ggc gcc atg gat ccg gaa ttc acc cac       96
Thr Glu Asn Leu Tyr Phe Gln Gly Ala Met Asp Pro Glu Phe Thr His
             20                  25                  30 gtc acc ggg gga aat gcc ggc cgc acc acg gct ggg ctt gtt ggt ctc      144
Val Thr Gly Gly Asn Ala Gly Arg Thr Thr Ala Gly Leu Val Gly Leu
         35                  40                  45 ctt aca cca ggc gcc aag cag aac atc caa ctg atc aac acc aac ggc      192
Leu Thr Pro Gly Ala Lys Gln Asn Ile Gln Leu Ile Asn Thr Asn Gly
     50                  55                  60 agt tgg cac atc aat agc acg gcc ttg aat tgc aat gaa agc ctt aac      240
Ser Trp His Ile Asn Ser Thr Ala Leu Asn Cys Asn Glu Ser Leu Asn
 65                  70                  75                  80 acc ggc tgg tta gca ggg ctc ttc tat caa cac aaa ttc aac tct tca      288
Thr Gly Trp Leu Ala Gly Leu Phe Tyr Gln His Lys Phe Asn Ser Ser
                 85                  90                  95 ggc tgt cct gag agg ttg gcc agc tgc cga cgc ctt acc gat ttt gcc      336
Gly Cys Pro Glu Arg Leu Ala Ser Cys Arg Arg Leu Thr Asp Phe Ala
             100                 105                 110 cag ggc tgg ggt cct atc agt tat gcc aac gga agc ggc ctc gac gaa      384
Gln Gly Trp Gly Pro Ile Ser Tyr Ala Asn Gly Ser Gly Leu Asp Glu
         115                 120                 125 cgc ccc tac tgc tgg cac tac cct cca aga cct tgt ggc att gtg ccc      432
Arg Pro Tyr Cys Trp His Tyr Pro Pro Arg Pro Cys Gly Ile Val Pro
     130                 135                 140 gca aag agc gtg tgt ggc ccg gta tat tgc ttc act ccc agc ccc gtg      480
Ala Lys Ser Val Cys Gly Pro Val Tyr Cys Phe Thr Pro Ser Pro Val
145                 150                 155                 160 gtg gtg gga acg acc gac agg tcg ggc gcg cct acc tac agc tgg ggt      528
Val Val Gly Thr Thr Asp Arg Ser Gly Ala Pro Thr Tyr Ser Trp Gly
                 165                 170                 175 gca aat gat acg gat gtc ttc gtc ctt aac aac acc agg cca ccg ctg      576
Ala Asn Asp Thr Asp Val Phe Val Leu Asn Asn Thr Arg Pro Pro Leu
             180                 185                 190 ggc aat tgg ttc ggt tgt acc tgg atg aac tca act gga ttc acc aaa      624
Gly Asn Trp Phe Gly Cys Thr Trp Met Asn Ser Thr Gly Phe Thr Lys
         195                 200                 205 gtg tgc gga gcg ccc cct tgt gtc atc gga ggg gtg ggc aac aac acc      672
Val Cys Gly Ala Pro Pro Cys Val Ile Gly Gly Val Gly Asn Asn Thr
     210                 215                 220 ttg ctc tgc ccc act gat tgc ttc cgc aaa cat ccg gaa gcc aca tac      720
Leu Leu Cys Pro Thr Asp Cys Phe Arg Lys His Pro Glu Ala Thr Tyr
225                 230                 235                 240 tct cgg tgc ggc tcc ggt ccc tgg att aca ccc agg tgc atg gtc gac      768
Ser Arg Cys Gly Ser Gly Pro Trp Ile Thr Pro Arg Cys Met Val Asp
                 245                 250                 255 tac ccg tat agg ctt tgg cac tat cct tgt acc atc aat tac acc ata      816
Tyr Pro Tyr Arg Leu Trp His Tyr Pro Cys Thr Ile Asn Tyr Thr Ile
             260                 265                 270 ttc aaa gtc agg atg tac gtg gga ggg gtc gag cac agg ctg gaa gcg      864
Phe Lys Val Arg Met Tyr Val Gly Gly Val Glu His Arg Leu Glu Ala
         275                 280                 285 gcc tgc aac tgg acg cgg ggc gaa cgc tgt gat ctg gaa gac agg gac      912
Ala Cys Asn Trp Thr Arg Gly Glu Arg Cys Asp Leu Glu Asp Arg Asp
     290                 295                 300 agg tcc gag ctc agc ccg ttg ctg ctg tcc acc aca cag tgg cag gtc      960
Arg Ser Glu Leu Ser Pro Leu Leu Leu Ser Thr Thr Gln Trp Gln Val
305                 310                 315                 320 ctt ccg tgt tct ttc acg acc ctg cca gcc ttg tcc acc ggc ctc atc     1008
Leu Pro Cys Ser Phe Thr Thr Leu Pro Ala Leu Ser Thr Gly Leu Ile
```

-continued

```
                    325                 330                 335
cac ctc cac cag aac att gtg gac gtg cag tac ttg tac ggg gta ggg       1056
His Leu His Gln Asn Ile Val Asp Val Gln Tyr Leu Tyr Gly Val Gly
            340                 345                 350 tca agc atc gcg tcc tgg gcc att aag tgg gag tac gtc gtt ctc ctg       1104
Ser Ser Ile Ala Ser Trp Ala Ile Lys Trp Glu Tyr Val Val Leu Leu
            355                 360                 365 ttc ctt ctg ctt gca gac gcg cgc gtc tgc tcc tgc ttg tgg atg atg       1152
Phe Leu Leu Leu Ala Asp Ala Arg Val Cys Ser Cys Leu Trp Met Met
            370                 375                 380 tta ctc ata tcc caa gcg gag gcg gct gga cta gtg cgg ccg caa ggc       1200
Leu Leu Ile Ser Gln Ala Glu Ala Ala Gly Leu Val Arg Pro Gln Gly
385                 390                 395                 400 ggc gga tcc gtg gac aag aaa att gtg ccc agg gat tgt ggt tgt aag       1248
Gly Gly Ser Val Asp Lys Lys Ile Val Pro Arg Asp Cys Gly Cys Lys
                405                 410                 415 cct tgc ata tgt aca gtc cca gaa gta tca tct gtc ttc atc ttc ccc       1296
Pro Cys Ile Cys Thr Val Pro Glu Val Ser Ser Val Phe Ile Phe Pro
                420                 425                 430 cca aag ccc aag gat gtg ctc acc att act ctg act cct aag gtc acg       1344
Pro Lys Pro Lys Asp Val Leu Thr Ile Thr Leu Thr Pro Lys Val Thr
            435                 440                 445 tgt gtt gtg gta gac atc agc aag gat gat ccc gag gtc cag ttc agc       1392
Cys Val Val Val Asp Ile Ser Lys Asp Asp Pro Glu Val Gln Phe Ser
450                 455                 460 tgg ttt gta gat gat gtg gag gtg cac aca gct cag acg caa ccc cgg       1440
Trp Phe Val Asp Asp Val Glu Val His Thr Ala Gln Thr Gln Pro Arg
465                 470                 475                 480 gag gag cag ttc aac agc act ttc cgc tca gtc agt gaa ctt ccc atc       1488
Glu Glu Gln Phe Asn Ser Thr Phe Arg Ser Val Ser Glu Leu Pro Ile
                485                 490                 495 atg cac cag gac tgg ctc aat ggc aag gag ttc aaa tgc agg gtc aac       1536
Met His Gln Asp Trp Leu Asn Gly Lys Glu Phe Lys Cys Arg Val Asn
                500                 505                 510 agt gca gct ttc cct gcc ccc atc gag aaa acc atc tcc aaa acc aaa       1584
Ser Ala Ala Phe Pro Ala Pro Ile Glu Lys Thr Ile Ser Lys Thr Lys
            515                 520                 525 ggc aga ccg aag gct cca cag gtg tac acc att cca cct ccc aag gag       1632
Gly Arg Pro Lys Ala Pro Gln Val Tyr Thr Ile Pro Pro Pro Lys Glu
530                 535                 540 cag atg gcc aag gat aaa gtc agt ctg acc tgc atg ata aca gac ttc       1680
Gln Met Ala Lys Asp Lys Val Ser Leu Thr Cys Met Ile Thr Asp Phe
545                 550                 555                 560 ttc cct gaa gac att act gtg gag tgg cag tgg aat ggg cag cca gcg       1728
Phe Pro Glu Asp Ile Thr Val Glu Trp Gln Trp Asn Gly Gln Pro Ala
                565                 570                 575 gag aac tac aag aac act cag ccc atc atg gac aca gat ggc tct tac       1776
Glu Asn Tyr Lys Asn Thr Gln Pro Ile Met Asp Thr Asp Gly Ser Tyr
            580                 585                 590 ttc gtc tac agc aag ctc aat gtg cag aag agc aac tgg gag gca gga       1824
Phe Val Tyr Ser Lys Leu Asn Val Gln Lys Ser Asn Trp Glu Ala Gly
            595                 600                 605 aat act ttc acc tgc tct gtg tta cat gag ggc ctg cac aac cac cat       1872
Asn Thr Phe Thr Cys Ser Val Leu His Glu Gly Leu His Asn His His
610                 615                 620 act gag aag agc ctc tcc cac tct cct ggg ctg caa agc ttg tcg aga       1920
Thr Glu Lys Ser Leu Ser His Ser Pro Gly Leu Gln Ser Leu Ser Arg
625                 630                 635                 640 agt act aga gga tca taa                                               1938
Ser Thr Arg Gly Ser
```

-continued

```
                                        645

<210> SEQ ID NO 74
<211> LENGTH: 645
<212> TYPE: PRT
<213> ORGANISM: Artificial
<220> FEATURE:
<223> OTHER INFORMATION: Synthetic Construct

<400> SEQUENCE: 74
```

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Thr His
            20                  25                  30

Val Thr Gly Gly Asn Ala Gly Arg Thr Thr Ala Gly Leu Val Gly Leu
        35                  40                  45

Leu Thr Pro Gly Ala Lys Gln Asn Ile Gln Leu Ile Asn Thr Asn Gly
    50                  55                  60

Ser Trp His Ile Asn Ser Thr Ala Leu Asn Cys Asn Glu Ser Leu Asn
65                  70                  75                  80

Thr Gly Trp Leu Ala Gly Leu Phe Tyr Gln His Lys Phe Asn Ser Ser
                85                  90                  95

Gly Cys Pro Glu Arg Leu Ala Ser Cys Arg Arg Leu Thr Asp Phe Ala
            100                 105                 110

Gln Gly Trp Gly Pro Ile Ser Tyr Ala Asn Gly Ser Gly Leu Asp Glu
        115                 120                 125

Arg Pro Tyr Cys Trp His Tyr Pro Pro Arg Pro Cys Gly Ile Val Pro
    130                 135                 140

Ala Lys Ser Val Cys Gly Pro Val Tyr Cys Phe Thr Pro Ser Pro Val
145                 150                 155                 160

Val Val Gly Thr Thr Asp Arg Ser Gly Ala Pro Thr Tyr Ser Trp Gly
                165                 170                 175

Ala Asn Asp Thr Asp Val Phe Val Leu Asn Asn Thr Arg Pro Pro Leu
            180                 185                 190

Gly Asn Trp Phe Gly Cys Thr Trp Met Asn Ser Thr Gly Phe Thr Lys
        195                 200                 205

Val Cys Gly Ala Pro Pro Cys Val Ile Gly Gly Val Gly Asn Asn Thr
    210                 215                 220

Leu Leu Cys Pro Thr Asp Cys Phe Arg Lys His Pro Glu Ala Thr Tyr
225                 230                 235                 240

Ser Arg Cys Gly Ser Gly Pro Trp Ile Thr Pro Arg Cys Met Val Asp
                245                 250                 255

Tyr Pro Tyr Arg Leu Trp His Tyr Pro Cys Thr Ile Asn Tyr Thr Ile
            260                 265                 270

Phe Lys Val Arg Met Tyr Val Gly Gly Val Glu His Arg Leu Glu Ala
        275                 280                 285

Ala Cys Asn Trp Thr Arg Gly Glu Arg Cys Asp Leu Glu Asp Arg Asp
    290                 295                 300

Arg Ser Glu Leu Ser Pro Leu Leu Leu Ser Thr Thr Gln Trp Gln Val
305                 310                 315                 320

Leu Pro Cys Ser Phe Thr Thr Leu Pro Ala Leu Ser Thr Gly Leu Ile
                325                 330                 335

His Leu His Gln Asn Ile Val Asp Val Gln Tyr Leu Tyr Gly Val Gly
            340                 345                 350

Ser Ser Ile Ala Ser Trp Ala Ile Lys Trp Glu Tyr Val Val Leu Leu
        355                 360                 365

| | | | | | | | | | | | | |
|---|---|---|---|---|---|---|---|---|---|---|---|---|
|Phe|Leu|Leu|Leu|Ala|Asp|Ala|Arg|Val|Cys|Ser|Cys|Leu|Trp|Met|Met|
| |370| | | |375| | | |380| | | | | | |

Phe Leu Leu Leu Ala Asp Ala Arg Val Cys Ser Cys Leu Trp Met Met
    370             375             380

Leu Leu Ile Ser Gln Ala Glu Ala Ala Gly Leu Val Arg Pro Gln Gly
385             390             395             400

Gly Gly Ser Val Asp Lys Lys Ile Val Pro Arg Asp Cys Gly Cys Lys
            405             410             415

Pro Cys Ile Cys Thr Val Pro Glu Val Ser Ser Val Phe Ile Phe Pro
            420             425             430

Pro Lys Pro Lys Asp Val Leu Thr Ile Thr Leu Thr Pro Lys Val Thr
            435             440             445

Cys Val Val Asp Ile Ser Lys Asp Pro Glu Val Gln Phe Ser
450             455             460

Trp Phe Val Asp Asp Val Glu Val His Thr Ala Gln Thr Gln Pro Arg
465             470             475             480

Glu Glu Gln Phe Asn Ser Thr Phe Arg Ser Val Ser Glu Leu Pro Ile
            485             490             495

Met His Gln Asp Trp Leu Asn Gly Lys Glu Phe Lys Cys Arg Val Asn
            500             505             510

Ser Ala Ala Phe Pro Ala Pro Ile Glu Lys Thr Ile Ser Lys Thr Lys
            515             520             525

Gly Arg Pro Lys Ala Pro Gln Val Tyr Thr Ile Pro Pro Lys Glu
530             535             540

Gln Met Ala Lys Asp Lys Val Ser Leu Thr Cys Met Ile Thr Asp Phe
545             550             555             560

Phe Pro Glu Asp Ile Thr Val Glu Trp Gln Trp Asn Gly Gln Pro Ala
            565             570             575

Glu Asn Tyr Lys Asn Thr Gln Pro Ile Met Asp Thr Asp Gly Ser Tyr
            580             585             590

Phe Val Tyr Ser Lys Leu Asn Val Gln Lys Ser Asn Trp Glu Ala Gly
            595             600             605

Asn Thr Phe Thr Cys Ser Val Leu His Glu Gly Leu His Asn His His
            610             615             620

Thr Glu Lys Ser Leu Ser His Ser Pro Gly Leu Gln Ser Leu Ser Arg
625             630             635             640

Ser Thr Arg Gly Ser
            645

<210> SEQ ID NO 75
<211> LENGTH: 1845
<212> TYPE: DNA
<213> ORGANISM: HCV E1E2
<220> FEATURE:
<221> NAME/KEY: CDS
<222> LOCATION: (1)..(1845)

<400> SEQUENCE: 75

| atg | tcg | tac | tac | cat | cac | cat | cac | cat | cac | gat | tac | gat | atc | cca | acg | 48 |
|---|---|---|---|---|---|---|---|---|---|---|---|---|---|---|---|---|
| Met | Ser | Tyr | Tyr | His | His | His | His | His | His | Asp | Tyr | Asp | Ile | Pro | Thr | |
| 1 | | | | 5 | | | | | 10 | | | | | 15 | | |

| acc | gaa | aac | ctg | tat | ttt | cag | ggc | gcc | atg | gat | ccg | gaa | ttc | tac | caa | 96 |
|---|---|---|---|---|---|---|---|---|---|---|---|---|---|---|---|---|
| Thr | Glu | Asn | Leu | Tyr | Phe | Gln | Gly | Ala | Met | Asp | Pro | Glu | Phe | Tyr | Gln | |
| | | | 20 | | | | | 25 | | | | | 30 | | | |

| gtg | cgc | aat | tcc | tcg | ggg | ctt | tac | cat | gtc | acc | aat | gat | tgc | cct | aac | 144 |
|---|---|---|---|---|---|---|---|---|---|---|---|---|---|---|---|---|
| Val | Arg | Asn | Ser | Ser | Gly | Leu | Tyr | His | Val | Thr | Asn | Asp | Cys | Pro | Asn | |
| | | 35 | | | | | 40 | | | | | 45 | | | | |

| tcg | agt | att | gtg | tac | gag | gcg | gcc | gat | gcc | atc | ctg | cac | act | ccg | ggg | 192 |
|---|---|---|---|---|---|---|---|---|---|---|---|---|---|---|---|---|
| Ser | Ser | Ile | Val | Tyr | Glu | Ala | Ala | Asp | Ala | Ile | Leu | His | Thr | Pro | Gly | |

```
                  50                  55                  60
tgt gtc cct tgc gtt cgc gag ggt aac gcc tcg agg tgt tgg gtg gcg        240
Cys Val Pro Cys Val Arg Glu Gly Asn Ala Ser Arg Cys Trp Val Ala
 65                  70                  75                  80 gtg acc ccc acg gtg gcc acc agg gac ggc aaa ctc ccc aca acg cag        288
Val Thr Pro Thr Val Ala Thr Arg Asp Gly Lys Leu Pro Thr Thr Gln
                     85                  90                  95 ctt cga cgt cat atc gat ctg ctt gtc ggg agc gcc acc ctc tgc tcg        336
Leu Arg Arg His Ile Asp Leu Leu Val Gly Ser Ala Thr Leu Cys Ser
                100                 105                 110 gcc ctc tac gtg ggg gac ctg tgc ggg tct gtc ttt ctt gtt ggt caa        384
Ala Leu Tyr Val Gly Asp Leu Cys Gly Ser Val Phe Leu Val Gly Gln
            115                 120                 125 ctg ttt acc ttc tct ccc agg cgc cac tgg acg acg caa gac tgc aat        432
Leu Phe Thr Phe Ser Pro Arg Arg His Trp Thr Thr Gln Asp Cys Asn
        130                 135                 140 tgt tct atc tat ccc ggc cat ata acg ggt cat cgc atg gca tgg gat        480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg        528
Met Met Met Asn Trp Ser Pro Thr Ala Ala Leu Val Val Ala Gln Leu
                    165                 170                 175 ctc cgg atc cca caa gcc atc atg gac atg atc gct ggt gct cac tgg        576
Leu Arg Ile Pro Gln Ala Ile Met Asp Met Ile Ala Gly Ala His Trp
                180                 185                 190 gga gtc ctg gcg ggc ata gcg tat ttc tcc atg gtg ggg aac tgg gcg        624
Gly Val Leu Ala Gly Ile Ala Tyr Phe Ser Met Val Gly Asn Trp Ala
            195                 200                 205 aag gtc ctg gta gtg ctg ctg cta ttt gcc ggc gtc gac gcg gaa acc        672
Lys Val Leu Val Val Leu Leu Leu Phe Ala Gly Val Asp Ala Glu Thr
        210                 215                 220 cac gtc acc ggg gga aat gcc ggc cgc acc acg gct ggg ctt gtt ggt        720
His Val Thr Gly Gly Asn Ala Gly Arg Thr Thr Ala Gly Leu Val Gly
225                 230                 235                 240 ctc ctt aca cca ggc gcc aag cag aac atc caa ctg atc aac acc aac        768
Leu Leu Thr Pro Gly Ala Lys Gln Asn Ile Gln Leu Ile Asn Thr Asn
                    245                 250                 255 ggc agt tgg cac atc aat agc acg gcc ttg aat tgc aat gaa agc ctt        816
Gly Ser Trp His Ile Asn Ser Thr Ala Leu Asn Cys Asn Glu Ser Leu
                260                 265                 270 aac acc ggc tgg tta gca ggg ctc ttc tat caa cac aaa ttc aac tct        864
Asn Thr Gly Trp Leu Ala Gly Leu Phe Tyr Gln His Lys Phe Asn Ser
            275                 280                 285 tca ggc tgt cct gag agg ttg gcc agc tgc cga cgc ctt acc gat ttt        912
Ser Gly Cys Pro Glu Arg Leu Ala Ser Cys Arg Arg Leu Thr Asp Phe
        290                 295                 300 gcc cag ggc tgg ggt cct atc agt tat gcc aac gga agc ggc ctc gac        960
Ala Gln Gly Trp Gly Pro Ile Ser Tyr Ala Asn Gly Ser Gly Leu Asp
305                 310                 315                 320 gaa cgc ccc tac tgc tgg cac tac cct cca aga cct tgt ggc att gtg       1008
Glu Arg Pro Tyr Cys Trp His Tyr Pro Pro Arg Pro Cys Gly Ile Val
                    325                 330                 335 ccc gca aag agc gtg tgt ggc ccg gta tat tgc ttc act ccc agc ccc       1056
Pro Ala Lys Ser Val Cys Gly Pro Val Tyr Cys Phe Thr Pro Ser Pro
                340                 345                 350 gtg gtg gtg gga acc acc gac agg tcg ggc gcg cct acc tac agc tgg       1104
Val Val Val Gly Thr Thr Asp Arg Ser Gly Ala Pro Thr Tyr Ser Trp
            355                 360                 365 ggt gca aat gat acg gat gtc ttc gtc ctt aac aac acc agg cca ccg       1152
Gly Ala Asn Asp Thr Asp Val Phe Val Leu Asn Asn Thr Arg Pro Pro
```

```
                370             375             380
ctg ggc aat tgg ttc ggt tgt acc tgg atg aac tca act gga ttc acc      1200
Leu Gly Asn Trp Phe Gly Cys Thr Trp Met Asn Ser Thr Gly Phe Thr
385             390             395             400 aaa gtg tgc gga gcg ccc cct tgt gtc atc gga ggg gtg ggc aac aac      1248
Lys Val Cys Gly Ala Pro Pro Cys Val Ile Gly Gly Val Gly Asn Asn
            405             410             415 acc ttg ctc tgc ccc act gat tgc ttc cgc aaa cat ccg gaa gcc aca      1296
Thr Leu Leu Cys Pro Thr Asp Cys Phe Arg Lys His Pro Glu Ala Thr
        420             425             430 tac tct cgg tgc ggc tcc ggt ccc tgg att aca ccc agg tgc atg gtc      1344
Tyr Ser Arg Cys Gly Ser Gly Pro Trp Ile Thr Pro Arg Cys Met Val
    435             440             445 gac tac ccg tat agg ctt tgg cac tat cct tgt acc atc aat tac acc      1392
Asp Tyr Pro Tyr Arg Leu Trp His Tyr Pro Cys Thr Ile Asn Tyr Thr
450             455             460 ata ttc aaa gtc agg atg tac gtg gga ggg gtc gag cac agg ctg gaa      1440
Ile Phe Lys Val Arg Met Tyr Val Gly Gly Val Glu His Arg Leu Glu
465             470             475             480 gcg gcc tgc aac tgg acg cgg ggc gaa cgc tgt gat ctg gaa gac agg      1488
Ala Ala Cys Asn Trp Thr Arg Gly Glu Arg Cys Asp Leu Glu Asp Arg
            485             490             495 gac agg tcc gag ctc agc ccg ttg ctg ctg tcc acc aca cag tgg cag      1536
Asp Arg Ser Glu Leu Ser Pro Leu Leu Leu Ser Thr Thr Gln Trp Gln
        500             505             510 gtc ctt ccg tgt tct ttc acg acc ctg cca gcc ttg tcc acc ggc ctc      1584
Val Leu Pro Cys Ser Phe Thr Thr Leu Pro Ala Leu Ser Thr Gly Leu
    515             520             525 atc cac ctc cac cag aac att gtg gac gtg cag tac ttg tac ggg gta      1632
Ile His Leu His Gln Asn Ile Val Asp Val Gln Tyr Leu Tyr Gly Val
530             535             540 ggg tca agc atc gcg tcc tgg gcc att aag tgg gag tac gtc gtt ctc      1680
Gly Ser Ser Ile Ala Ser Trp Ala Ile Lys Trp Glu Tyr Val Val Leu
545             550             555             560 ctg ttc ctt ctg ctt gca gac gcg cgc gtc tgc tcc tgc ttg tgg atg      1728
Leu Phe Leu Leu Leu Ala Asp Ala Arg Val Cys Ser Cys Leu Trp Met
            565             570             575 atg tta ctc ata tcc caa gcg gag gcg gct gga cta gtg cgg ccg ctt      1776
Met Leu Leu Ile Ser Gln Ala Glu Ala Ala Gly Leu Val Arg Pro Leu
        580             585             590 tcg aat cta gag cct gca gtc tcg agg cat gcg gta cca agc ttg tcg      1824
Ser Asn Leu Glu Pro Ala Val Ser Arg His Ala Val Pro Ser Leu Ser
    595             600             605 aga agt act aga gga tca taa                                          1845
Arg Ser Thr Arg Gly Ser
    610

<210> SEQ ID NO 76
<211> LENGTH: 614
<212> TYPE: PRT
<213> ORGANISM: HCV E1E2

<400> SEQUENCE: 76

Met Ser Tyr Tyr His His His His His His Asp Tyr Asp Ile Pro Thr
1               5

-continued

```
             50                  55                  60
Cys Val Pro Cys Val Arg Glu Gly Asn Ala Ser Arg Cys Trp Val Ala
 65                  70                  75                  80

Val Thr Pro Thr Val Ala Thr Arg Asp Gly Lys Leu Pro Thr Thr Gln
                     85                  90                  95

Leu Arg Arg His Ile Asp Leu Leu Val Gly Ser Ala Thr Leu Cys Ser
                    100                 105                 110

Ala Leu Tyr Val Gly Asp Leu Cys Gly Ser Val Phe Leu Val Gly Gln
                115                 120                 125

Leu Phe Thr Phe Ser Pro Arg Arg His Trp Thr Thr Gln Asp Cys Asn
            130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
                180                 185                 190

Gly Val Leu Ala Gly Ile Ala Tyr Phe Ser Met Val Gly Asn Trp Ala
                195                 200                 205

Lys Val Leu Val Val Leu Leu Leu Phe Ala Gly Val Asp Ala Glu Thr
210                 215                 220

His Val Thr Gly Gly Asn Ala Gly Arg Thr Thr Ala Gly Leu Val Gly
225                 230                 235                 240

Leu Leu Thr Pro Gly Ala Lys Gln Asn Ile Gln Leu Ile Asn Thr Asn
                245                 250                 255

Gly Ser Trp His Ile Asn Ser Thr Ala Leu Asn Cys Asn Glu Ser Leu
                260                 265                 270

Asn Thr Gly Trp Leu Ala Gly Leu Phe Tyr Gln His Lys Phe Asn Ser
                275                 280                 285

Ser Gly Cys Pro Glu Arg Leu Ala Ser Cys Arg Arg Leu Thr Asp Phe
                290                 295                 300

Ala Gln Gly Trp Gly Pro Ile Ser Tyr Ala Asn Gly Ser Gly Leu Asp
305                 310                 315                 320

Glu Arg Pro Tyr Cys Trp His Tyr Pro Pro Arg Pro Cys Gly Ile Val
                325                 330                 335

Pro Ala Lys Ser Val Cys Gly Pro Val Tyr Cys Phe Thr Pro Ser Pro
                340                 345                 350

Val Val Val Gly Thr Thr Asp Arg Ser Gly Ala Pro Thr Tyr Ser Trp
                355                 360                 365

Gly Ala Asn Asp Thr Asp Val Phe Val Leu Asn Asn Thr Arg Pro Pro
                370                 375                 380

Leu Gly Asn Trp Phe Gly Cys Thr Trp Met Asn Ser Thr Gly Phe Thr
385                 390                 395                 400

Lys Val Cys Gly Ala Pro Pro Cys Val Ile Gly Val Gly Asn Asn
                405                 410                 415

Thr Leu Leu Cys Pro Thr Asp Cys Phe Arg Lys His Pro Glu Ala Thr
                420                 425                 430

Tyr Ser Arg Cys Gly Ser Gly Pro Trp Ile Thr Pro Arg Cys Met Val
                435                 440                 445

Asp Tyr Pro Tyr Arg Leu Trp His Tyr Pro Cys Thr Ile Asn Tyr Thr
                450                 455                 460

Ile Phe Lys Val Arg Met Tyr Val Gly Gly Val Glu His Arg Leu Glu
465                 470                 475                 480
```

```
Ala Ala Cys Asn Trp Thr Arg Gly Glu Arg Cys Asp Leu Glu Asp Arg
            485                 490                 495

Asp Arg Ser Glu Leu Ser Pro Leu Leu Leu Ser Thr Thr Gln Trp Gln
        500                 505                 510

Val Leu Pro Cys Ser Phe Thr Thr Leu Pro Ala Leu Ser Thr Gly Leu
            515                 520                 525

Ile His Leu His Gln Asn Ile Val Asp Val Gln Tyr Leu Tyr Gly Val
        530                 535                 540

Gly Ser Ser Ile Ala Ser Trp Ala Ile Lys Trp Glu Tyr Val Val Leu
545                 550                 555                 560

Leu Phe Leu Leu Leu Ala Asp Ala Arg Val Cys Ser Cys Leu Trp Met
            565                 570                 575

Met Leu Leu Ile Ser Gln Ala Glu Ala Ala Gly Leu Val Arg Pro Leu
        580                 585                 590

Ser Asn Leu Glu Pro Ala Val Ser Arg His Ala Val Pro Ser Leu Ser
            595                 600                 605

Arg Ser Thr Arg Gly Ser
        610

<210> SEQ ID NO 77
<211> LENGTH: 2517
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2517)

<400> SEQUENCE: 77 atg tcg tac tac cat cac cat cac cat cac gat tac gat atc cca acg     48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa     96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac    144
Val Arg Asn Ser Ser Gly Leu Tyr His Val Thr Asn Asp Cys Pro Asn
        35                  40                  45 tcg agt att gtg tac gag gcg gcc gat gcc atc ctg cac act ccg ggg    192
Ser Ser Ile Val Tyr Glu Ala Ala Asp Ala Ile Leu His Thr Pro Gly
    50                  55                  60 tgt gtc cct tgc gtt cgc gag ggt aac gcc tcg agg tgt tgg gtg gcg    240
Cys Val Pro Cys Val Arg Glu Gly Asn Ala Ser Arg Cys Trp Val Ala
65                  70                  75                  80 gtg acc ccc acg gtg gcc acc agg gac ggc aaa ctc ccc aca acg cag    288
Val Thr Pro Thr Val Ala Thr Arg Asp Gly Lys Leu Pro Thr Thr Gln
            85                  90                  95 ctt cga cgt cat atc gat ctg ctt gtc ggg agc gcc acc ctc tgc tcg    336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa    384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat    432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat    480
Cys Ser Ile Tyr Pro Gly His Ile Thr Gly His Arg Met Ala Trp Asp
145                 150                 155                 160
```

```
atg atg atg aac tgg tcc cct acg gca gcg ttg gtg gta gct cag ctg        528
Met Met Met Asn Trp Ser Pro Thr Ala Ala Leu Val Val Ala Gln Leu
            165                 170                 175 ctc cgg atc cca caa gcc atc atg gac atg atc gct ggt gct cac tgg        576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg        624
Gly Val Leu Ala Gly Ile Ala Tyr Phe Ser Met Val Gly Asn Trp Ala
        195                 200                 205 aag gtc ctg gta gtg ctg ctg cta ttt gcc ggc gtc gac gcg gaa acc        672
Lys Val Leu Val Val Leu Leu Leu Phe Ala Gly Val Asp Ala Glu Thr
    210                 215                 220 cac gtc acc ggg gga aat gcc ggc cgc acc acg gct ggg ctt gtt ggt        720
His Val Thr Gly Gly Asn Ala Gly Arg Thr Thr Ala Gly Leu Val Gly
225                 230                 235                 240 ctc ctt aca cca ggc gcc aag cag aac atc caa ctg atc aac acc aac        768
Leu Leu Thr Pro Gly Ala Lys Gln Asn Ile Gln Leu Ile Asn Thr Asn
                245                 250                 255 ggc agt tgg cac atc aat agc acg gcc ttg aat tgc aat gaa agc ctt        816
Gly Ser Trp His Ile Asn Ser Thr Ala Leu Asn Cys Asn Glu Ser Leu
            260                 265                 270 aac acc ggc tgg tta gca ggg ctc ttc tat caa cac aaa ttc aac tct        864
Asn Thr Gly Trp Leu Ala Gly Leu Phe Tyr Gln His Lys Phe Asn Ser
        275                 280                 285 tca ggc tgt cct gag agg ttg gcc agc tgc cga cgc ctt acc gat ttt        912
Ser Gly Cys Pro Glu Arg Leu Ala Ser Cys Arg Arg Leu Thr Asp Phe
    290                 295                 300 gcc cag ggc tgg ggt cct atc agt tat gcc aac gga agc ggc ctc gac        960
Ala Gln Gly Trp Gly Pro Ile Ser Tyr Ala Asn Gly Ser Gly Leu Asp
305                 310                 315                 320 gaa cgc ccc tac tgc tgg cac tac cct cca aga cct tgt ggc att gtg       1008
Glu Arg Pro Tyr Cys Trp His Tyr Pro Pro Arg Pro Cys Gly Ile Val
                325                 330                 335 ccc gca aag agc gtg tgt ggc ccg gta tat tgc ttc act ccc agc ccc       1056
Pro Ala Lys Ser Val Cys Gly Pro Val Tyr Cys Phe Thr Pro Ser Pro
            340                 345                 350 gtg gtg gtg gga acg acc gac agg tcg ggc gcg cct acc tac agc tgg       1104
Val Val Val Gly Thr Thr Asp Arg Ser Gly Ala Pro Thr Tyr Ser Trp
        355                 360                 365 ggt gca aat gat acg gat gtc ttc gtc ctt aac aac acc agg cca ccg       1152
Gly Ala Asn Asp Thr Asp Val Phe Val Leu Asn Asn Thr Arg Pro Pro
    370                 375                 380 ctg ggc aat tgg ttc ggt tgt acc tgg atg aac tca act gga ttc acc       1200
Leu Gly Asn Trp Phe Gly Cys Thr Trp Met Asn Ser Thr Gly Phe Thr
385                 390                 395                 400 aaa gtg tgc gga gcg ccc cct tgt gtc atc gga ggg gtg ggc aac aac       1248
Lys Val Cys Gly Ala Pro Pro Cys Val Ile Gly Gly Val Gly Asn Asn
                405                 410                 415 acc ttg ctc tgc ccc act gat tgc ttc cgc aaa cat ccg gaa gcc aca       1296
Thr Leu Leu Cys Pro Thr Asp Cys Phe Arg Lys His Pro Glu Ala Thr
            420                 425                 430 tac tct cgg tgc ggc tcc ggt ccc tgg att aca ccc agg tgc atg gtc       1344
Tyr Ser Arg Cys Gly Ser Gly Pro Trp Ile Thr Pro Arg Cys Met Val
        435                 440                 445 gac tac ccg tat agg ctt tgg cac tat cct tgt acc atc aat tac acc       1392
Asp Tyr Pro Tyr Arg Leu Trp His Tyr Pro Cys Thr Ile Asn Tyr Thr
    450                 455                 460 ata ttc aaa gtc agg atg tac gtg gga ggg gtc gag cac agg ctg gaa       1440
Ile Phe Lys Val Arg Met Tyr Val Gly Gly Val Glu His Arg Leu Glu
465                 470                 475                 480
```

```
gcg gcc tgc aac tgg acg cgg ggc gaa cgc tgt gat ctg gaa gac agg      1488
Ala Ala Cys Asn Trp Thr Arg Gly Glu Arg Cys Asp Leu Glu Asp Arg
            485                 490                 495 gac agg tcc gag ctc agc ccg ttg ctg ctg tcc acc aca cag tgg cag      1536
Asp Arg Ser Glu Leu Ser Pro Leu Leu Leu Ser Thr Thr Gln Trp Gln
        500                 505                 510 gtc ctt ccg tgt tct ttc acg acc ctg cca gcc ttg tcc acc ggc ctc      1584
Val Leu Pro Cys Ser Phe Thr Thr Leu Pro Ala Leu Ser Thr Gly Leu
    515                 520                 525 atc cac ctc cac cag aac att gtg gac gtg cag tac ttg tac ggg gta      1632
Ile His Leu His Gln Asn Ile Val Asp Val Gln Tyr Leu Tyr Gly Val
530                 535                 540 ggg tca agc atc gcg tcc tgg gcc att aag tgg gag tac gtc gtt ctc      1680
Gly Ser Ser Ile Ala Ser Trp Ala Ile Lys Trp Glu Tyr Val Val Leu
545                 550                 555                 560 ctg ttc ctt ctg ctt gca gac gcg cgc gtc tgc tgc ttg tgg atg          1728
Leu Phe Leu Leu Leu Ala Asp Ala Arg Val Cys Ser Cys Leu Trp Met
            565                 570                 575 atg tta ctc ata tcc caa gcg gag gcg gct gga cta gtg cgg ccg caa      1776
Met Leu Leu Ile Ser Gln Ala Glu Ala Ala Gly Leu Val Arg Pro Gln
        580                 585                 590 ggc ggc gga tcc gtg gac aag aaa att gtg ccc agg gat tgt ggt tgt      1824
Gly Gly Gly Ser Val Asp Lys Lys Ile Val Pro Arg Asp Cys Gly Cys
    595                 600                 605 aag cct tgc ata tgt aca gtc cca gaa gta tca tct gtc ttc atc ttc      1872
Lys Pro Cys Ile Cys Thr Val Pro Glu Val Ser Ser Val Phe Ile Phe
610                 615                 620 ccc cca aag ccc aag gat gtg ctc acc att act ctg act cct aag gtc      1920
Pro Pro Lys Pro Lys Asp Val Leu Thr Ile Thr Leu Thr Pro Lys Val
625                 630                 635                 640 acg tgt gtt gtg gta gac atc agc aag gat gat ccc gag gtc cag ttc      1968
Thr Cys Val Val Val Asp Ile Ser Lys Asp Asp Pro Glu Val Gln Phe
            645                 650                 655 agc tgg ttt gta gat gat gtg gag gtg cac aca gct cag acg caa ccc      2016
Ser Trp Phe Val Asp Asp Val Glu Val His Thr Ala Gln Thr Gln Pro
        660                 665                 670 cgg gag gag cag ttc aac agc act ttc cgc tca gtc agt gaa ctt ccc      2064
Arg Glu Glu Gln Phe Asn Ser Thr Phe Arg Ser Val Ser Glu Leu Pro
    675                 680                 685 atc atg cac cag gac tgg ctc aat ggc aag gag ttc aaa tgc agg gtc      2112
Ile Met His Gln Asp Trp Leu Asn Gly Lys Glu Phe Lys Cys Arg Val
690                 695                 700 aac agt gca gct ttc cct gcc ccc atc gag aaa acc atc tcc aaa acc      2160
Asn Ser Ala Ala Phe Pro Ala Pro Ile Glu Lys Thr Ile Ser Lys Thr
705                 710                 715                 720 aaa ggc aga ccg aag gct cca cag gtg tac acc att cca cct ccc aag      2208
Lys Gly Arg Pro Lys Ala Pro Gln Val Tyr Thr Ile Pro Pro Pro Lys
            725                 730                 735 gag cag atg gcc aag gat aaa gtc agt ctg acc tgc atg ata aca gac      2256
Glu Gln Met Ala Lys Asp Lys Val Ser Leu Thr Cys Met Ile Thr Asp
        740                 745                 750 ttc ttc cct gaa gac att act gtg gag tgg cag tgg aat ggg cag cca      2304
Phe Phe Pro Glu Asp Ile Thr Val Glu Trp Gln Trp Asn Gly Gln Pro
    755                 760                 765 gcg gag aac tac aag aac act cag ccc atc atg gac aca gat ggc tct      2352
Ala Glu Asn Tyr Lys Asn Thr Gln Pro Ile Met Asp Thr Asp Gly Ser
770                 775                 780 tac ttc gtc tac agc aag ctc aat gtg cag aag agc aac tgg gag gca      2400
Tyr Phe Val Tyr Ser Lys Leu Asn Val Gln Lys Ser Asn Trp Glu Ala
785                 790                 795                 800
```

-continued

```
gga aat act ttc acc tgc tct gtg tta cat gag ggc ctg cac aac cac    2448
Gly Asn Thr Phe Thr Cys Ser Val Leu His Glu Gly Leu His Asn His
            805                 810                 815 cat act gag aag agc ctc tcc cac tct cct ggg ctg caa agc ttg tcg    2496
His Thr Glu Lys Ser Leu Ser His Ser Pro Gly Leu Gln Ser Leu Ser
        820                 825                 830 aga agt act aga gga tca taa                                        2517
Arg Ser Thr Arg Gly Ser
        835
```

<210> SEQ ID NO 78
<211> LENGTH: 838
<212> TYPE: PRT
<213> ORGANISM: Artificial
<220> FEATURE:
<223> OTHER INFORMATION: Synthetic Construct

<400> SEQUENCE: 78

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Tyr Gln
            20                  25                  30

Val Arg Asn Ser Ser Gly Leu Tyr His Val Thr Asn Asp Cys Pro Asn
        35                  40                  45

Ser Ser Ile Val Tyr Glu Ala Ala Asp Ala Ile Leu His Thr Pro Gly
    50                  55                  60

Cys Val Pro Cys Val Arg Glu Gly Asn Ala Ser Arg Cys Trp Val Ala
65                  70                  75                  80

Val Thr Pro Thr Val Ala Thr Arg Asp Gly Lys Leu Pro Thr Thr Gln
            85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Thr
    210                 215                 220

His Val Thr Gly Gly Asn Ala Gly Arg Thr Thr Ala Gly Leu Val Gly
225                 230                 235                 240

Leu Leu Thr Pro Gly Ala Lys Gln Asn Ile Gln Leu Ile Asn Thr Asn
                245                 250                 255

Gly Ser Trp His Ile Asn Ser Thr Ala Leu Asn Cys Asn Glu Ser Leu
            260                 265                 270

Asn Thr Gly Trp Leu Ala Gly Leu Phe Tyr Gln His Lys Phe Asn Ser
        275                 280                 285

Ser Gly Cys Pro Glu Arg Leu Ala Ser Cys Arg Arg Leu Thr Asp Phe
    290                 295                 300

Ala Gln Gly Trp Gly Pro Ile Ser Tyr Ala Asn Gly Ser Gly Leu Asp
```

-continued

```
            305                 310                 315                 320
Glu Arg Pro Tyr Cys Trp His Tyr Pro Pro Arg Pro Cys Gly Ile Val
                    325                 330                 335
Pro Ala Lys Ser Val Cys Gly Pro Val Tyr Cys Phe Thr Pro Ser Pro
                    340                 345                 350
Val Val Gly Thr Thr Asp Arg Ser Gly Ala Pro Thr Tyr Ser Trp
                355                 360                 365
Gly Ala Asn Asp Thr Asp Val Phe Val Leu Asn Thr Arg Pro Pro
            370                 375                 380
Leu Gly Asn Trp Phe Gly Cys Thr Trp Met Asn Ser Thr Gly Phe Thr
385                 390                 395                 400
Lys Val Cys Gly Ala Pro Pro Cys Val Ile Gly Val Gly Asn Asn
                    405                 410                 415
Thr Leu Leu Cys Pro Thr Asp Cys Phe Arg Lys His Pro Glu Ala Thr
                420                 425                 430
Tyr Ser Arg Cys Gly Ser Gly Pro Trp Ile Thr Pro Arg Cys Met Val
                435                 440                 445
Asp Tyr Pro Tyr Arg Leu Trp His Tyr Pro Cys Thr Ile Asn Tyr Thr
        450                 455                 460
Ile Phe Lys Val Arg Met Tyr Val Gly Gly Val Glu His Arg Leu Glu
465                 470                 475                 480
Ala Ala Cys Asn Trp Thr Arg Gly Glu Arg Cys Asp Leu Glu Asp Arg
                    485                 490                 495
Asp Arg Ser Glu Leu Ser Pro Leu Leu Leu Ser Thr Thr Gln Trp Gln
                500                 505                 510
Val Leu Pro Cys Ser Phe Thr Thr Leu Pro Ala Leu Ser Thr Gly Leu
                515                 520                 525
Ile His Leu His Gln Asn Ile Val Asp Val Gln Tyr Leu Tyr Gly Val
            530                 535                 540
Gly Ser Ser Ile Ala Ser Trp Ala Ile Lys Trp Glu Tyr Val Val Leu
545                 550                 555                 560
Leu Phe Leu Leu Leu Ala Asp Ala Arg Val Cys Ser Cys Leu Trp Met
                    565                 570                 575
Met Leu Leu Ile Ser Gln Ala Glu Ala Ala Gly Leu Val Arg Pro Gln
                580                 585                 590
Gly Gly Gly Ser Val Asp Lys Lys Ile Val Pro Arg Asp Cys Gly Cys
            595                 600                 605
Lys Pro Cys Ile Cys Thr Val Pro Glu Val Ser Ser Val Phe Ile Phe
        610                 615                 620
Pro Pro Lys Pro Lys Asp Val Leu Thr Ile Thr Leu Thr Pro Lys Val
625                 630                 635                 640
Thr Cys Val Val Val Asp Ile Ser Lys Asp Asp Pro Glu Val Gln Phe
                    645                 650                 655
Ser Trp Phe Val Asp Asp Val Glu Val His Thr Ala Gln Thr Gln Pro
                660                 665                 670
Arg Glu Glu Gln Phe Asn Ser Thr Phe Arg Ser Val Ser Glu Leu Pro
                675                 680                 685
Ile Met His Gln Asp Trp Leu Asn Gly Lys Glu Phe Lys Cys Arg Val
            690                 695                 700
Asn Ser Ala Ala Phe Pro Ala Pro Ile Glu Lys Thr Ile Ser Lys Thr
705                 710                 715                 720
Lys Gly Arg Pro Lys Ala Pro Gln Val Tyr Thr Ile Pro Pro Pro Lys
                    725                 730                 735
```

```
Glu Gln Met Ala Lys Asp Lys Val Ser Leu Thr Cys Met Ile Thr Asp
            740             745             750

Phe Phe Pro Glu Asp Ile Thr Val Glu Trp Gln Trp Asn Gly Gln Pro
        755             760             765

Ala Glu Asn Tyr Lys Asn Thr Gln Pro Ile Met Asp Thr Asp Gly Ser
    770             775             780

Tyr Phe Val Tyr Ser Lys Leu Asn Val Gln Lys Ser Asn Trp Glu Ala
785             790             795                         800

Gly Asn Thr Phe Thr Cys Ser Val Leu His Glu Gly Leu His Asn His
                805             810             815

His Thr Glu Lys Ser Leu Ser His Ser Pro Gly Leu Gln Ser Leu Ser
            820             825             830

Arg Ser Thr Arg Gly Ser
        835

<210> SEQ ID NO 79
<211> LENGTH: 5
<212> TYPE: PRT
<213> ORGANISM: Mus musculus

<400> SEQUENCE: 79

Val Asp Lys Lys Ile
1               5
```

What is claimed is:

1. A purified chimeric antigen for eliciting an immune response against Hepatitis C in a host, said chimeric antigen comprising:
    an immune response domain, wherein the immune response domain comprises at least one immunogenic portion of an HCV protein selected from the group consisting of a HCV E1 protein, a HCV E2 protein, a HCV E1-E2 protein, a HCV NS3 protein, a HCV NS4B protein, and a HCV NS5A protein, and a combination thereof,
    a target binding domain, wherein the target binding domain consists of a hinge region, at least a portion of a $C_H1$ region and a xenotypic Fc antibody fragment comprising at least part of a $C_H2$ and $C_H3$ domain, wherein the immune response domain and the target binding domain are linked by peptide linkage.

2. The chimeric antigen of claim 1, wherein the chimeric antigen elicits a humoral immune response, a cellular immune response, or a both humoral immune response and a cellular immune response.

3. The chimeric antigen of claim 1, wherein the chimeric antigen elicits a Th1 immune response, a Th2 immune response or both a Th1 and a Th2 immune response.

4. The chimeric antigen of claim 1, wherein the immune response is an in vivo immune response.

5. The chimeric antigen of claim 1, wherein the target binding domain is capable of binding to an antigen presenting cell (APC).

6. The chimeric antigen of claim 1, further comprising one or more of a 6×His tag, a protease cleavage site, and a linker for linking the immune response domain and the target binding domain.

7. The chimeric antigen of claim 1, wherein the linker is selected from the group consisting of leucine zippers, biotin bound to avidin, or a covalent peptide linkage.

8. The chimeric antigen of claim 1, wherein the chimeric antigen is glycosylated.

9. The chimeric antigen of claim 1, wherein the chimeric antigen is mannose glycosylated.

10. A method of producing a chimeric antigen comprising:
    (a) providing a microorganism or a cell, the microorganism or cell comprising a polynucleotide that encodes a target binding domain bound to a linker molecule;
    (b) culturing said microorganism or cell under conditions whereby the target binding domain-linker molecule is expressed; and
    (c) contacting the target binding domain-linker molecule and an immune response domain under conditions that allow for the binding of the linker to the immune response domain, the binding resulting in a chimeric antigen.

11. A method of delivering an antigen to an antigen presenting cell, the method comprising administering to the antigen presenting cell a chimeric antigen of claim 1.

12. The method of claim 11, wherein the antigen presenting cell is a dendritic cell.

13. A method of activating an antigen presenting cell, the method comprising contacting the antigen presenting cell with a chimeric antigen of claim 1.

14. The method of claim 13, wherein the contacting takes place ex vivo.

15. The method of claim 13, wherein the contacting takes places in vivo.

16. The method of claim 15, wherein the contacting takes place in a human.

17. The method of claim 15, wherein the method comprises administering to a subject a composition comprising a chimeric antigen comprising an immune response domain and a target binding domain, wherein the immune response domain comprises one or more immunogenic portions of one or more proteins selected from the group consisting of a HCV E1 protein, a HCV E2 protein, a HCV E1-E2 protein, a HCV NS3 protein, a HCV NS4B protein, and a HCV NS5A protein, and a combination thereof, and the target binding domain comprises an antibody fragment, and wherein the antigen presenting cell is in the subject.

18. The method of claim 15, wherein the contacting results in a humoral immune response, a cellular immune response, or both a humoral immune response and a cellular immune response.

19. The method of claim 18 wherein the cellular immune response is one or more of a Th1 response, a Th2 response, and a CTL response.

20. The method of claim 17, wherein the subject has, or is likely to have, an immune-treatable condition.

21. The method of claim 20, wherein the immune-treatable condition is an acute infection.

22. The method of claim 20, wherein the immune-treatable condition is a chronic infection.

23. The method of claim 22, wherein the chronic infection is a chronic hepatitis C viral infection.

24. The method of claim 20, wherein the immune treatable condition is a hepatitis C viral infection and the immune response domain comprises one or more antigenic portions of one or more proteins selected from the group consisting of a HCV E1 protein, a HCV E2 protein, a HCV E1-E2 protein, a HCV NS5A protein, and a combination thereof.

25. The method of claim 17, wherein the subject is vaccinated against a viral infection.

26. The method of claim 25, wherein the subject is therapeutically vaccinated against an existing viral infection.

* * * * *

UNITED STATES PATENT AND TRADEMARK OFFICE
CERTIFICATE OF CORRECTION

PATENT NO. : 8,465,745 B2
APPLICATION NO. : 13/209979
DATED : June 18, 2013
INVENTOR(S) : Rajan George et al.

It is certified that error appears in the above-identified patent and that said Letters Patent is hereby corrected as shown below:

In the Claims:

In claim 2, column 205, line 49, please delete "a both" and insert --both a--

In column 206, line 32, please cancel the entire text of claim 10 beginning with "A method of producing" and ending "a chimeric antigen."

In claim 11, column 206, line 45, please delete claim reference numeral "11." and insert numeral --10.--

In claim 12, column 206, line 48, please delete claim reference numeral "12." and insert numeral --11.--

In claim 12, column 206, line 48, please delete "The method of claim 11," and insert --The method of claim 10,--

In claim 13, column 206, line 50, please delete claim reference numeral "13." and insert numeral --12.--

In claim 14, column 206, line 53, please delete claim reference numeral "14." and insert numeral --13.--

In claim 14, column 206, line 53, please delete "The method of claim 13," and insert --The method of claim 12,--

In claim 15, column 206, line 55, please delete claim reference numeral "15." and insert numeral --14.--

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,465,745 B2

In claim 15, column 206, line 55, please delete "The method of claim 13," and insert
--The method of claim 12,--

In claim 16, column 206, line 57, please delete claim reference numeral "16." and insert
numeral --15.--

In claim 16, column 206, line 57, please delete "The method of claim 15," and insert
--The method of claim 14,--

In claim 17, column 206, line 59, please delete "The method of claim 15," and insert
--The method of claim 14,--

In claim 17, column 206, line 59, please delete claim reference numeral "17." and insert
numeral --16.--

In claim 18, column 207, line 3, please delete claim reference numeral "18." and insert numeral --17.--

In claim 18, column 207, line 3, please delete "The method of claim 15," and insert
--The method of claim 14,--

In claim 19, column 207, line 7, please delete claim reference numeral "19." and insert numeral --18.--

In claim 19, column 207, line 7, please delete "The method of claim 18," and insert
--The method of claim 17,--

In claim 20, column 207, line 10, please delete claim reference numeral "20." and insert
numeral --19.--

In claim 20, column 207, line 10, please delete "The method of claim 17," and insert
--The method of claim 16,--

In claim 21, column 207, line 12, please delete claim reference numeral "21." and insert
numeral --20.--

In claim 21, column 207, line 12, please delete "The method of claim 20," and insert
--The method of claim 19,--

In claim 22, column 207, line 14, please delete claim reference numeral "22." and insert
numeral --21.--

In claim 22, column 207, line 14, please delete "The method of claim 20," and insert
--The method of claim 19,--

In claim 23, column 207, line 16, please delete claim reference numeral "23." and insert
numeral --22.--

CERTIFICATE OF CORRECTION (continued)
U.S. Pat. No. 8,465,745 B2

In claim 23, column 207, line 16, please delete "The method of claim 22," and insert
--The method of claim 21,--

In claim 24, column 207, line 18, please delete claim reference numeral "24." and insert numeral --23.--

In claim 24, column 207, line 18, please delete "The method of claim 20," and insert
--The method of claim 19,--

In claim 25, column 207, line 24, please delete claim reference numeral "25." and insert numeral --24.--

In claim 25, column 207, line 24, please delete "The method of claim 17," and insert
--The method of claim 16,--

In column 207, line 26, please insert the following claim:
--25. The method of claim 24, wherein the subject is prophylactically vaccinated against a viral infection.--

In claim 26, column 207, line 26, please delete "The method of claim 25," and insert
--The method of claim 24,--

In column 207, line 28, please insert the following claim:
--27. A pharmaceutical composition comprising a chimeric antigen of claim 1 and a pharmaceutically acceptable excipient--